US012685012B2

(12) United States Patent
Park et al.

(10) Patent No.: US 12,685,012 B2
(45) Date of Patent: Jul. 14, 2026

(54) LIGHT-EMITTING DEVICE AND ELECTRONIC APPARATUS INCLUDING THE SAME

(71) Applicant: Samsung Display Co., Ltd., Yongin-si (KR)

(72) Inventors: Hyunbin Park, Yongin-si (KR); Minji Kim, Yongin-si (KR); Jeongmin Lee, Yongin-si (KR); Eunjae Jeong, Yongin-si (KR); Jiyong Choi, Yongin-si (KR); Sanghyun Han, Yongin-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 837 days.

(21) Appl. No.: 18/102,869

(22) Filed: Jan. 30, 2023

(65) Prior Publication Data

US 2023/0363259 A1 Nov. 9, 2023

(30) Foreign Application Priority Data

Feb. 9, 2022 (KR) ........................ 10-2022-0016967
May 24, 2022 (KR) ........................ 10-2022-0063592

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C07D 209/88* (2013.01);
(Continued)

(58) Field of Classification Search
CPC .. H10K 85/633; H10K 85/636; C07C 211/61; C07D 209/88; C07D 307/91; C07D 333/76; C07D 405/10; C09K 11/06
(Continued)

(56) References Cited

U.S. PATENT DOCUMENTS 4,720,432 A 1/1988 Vanslyke et al.
5,061,569 A 10/1991 Vanslyke et al.
(Continued)

FOREIGN PATENT DOCUMENTS

JP 11-144873 5/1999
JP 2000-302756 10/2000
(Continued)

*Primary Examiner* — James D Sells
(74) *Attorney, Agent, or Firm* — CANTOR COLBURN LLP

(57) ABSTRACT

Embodiments provide a light-emitting device that includes a first electrode, a second electrode facing the first electrode, an interlayer between the first electrode and the second electrode and including an emission layer, a first compound represented by Formula 1, a second compound represented by Formula 2, and at least one of a third compound represented by Formula 3 and a fourth compound represented by
(Continued)

Formula 4, wherein the first compound to the fourth compound are different from each other, and Formulae 1 to 4 are described in the specification:

[Formula 1]

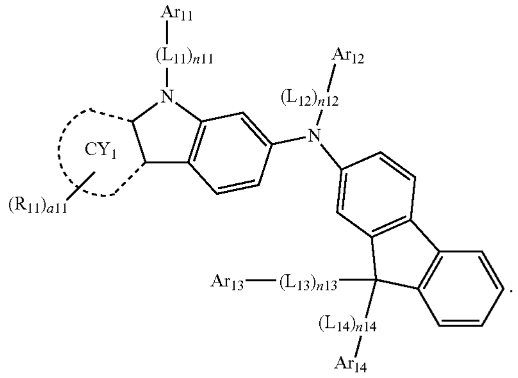

20 Claims, 3 Drawing Sheets

(51) Int. Cl.

| | |
|---|---|
| ***C07D 209/88*** | (2006.01) |
| ***C07D 307/91*** | (2006.01) |
| ***C07D 333/76*** | (2006.01) |
| ***C07D 405/10*** | (2006.01) |
| ***C09K 11/06*** | (2006.01) |
| *H10K 50/15* | (2023.01) |
| *H10K 50/17* | (2023.01) |
| *H10K 50/18* | (2023.01) |

(52) U.S. Cl.
CPC ......... *C07D 307/91* (2013.01); *C07D 333/76* (2013.01); *C07D 405/10* (2013.01); *C09K 11/06* (2013.01); *H10K 85/636* (2023.02); *C07C 2601/14* (2017.05); *C07C 2602/42* (2017.05); *C07C 2603/18* (2017.05); *C07C 2603/74* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/156* (2023.02); *H10K 50/17* (2023.02); *H10K 50/181* (2023.02); *H10K 85/615* (2023.02); *H10K 85/626* (2023.02); *H10K 85/6572* (2023.02); *H10K 85/6574* (2023.02); *H10K 85/6576* (2023.02)

(58) Field of Classification Search
USPC .......................................................... 428/690
See application file for complete search history.

(56) References Cited

U.S. PATENT DOCUMENTS

| | | | | |
|---|---|---|---|---|
| 6,242,115 | B1 | 6/2001 | Thomson et al. | |
| 8,021,764 | B2 | 9/2011 | Hwang et al. | |
| 10,079,348 | B2 | 9/2018 | Jin et al. | |
| 10,941,108 | B2 | 3/2021 | Jeong et al. | |
| 11,440,901 | B2 * | 9/2022 | Yang ..................... | C07F 7/0816 |
| 2014/0001444 | A1 | 1/2014 | Kim et al. | |
| 2019/0288220 | A1 | 9/2019 | Kim et al. | |

FOREIGN PATENT DOCUMENTS

| | | |
|---|---|---|
| JP | 2003-133075 | 5/2003 |
| JP | 2004-79265 | 3/2004 |
| JP | 2006-151979 | 6/2006 |
| JP | 2007-77064 | 3/2007 |
| KR | 1020140001581 A | 1/2014 |
| KR | 10-2017-0007683 | 1/2017 |
| KR | 10-1708176 | 2/2017 |
| KR | 10-1790321 | 10/2017 |
| KR | 10-2019-0108222 | 9/2019 |

* cited by examiner

LIGHT-EMITTING DEVICE AND ELECTRONIC APPARATUS INCLUDING THE SAME

CROSS-REFERENCE TO RELATED APPLICATION(S)

This application claims priority to and benefits of Korean Patent Application Nos. 10-2022-0016967 and 10-2022-0063592, under 35 U.S.C. § 119, filed on Feb. 9, 2022 and May 24, 2022, respectively, in the Korean Intellectual Property Office, the entire contents of which are incorporated herein by reference.

BACKGROUND

1. Technical Field

The disclosure relates to a light-emitting device and an electronic apparatus including the same.

2. Description of the Related Art

Light-emitting devices are self-emissive devices that have wide viewing angles, high contrast ratios, short response times, and excellent characteristics in terms of luminance, driving voltage, and response speed, and produce multicolor images, compared to devices of the related art.

In a light-emitting device, a first electrode is arranged on a substrate, and a hole transport region, an emission layer, an electron transport region, and a second electrode are sequentially formed on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. The excitons may transition from an excited state to a ground state, thus generating light.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Embodiments include a light-emitting device having a low driving voltage, high efficiency, and a long lifespan, and an electronic apparatus including the light-emitting device.

Additional aspects will be set forth in part in the description which follows and, in part, will be apparent from the description, or may be learned by practice of the embodiments of the disclosure.

According to embodiments, a light-emitting device may include: a first electrode; a second electrode facing the first electrode; an interlayer between the first electrode and the second electrode and including an emission layer; a first compound represented by Formula 1; a second compound represented by Formula 2; and at least one of a third compound represented by Formula 3 and a fourth compound represented by Formula 4, wherein the first compound to the fourth compound may be different from each other:

[Formula 1]

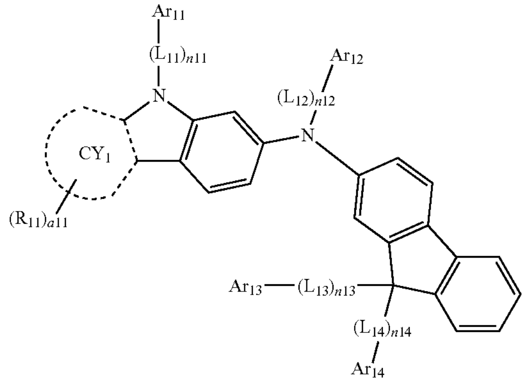

[Formula 2]

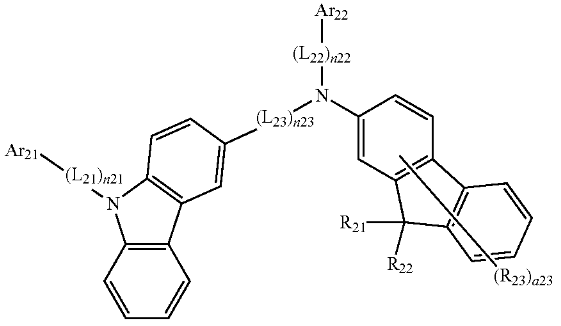

[Formula 3]

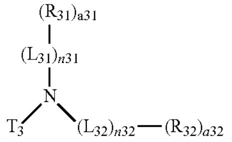

[Formula 4]

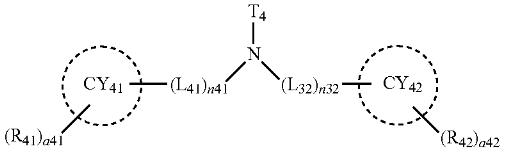

[Formula 5]

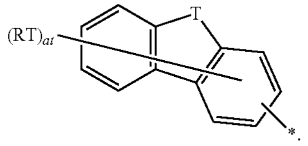

In Formulae 1 to 4, $L_{11}$ to $L_{14}$, $L_{21}$ to $L_{23}$, $L_{31}$, $L_{32}$, $L_{41}$, and $L_{42}$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, n11 to n14, n21 to n23, n31, n32, n41, and n42 may each independently be an integer from 1 to 3, $Ar_{11}$ to $Ar_{14}$, $Ar_{21}$, and $Ar_{22}$ may each independently be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{21}$ and $R_{22}$ may each independently be a $C_1$-$C_{30}$ alkyl group or a $C_3$-$C_{30}$ cycloalkyl group, each unsubstituted or substituted with deuterium, —F, a cyano group, a $C_1$-$C_{10}$ alkyl group, or any combination thereof, $R_{31}$ and $R_{32}$ may each independently be a $C_3$-$C_{30}$ cycloalkyl group that is unsubstituted or substituted with deuterium, —F, a cyano group, a $C_1$-$C_{10}$ alkyl group, or any combination thereof, $CY_1$ may be a benzene group or a naphthalene group, $CY_{41}$ and $CY_{42}$ may each independently be a $C_5$-$C_{30}$ carbocyclic group, $T_3$ and $T_4$ may each independently be a group represented by Formula 5, wherein in Formula 5, T may be $C(X_1)(X_2)$, O, S, or $N(X_1)$, $X_1$ and $X_2$ may each independently be a $C_1$-$C_{30}$ alkyl group unsubstituted or substituted with at least one $R_{10a}$, a $C_2$-$C_{30}$ alkenyl group unsubstituted or substituted with at least one $R_{10a}$, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, $X_1$ and $X_2$ may optionally be linked to each other to form a $C_5$-$C_{30}$ carbocyclic group that is unsubstituted or substituted with at least one $R_{10a}$ or a $C_1$-$C_{30}$ heterocyclic group that is unsubstituted or substituted with at least one $R_{10a}$, wherein in Formulae 1 to 5, $R_{11}$, $R_{23}$, $R_{41}$, $R_{42}$, and RT may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)_2(Q_1)$, or —$P(=O)(Q_1)(Q_2)$, a11 may be an integer from 0 to 6, a23 may be an integer from 0 to 7, a31 and a32 may each independently be an integer from 1 to 5, a41 and a42 may each independently be an integer from 0 to 9, at may be an integer from 0 to 7,

* indicates a binding site to a neighboring atom, $R_{10a}$ may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, or a $C_2$-$C_{60}$ heteroarylalkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, $C_7$-$C_{60}$ aryl alkyl group, or a $C_2$-$C_{60}$ heteroarylalkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, the first electrode may be an anode; the second electrode may be a cathode; the interlayer may further include a hole transport region between the emission layer and the first electrode, and an electron transport region between the emission layer and the second electrode; the hole transport region may include a hole injection layer, a hole transport layer, an emission auxiliary layer, an electron blocking layer, or any combination thereof; and the electron transport region may include a buffer layer, a hole blocking layer, an electron control layer, an electron transport layer, an electron injection layer, or any combination thereof.

In an embodiment, the hole transport region may include at least one of a hole injection layer, a hole transport layer, and an electron blocking layer; and the at least one of the hole injection layer, the hole transport layer, and the electron blocking layer may include the first compound, the second compound, and at least one of the third compound and the fourth compound.

In an embodiment, the hole transport region may include a hole transport layer; the hole transport layer may include a first hole transport layer, a second hole transport layer, and a third hole transport layer; the first hole transport layer may be between the first electrode and the second hole transport layer; the first hole transport layer may include the first compound; the second hole transport layer may be between the first hole transport layer and the third hole transport layer; the second hole transport layer may include the second compound; and the third hole transport layer may include at least one of the third compound and the fourth compound.

In an embodiment, the hole transport region may include a hole transport layer; the hole transport layer may include a first hole transport layer, a second hole transport layer, a third hole transport layer, and a fourth hole transport layer; the first hole transport layer may be between the first electrode and the second hole transport layer; the first hole transport layer may include the first compound; the second hole transport layer may be between the first hole transport layer and the third hole transport layer; the second hole transport layer may include the second compound; the third hole transport layer may be between the second hole transport layer and the fourth hole transport layer; the third hole transport layer may include the third compound, and the fourth hole transport layer may include the fourth compound.

In an embodiment, in Formulae 1 to 4, $L_{11}$ to $L_{14}$, $L_{21}$ to $L_{23}$, $L_{31}$, $L_{32}$, $L_{41}$, and $L_{42}$ may each independently be: a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ is the same as defined in Formulae 1 to 4.

In an embodiment, in Formulae 1 to 4, $L_{11}$ to $L_{14}$, $L_{21}$ to $L_{23}$, $L_{31}$, $L_{32}$, $L_{41}$, and $L_{42}$ may each independently be a single bond or phenylene.

In an embodiment, in Formulae 1 and 2, $Ar_{11}$ to $Ar_{14}$, $Ar_{21}$, and $Ar_{22}$ may each independently be a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, $—P(=O)(Q_{31})(Q_{32})$, or any combination thereof, and $Q_{31}$ to $Q_{33}$ may each independently be: $CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, or $—CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, or any combination thereof.

In an embodiment, in Formulae 1 and 2, $Ar_{11}$ to $Ar_{14}$, $Ar_{21}$, and $Ar_{22}$ may each independently be a phenyl group, a naphthyl group, a phenanthrenyl group, an anthracenyl group, a dibenzothiophenyl group, or a dibenzofuranyl group, each unsubstituted or substituted with deuterium, —F, a cyano group, a $C_1$-$C_{20}$ alkyl group, a $C_1$-$C_{20}$ alkoxy group, a phenyl group, or any combination thereof.

In an embodiment, in Formula 2, $R_{21}$ and $R_{22}$ may be identical to each other.

In an embodiment, in Formula 3, $R_{31}$ and $R_{32}$ may each independently be a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, or a bicyclo[2.2.2]octyl group, each unsubstituted or substituted with deuterium, —F, a cyano group, a $C_1$-$C_{10}$ alkyl group, or any combination thereof.

In an embodiment, in Formula 4, $CY_{41}$ and $CY_{42}$ may each be a naphthalene group; or one of $CY_{41}$ and $CY_{42}$ may be a naphthalene group, and the other of $CY_{41}$ and $CY_{42}$ may be a benzene group or a phenanthrene group.

In an embodiment, in Formulae 1, 2, and 4, $R_{11}$ may be hydrogen, deuterium, or —F, and $R_{23}$, $R_{41}$, and $R_{42}$ may each independently be: hydrogen, deuterium, or —F; or a phenyl group that is unsubstituted or substituted with deuterium, —F, a cyano group, a $C_1$-$C_{20}$ alkyl group, or any combination thereof.

In an embodiment, in Formula 5, $X_1$ and $X_2$ may each independently be: a $C_1$-$C_{10}$ alkyl group that is unsubstituted or substituted with deuterium, —F, a cyano group, or any combination thereof; or a $C_2$-$C_{10}$ alkenyl group, a cyclopropyl group, a cyclobutyl group, a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, a bicyclo[2.2.2]octyl group, phenyl group, a naphthyl group, a pyridinyl group, a pyrimidinyl group, a pyrazinyl group, a pyridazinyl group, or a triazinyl group, each unsubstituted or substituted with deuterium, —F, a cyano group, a $C_1$-$C_{10}$ alkyl group, or any combination thereof.

In an embodiment, in Formula 5, when T is $C(X_1)(X_2)$, $X_1$ and $X_2$ may be identical to each other.

In an embodiment, in Formula 5, RT may be: hydrogen, deuterium, —F, or a cyano group; or a $C_6$-$C_{10}$ aryl group that is unsubstituted or substituted with deuterium, —F, a cyano group, a $C_1$-$C_{10}$ alkyl group, a $C_1$-$C_{10}$ alkoxy group, or any combination thereof.

In an embodiment, the emission layer may emit blue light having a maximum emission wavelength in a range of about 430 nm to about 490 nm.

According to embodiments, an electronic apparatus may include the light-emitting device.

In an embodiment, the electronic apparatus may further include a thin-film transistor, wherein the thin-film transistor may include a source electrode and a drain electrode, and the first electrode of the light-emitting device may be electrically connected to the source electrode or the drain electrode.

In an embodiment, the electronic apparatus may further include a color filter, a color conversion layer, a touch screen layer, a polarizing layer, or any combination thereof.

It is to be understood that the embodiments above are described in a generic and explanatory sense only and not for the purpose of limitation, and the disclosure is not limited to the embodiments described above.

BRIEF DESCRIPTION OF THE DRAWINGS

The above and other aspects and features of the disclosure will be more apparent by describing in detail embodiments thereof with reference to the accompanying drawings, in which.

DETAILED DESCRIPTION OF THE EMBODIMENTS

Figure 1:
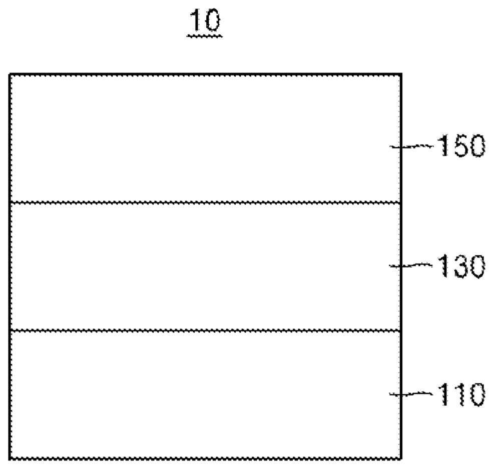
FIG. 1 is a schematic cross-sectional view of a light-emitting device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

In the specification and the claims, the term "at least one of" is intended to include the meaning of "at least one selected from the group consisting of" for the purpose of its meaning and interpretation. For example, "at least one of A, B, and C" may be understood to mean A only, B only, C only, or any combination of two or more of A, B, and C, such as ABC, ACC, BC, or CC. When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within +20%, +10%, or +5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

The term "interlayer" as used herein may refer to a single layer and/or multiple layers between the first electrode and the second electrode of a light-emitting device.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

An aspect provides a light-emitting device which may include:

a first electrode;

a second electrode facing the first electrode;

an interlayer between the first electrode and the second electrode and comprising an emission layer;

a first compound represented by Formula 1;

a second compound represented by Formula 2; and at least one of a third compound represented by Formula 3 and a fourth compound represented by Formula 4, wherein the first compound to the fourth compound may be different from each other.

Hereinafter, the first compound, the second compound, the third compound, and the fourth compound will be described:

[Formula 1]

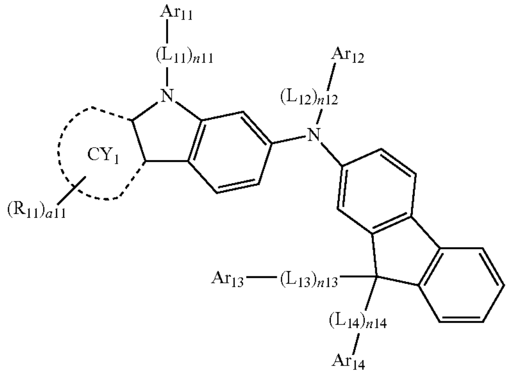

[Formula 2]

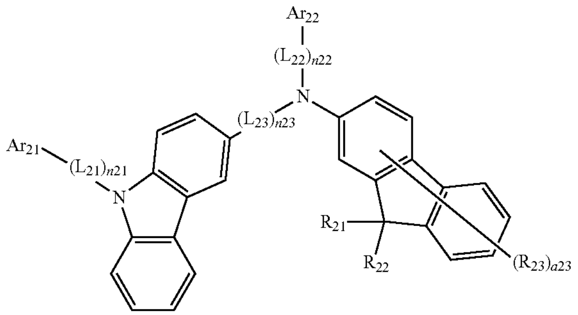

[Formula 3]

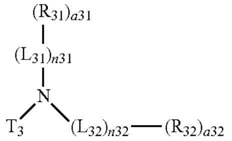

[Formula 4]

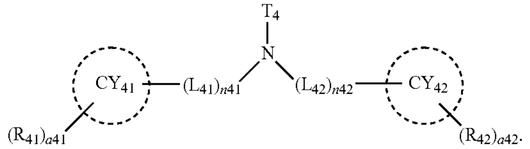

In Formulae 1 to 4, $L_{11}$ to $L_{14}$, $L_{21}$ to $L_{23}$, $L_{31}$, $L_{32}$, $L_{41}$ and $L_{42}$ may each independently be a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, and n11 to n14, n21 to n23, n31, n32, n41, and n42 may each independently be an integer from 1 to 3.

In an embodiment, in Formulae 1 to 4, $L_{11}$ to $L_{14}$, $L_{21}$ to $L_{23}$, $L_{31}$, $L_{32}$, $L_{41}$, and $L_{42}$ may each independently be:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluoren-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ may be the same as defined herein.

In an embodiment, in Formulae 1 to 4, $L_{11}$ to $L_{14}$, $L_{21}$ to $L_{23}$, $L_{31}$, $L_{32}$, $L_{41}$, and $L_{42}$ may each independently be a single bond or phenylene.

In an embodiment, $L_{31}$ and $L_{32}$ may each independently be a group represented by one of Formulae 2-1 to 2-3, and * and *' in Formulae 2-1 to 2-3 each indicate a binding site to a neighboring atom:

2-1

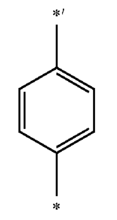

2-2

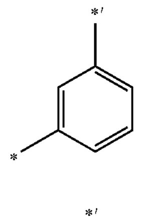

2-3

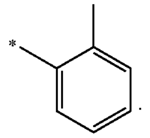

In an embodiment, in Formulae 1 to 4, n11 to n14, n21 to n23, n31, n32, n41, and n42 may each independently be 1 or 2.

In Formulae 1 and 2, $Ar_{11}$ to $Ar_{14}$, $Ar_{21}$, and $Ar_{22}$ may each independently be a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$.

In an embodiment, in Formulae 1 and 2, $Ar_{11}$ to $Ar_{14}$, $Ar_{21}$, and $Ar_{22}$ may each independently be:

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, $—CD_3$, $—CD_2H$, $—CDH_2$, $—CF_3$, $—CF_2H$, $—CFH_2$, hydroxyl group, cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolecarbazolyl group, an imidazopyridinyl group, an imidazopyrimidinyl group, —Si$(Q_{31})(Q_{32})(Q_{33})$, —N$(Q_{31})(Q_{32})$, —B$(Q_{31})(Q_{32})$, —P$(Q_{31})(Q_{32})$, —C(=O)$(Q_{31})$, —S$(=O)_2(Q_{31})$, —P(=O)$(Q_{31})(Q_{32})$, or any combination thereof, and $Q_{31}$ to $Q_{33}$ may each independently be:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, or any combination thereof.

In an embodiment, in Formulae 1 and 2, $Ar_{11}$ to $Ar_{14}$, $Ar_{21}$, and $Ar_{22}$ may each independently be a phenyl group, a naphthyl group, a phenanthrenyl group, an anthracenyl group, a dibenzothiophenyl group, or a dibenzofuranyl group, each unsubstituted or substituted with deuterium, —F, a cyano group, a $C_1$-$C_{20}$ alkyl group, a $C_1$-$C_{20}$ alkoxy group, a phenyl group, or any combination thereof.

In an embodiment, in Formula 1, $Ar_{11}$ to $Ar_{14}$ may each independently be a phenyl group or a naphthyl group, each unsubstituted or substituted with deuterium, —F, a cyano group, a $C_1$-$C_{20}$ alkyl group, a $C_1$-$C_{20}$ alkoxy group, a phenyl group, or any combination thereof, and in Formula 2, $Ar_{21}$ and $Ar_{22}$ may each independently be a phenyl group, a naphthyl group, or a dibenzofuranyl group, each unsubstituted or substituted with deuterium, —F, a cyano group, a $C_1$-$C_{20}$ alkyl group, a $C_1$-$C_{20}$ alkoxy group, a phenyl group, or any combination thereof.

For example, in Formula 1, $Ar_{11}$ to $Ar_{14}$ may each independently be a phenyl group or a naphthyl group, and in Formula 2, $Ar_{21}$ and $Ar_{22}$ may each independently be a phenyl group, a naphthyl group, or a dibenzofuranyl group.

In Formula 2, $R_{21}$ and $R_{22}$ may each independently be a $C_1$-$C_{30}$ alkyl group or a $C_3$-$C_{30}$ cycloalkyl group, each unsubstituted or substituted with deuterium, —F, a cyano group, a $C_1$-$C_{10}$ alkyl group, or any combination thereof.

The term 'cycloalkyl group' as used herein may refer to not only a monocyclic group such as a cyclohexyl group, but may also refer to a condensed-cyclic unsaturated hydrocarbon group such as an adamantanyl group.

In an embodiment, in Formula 2, $R_{21}$ and $R_{22}$ may each independently be a $C_1$-$C_{10}$ alkyl group or a $C_3$-$C_{10}$ cycloalkyl group, each unsubstituted or substituted with deuterium, —F, a cyano group, or any combination thereof.

In an embodiment, in Formula 2, $R_{21}$ and $R_{22}$ may each independently be:

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each unsubstituted or substituted with deuterium, —F, a cyano group, or any combination thereof; or a cyclopropyl group, a cyclobutyl group, a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, or a bicyclo[2.2.2]octyl group.

In an embodiment, in Formula 2, $R_{21}$ and $R_{22}$ may be identical to each other.

In Formula 3, $R_{31}$ and $R_{32}$ may each independently be a $C_3$-$C_{30}$ cycloalkyl group that is unsubstituted or substituted with deuterium, —F, a cyano group, a $C_1$-$C_{10}$ alkyl group, or any combination thereof. In Formula 2, $R_{31}$ and $R_{32}$ may be identical to each other or different from each other.

In an embodiment, in Formula 3, $R_{31}$ and $R_{32}$ may each independently be a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, or a bicyclo[2.2.2]octyl group, each unsubstituted or substituted with deuterium, —F, a cyano group, a $C_1$-$C_{10}$ alkyl group, or any combination thereof.

In an embodiment, in Formula 3, $R_{31}$ and $R_{32}$ may each independently be a cyclopentyl group, a cyclohexyl group, a cycloheptyl group, a cyclooctyl group, an adamantanyl group, a bicyclo[2.2.1]heptyl group, or a bicyclo[2.2.2]octyl group.

For example, in Formula 3, $R_{31}$ may be a cyclohexyl group, an adamantanyl group, or a bicyclo[2.2.1]heptyl group, and $R_{32}$ may be a bicyclo[2.2.1]heptyl group, but embodiments are not limited thereto.

In Formula 1, $CY_1$ may be a benzene group or a naphthalene group.

In an embodiment, in Formula 1, $CY_1$ may be a group represented by one of Formulae 1-1 to 1-4:

1-1

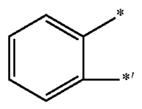

1-2

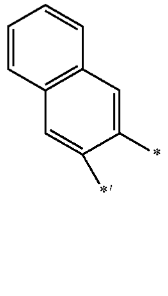

-continued 1-3

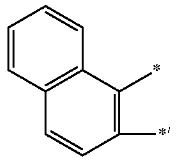

1-4

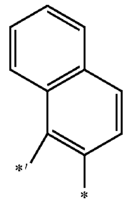

In Formulae 1-1 to 1-4, * indicates a binding site to a nitrogen atom, and *' indicates a binding site to a carbon atom.

In Formula 4, $CY_{41}$ and $CY_{42}$ may each independently be a $C_5$-$C_{30}$ carbocyclic group.

In an embodiment, in Formula 4, $CY_{41}$ and $CY_{42}$ in Formula 4 may each independently be a $C_6$-$C_{20}$ arene group.

For example, in Formula 4, $CY_{41}$ and $CY_{42}$ may each independently be a benzene group, a naphthalene group, an anthracene group, or a phenanthrene group.

In an embodiment, in Formula 4, $CY_{41}$ and $CY_{42}$ may each independently be a benzene group, a naphthalene group, or a phenanthrene group.

In an embodiment, in Formula 4, $CY_{41}$ and $CY_{42}$ may each be a naphthalene group; or one of $CY_{41}$ and $CY_{42}$ may be a naphthalene group, and the other of $CY_{41}$ and $CY_{42}$ may be a benzene group or a phenanthrene group.

In Formulae 3 and 4, $T_3$ and $T_4$ may each independently be a group represented by Formula 5:

[Formula 5]

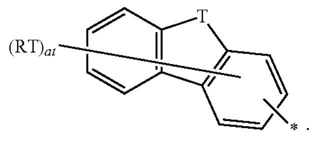

In Formula 5,

T may be $C(X_1)(X_2)$, O, S, or $N(X_1)$, $X_1$ and $X_2$ may each independently be a $C_1$-$C_{30}$ alkyl group unsubstituted or substituted with at least one $R_{10a}$, a $C_2$-$C_{30}$ alkenyl group unsubstituted or substituted with at least one $R_{10a}$, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, and $X_1$ and $X_2$ may optionally be linked to each other to form a $C_5$-$C_{30}$ carbocyclic group that is unsubstituted or substituted with at least one $R_{10a}$ or a $C_1$-$C_{30}$ heterocyclic group that is unsubstituted or substituted with at least one $R_{10a}$.

In Formula 5, * indicates a binding site to a neighboring atom.

In Formulae 1 to 5, $R_{11}$, $R_{23}$, $R_{41}$, $R_{42}$, and RT may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-Si(Q_1)(Q_2)(Q_3)$, $-N(Q_1)(Q_2)$, $-B(Q_1)(Q_2)$, $-P(Q_1)(Q_2)$, $-C(=O)(Q_1)$, $-S(=O)_2(Q_1)$, or $-P(=O)(Q_1)(Q_2)$, a11 may be an integer from 0 to 6, a23 may be an integer from 0 to 7, a31 and a32 may each independently be an integer from 1 to 5, a41 and a42 may each independently be an integer from 0 to 9, and at may be an integer from 0 to 7.

In an embodiment, a11 indicates the number of substituents bonded to $CY_1$. For example, when $CY_1$ is a group represented by Formula 1-1, a11 may be an integer from 0 to 4, and when $CY_1$ is a group represented by one of Formulae 1-2 to 1-4, a11 may be an integer from 0 to 6.

In an embodiment, a41 and a42 indicate the number of substituents bonded to $CY_{41}$ and $CY_{42}$, respectively. For example, when $CY_{41}$ is a benzene group, a41 may be an integer from 0 to 5, when $CY_{41}$ is a naphthalene group, a41 may be an integer from 0 to 7, and when $CY_{41}$ is a phenanthrene group, a41 may be an integer from 0 to 9.

In an embodiment, in Formulae 1, 2, and 4, a11, a23, a41, and a42 may each independently be 0, 1, or 2.

In an embodiment, in Formula 3, a31 and a32 may each independently be 1 or 2. For example, a31 and a32 may each be 1.

In an embodiment, in Formulae 1, 2, 4, and 5, $R_{11}$, $R_{23}$, $R_{41}$, $R_{42}$, and RT may each independently be:

hydrogen, deuterium, —F, —Cl, —Br, —I, a hydroxyl group, a cyano group, a nitro group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, $-CD_3$, $-CD_2H$, $-CDH_2$, $-CF_3$, $-CF_2H$, $-CFH_2$, a hydroxyl group, a cyano group, a nitro group, a $C_1$-$C_{20}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, $—CD_3$, $—CD_2H$, $—CDH_2$, $—CF_3$, $—CF_2H$, $—CFH_2$, hydroxyl group, cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolecarbazolyl group, an imidazopyridinyl group, an imidazopyrimidinyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, $—P(=O)(Q_{31})(Q_{32})$, or any combination thereof; or $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, and $Q_1$ to $Q_3$ and $Q_{31}$ to $Q_{33}$ may each independently be:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, or $—CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, or any combination thereof.

In an embodiment, in Formulae 1, 2, and 4, $R_{11}$ may be hydrogen, deuterium, or —F, and $R_{23}$, $R_{41}$, and $R_{42}$ may each independently be: hydrogen, deuterium, or —F; or a phenyl group that is unsubstituted or substituted with deuterium, —F, a cyano group, a $C_1$-$C_{20}$ alkyl group, or any combination thereof.

For example, $R_{11}$ may be hydrogen.

For example, $R_{23}$ may be hydrogen or a phenyl group, but embodiments are not limited thereto.

For example, $R_{41}$ and $R_{42}$ may each independently be hydrogen or a phenyl group.

For example, one of $R_{41}$ and $R_{42}$ may be hydrogen, and the other of $R_{41}$ and $R_{42}$ may be a phenyl group, but embodiments are not limited thereto.

In embodiments, $T_3$ in Formula 3 and $T_4$ in Formula 4 may be identical to or different from each other.

With respect to Formula 5, the expression "$X_1$ and $X_2$ are linked to each other to form a cyclic group" as used herein may include:

a case in which $X_1$ and $X_2$ are directly linked to each other to form a cyclic group; or a case in which $X_1$ and $X_2$ are directly linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a cyclic group.

For example, in Compound 129, T may be $C(X_1)(X_2)$, wherein $X_1$ and $X_2$ may each be a phenyl group and may be linked to each other via a single bond to form a fluorene group. However, embodiments are not limited thereto, and may be implemented in various forms.

For example, in Compound 143, T may be $C(X_1)(X_2)$, wherein $X_1$ and $X_2$ may each be an ethyl group and may be linked to each other via a single bond to form a cyclopentane group. However, embodiments are not limited thereto, and may be implemented in various forms.

In an embodiment, in Formula 5, $X_1$ and $X_2$ may each independently be:

a $C_1$-$C_{10}$ alkyl group that is unsubstituted or substituted with deuterium, —F, a cyano group, or any combination thereof; or a $C_2$-$C_{10}$ alkenyl group, a cyclopropyl group, a cyclobutyl group, a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, a bicyclo[2.2.2]octyl group, phenyl group, a naphthyl group, a pyridinyl group, a pyrimidinyl group, a pyrazinyl group, a pyridazinyl group, or a triazinyl group, each unsubstituted or substituted with deuterium, —F, a cyano group, a $C_1$-$C_{10}$ alkyl group, or any combination thereof.

For example, $X_1$ and $X_2$ may each independently be:

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group;

an ethenyl group, a propenyl group, a butenyl group, a pentenyl group, or a hexenyl group;

a cyclopropyl group, a cyclobutyl group, a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, or a bicyclo[2.2.2]octyl group; or a phenyl group, a naphthyl group, a pyridinyl group, a pyrimidinyl group, a pyrazinyl group, a pyridazinyl group, or a triazinyl group.

In an embodiment, in Formula 5, when T is $C(X_1)(X_2)$, $X_1$ and $X_2$ may be identical to each other.

In an embodiment, in Formula 5, RT may be:

hydrogen, deuterium, —F, or a cyano group; or a $C_6$-$C_{10}$ aryl group that is unsubstituted or substituted with deuterium, —F, a cyano group, a $C_1$-$C_{10}$ alkyl group, a $C_1$-$C_{10}$ alkoxy group, or any combination thereof.

In an embodiment, in Formula 5, RT may be:

hydrogen; or a phenyl group unsubstituted or substituted with deuterium, —F, a cyano group, or any combination thereof.

For example, in Formula 5, RT may be hydrogen or a phenyl group.

In an embodiment, in Formula 5, at may be 0 or 1.

In an embodiment, a group represented by Formula 5 may be a group represented by one of Formulae 5-1 to 5-5:

5-1

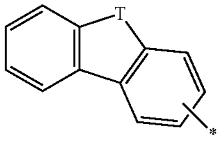

5-2

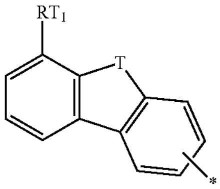

5-3

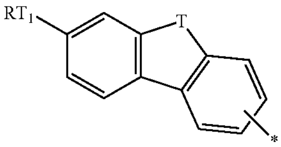

-continued 5-4

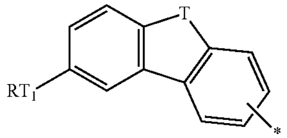

5-5

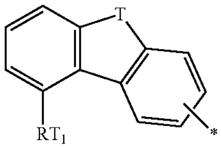

In Formulae 5-1 to 5-5, $RT_1$ may be the same as defined in connection with RT in Formula 5, except that $RT_1$ may not be hydrogen;

T may be the same as defined in Formula 5; and

* indicates a binding site to a neighboring atom.

In an embodiment, $R_{10a}$ may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, or a $C_2$-$C_{60}$ heteroarylalkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, a $C_7$-$C_{60}$ arylalkyl group, or a $C_2$-$C_{60}$ heteroarylalkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

In an embodiment, the first compound may include at least one of Compounds 1 to 93, the second compound may include at least one of Compounds 94 to 123, the third compound may include at least one of Compounds 124 to 183, and the fourth compound may include at least one of Compounds 184 to 207, but embodiments are not limited thereto:

-continued
1
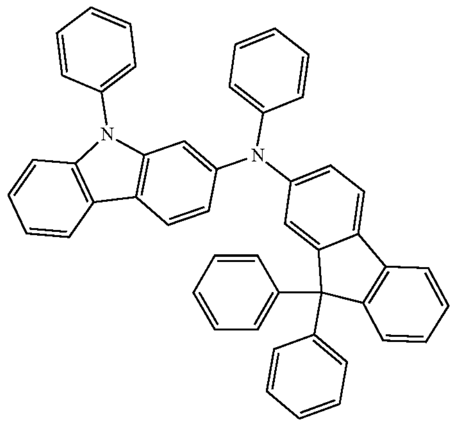
2
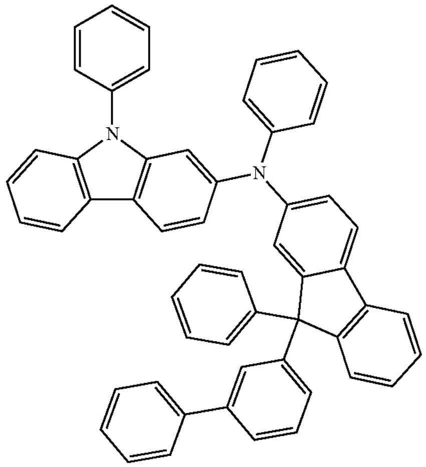
3
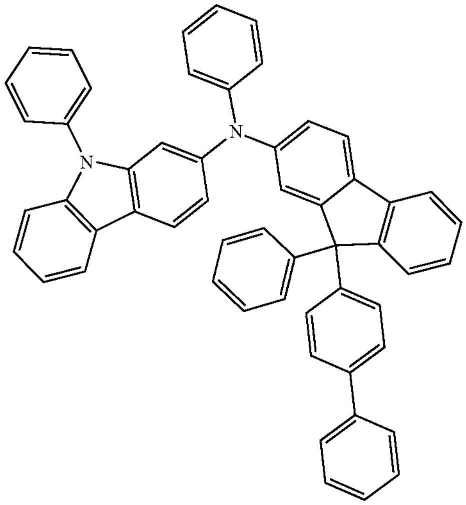
4
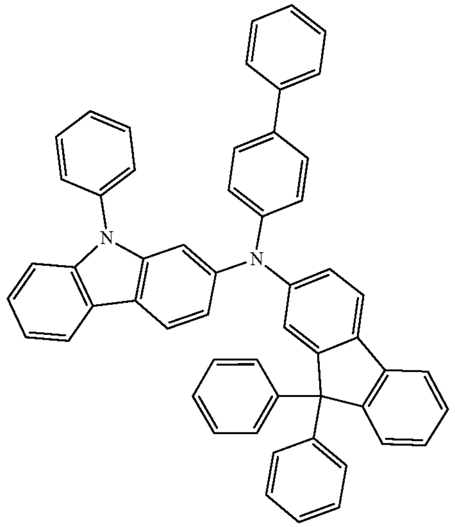
5
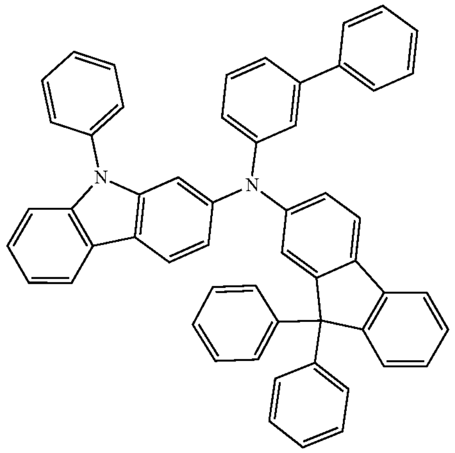
6
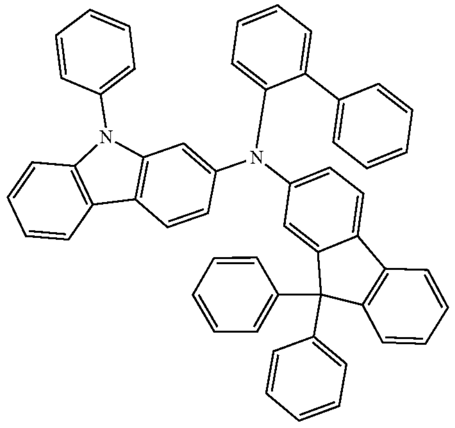

-continued
7
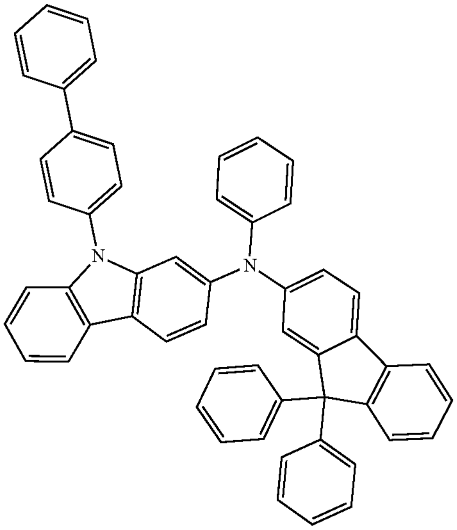
8
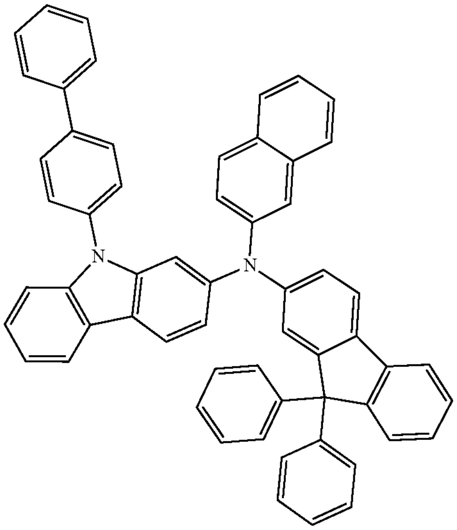
9
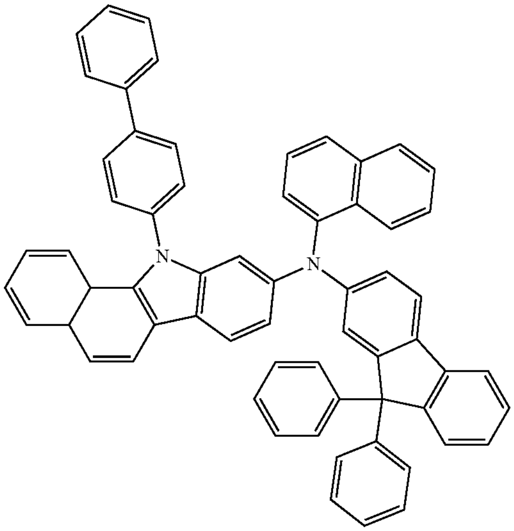
-continued
10
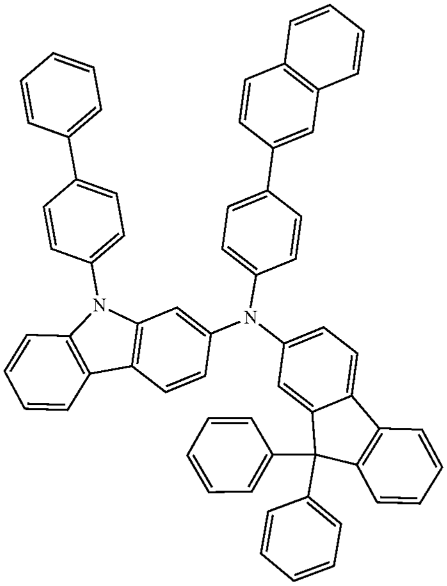
11
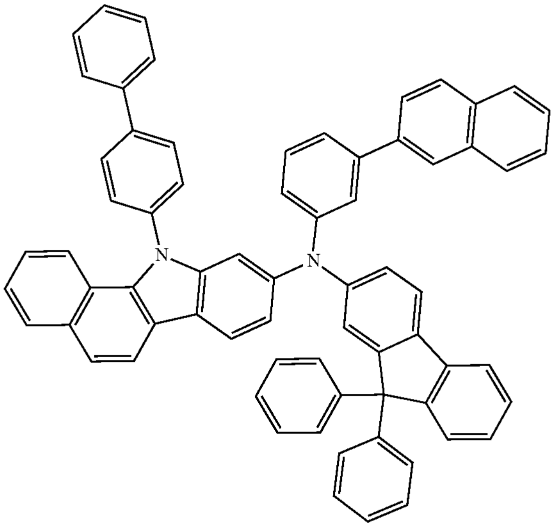
12
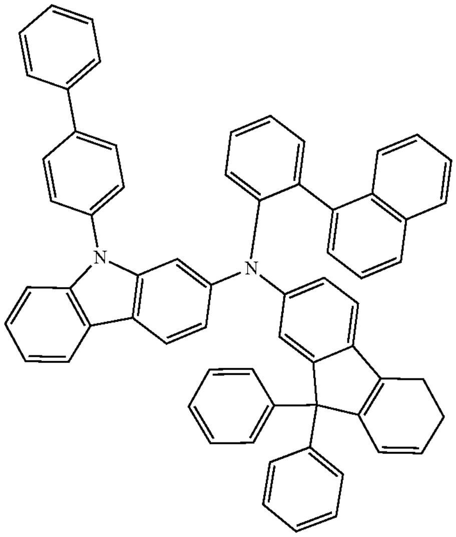

-continued
13
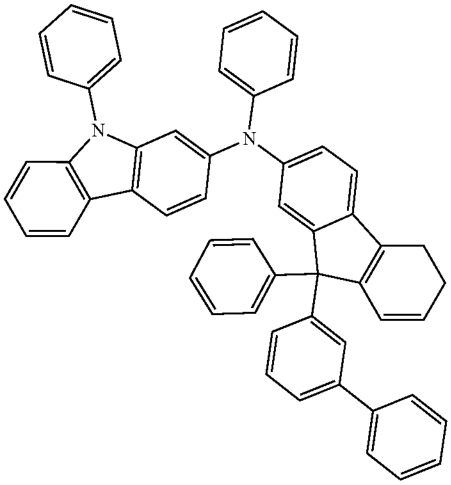
14
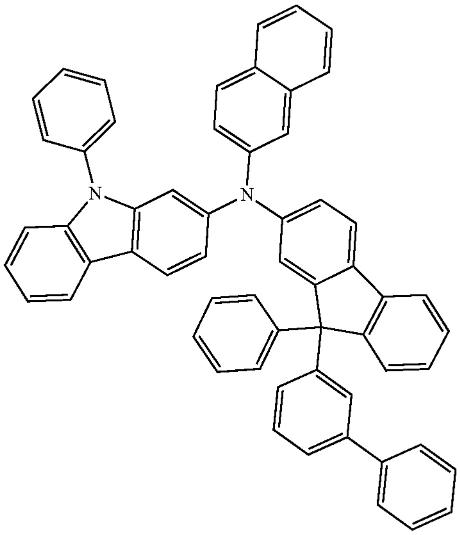
15
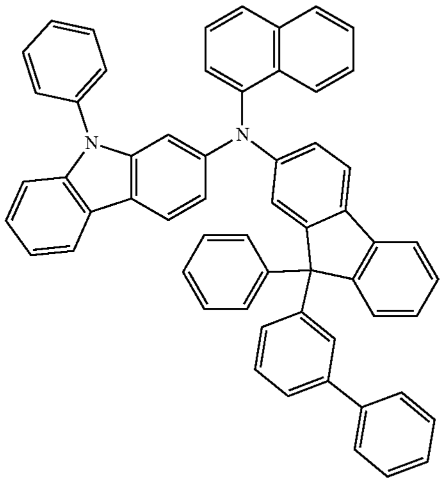
-continued
16
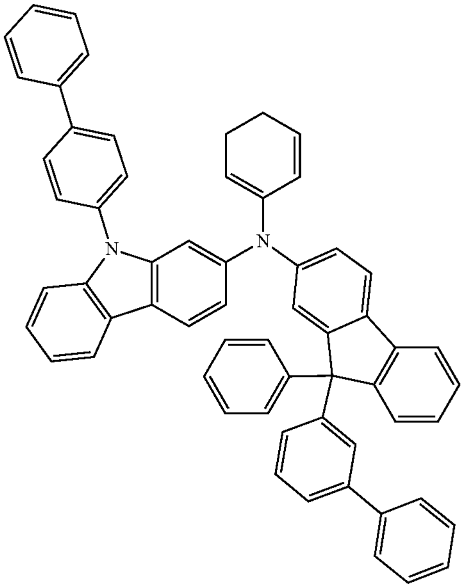
17
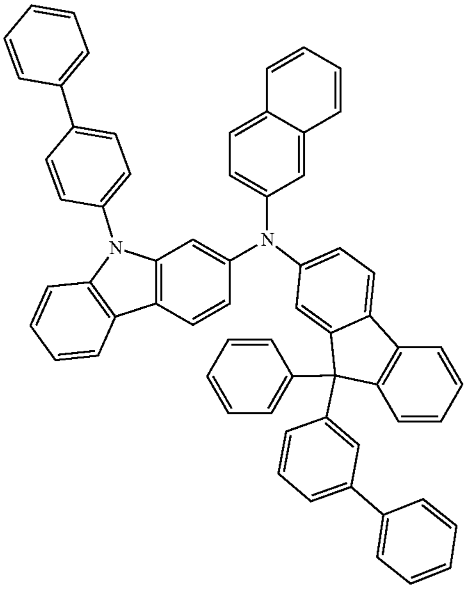

-continued
18
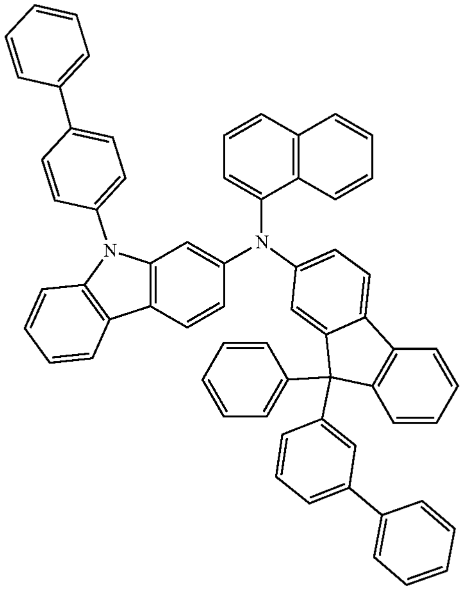
19
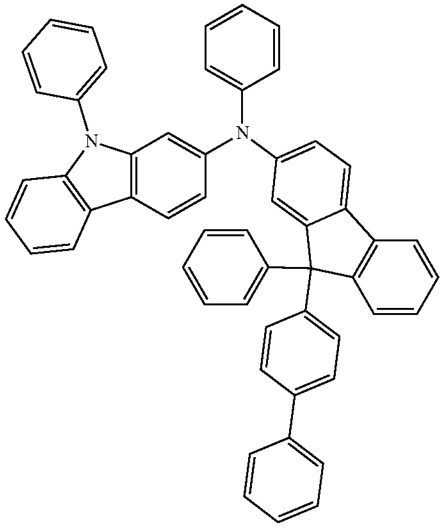
-continued
20
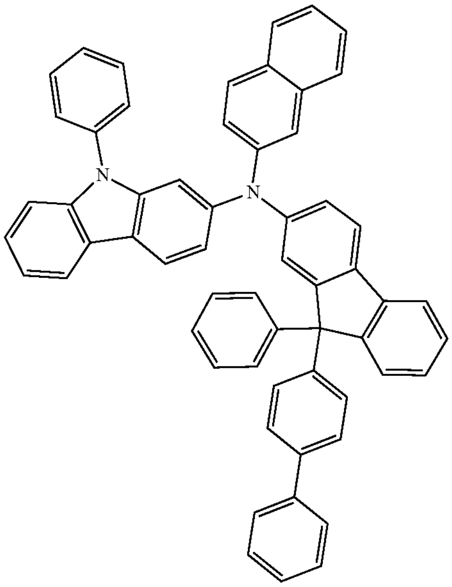
21
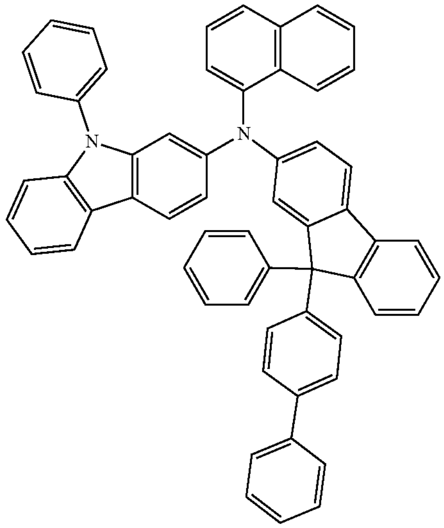

22
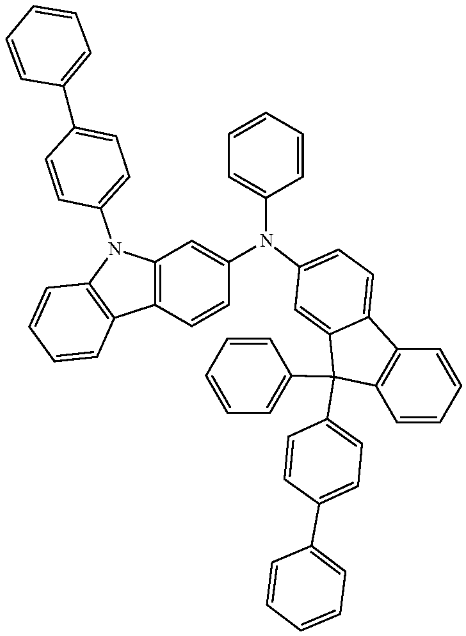
23
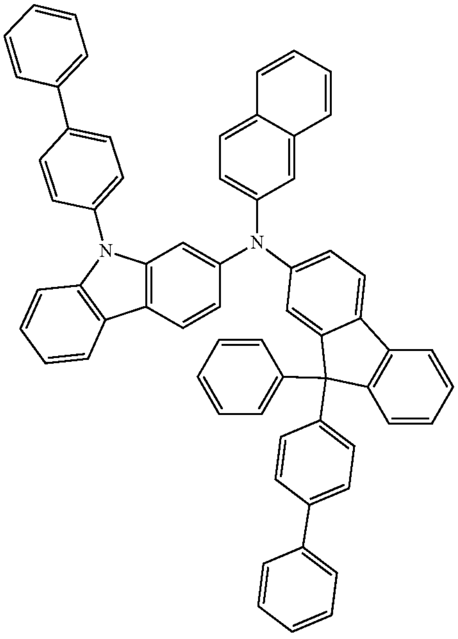
24
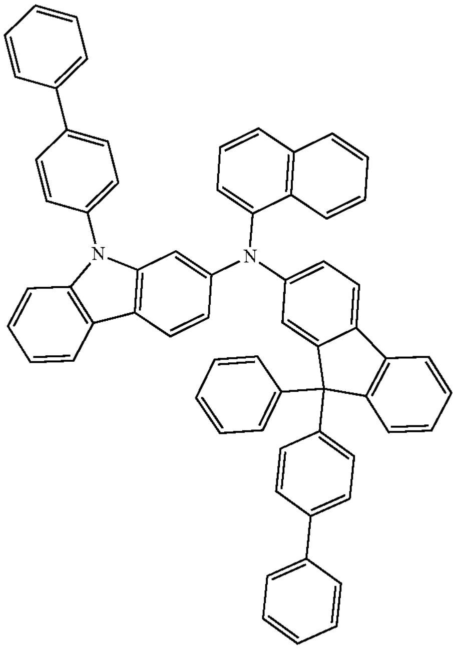
25
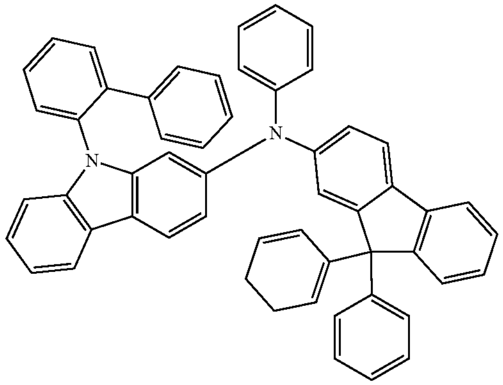
26
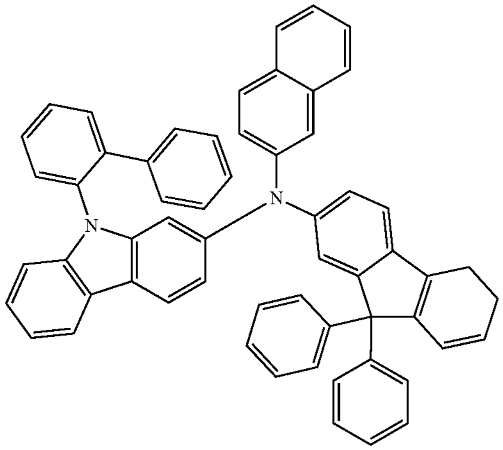

27
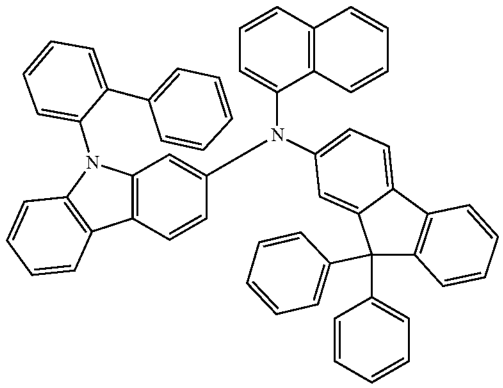
28
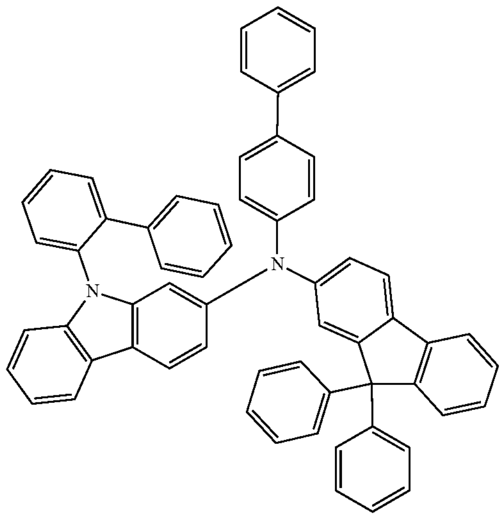
29
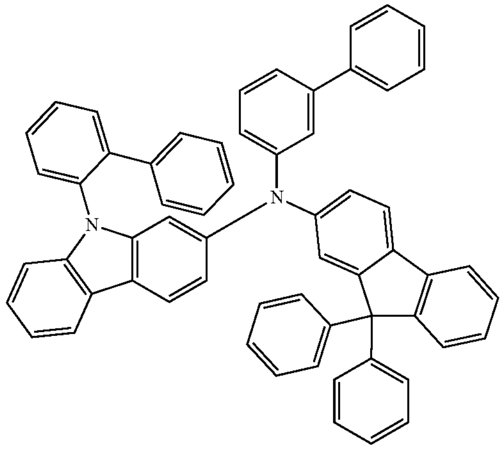
30
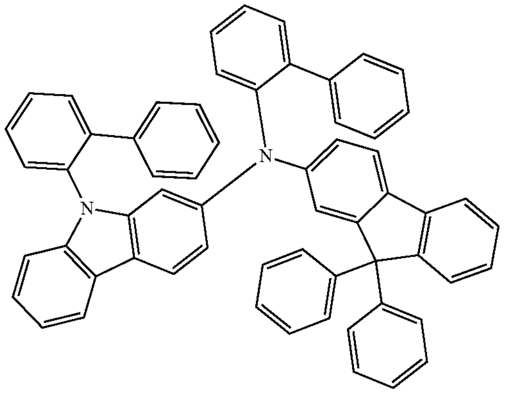
31
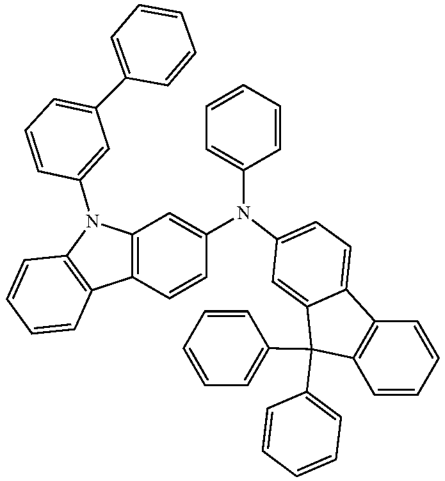
32
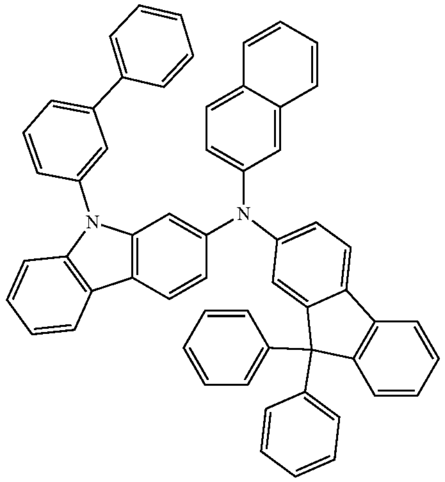

-continued
33
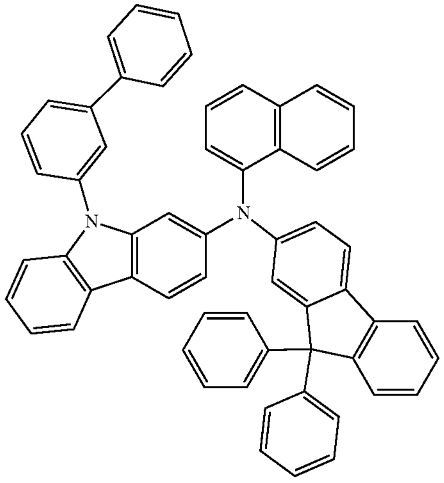
34
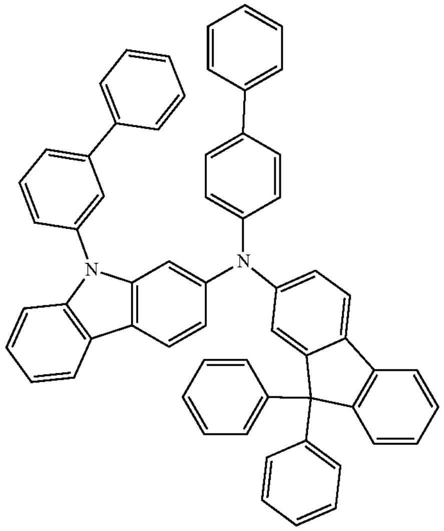
35
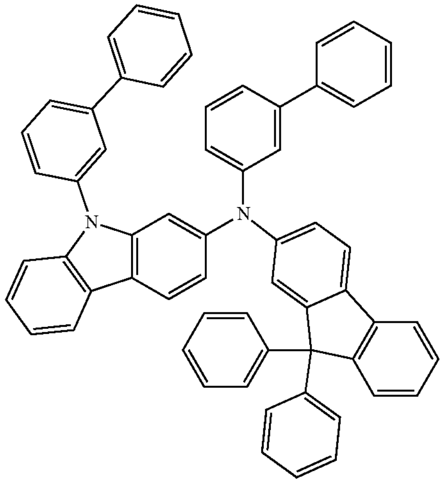
-continued
36
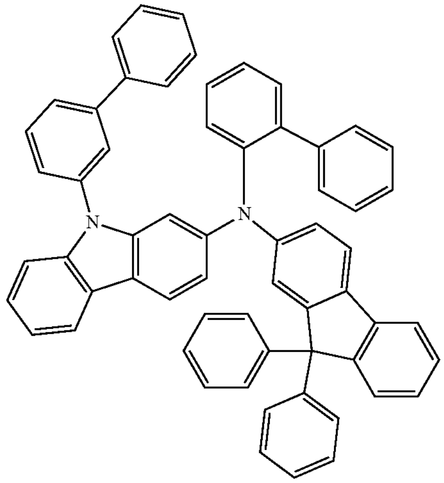
37
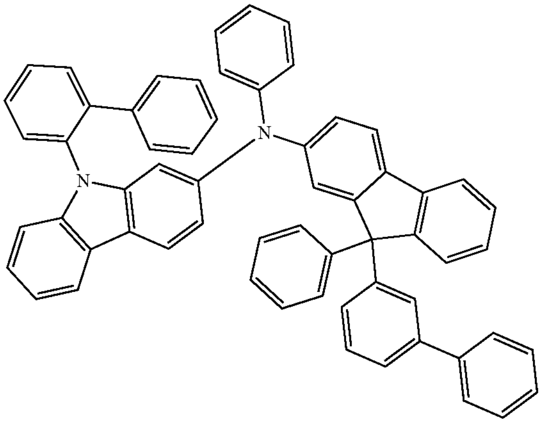
38
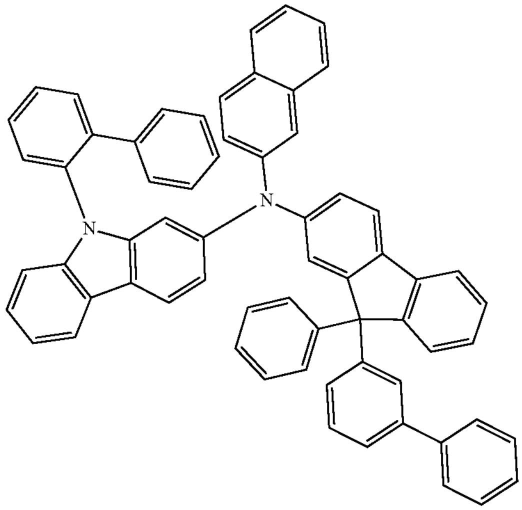

-continued
39
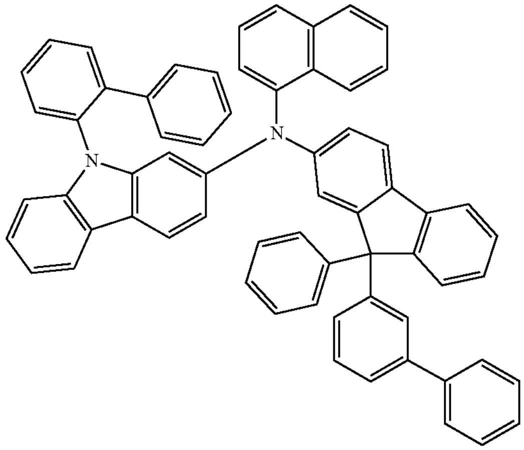
40
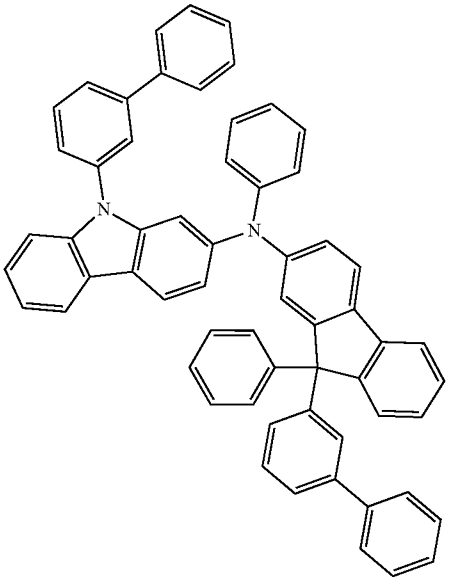
41
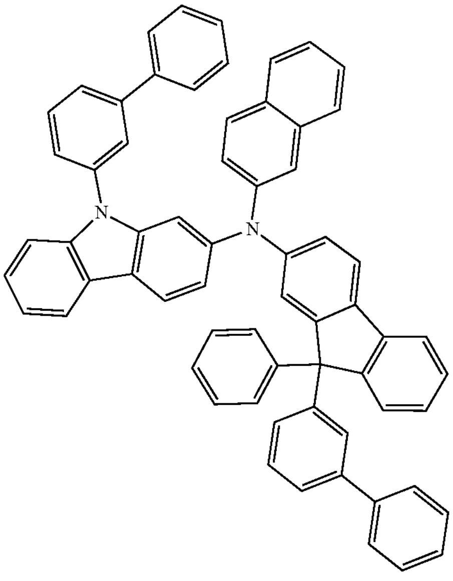
-continued
42
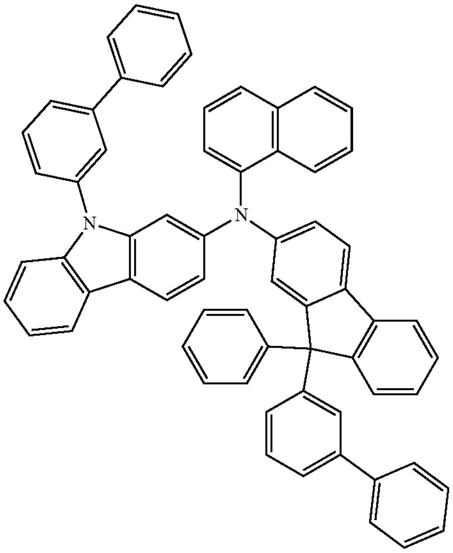
43
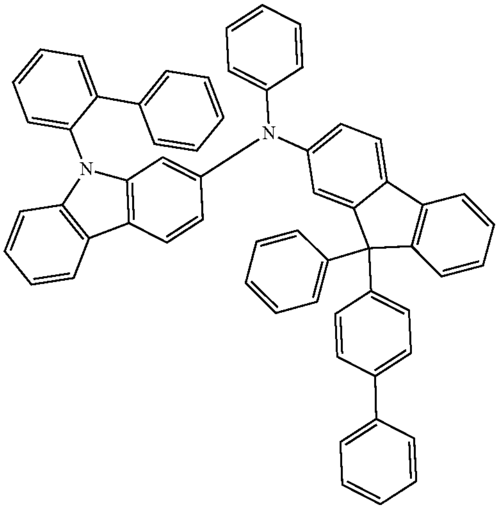
44
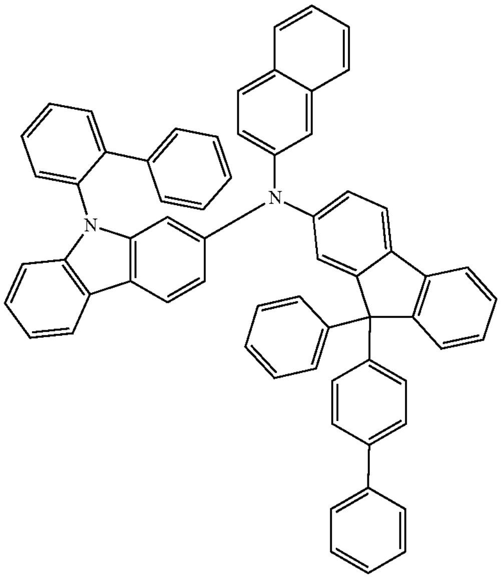

-continued
45
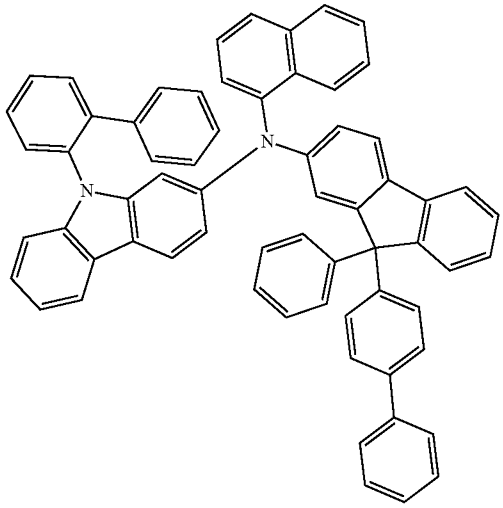
47
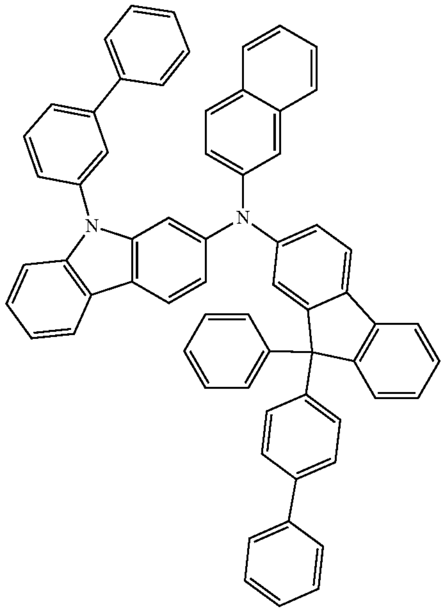
46
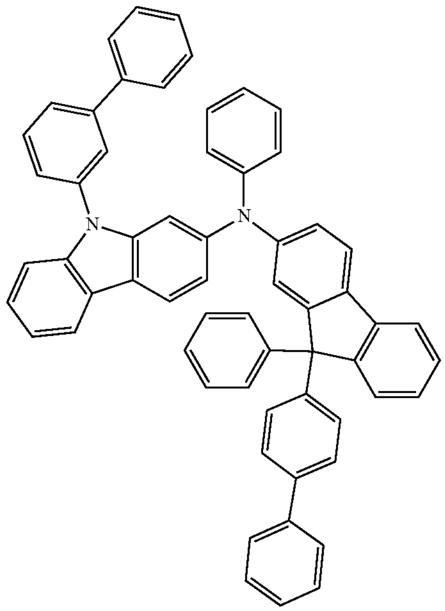
48
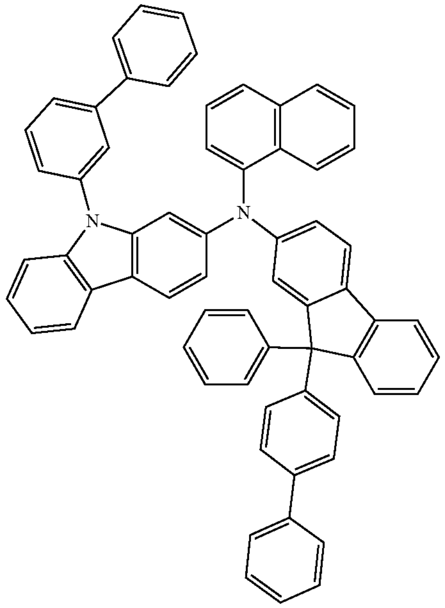

-continued
49
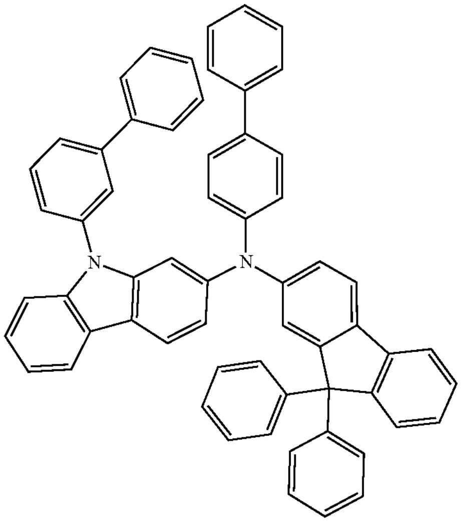
50
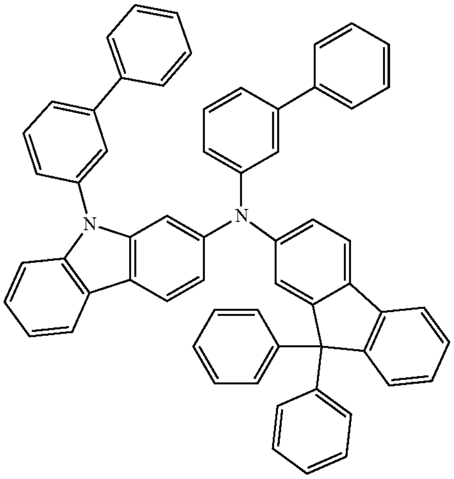
51
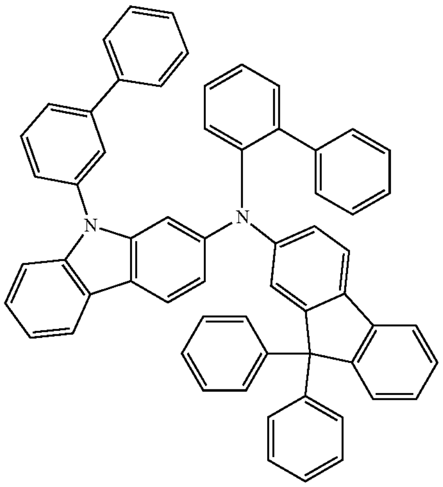
-continued
52
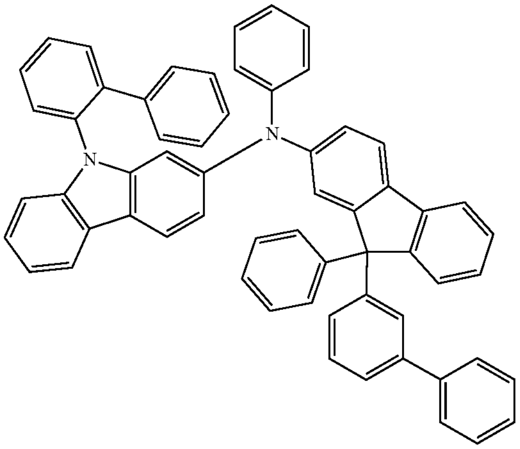
53
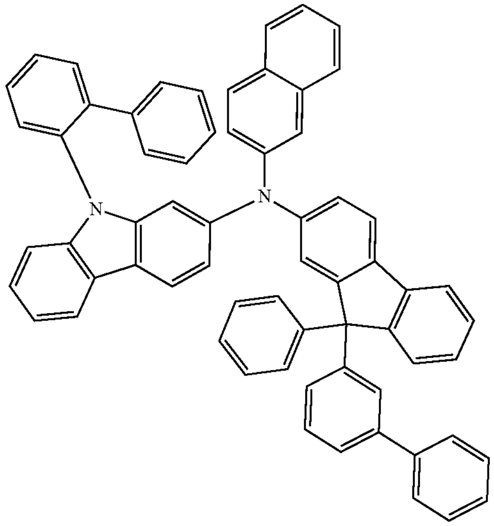
54
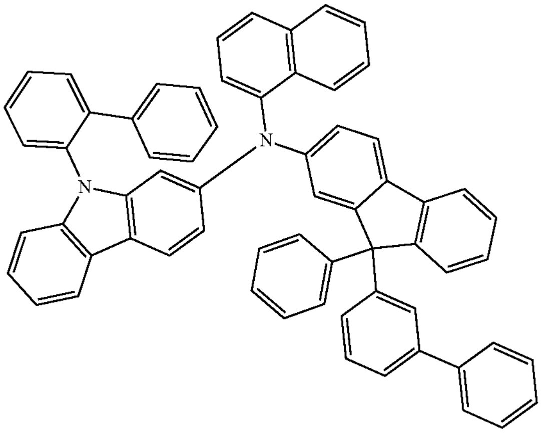

-continued
55
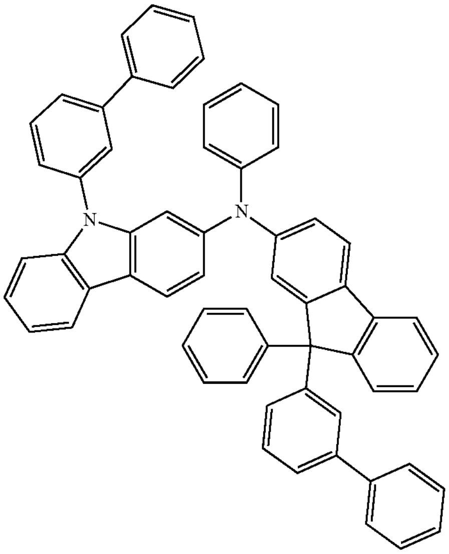
56
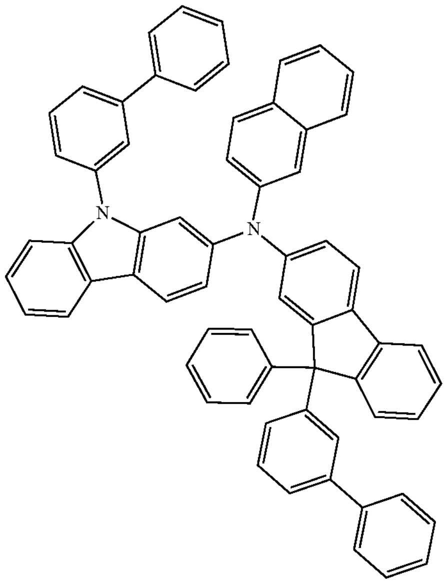
-continued
57
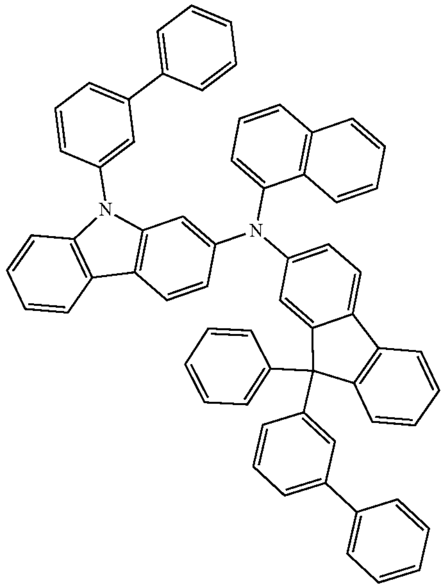
58
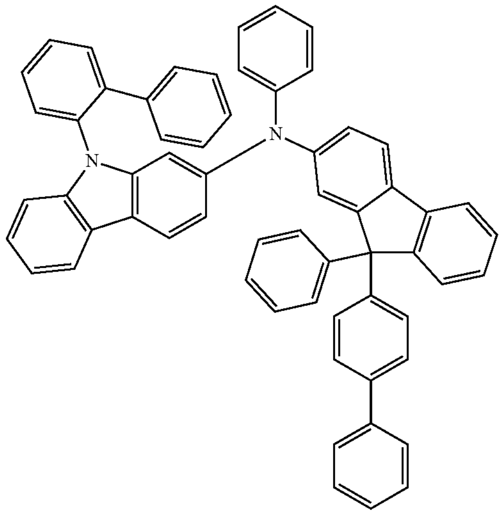

-continued
59
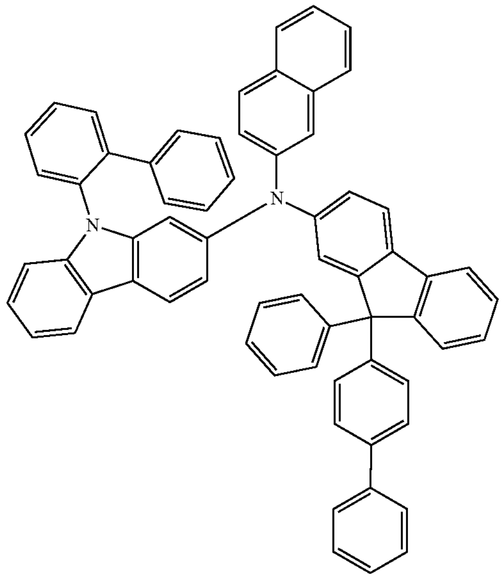
60
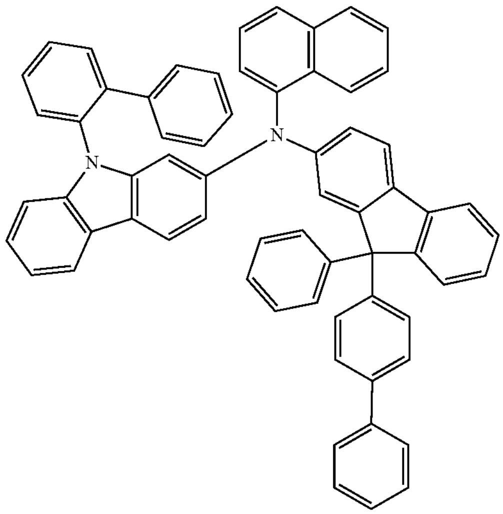
-continued
61
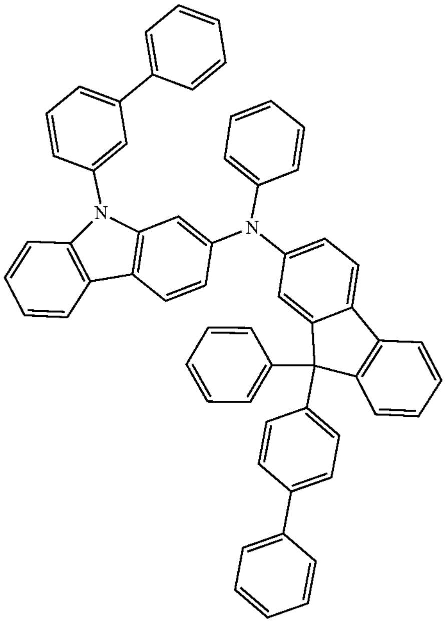
62
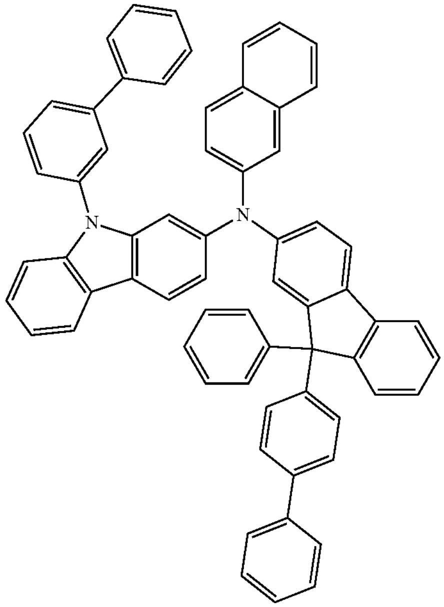

-continued
63
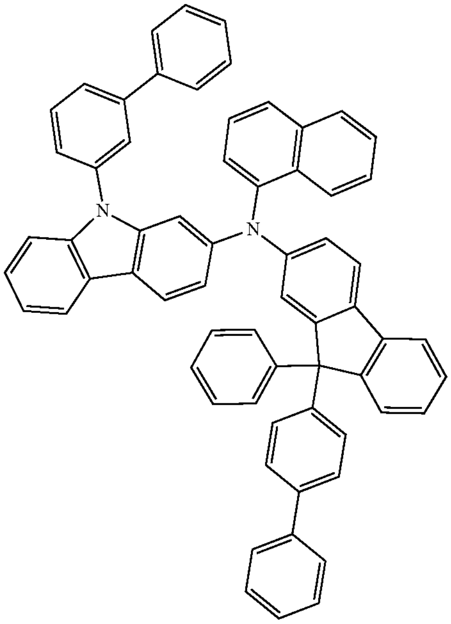
64
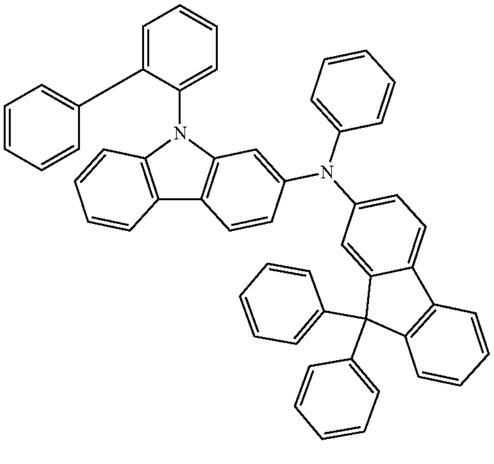
65
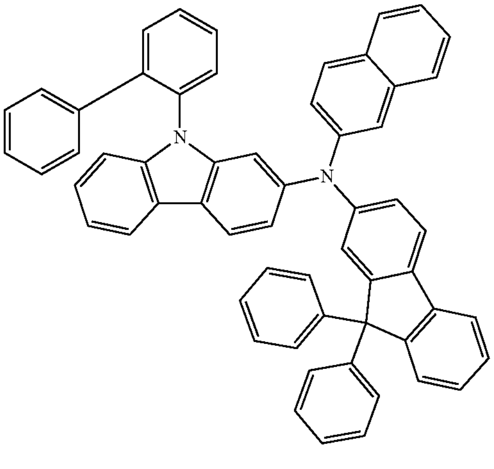
-continued
66
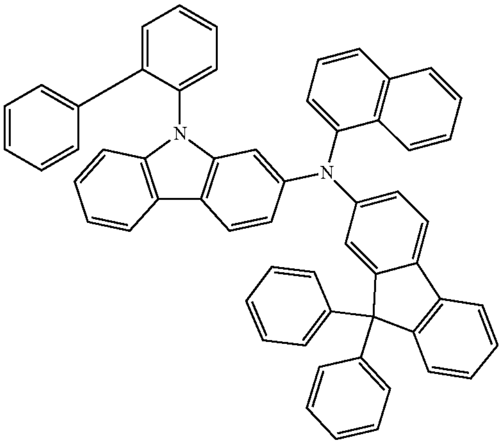
67
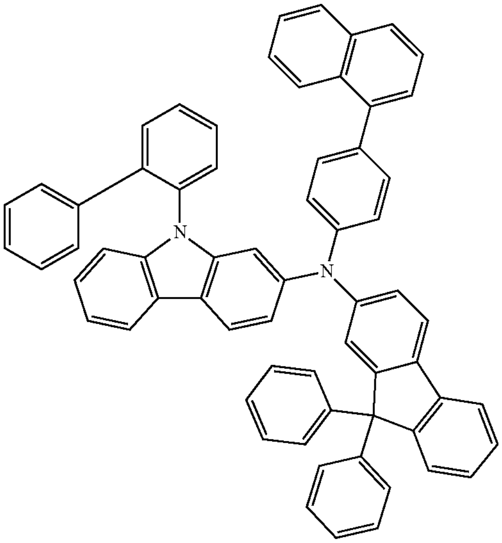
68
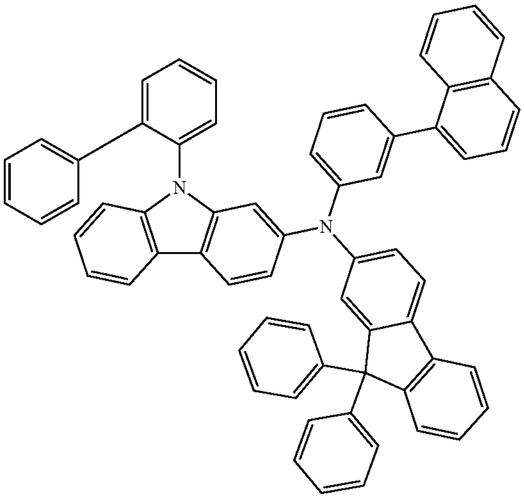

-continued
69
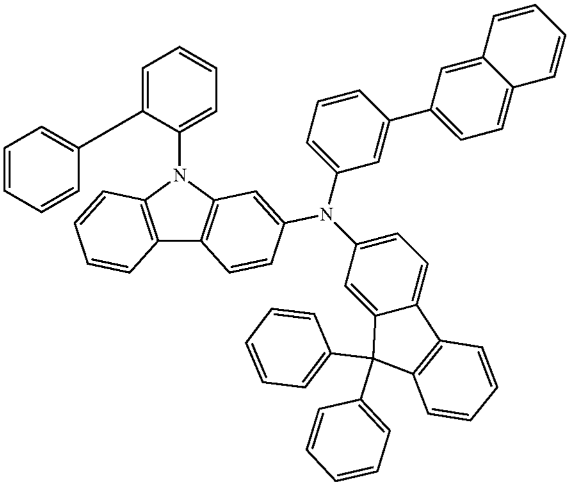
70
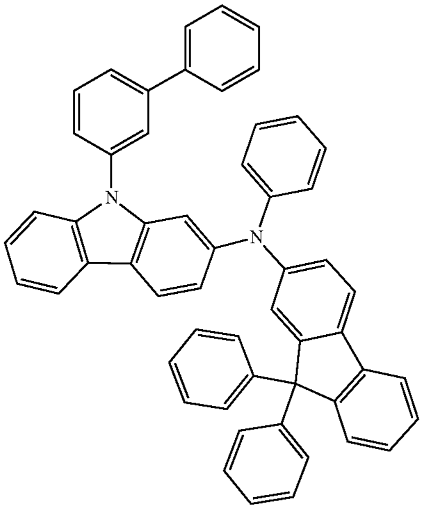
71
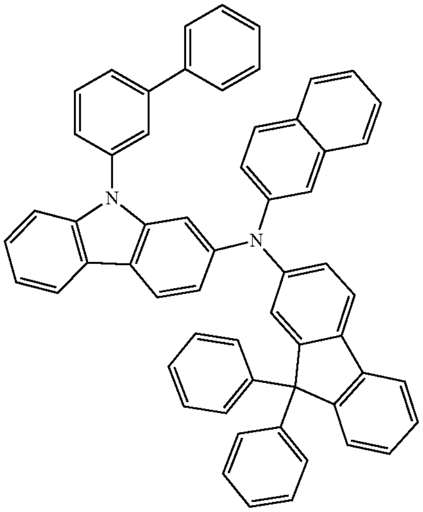
-continued
72
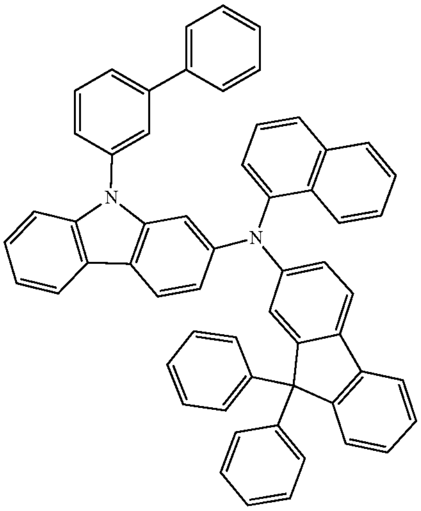
73
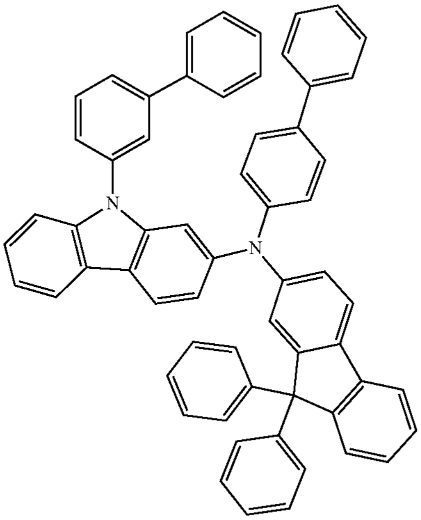
74
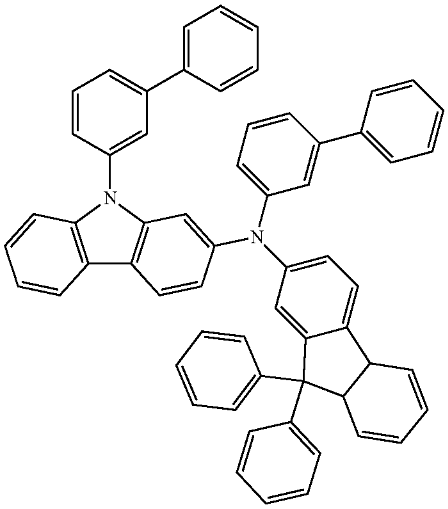

-continued
75
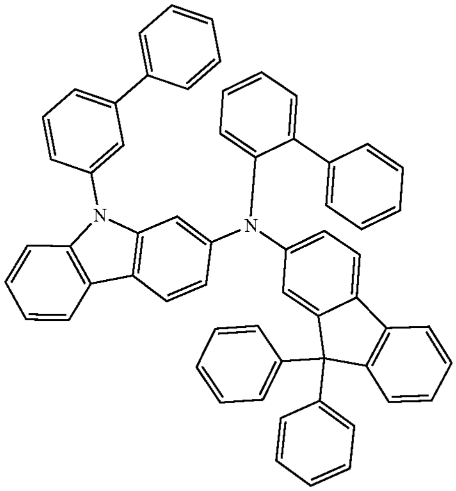
76
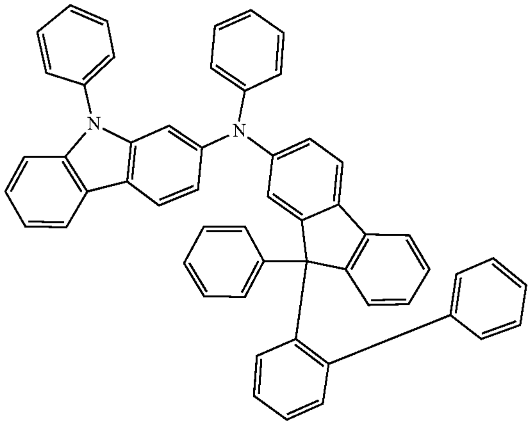
77
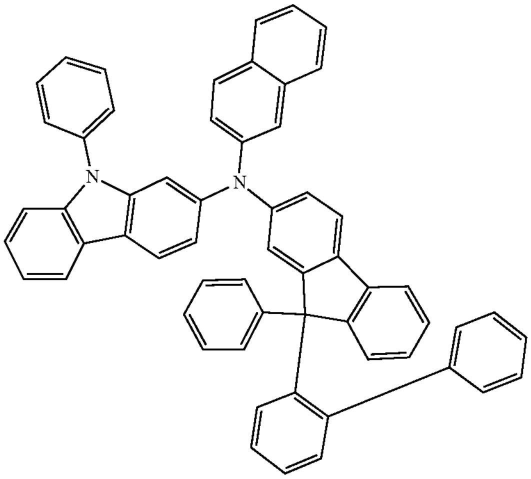
-continued
78
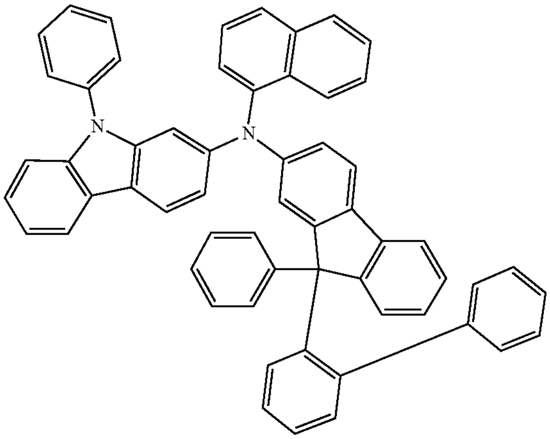
79
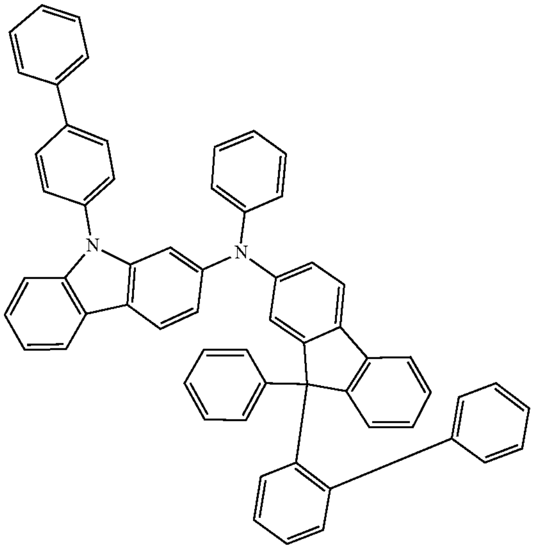
80
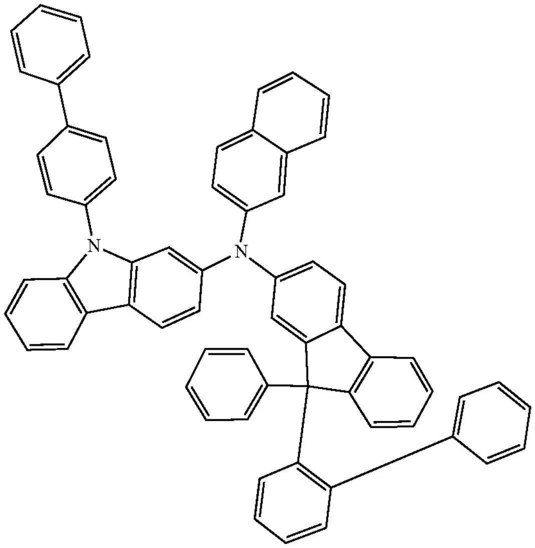

-continued
81
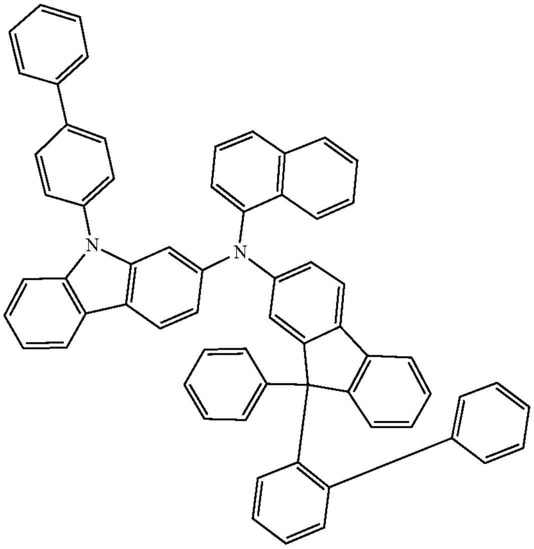
82
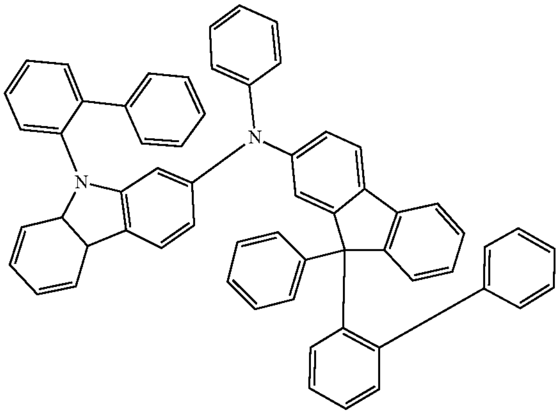
,
83
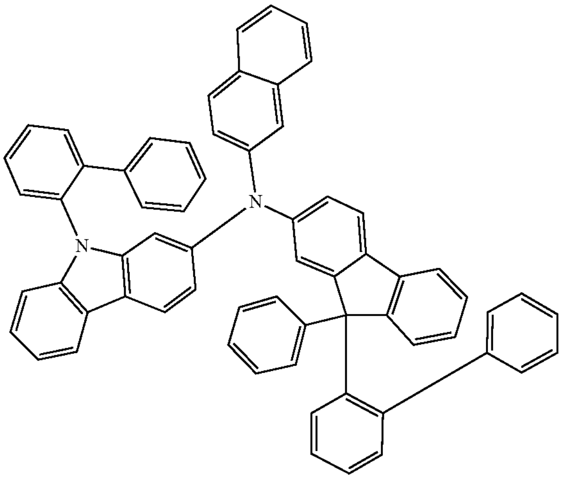
-continued
84
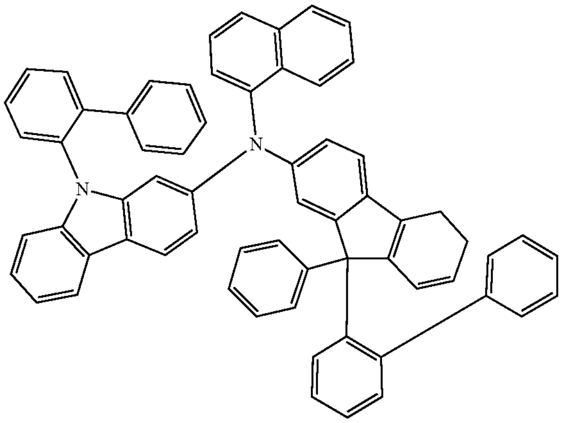
85
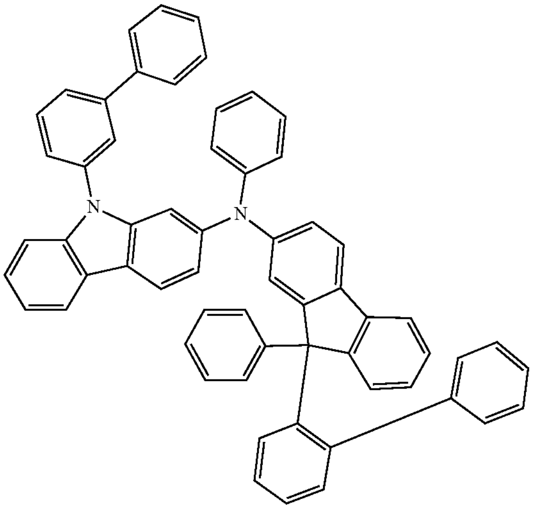
86
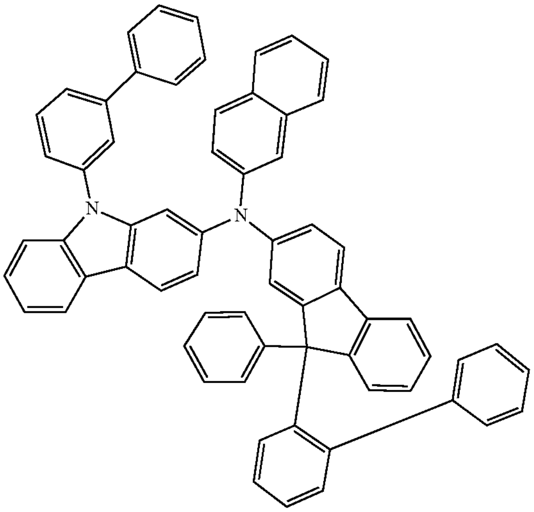

-continued
87
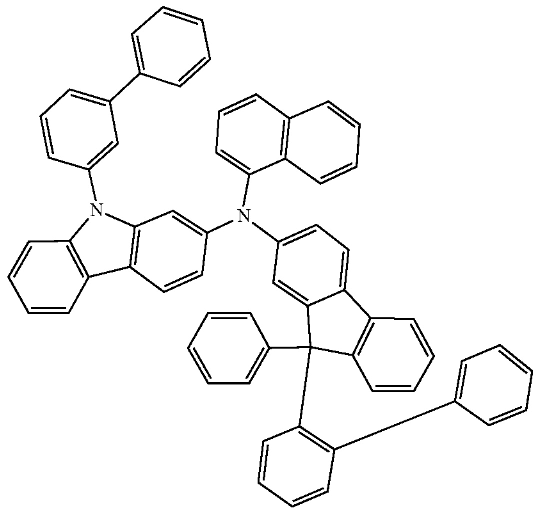
88
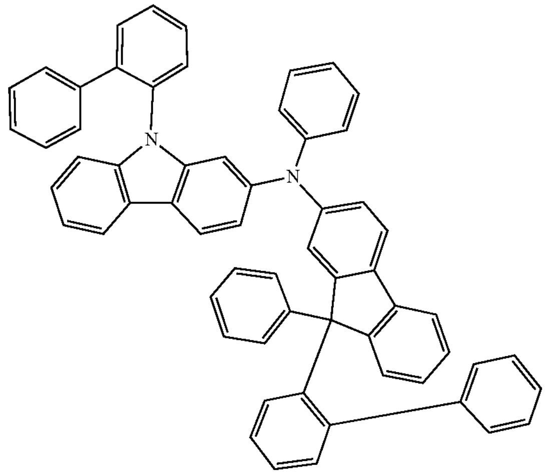
89
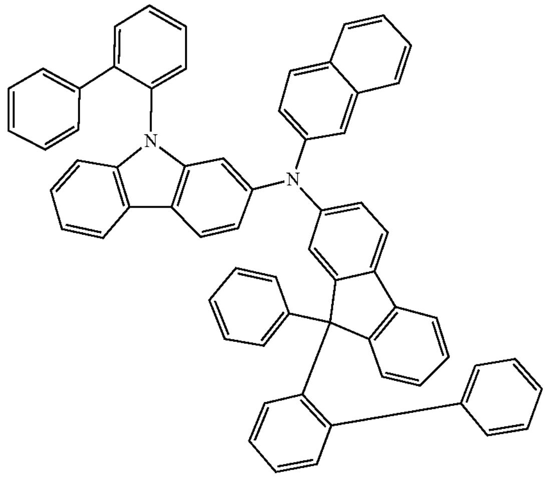
-continued
90
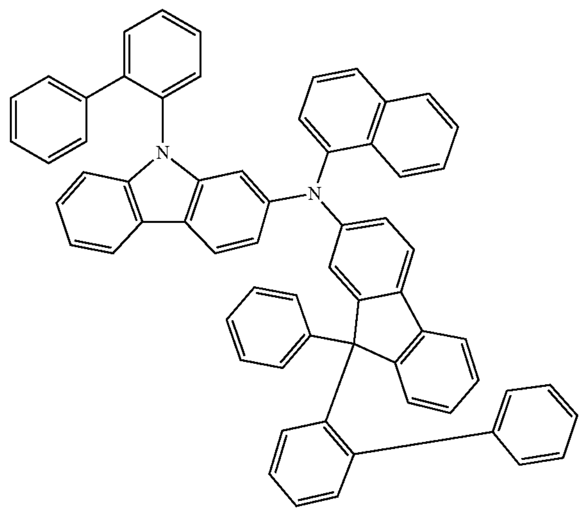
91
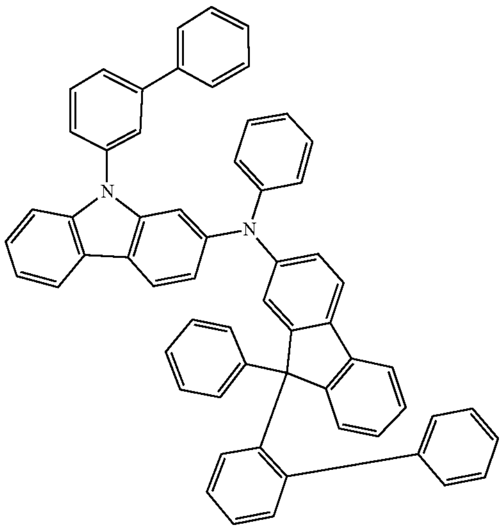
92
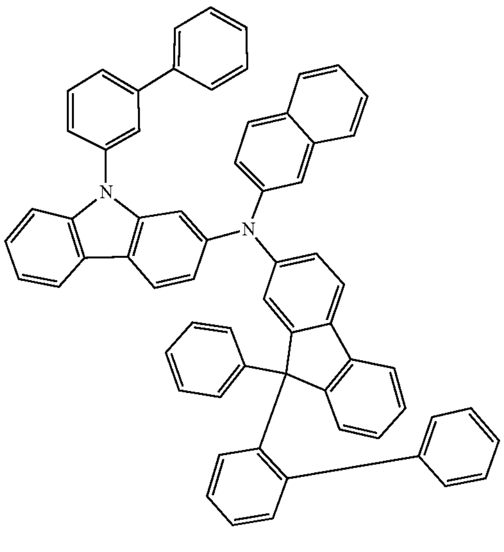

-continued
93
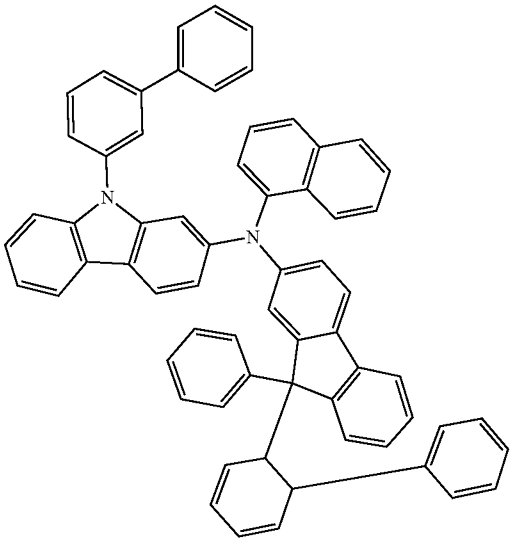
94
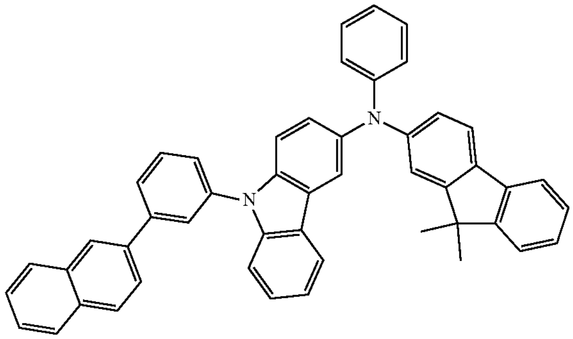
95
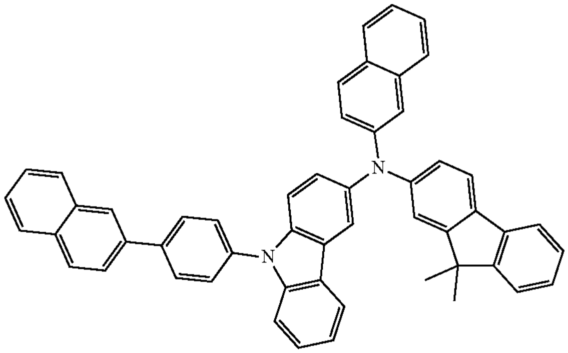
96
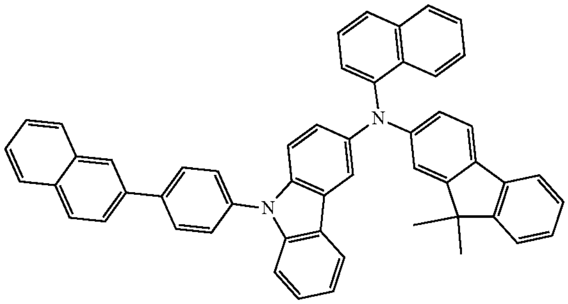
-continued
97
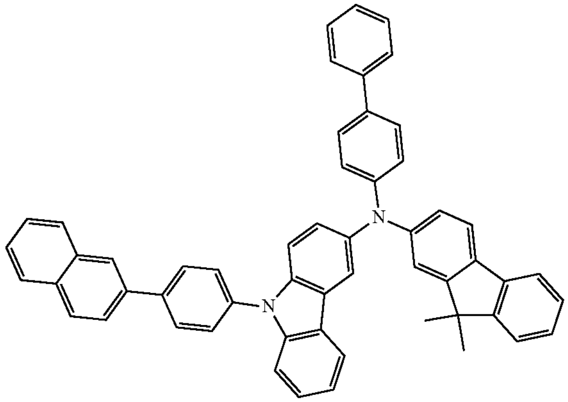
98
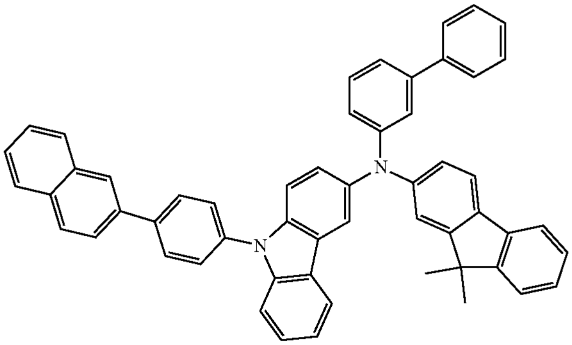
99
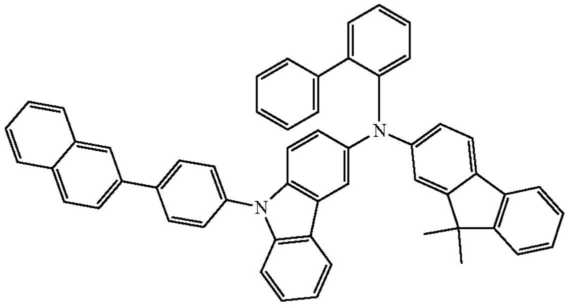
100
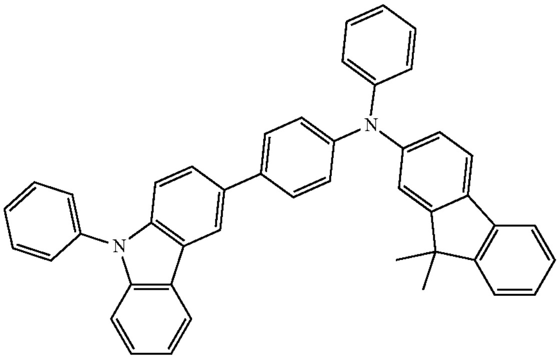

-continued
101
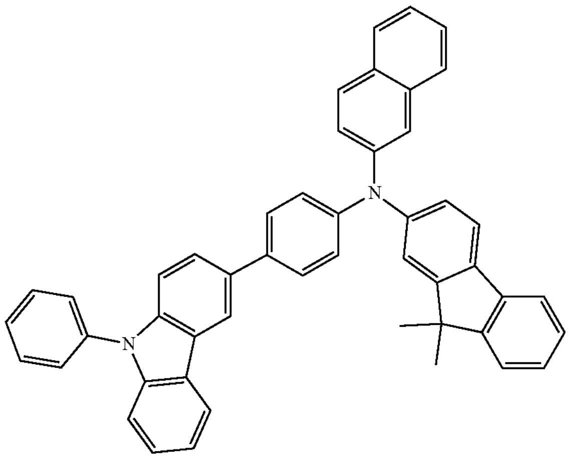
102
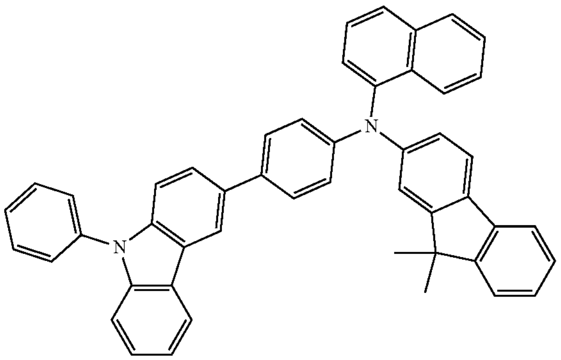
103
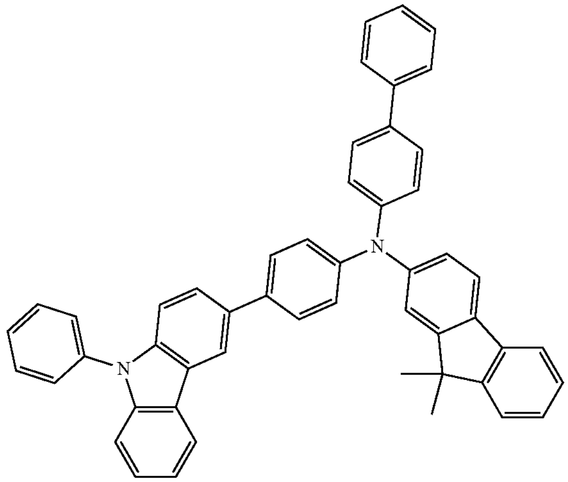
-continued
104
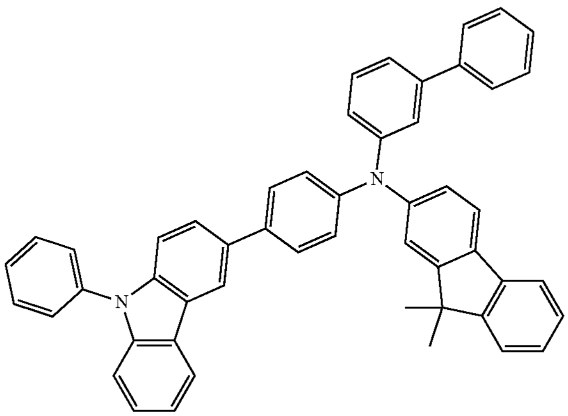
105
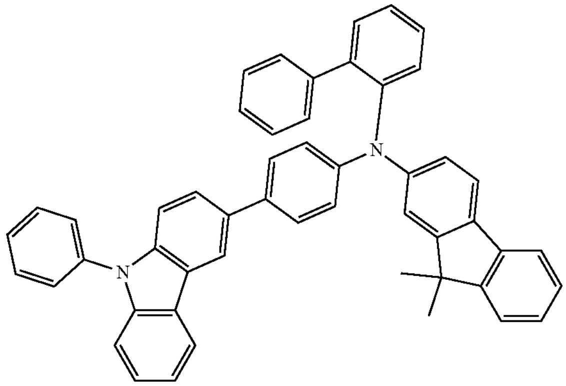
106
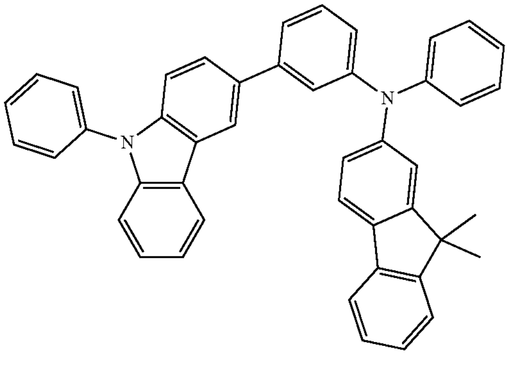
107
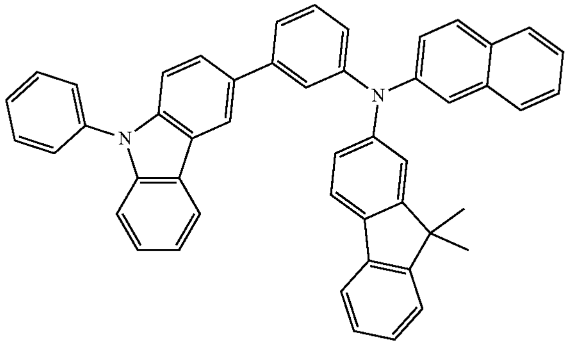

108
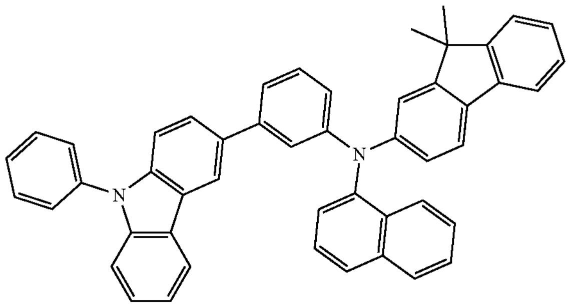
109
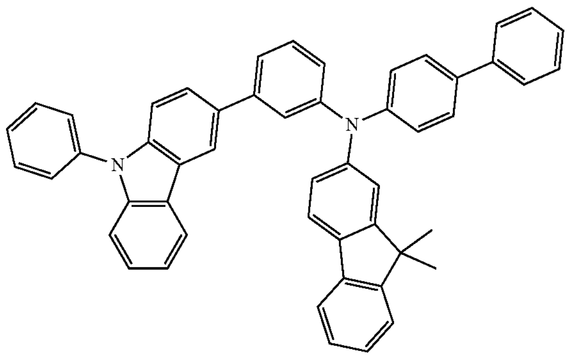
110
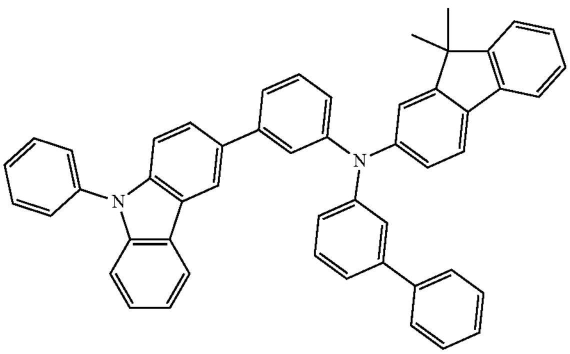
111
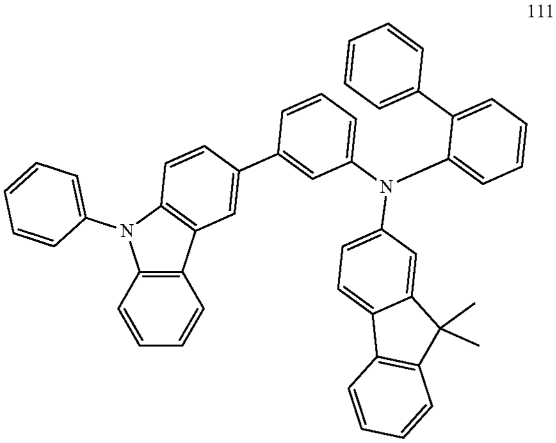
112
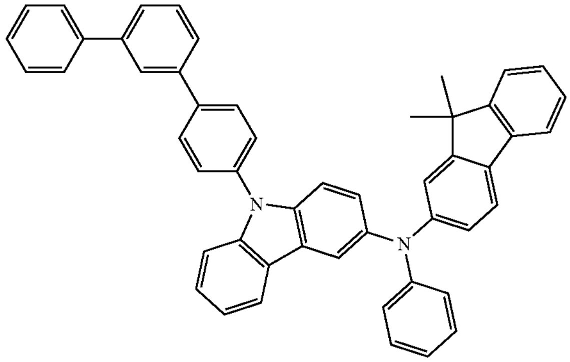
113
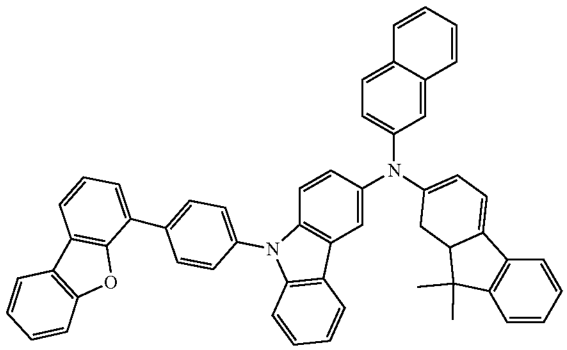
114
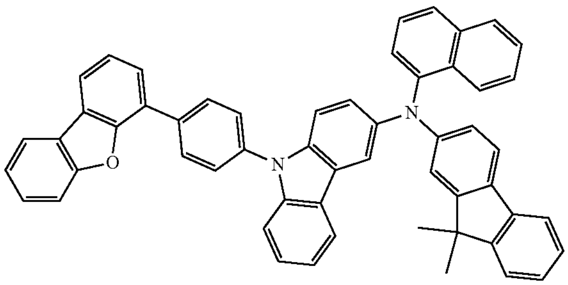
115
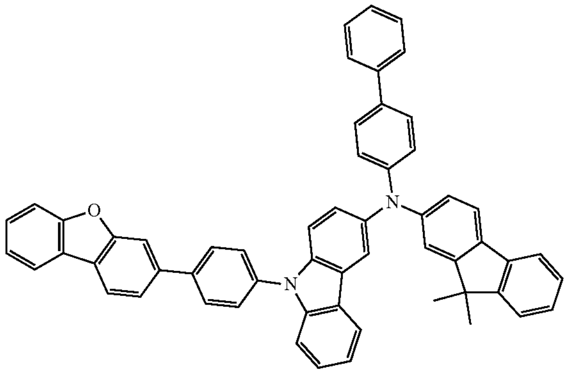

-continued
116
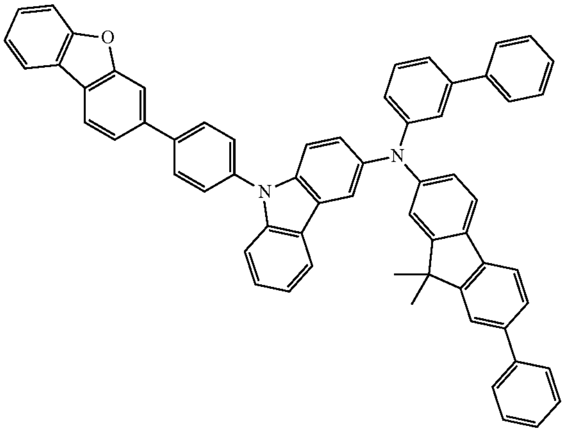
117
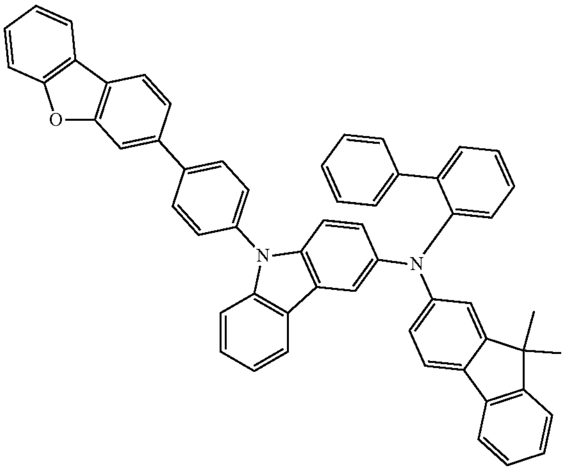
118
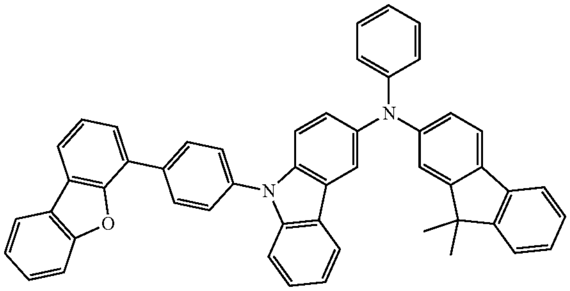
119
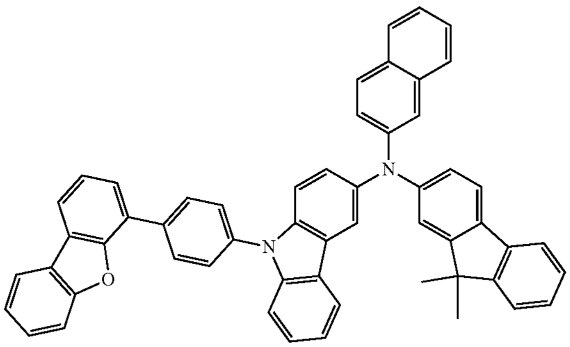
-continued
120
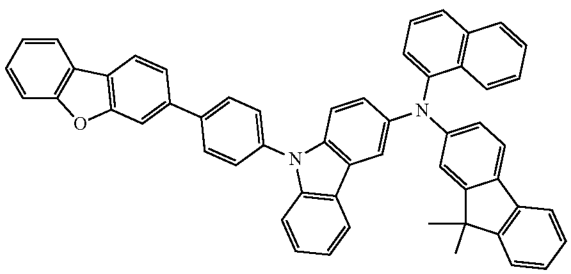
121
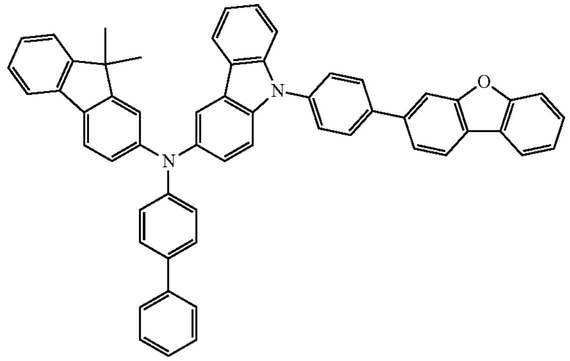
122
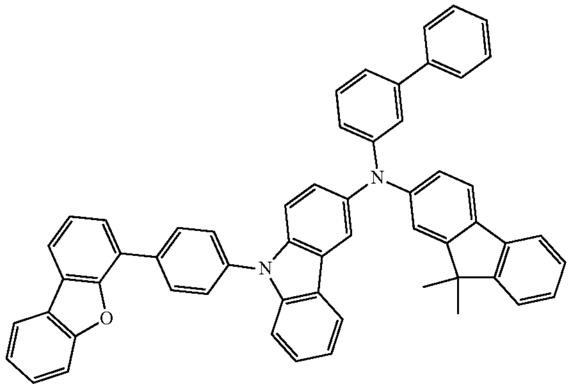
123
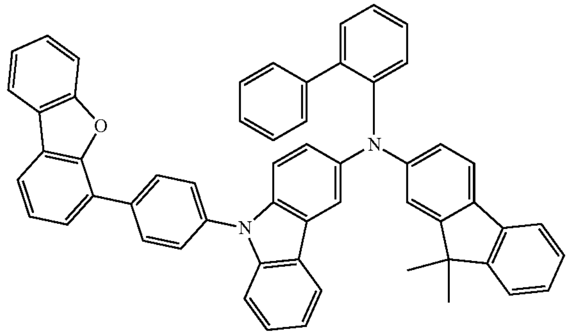

-continued
124
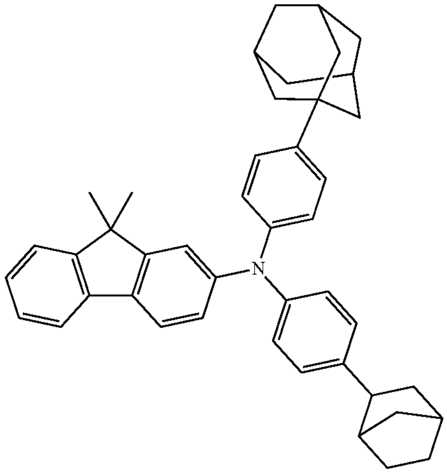
125
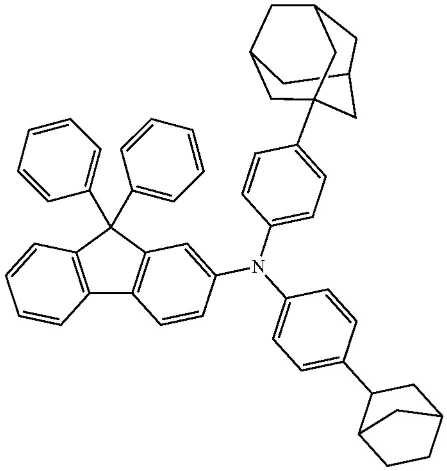
126
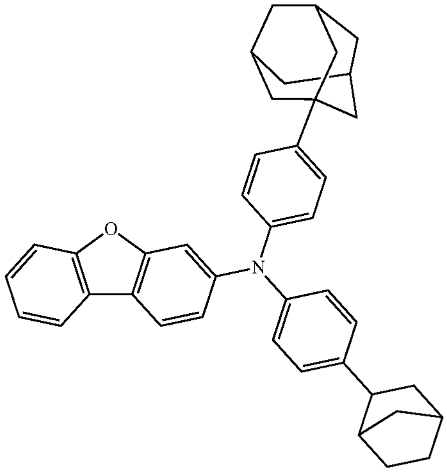
-continued
127
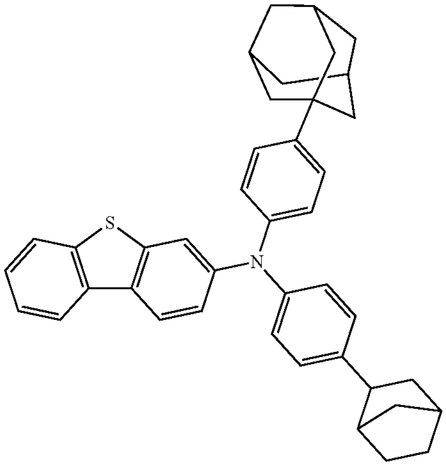
128
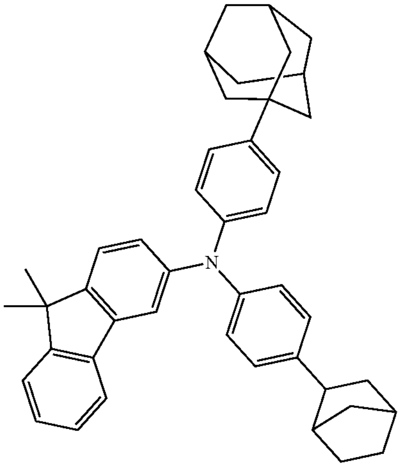
129
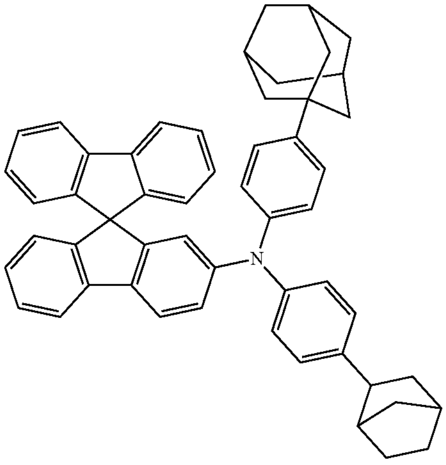

-continued
130
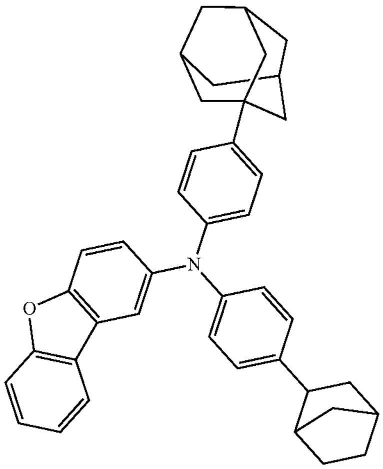
131
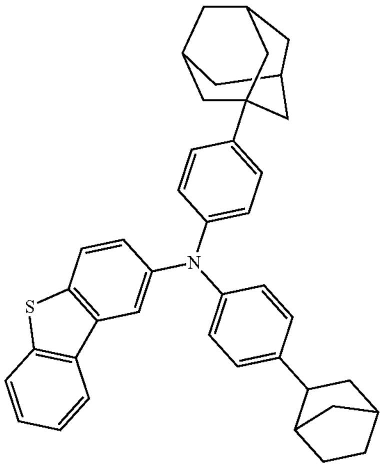
132
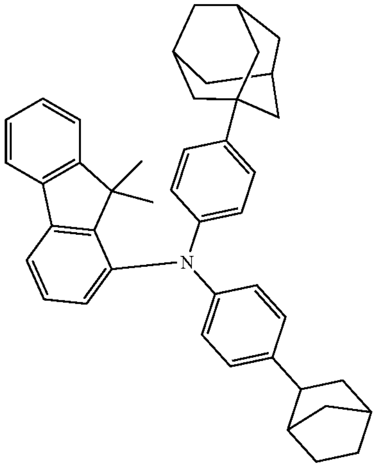
-continued
133
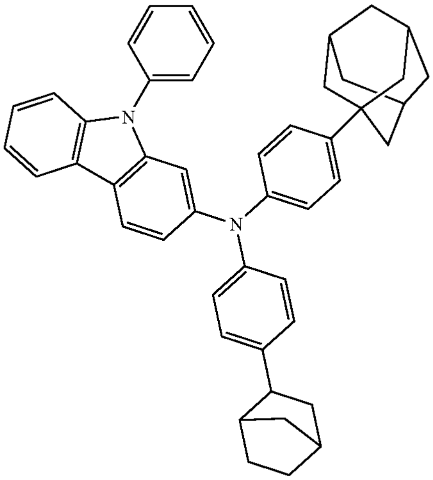
134
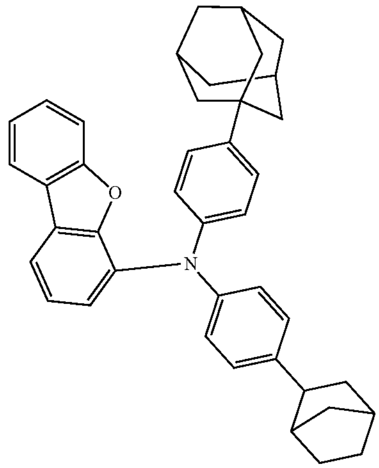
135
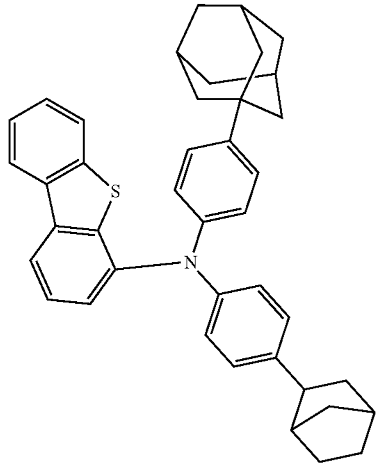

-continued
136
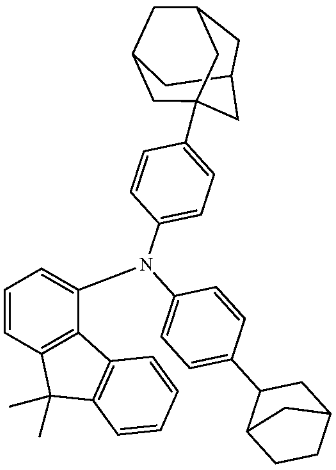
137
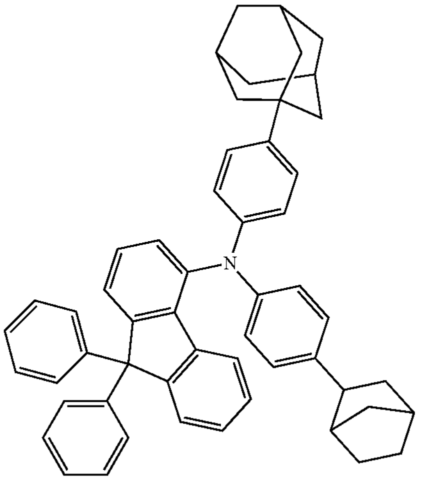
138
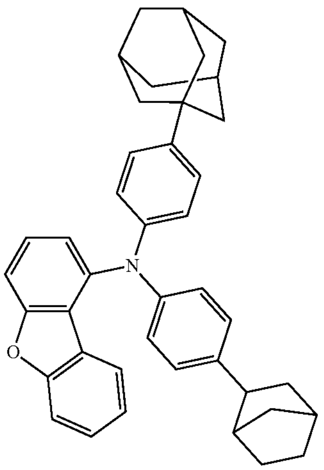
-continued
139
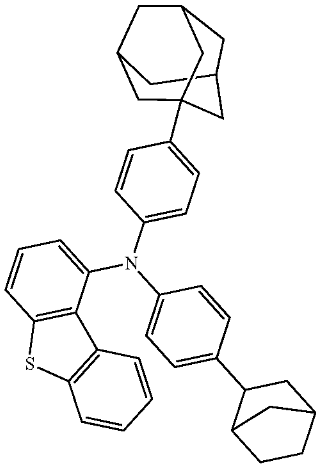
140
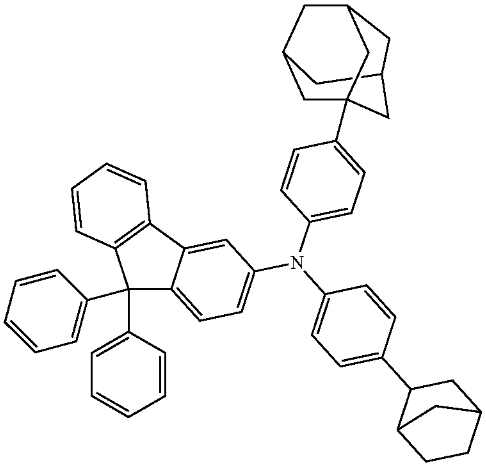
141
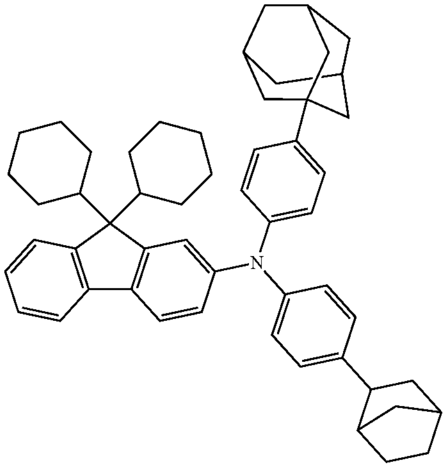

-continued
142
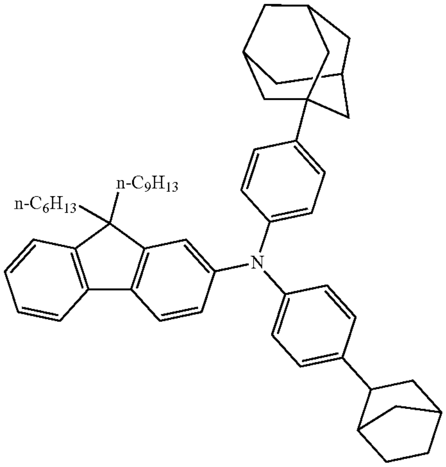
143
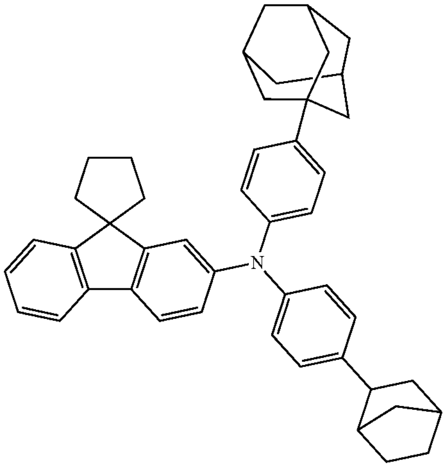
144
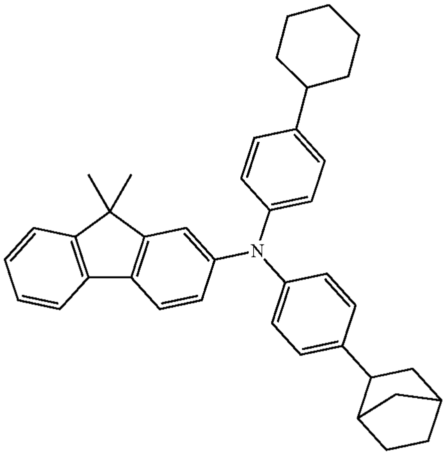
-continued
145
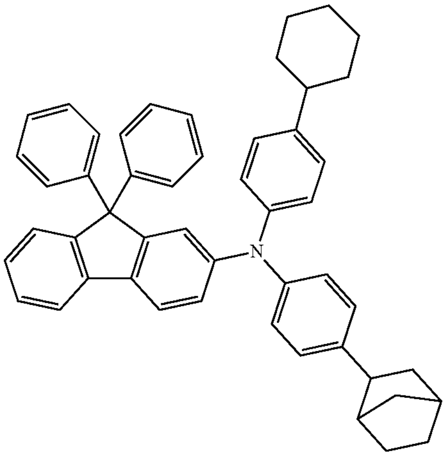
146
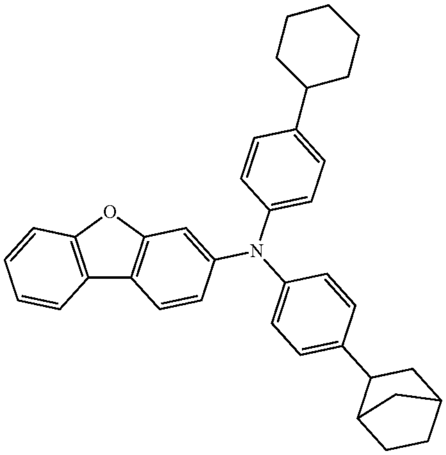
147
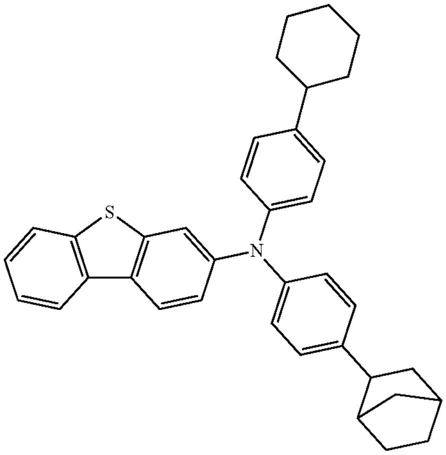

-continued
148
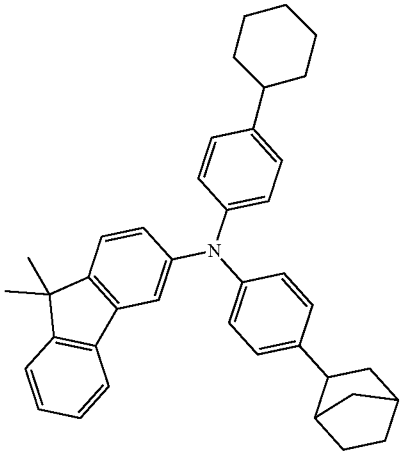
149
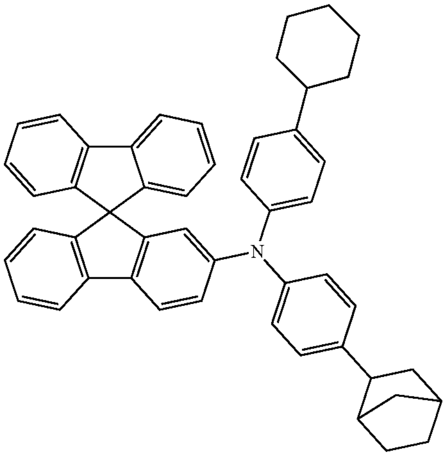
150
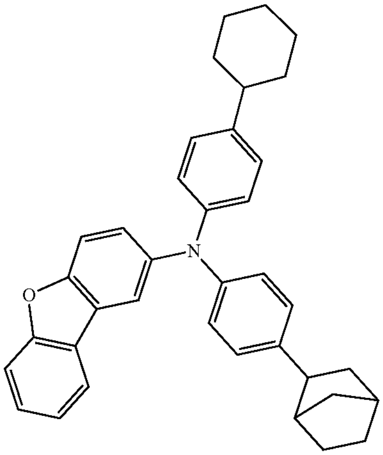
-continued
151
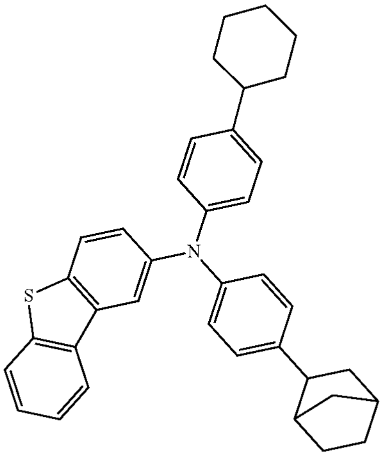
152
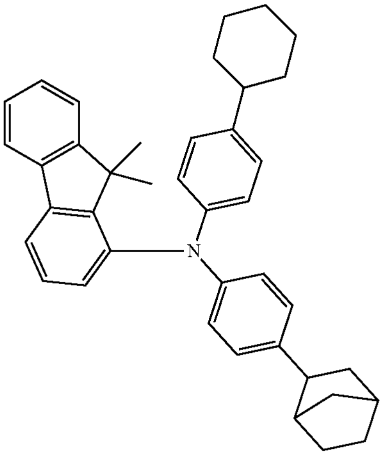
153
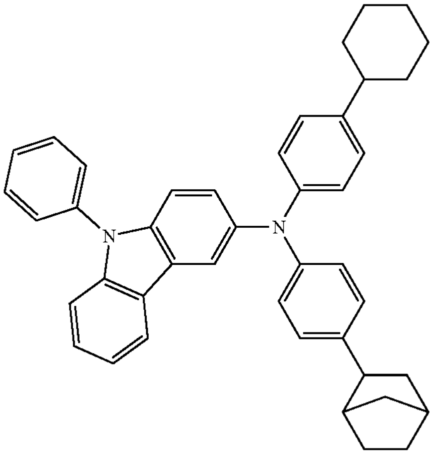

-continued
154
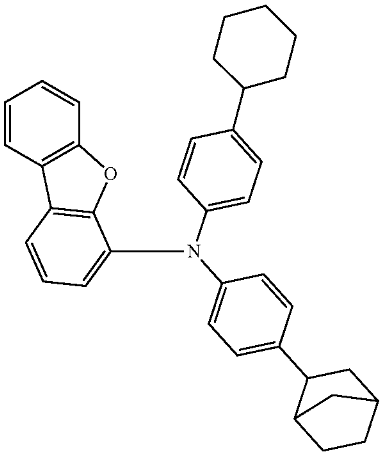
155
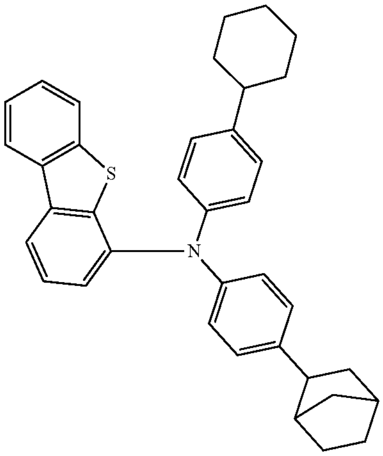
156
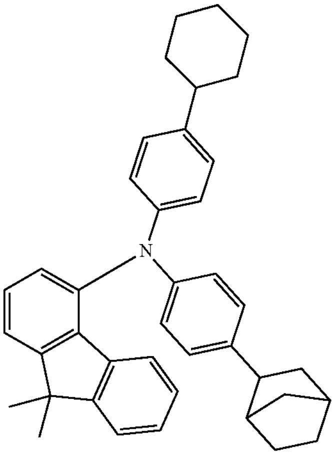
-continued
157
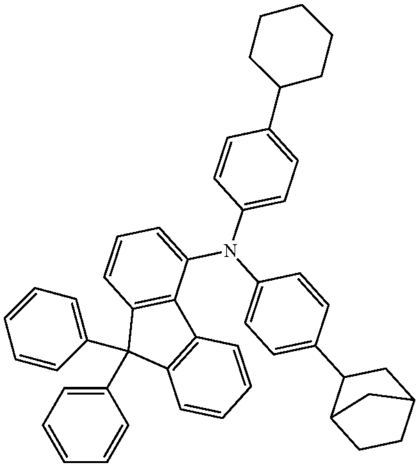
158
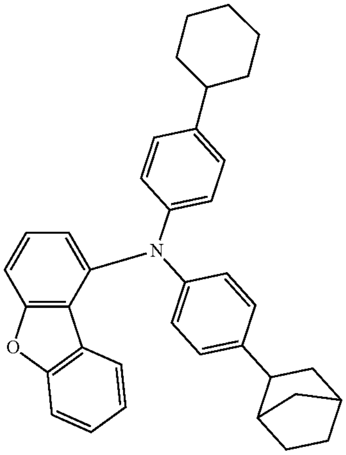
159
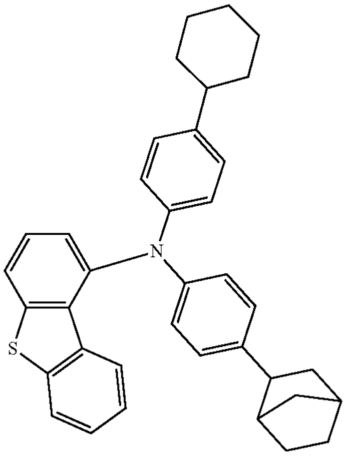

-continued
160
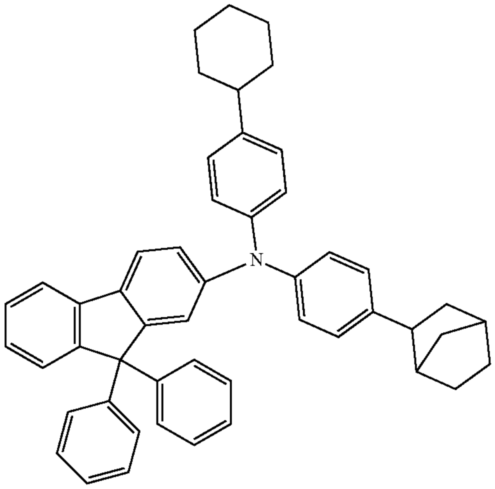
161
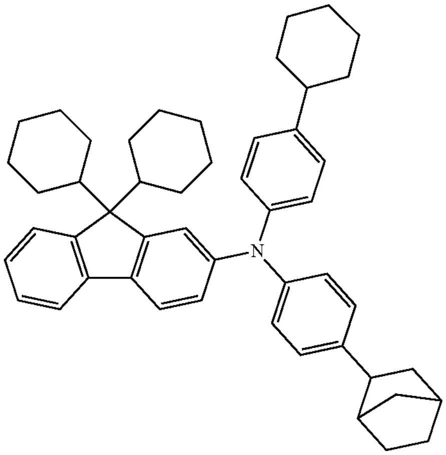
162
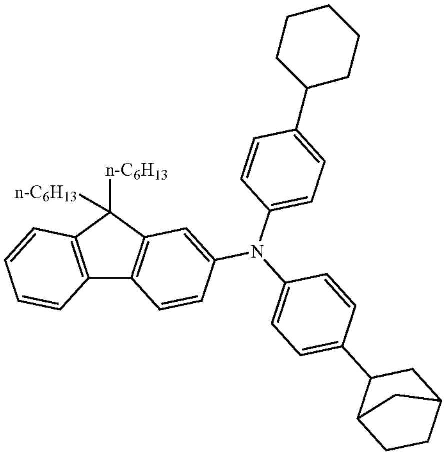
-continued
163
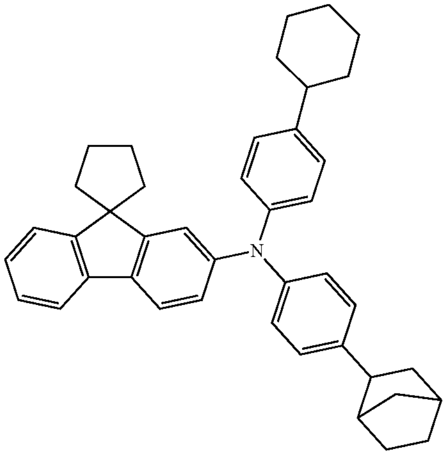
164
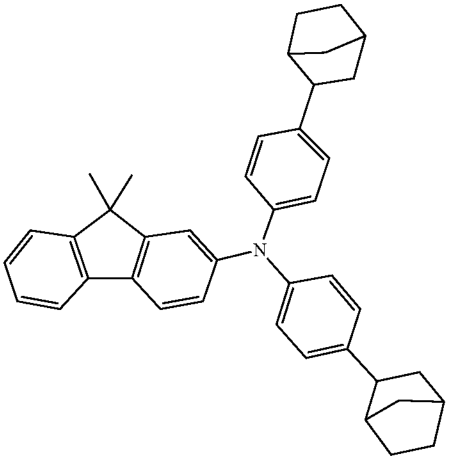
165
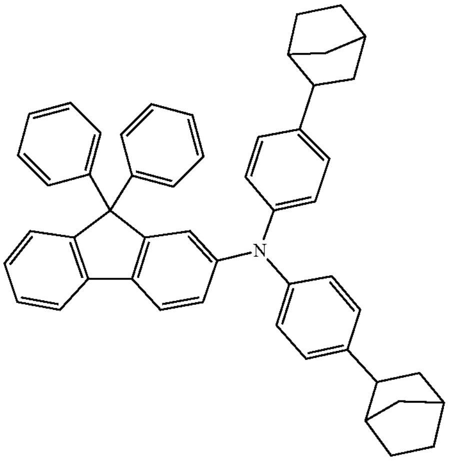

-continued
166
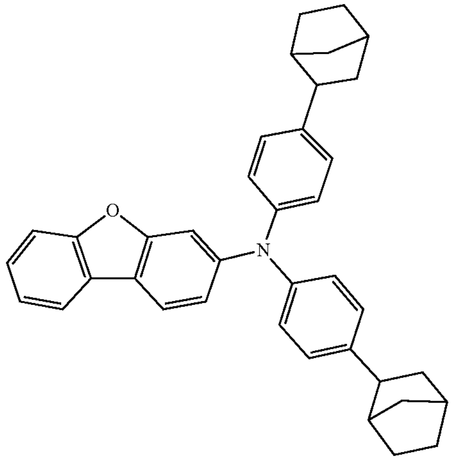
167
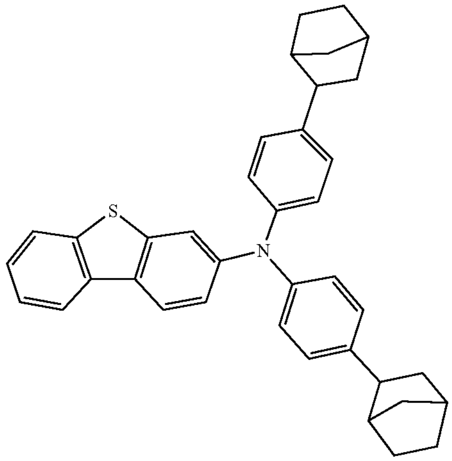
168
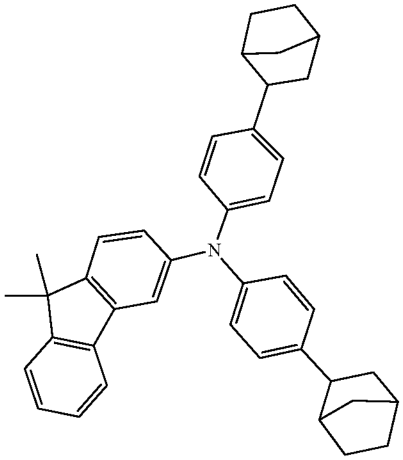
-continued
169
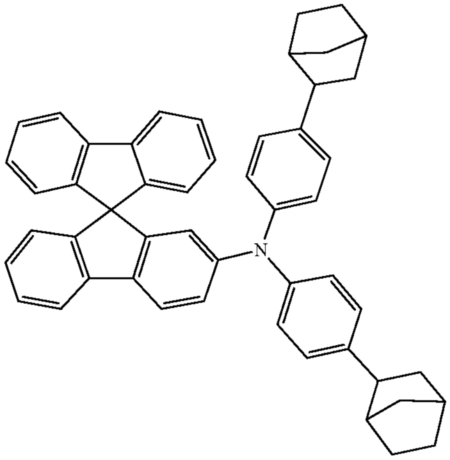
170
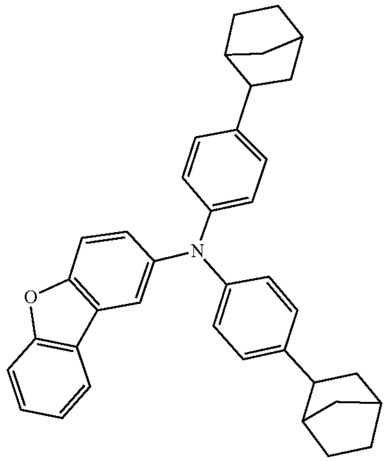
171
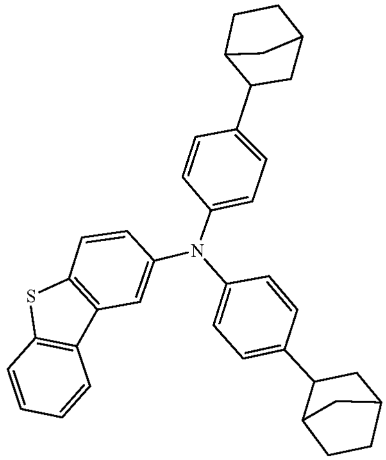

-continued
172
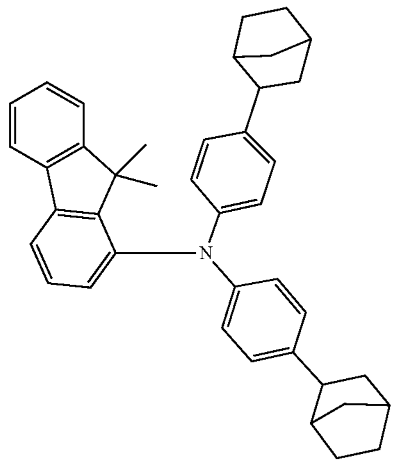
173
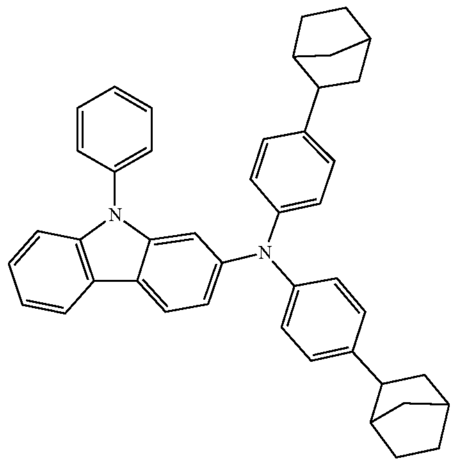
174
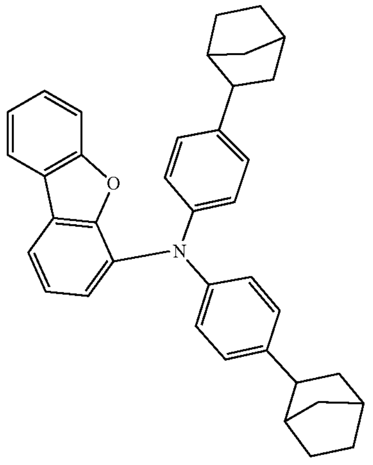
-continued
175
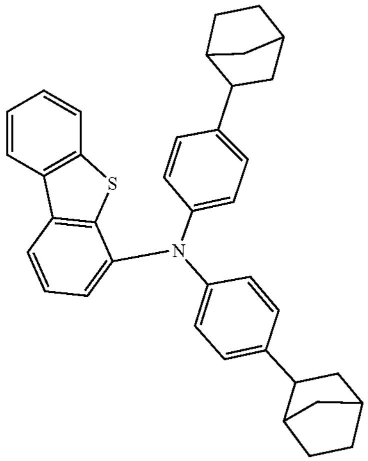
176
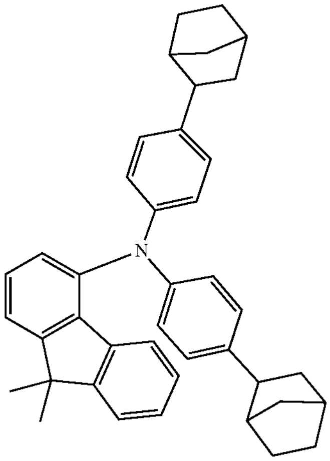
177
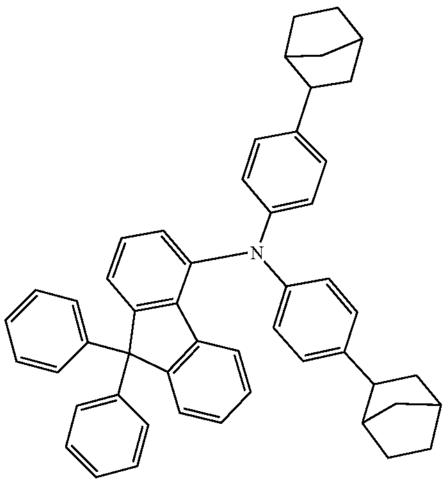

-continued
178
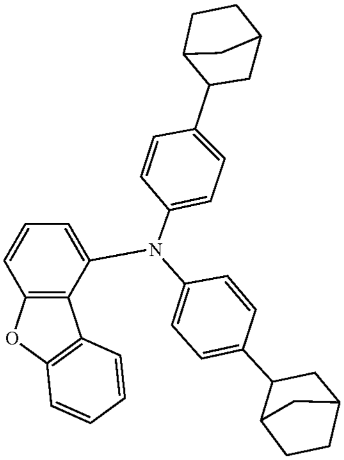
179
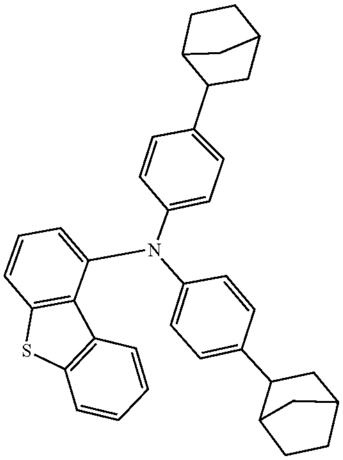
180
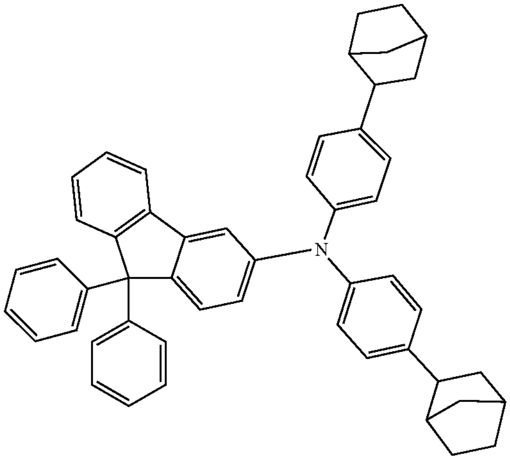
-continued
181
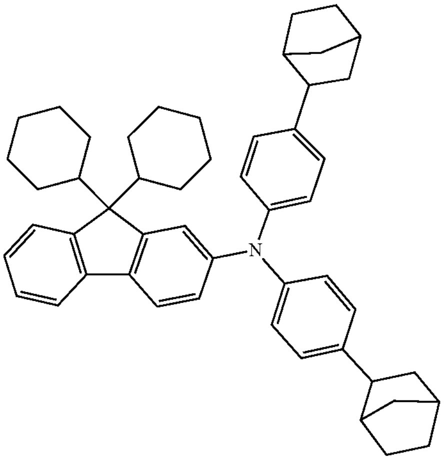
182
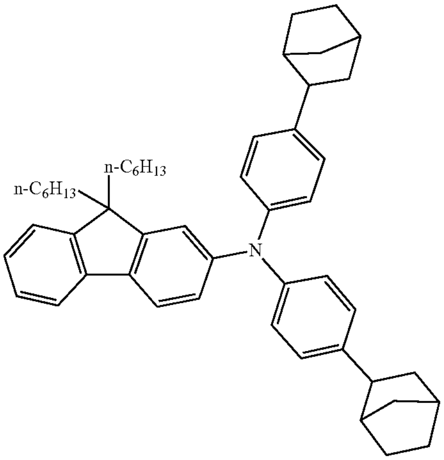
183
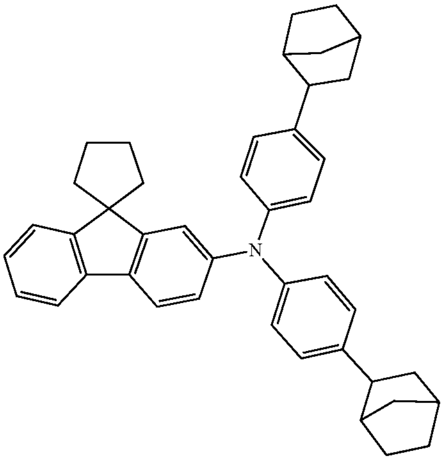

-continued
184
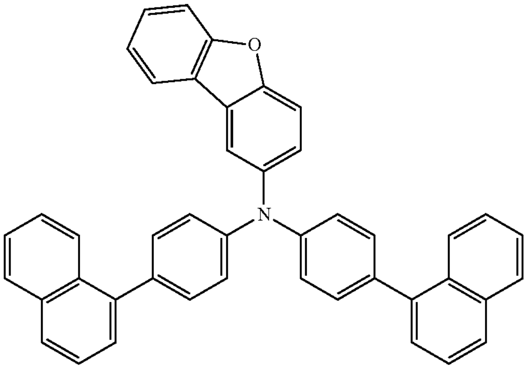
185
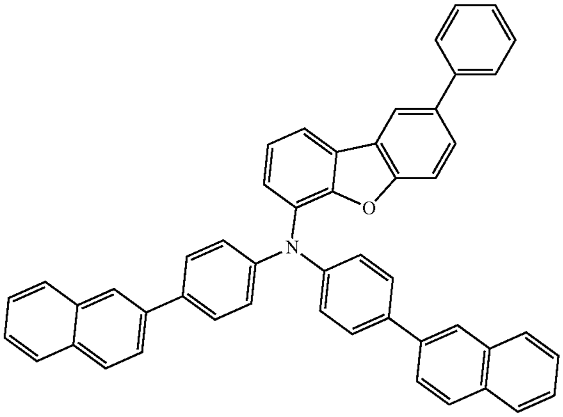
186
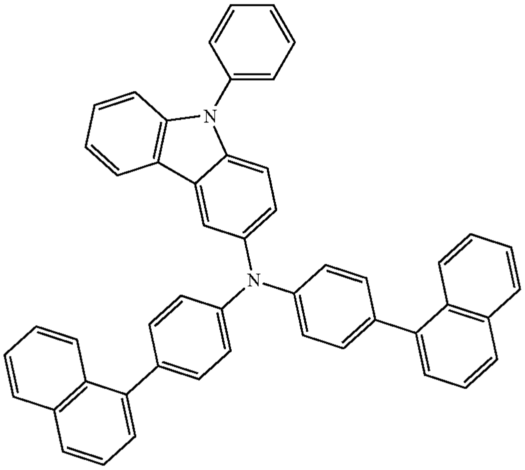
-continued
187
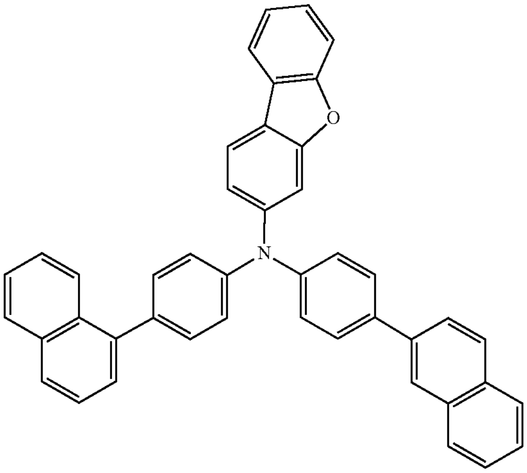
188
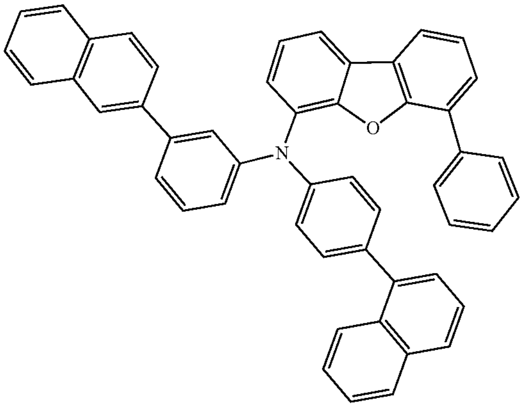
189
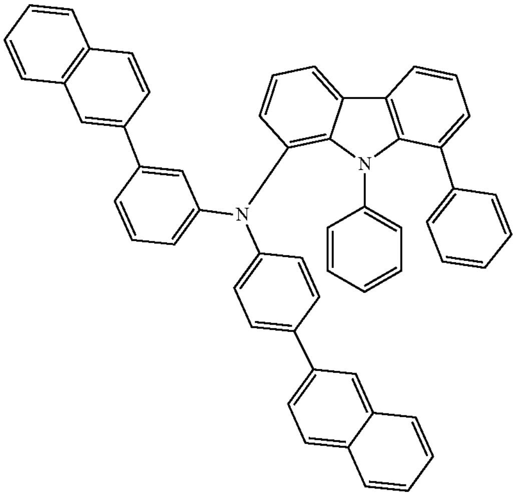

-continued
190
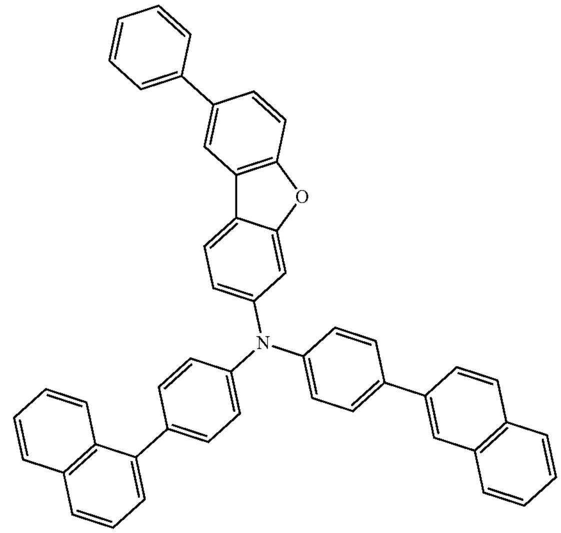
191
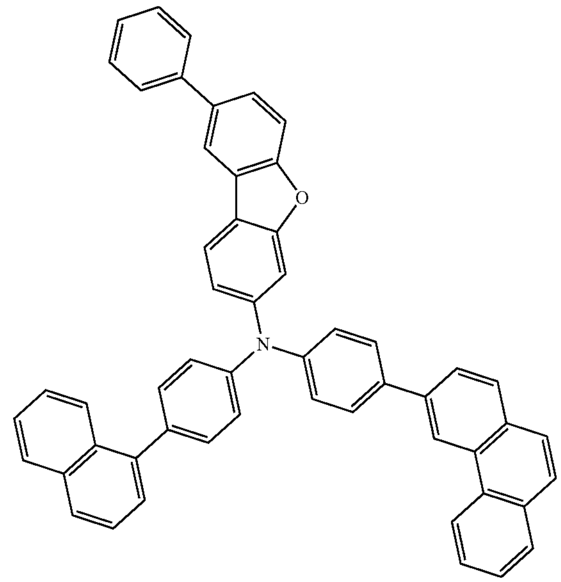
192
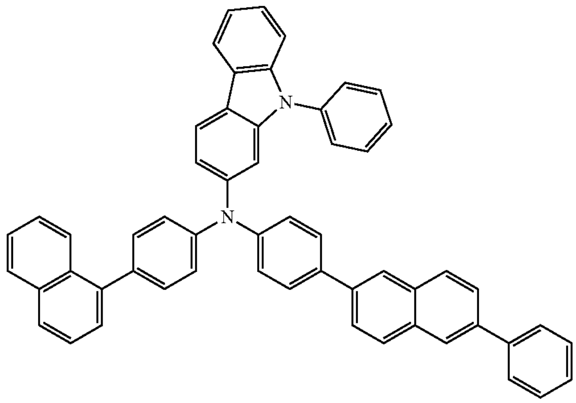
-continued
193
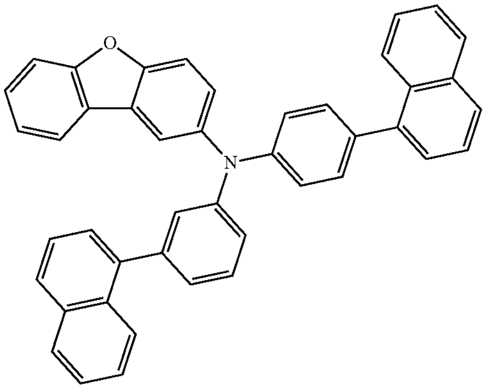
194
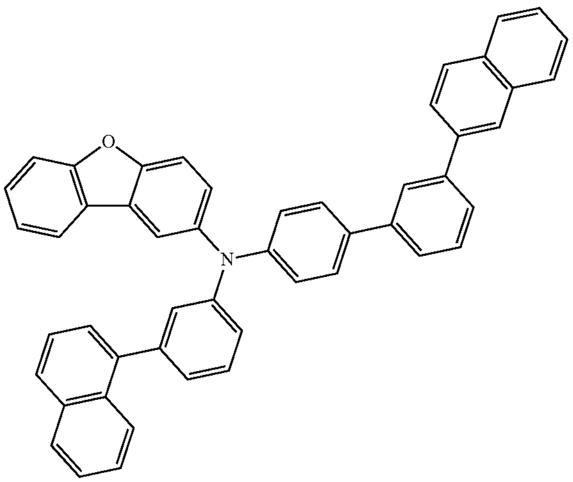
195
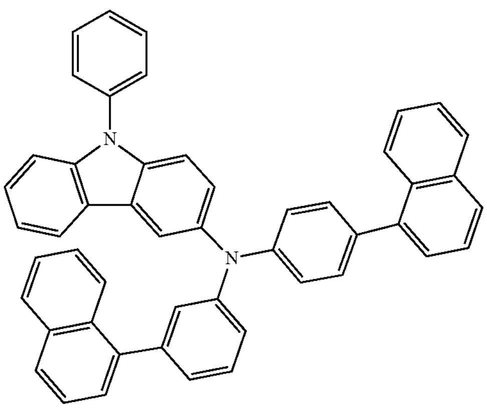

-continued
196
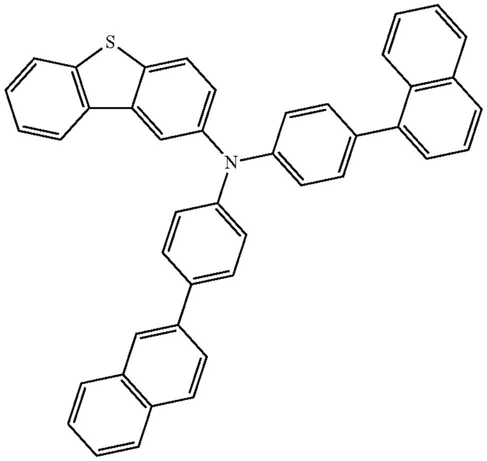
197
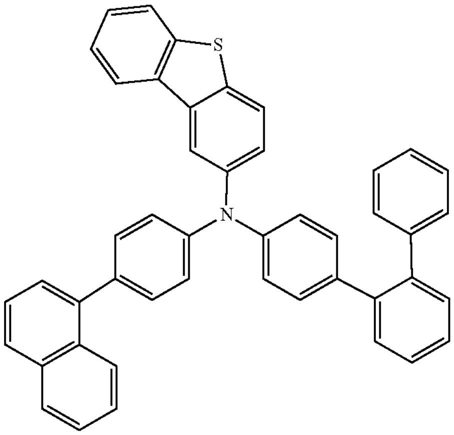
198
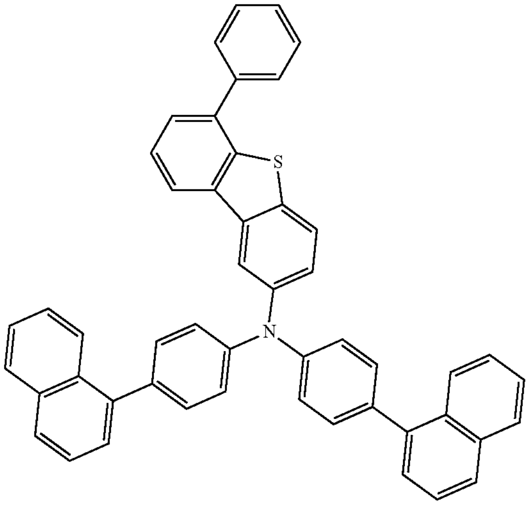
-continued
199
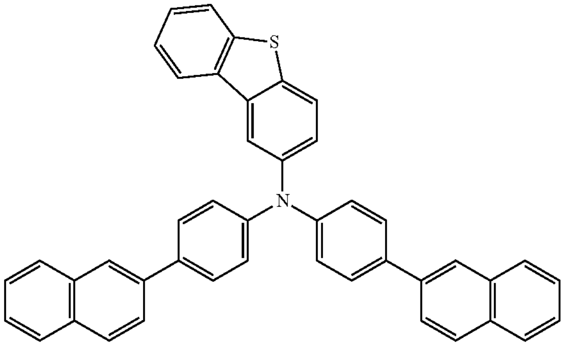
200
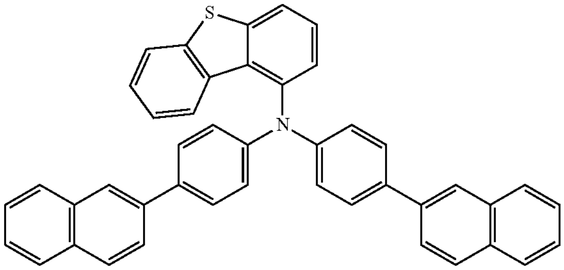
201
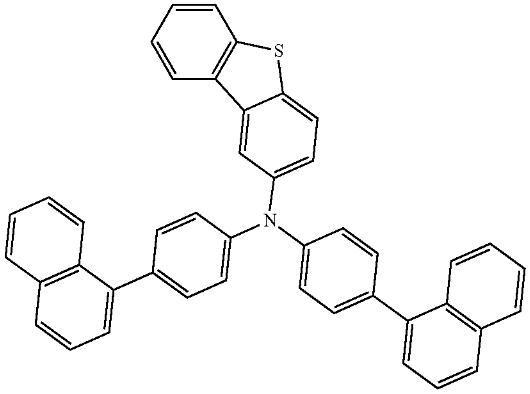
202
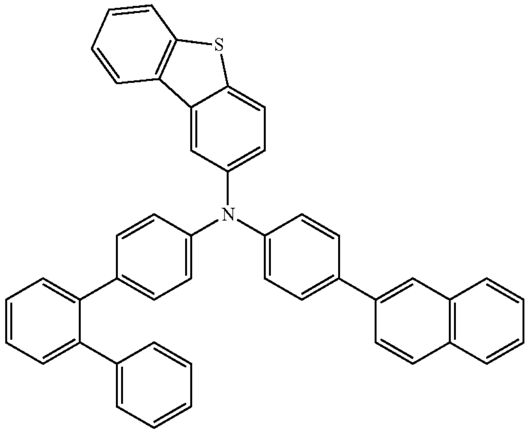

-continued

203

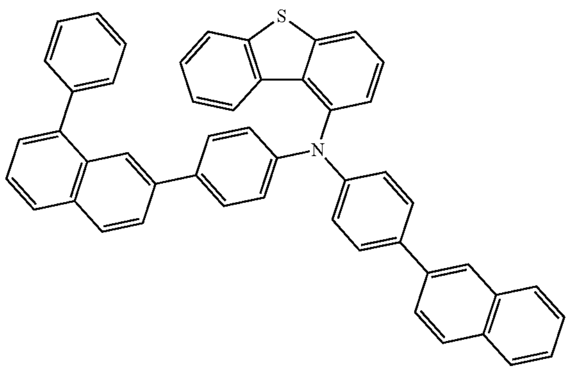

204

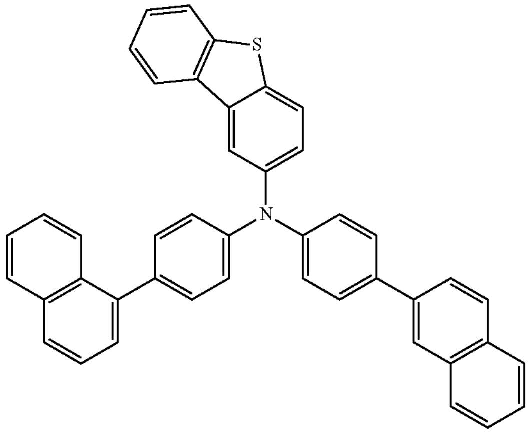

205

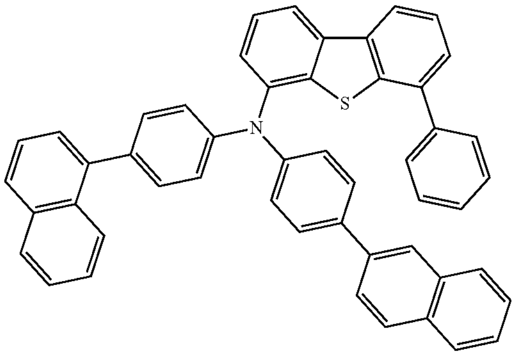

206

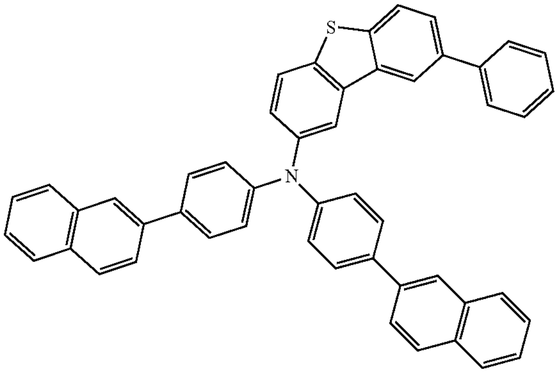

-continued

207

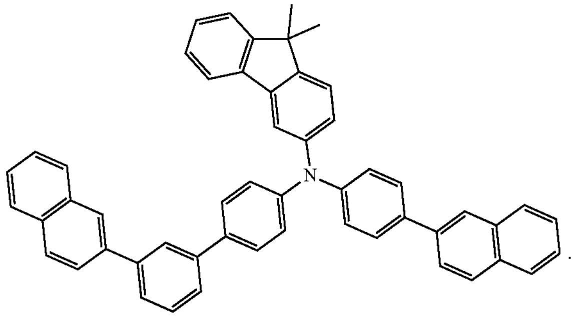

Synthesis methods of the first compound to fourth compound (hereinafter referred to as 'amine-based compound' in some embodiments) may be recognized by one of ordinary skill in the art by referring to the Synthesis Examples and/or the Examples below.

In an embodiment, the first compound; the second compound; and at least one of the third compound and the fourth compound may be included between the first electrode and the second electrode of the light-emitting device. For example, the first compound; the second compound; and at least one of the third compound and the fourth compound may be included in the interlayer of the light-emitting device.

In an embodiment, the first electrode of the light-emitting device may be an anode, the second electrode of the light-emitting device may be a cathode, the interlayer may further include a hole transport region between the first electrode and the emission layer, and an electron transport region between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In an embodiment, the hole transport region may include: the first compound; the second compound; and at least one of the third compound and the fourth compound.

In an embodiment, the hole transport region may include at least one of a hole injection layer, a hole transport layer, and an electron blocking layer, and the at least one of the hole injection layer, the hole transport layer, and the electron blocking layer may include: the first compound; the second compound; and at least one of the third compound and the fourth compound.

In an embodiment, the hole transport region may include a hole transport layer, and the hole transport layer may include: the first compound; the second compound; and at least one of the third compound and the fourth compound.

In an embodiment, the hole transport region may include a hole injection layer and a hole transport layer, and the hole transport layer may include: the first compound; the second compound; and at least one of the third compound and the fourth compound.

When the hole transport layer has a multilayer structure, the driving voltage and luminescence efficiency of the light-emitting device may be significantly affected by compounds included in the hole transport layer that is arranged close to the emission layer, whereas the lifespan characteristics of the light-emitting device may be relatively significantly affected by compounds included in the hole transport layer that is arranged far from the emission layer.

The third compound includes a cycloalkane group having high rigidity (see $R_{31}$ and $R_{32}$ in Formula 3), and thus may have excellent optical properties. The fourth compound includes, in addition to $T_4$ which is a group represented by Formula 5, carbocyclic groups such as $CY_{41}$ and $CY_{42}$, and thus may have excellent charge transport properties due to high planarity of the entire molecule, and in this regard, may have excellent stability during charge transport. Therefore, when at least one of the third compound and the fourth compound is included in the hole transport layer that is arranged close to the emission layer, the driving voltage and luminescence efficiency of the light-emitting device may be significantly improved.

In an embodiment, the hole transport region may include a hole transport layer,

- the hole transport layer may include a first hole transport layer, a second hole transport layer, and a third hole transport layer,
- the first hole transport layer may be between the first electrode and the second hole transport layer,
- the first hole transport layer may include the first compound,
- the second hole transport layer may be between the first hole transport layer and the third hole transport layer,
- the second hole transport layer may include the second compound, and
- the third hole transport layer may include at least one of the third compound and the fourth compound.

In the embodiment described above, the first hole transport layer, the second hole transport layer, and the third hole transport layer may directly contact one another, or other organic layers and/or inorganic layers may be arranged between the first hole transport layer and the second hole transport layer and/or between the second hole transport layer and the third hole transport layer.

In an embodiment, the first hole transport layer, the second hole transport layer, and the third hole transport layer may directly contact one another. For example, the second hole transport layer may directly contact each of the first hole transport layer and the third hole transport layer.

When at least one of the third compound and the fourth compound is included in the third hole transport layer that is arranged close to the emission layer, the driving voltage and luminescence efficiency of the light-emitting device may be significantly improved.

For example, the third hole transport layer may include only the third compound.

For example, the third hole transport layer may include both the third compound and the fourth compound.

In an embodiment, the hole transport region may include a hole transport layer, the hole transport layer may include a first hole transport layer, a second hole transport layer, a third hole transport layer, and a fourth hole transport layer,

- the first hole transport layer may be between the first electrode and the second hole transport layer, the first hole transport layer may include the first compound,
- the second hole transport layer may be between the first hole transport layer and the third hole transport layer,
- the second hole transport layer may include the second compound,
- the third hole transport layer may be between the second hole transport layer and the fourth hole transport layer,
- the third hole transport layer may include the third compound, and
- the fourth hole transport layer may include the fourth compound.

In the embodiment described above, the first hole transport layer, the second hole transport layer, the third hole transport layer, and the fourth hole transport layer may directly contact one another, or other organic layers and/or inorganic layers may be arranged between the first hole transport layer and the second hole transport layer, and/or between the second hole transport layer and the third hole transport layer, and/or between the third hole transport layer and the fourth hole transport layer.

In an embodiment, the first hole transport layer, the second hole transport layer, the third hole transport layer, and the fourth hole transport layer may directly contact one another. For example, the second hole transport layer may directly contact each of the first hole transport layer and the third hole transport layer, and the third hole transport layer may directly contact each of the second hole transport layer and the fourth hole transport layer.

When the third compound and the fourth compound are respectively included in the third hole transport layer and the fourth hole transport layer that are arranged close to the emission layer, the driving voltage and luminescence efficiency of the light-emitting device may be significantly improved.

In an embodiment, the emission layer of the interlayer in the light-emitting device may include a dopant and a host. For example, the host may include an anthracene compound, but is not limited thereto, and the dopant may include a compound including a $C_8$-$C_{60}$ polycyclic group in which at least two cyclic groups are condensed while sharing boron (B). However, embodiments are not limited thereto.

An amount of the host may be greater than an amount of the dopant. For example, an amount of the dopant in the emission layer may be in a range of about 0.01 parts by weight to about 5 parts by weight, based on a total of 100 parts by weight of the host and the dopant. For example, an amount of the dopant in the emission layer may be in a range of about 0.01 parts by weight to about 3 parts by weight, based a total of 100 parts by weight of the host and the dopant. However, embodiments are not limited thereto.

The emission layer may emit red light, green light, blue light, and/or white light. For example, the emission layer may emit blue light. The blue light may have a maximum emission wavelength in a range of, for example, about 400 nm to about 490 nm. For example, in an embodiment, the emission layer may emit blue light having a maximum emission wavelength in a range of about 430 nm to about 490 nm.

In an embodiment, the light-emitting device may include a capping layer outside the first electrode or outside the second electrode.

For example, the light-emitting device may further include at least one of a first capping layer outside the first electrode and a second capping layer outside the second electrode, and at least one of the first capping layer and the second capping layer may include at least one of the first compound to the fourth compound. The first capping layer and/or the second capping layer may each be the same as described herein.

In an embodiment, the light-emitting device may further include:

a first capping layer outside the first electrode and includes at least one of the first compound to the fourth compound;

a second capping layer outside the second electrode and includes at least one of the first compound to the fourth compound; or both the first capping layer and the second capping layer.

The wording "(interlayer and/or capping layer) includes a first compound" as used herein refers to a case in which "(interlayer and/or capping layer) may include one kind of first compound represented by Formula 1" or a case in which "(interlayer and/or capping layer) may include two or more different kinds of first compounds represented by Formula 1. The second compound to the fourth compound may each be interpreted in a same manner.

For example, the interlayer and/or the capping layer may include Compound 1 only as the amine-based compound. Thus, Compound 1 may be included in the hole transport region of the light-emitting device. For example, the interlayer may include, as the amine-based compound, both Compound 1 and Compound 2. Compound 1 and Compound 2 may be present in a same layer (for example, both Compound 1 and Compound 2 may be present in the hole transport region), or may be present in different layers (for example, Compound 1 may be present in the emission layer, and Compound 2 may be present in the hole transport region).

Another aspect provides an electronic apparatus which may include the light-emitting device. The electronic apparatus may further include a thin-film transistor.

For example, in an embodiment, the electronic apparatus may further include a thin-film transistor including a source electrode and a drain electrode, wherein the first electrode of the light-emitting device may be electrically connected to the source electrode or the drain electrode. In an embodiment, the electronic apparatus may further include a color filter, a color conversion layer, a touch screen layer, a polarizing layer, or any combination thereof. The electronic apparatus may be the same as described herein.

The first compound to the fourth compound that are each an amine-based compound and have a condensed cyclic structure in its molecule (see a fluorene group or the like in Formula 1; a carbazole group, a fluorene group, and the like in Formula 2; $T_3$ or the like in Formula 3; and $T_4$ or the like in Formula 4) may have a high glass transition temperature (Tg) and/or a high melting point so that crystallization may be prevented. In the first compound to the fourth compound, resistance to heat generated during light emission and resistance under high-temperature environments may be increased, resulting in excellent electrical stability and excellent charge transport ability.

Since the third compound includes a cycloalkane group having high rigidity (see $R_{31}$ and $R_{32}$ in Formula 3), the third compound may have excellent optical properties. Since the fourth compound has high planarity of the entire molecule, the fourth compound may have excellent charge transport properties and thus, is also highly stable during charge transport.

Therefore, when the first compound to the third compound, or the first compound to the fourth compound are used as hole-transporting materials, an electronic device (for example, an organic light-emitting device) having a low driving voltage, high luminance, high efficiency, and long lifespan characteristics may be implemented.

[Description of FIG. 1]

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described with reference to FIG. 1.

[First Electrode 110]

In FIG. 1, a substrate may be further included under the first electrode 110 or on the second electrode 150. In an embodiment, the substrate may be a glass substrate or a plastic substrate. In embodiments, the substrate may be a flexible substrate, and for example, may include plastics with excellent heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high-work function material that facilitates the injection of holes.

The first electrode 110 may be a reflective electrode, a semi-transmissive electrode, or a transmissive electrode. In an embodiment, when the first electrode 110 is a transmissive electrode, a material for forming the first electrode 110 may include indium tin oxide (ITO), indium zinc oxide (IZO), tin oxide ($SnO_2$), zinc oxide (ZnO), or any combination thereof. In embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a structure consisting of a single layer or a structure including multiple layers. For example, the first electrode 110 may have a three-layered structure of ITO/Ag/ITO.

[Interlayer 130]

The interlayer 130 is arranged on the first electrode 110. The interlayer 130 may include an emission layer.

The interlayer 130 may further include a hole transport region between the first electrode 110 and the emission layer, and an electron transport region between the emission layer and the second electrode 150.

In an embodiment, the interlayer 130 may further include, in addition to various organic materials, a metal-containing compound such as an organometallic compound, an inorganic material such as a quantum dot, and the like.

The interlayer 130 may include two or more emitting units stacked between the first electrode 110 and the second electrode 150, and at least one charge generation layer located between the two or more emitting units. When the interlayer 130 includes the two or more emitting units and the at least one charge generation layer, the light-emitting device 10 may be a tandem light-emitting device.

[Hole Transport Region in Interlayer 130]

The hole transport region may have a structure consisting of a layer consisting of a single material, a structure consisting of a layer including multiple materials that are different from each other, or a structure including multiple layers including multiple materials that are different from each other.

The hole transport region may include a hole injection layer, a hole transport layer, an emission auxiliary layer, an electron blocking layer, or any combination thereof.

In embodiments, the hole transport region may have a multi-layer structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein the layers of each structure may be stacked from the first electrode 110 in its respective stated order, but the structure of the hole transport region is not limited thereto.

The hole transport region may include: the first compound; the second compound; and at least one of the third compound and the fourth compound.

The hole transport region may further include, in addition to the first compound to the fourth compound, a compound represented by Formula 201, a compound represented by Formula 202, or any combination thereof:

[Formula 201]

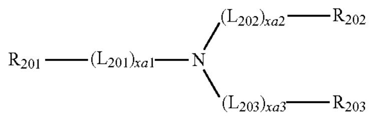

[Formula 202]

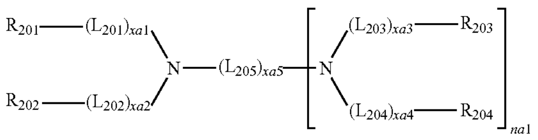

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be bonded to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group, etc.) unsubstituted or substituted with at least one $R_{10a}$ (for example, Compound HT16, etc.), $R_{203}$ and $R_{204}$ may optionally be bonded to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In embodiments, the compound represented by Formula 201 and the compound represented by Formula 202 may each independently include at least one of groups represented by Formulae CY201 to CY217:

CY201

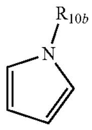

CY202

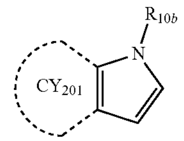

CY203

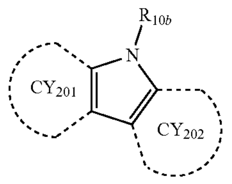

CY204

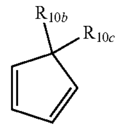

CY205

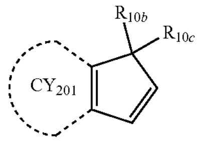

CY206

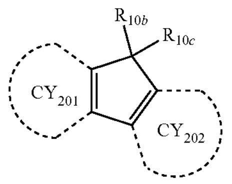

CY207

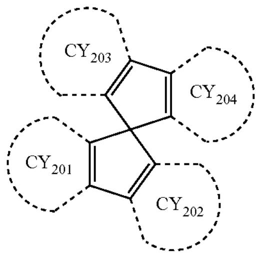

CY208

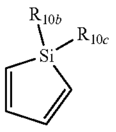

-continued

CY209

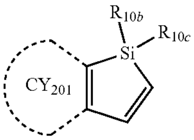

CY210

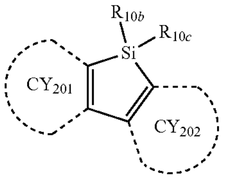

CY211

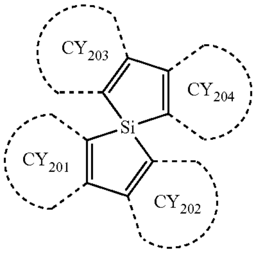

CY212

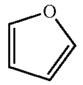

CY213

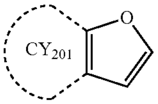

CY214

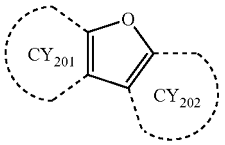

CY215

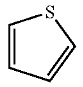

CY216

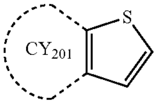

CY217

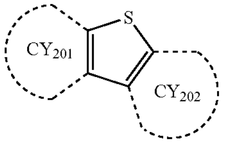

In Formulae CY201 to CY217, $R_{10b}$ and $R_{10c}$ may each independently be the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$ as described herein.

In an embodiment, in Formulae CY201 to CY217, ring $CY_{201}$ to ring $CY_{204}$ may each independently be a benzene group, a naphthalene group, a phenanthrene group, or an anthracene group.

In embodiments, the compound represented by Formula 201 and the compound represented by Formula 202 may each independently include at least one of groups represented by Formulae CY201 to CY203.

In embodiments, the compound represented by Formula 201 may include at least one of groups represented by Formulae CY201 to CY203 and at least one of groups represented by Formulae CY204 to CY217.

In embodiments, in Formula 201, xa1 may be 1, $R_{201}$ may be one of groups represented by Formulae CY201 to CY203, xa2 may be 0, and $R_{202}$ may be one of groups represented by Formulae CY204 to CY207.

In embodiments, the compound represented by 201 and the compound represented by 202 may each not include groups represented by Formulae CY201 to CY203.

In embodiments, the compound represented by 201 and the compound represented by 202 may each not include groups represented by Formulae CY201 to CY203, and may each independently include at least one of groups represented by Formulae CY204 to CY217.

In embodiments, the compound represented by 201 and the compound represented by 202 may each not include groups represented by Formulae CY201 to CY217.

In an embodiment, the hole transport region may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof.

HT1

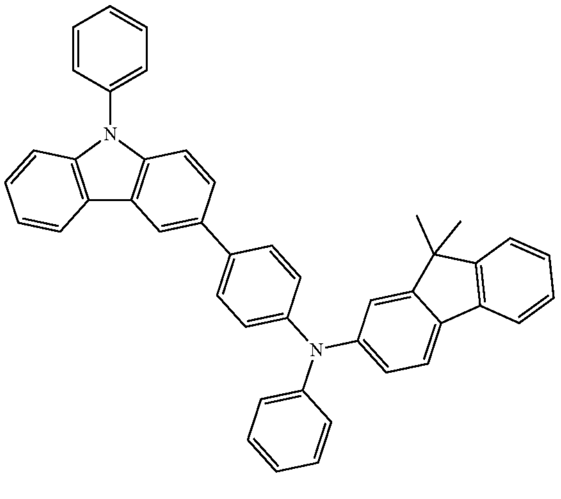

-continued
HT2
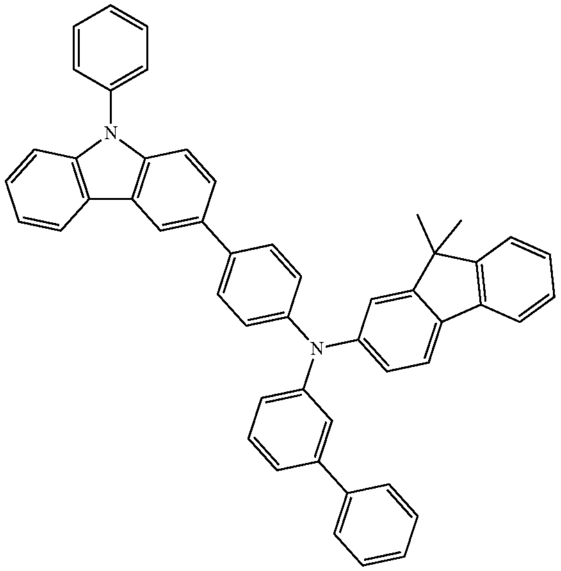
HT3
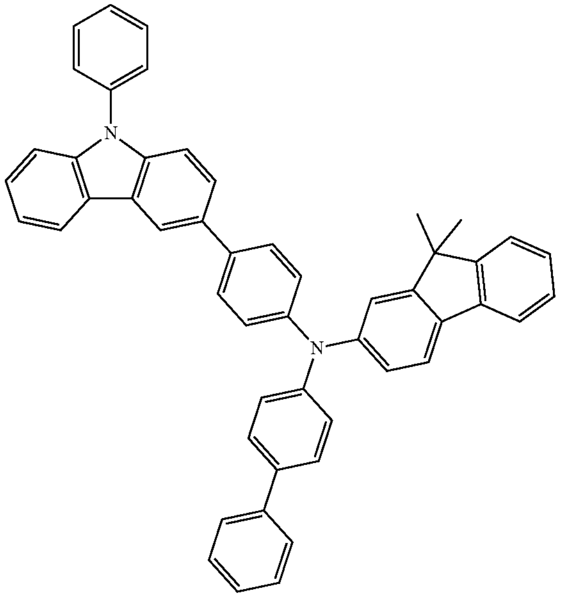
-continued
HT4
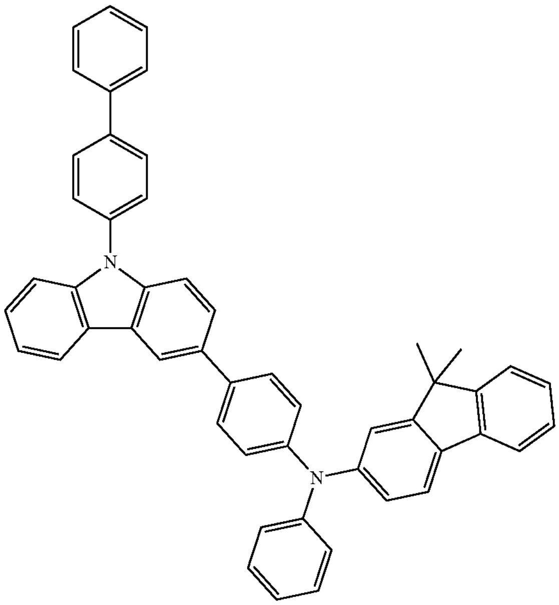
HT5
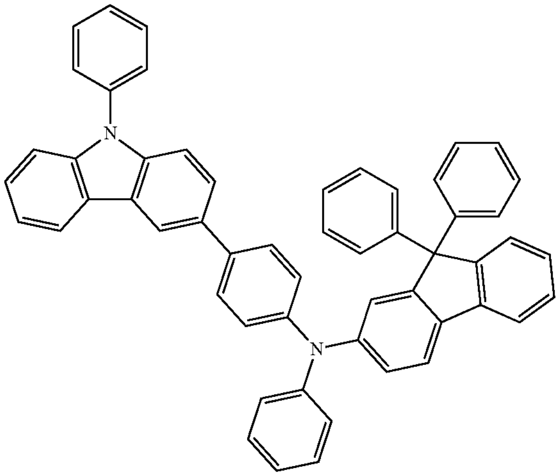

-continued
HT6
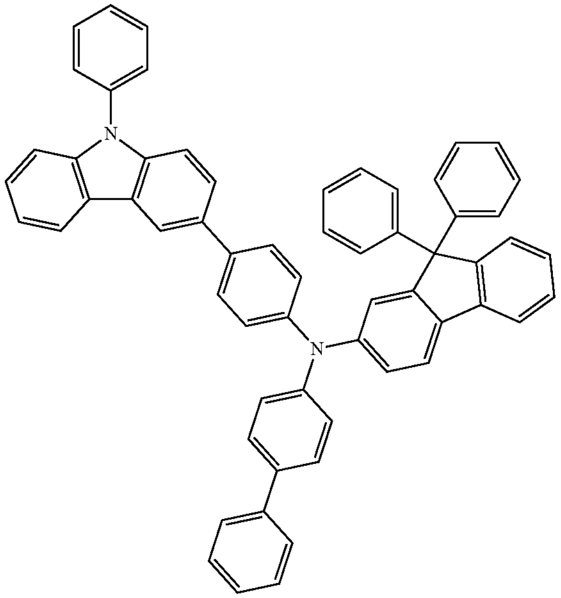
HT7
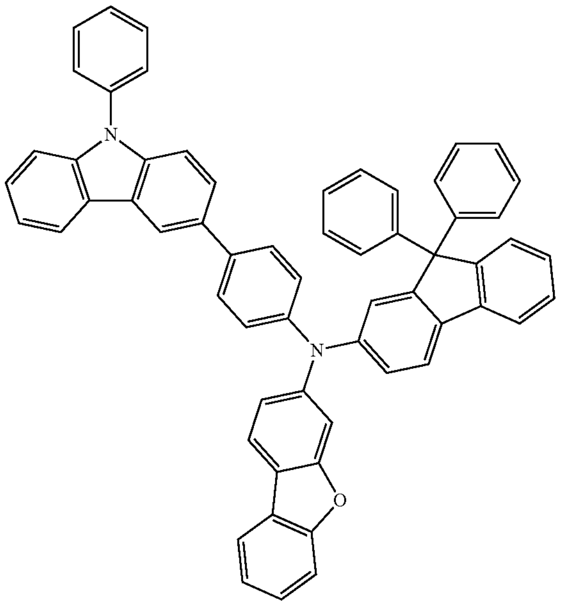
-continued
HT8
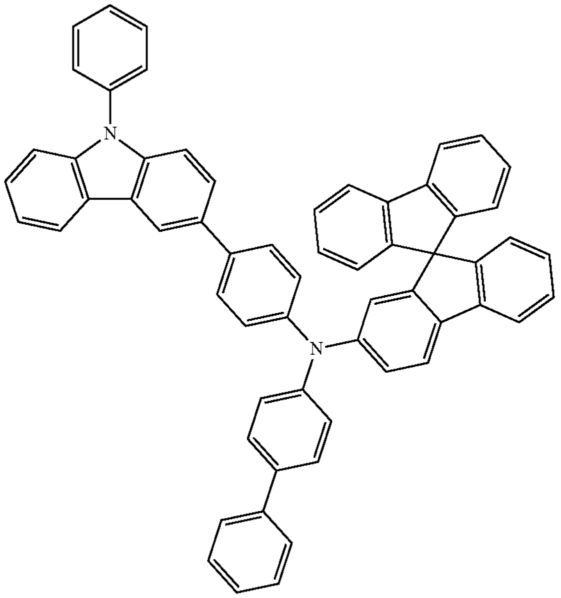
HT9
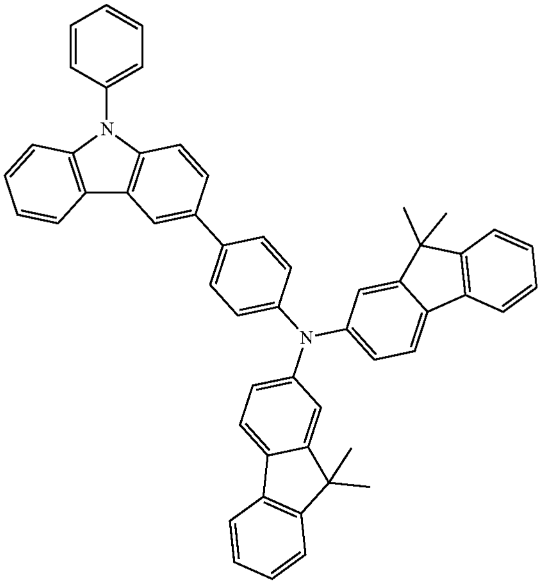

-continued
HT10
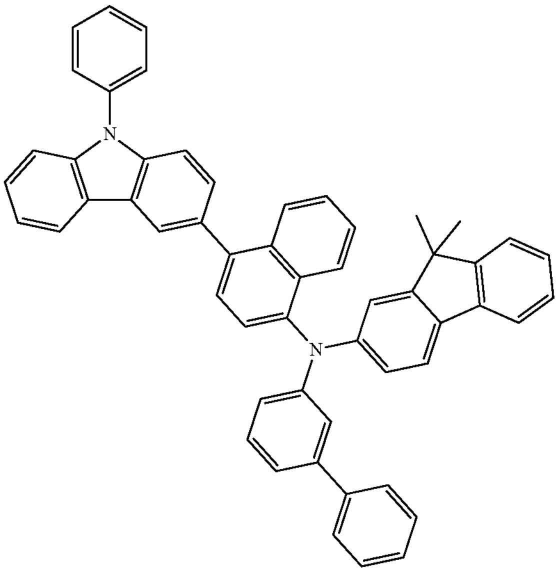
HT11
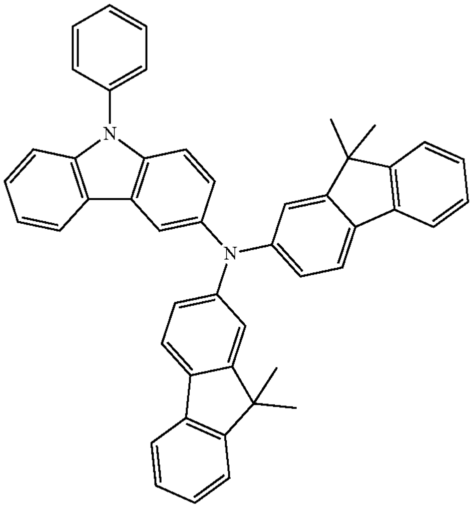
HT12
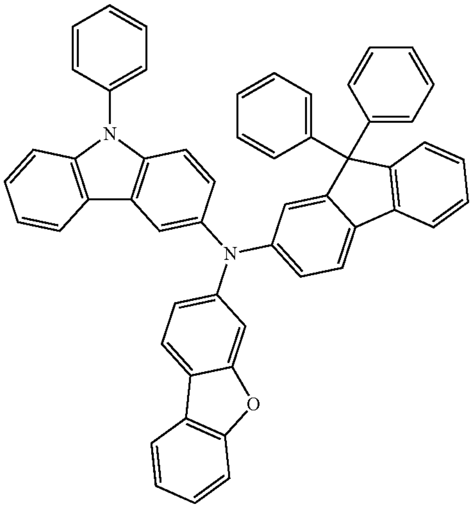
-continued
HT13
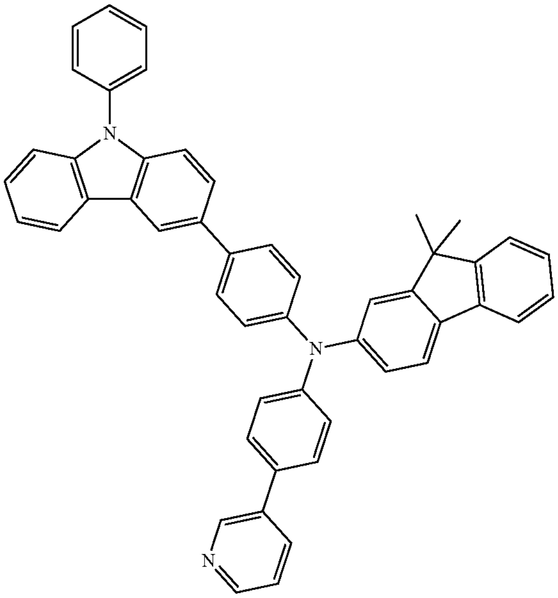
HT14
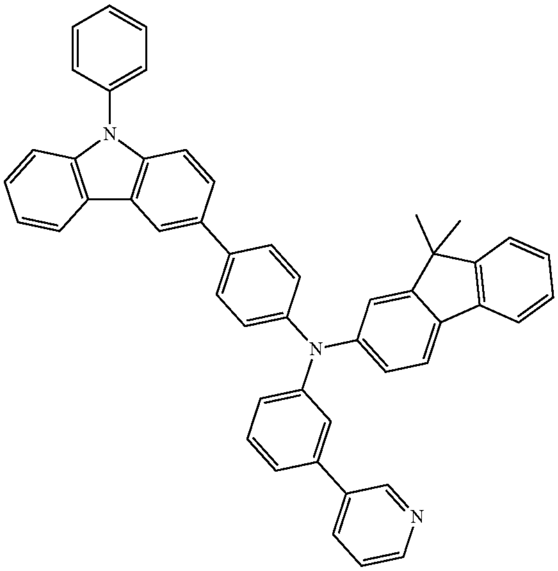

-continued
HT15
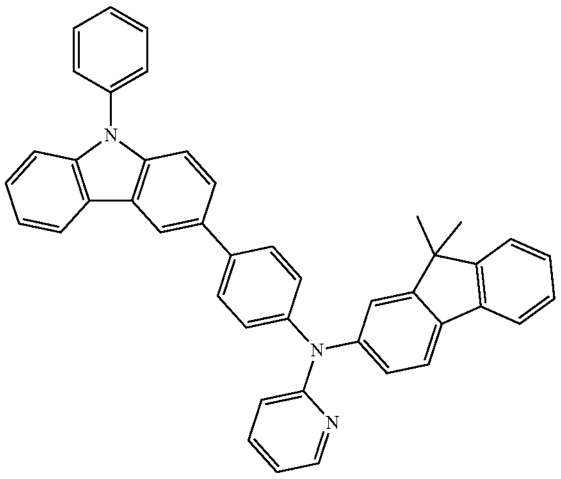
HT16
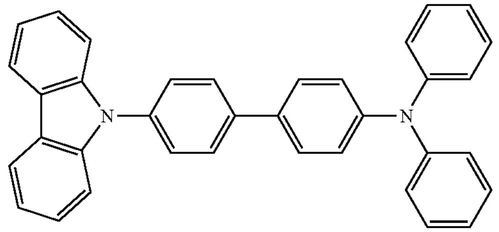
HT17
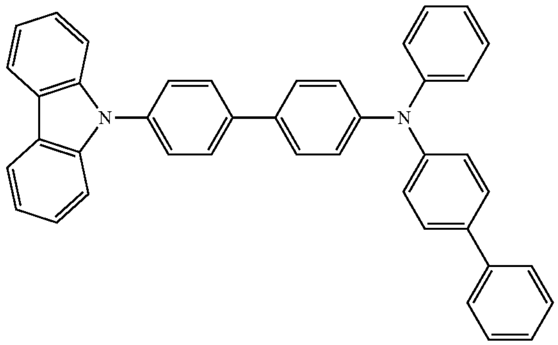
HT18
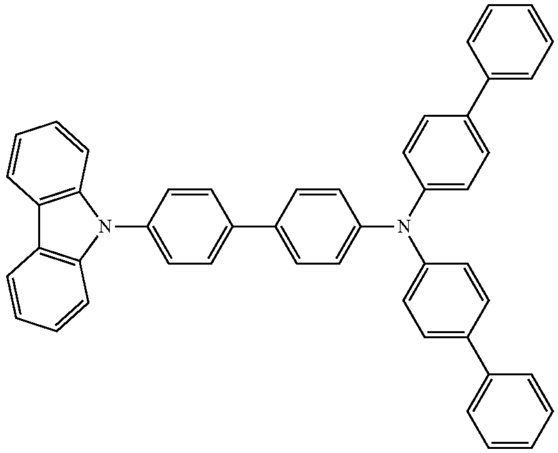
-continued
HT19
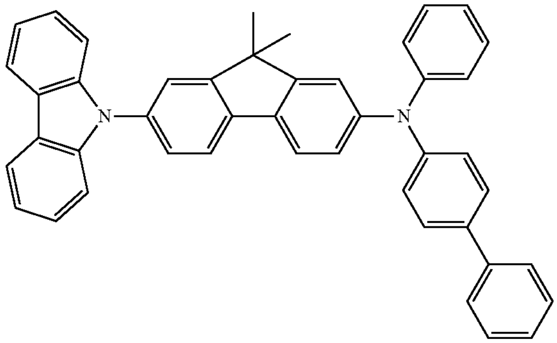
HT20
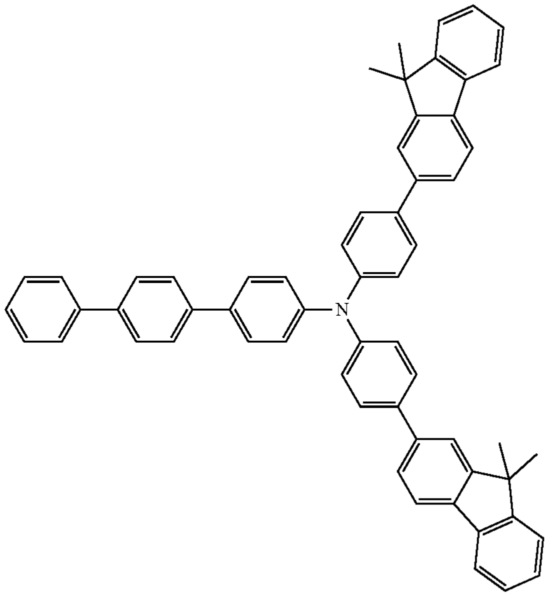
HT21
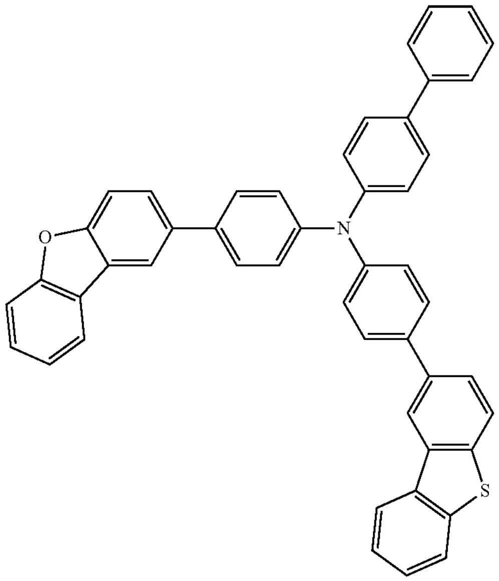

-continued
HT22
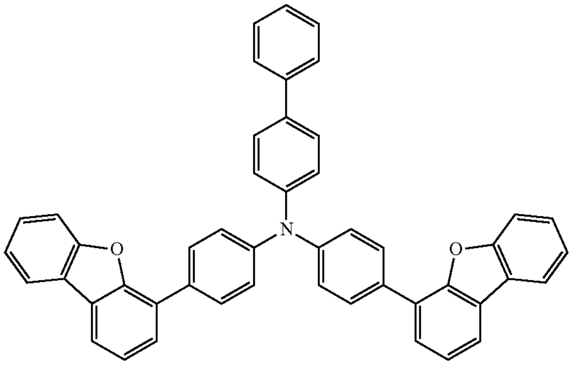
HT23
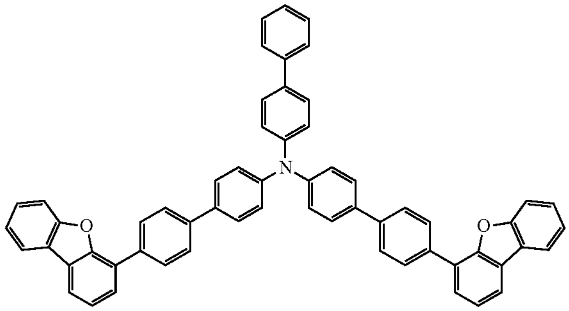
HT24
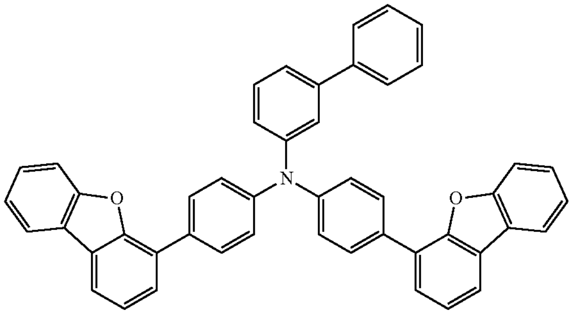
HT25
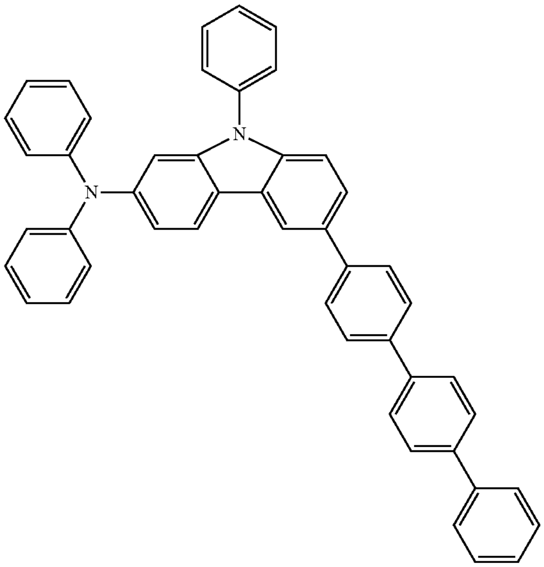
-continued
HT26
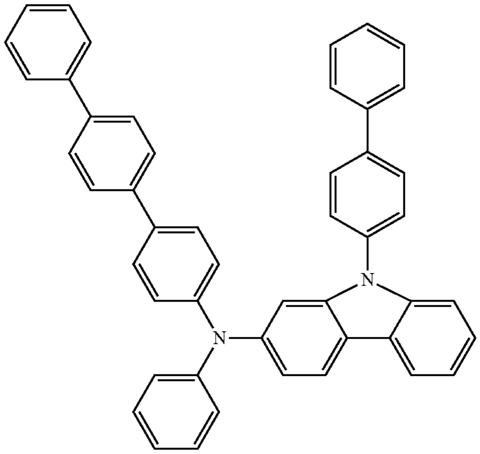
HT27
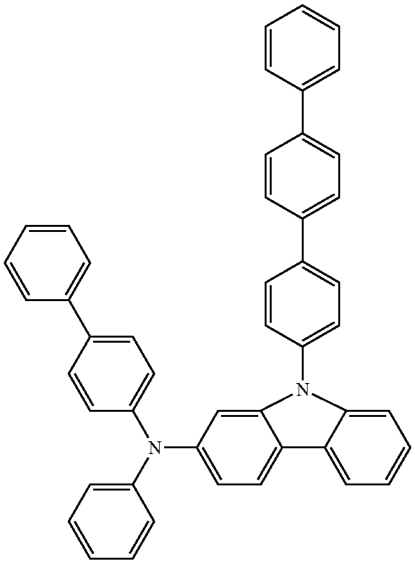
HT28
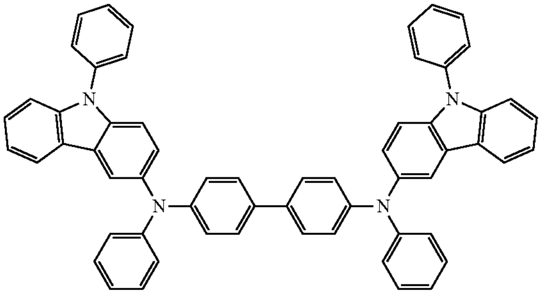

-continued
HT29
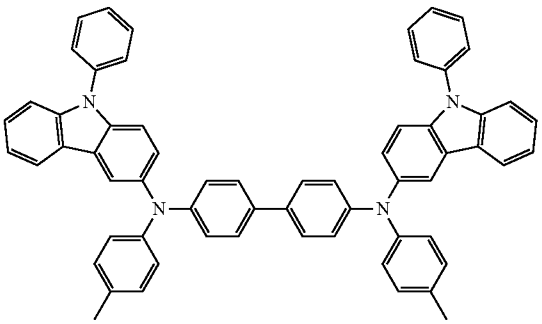
HT30
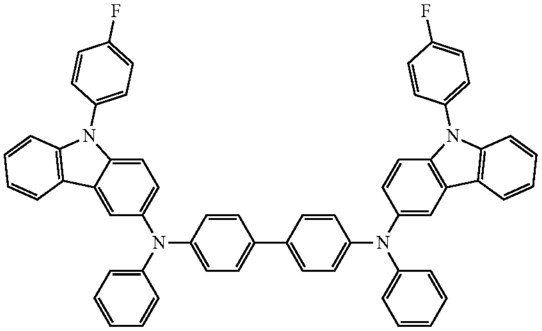
HT31
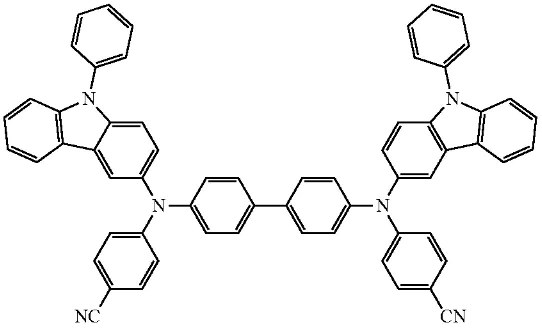
HT32
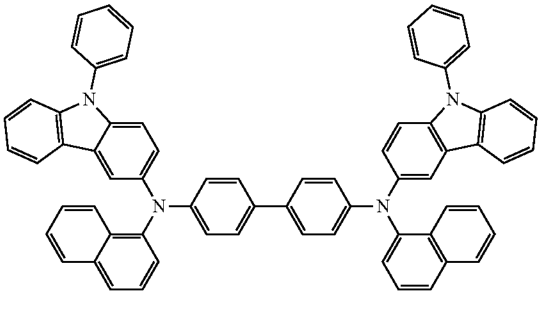
-continued
HT33
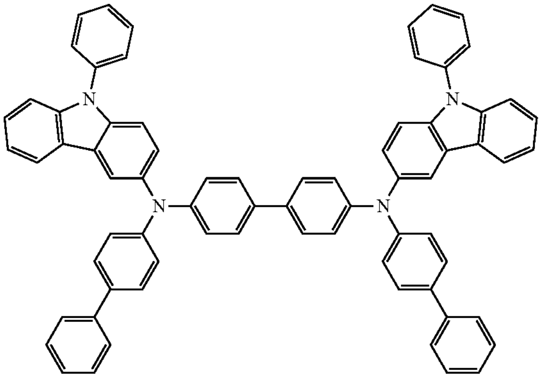
HT34
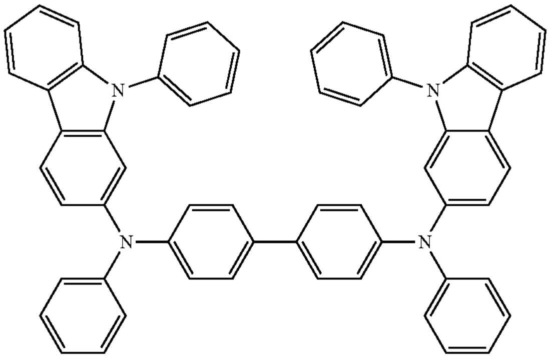
HT35
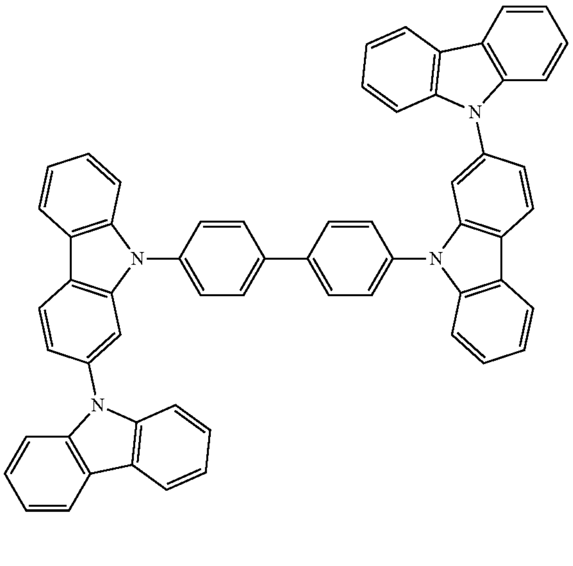

-continued
HT36
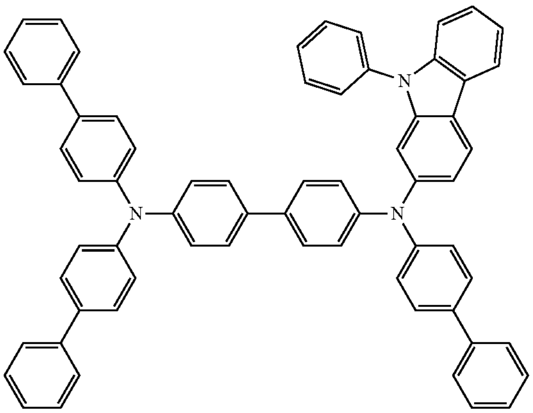
HT37
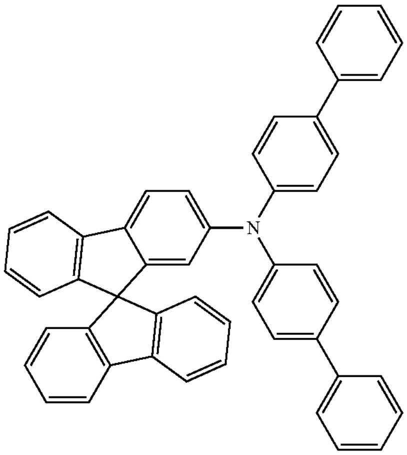
HT38
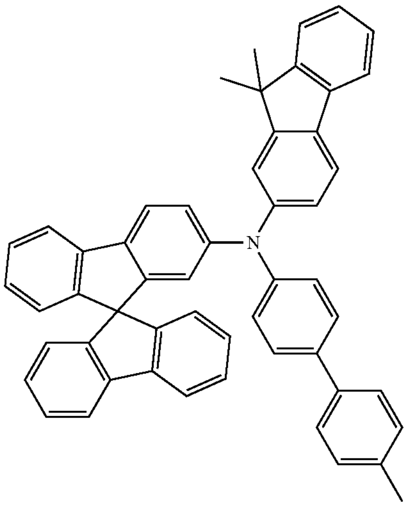
-continued
HT39
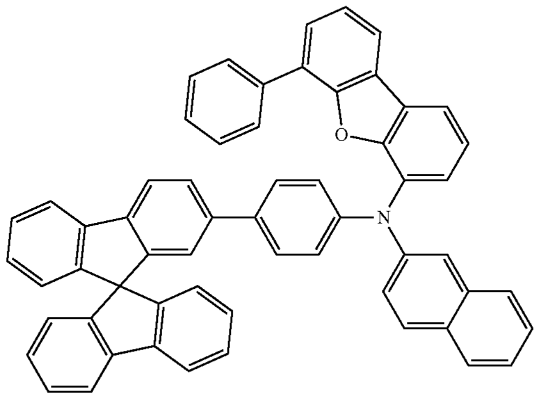
HT40
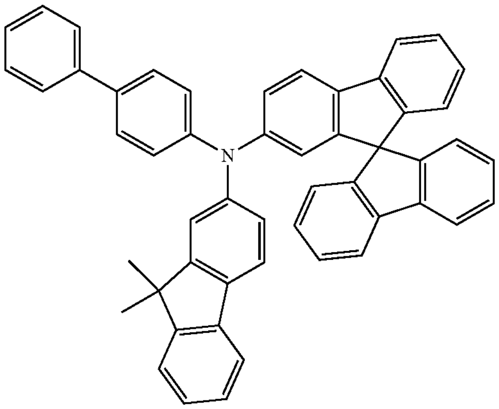
HT41
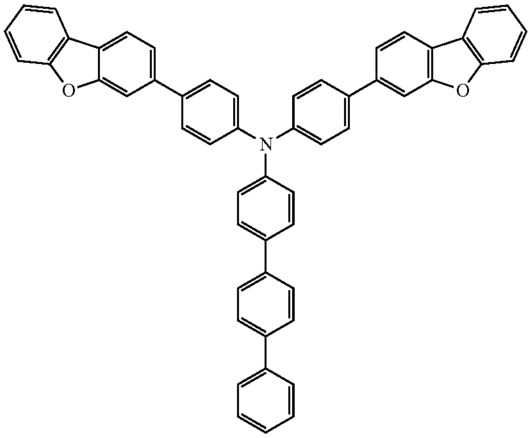
HT42
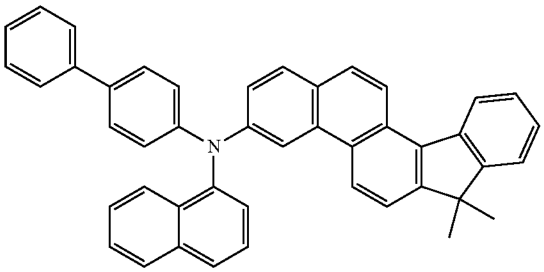

-continued
HT43
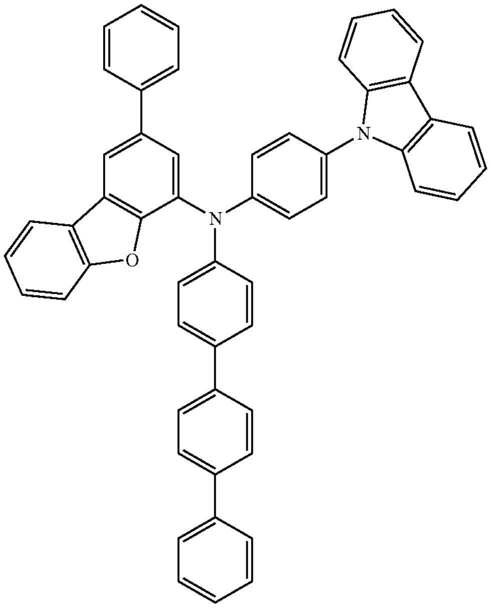
HT44
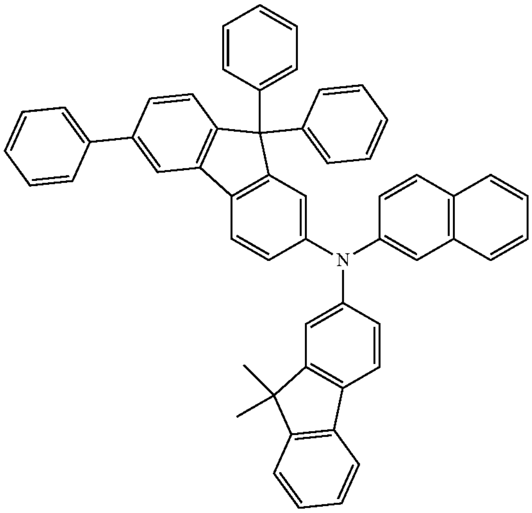
HT45
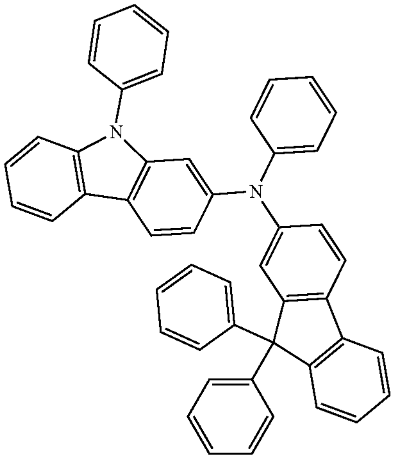
-continued
HT46
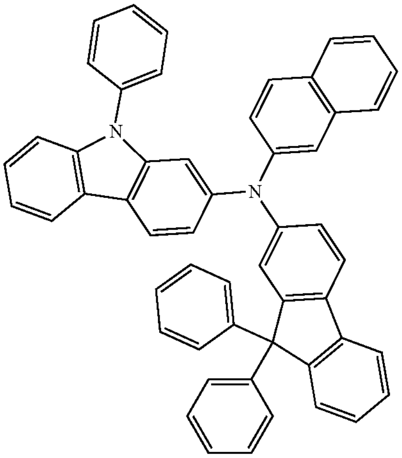
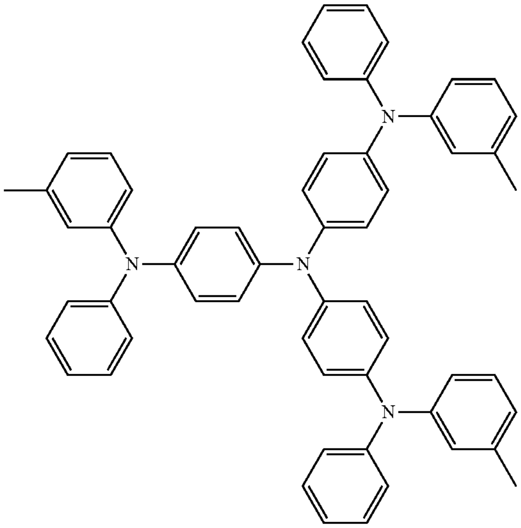
m-MTDATA
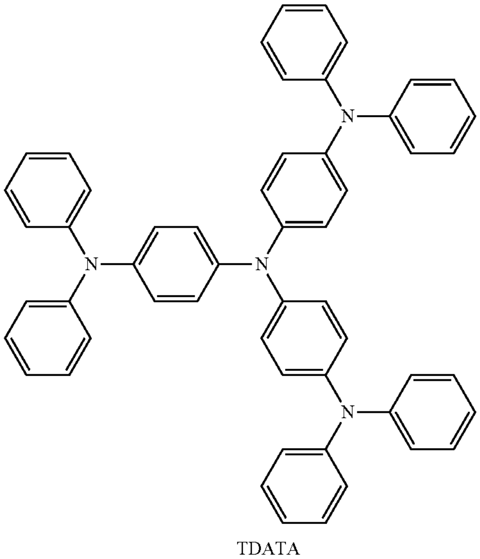
TDATA -continued

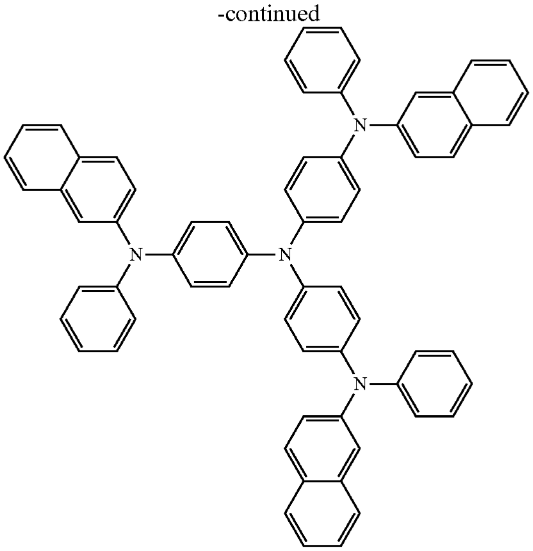

2-TNATA

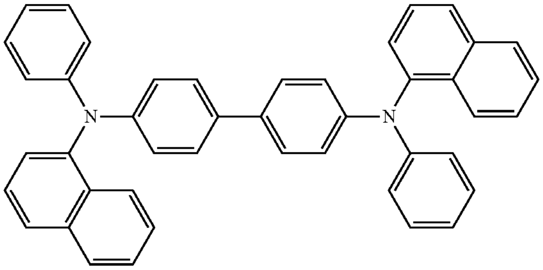

NPB

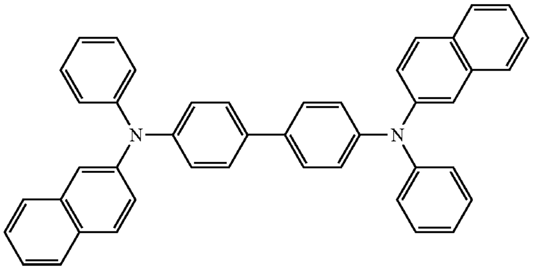

β-NPB

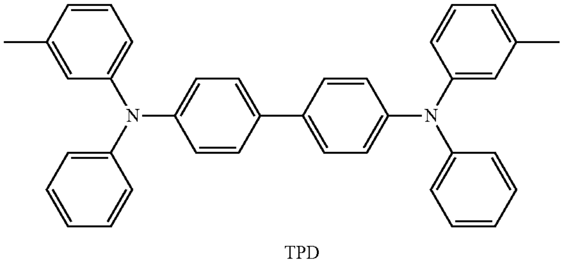

TPD

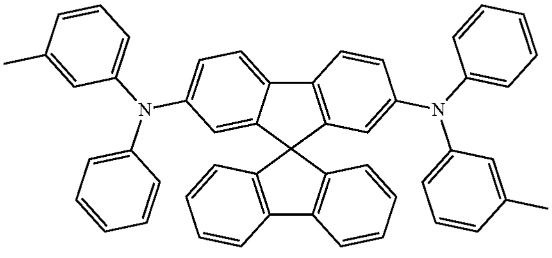

Spiro-TPD

-continued

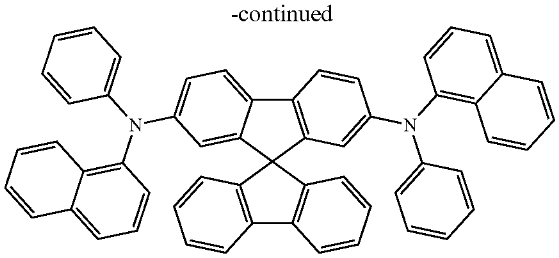

Spiro-NPB

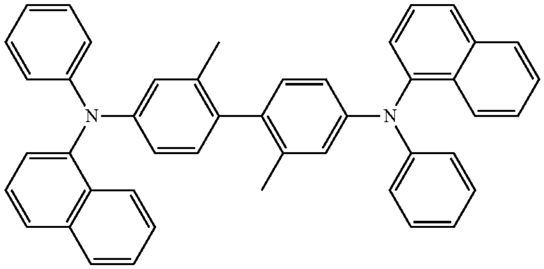

methylated-NPB

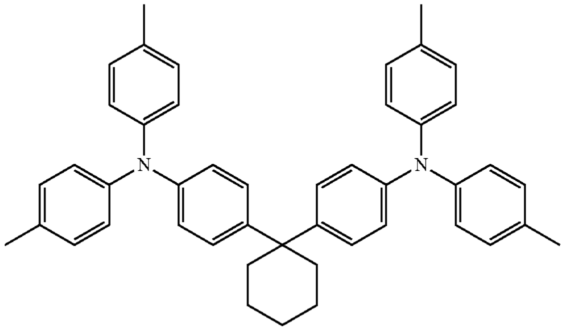

TAPC

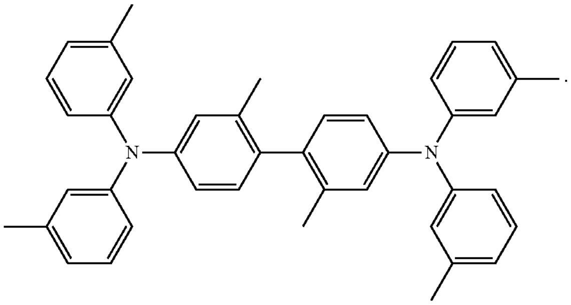

HMTPD

A thickness of the hole transport region may be in a range of about 50 Å to about 10,000 Å. For example, the thickness of the hole transport region may be in a range of about 100 Å to about 4,000 Å. When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of about 100 Å to about 1,000 Å. For example, the thickness of the hole transport layer may be in a range of about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to a wavelength of light emitted by the emission layer, and the electron blocking layer may block the leakage of electrons from the emission layer to the hole transport region. Materials that may be included in the hole transport region may be included in the emission auxiliary layer and the electron blocking layer.

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

For example, the p-dopant may have a lowest unoccupied molecular orbital (LUMO) energy level equal to or less than about-3.5 eV.

In an embodiment, the p-dopant may include a quinone derivative, a cyano group-containing compound, a compound including element EL1 and element EL2, or any combination thereof.

Examples of the quinone derivative may include TCNQ, F4-TCNQ, and the like.

Examples of the cyano group-containing compound may include HAT-CN, a compound represented by Formula 221, and the like:

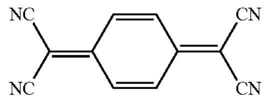

TCNQ

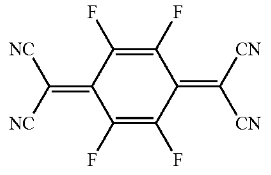

F4-TCNQ

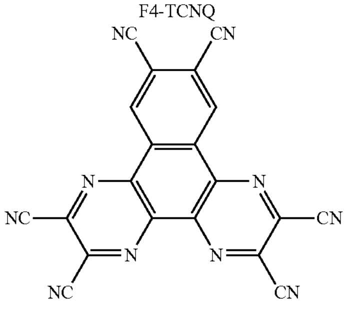

HAT-CN

[Formula 221]

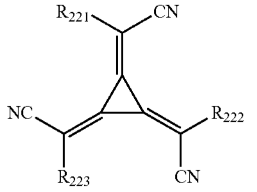

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.

In the compound including element EL1 and element EL2, element EL1 may be a metal, a metalloid, or any combination thereof, and element EL2 may be a non-metal, a metalloid, or any combination thereof.

Examples of the metal may include: an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.); and the like.

Examples of the metalloid may include silicon (Si), antimony (Sb), tellurium (Te), and the like.

Examples of the non-metal may include oxygen (O), a halogen (for example, F, Cl, Br, I, etc.), and the like.

Examples of the compound including element EL1 and element EL2 may include a metal oxide, a metal halide (for example, a metal fluoride, a metal chloride, a metal bromide, a metal iodide, etc.), a metalloid halide (for example, a metalloid fluoride, a metalloid chloride, a metalloid bromide, a metalloid iodide, etc.), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), rhenium oxide (for example, $ReO_3$, etc.), and the like.

Examples of the metal halide may include an alkali metal halide, an alkaline earth metal halide, a transition metal halide, a post-transition metal halide, a lanthanide metal halide, and the like.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, $BaI_2$, and the like.

Examples of the transition metal halide may include a titanium halide (for example, $TiF_4$, $TiCl_4$, $TiBr_4$, $TiI_4$, etc.), a zirconium halide (for example, $ZrF_4$, $ZrCl_4$, $ZrBr_4$, $ZrI_4$, etc.), a hafnium halide (for example, $HfF_4$, $HfCl_4$, $HfBr_4$, $HfI_4$, etc.), a vanadium halide (for example, $VF_3$, $VCl_3$, $VBr_3$, $VI_3$, etc.), a niobium halide (for example, $NbF_3$, $NbCl_3$, $NbBr_3$, $NbI_3$, etc.), a tantalum halide (for example, $TaF_3$, $TaCl_3$, $TaBr_3$, $TaI_3$, etc.), a chromium halide (for example, $CrF_3$, $CrCl_3$, $CrBr_3$, $CrI_3$, etc.), a molybdenum halide (for example, $MoF_3$, $MoCl_3$, $MoBr_3$, $MoI_3$, etc.), a tungsten halide (for example, $WF_3$, $WCl_3$, $WBr_3$, $WI_3$, etc.), a manganese halide (for example, $MnF_2$, $MnCl_2$, $MnBr_2$, $MnI_2$, etc.), a technetium halide (for example, $TcF_2$, $TcCl_2$, $TcBr_2$, $TcI_2$, etc.), a rhenium halide (for example, $ReF_2$, $ReCl_2$, $ReBr_2$, $ReI_2$, etc.), an iron halide (for example, $FeF_2$, $FeCl_2$, $FeBr_2$, $FeI_2$, etc.), a ruthenium halide (for example, $RuF_2$, $RuCl_2$, $RuBr_2$, $RuI_2$, etc.), an osmium halide (for example, $OsF_2$, $OsCl_2$, $OsBr_2$, $OsI_2$, etc.), a cobalt halide (for example, $CoF_2$, $CoCl_2$, $CoBr_2$, $CoI_2$, etc.), a rhodium halide (for example, $RhF_2$, $RhCl_2$, $RhBr_2$, $RhI_2$, etc.), an iridium halide (for example, $IrF_2$, $IrCl_2$, $IrBr_2$, $IrI_2$, etc.), a nickel halide (for example, $NiF_2$, $NiCl_2$, $NiBr_2$, $NiI_2$, etc.), a palladium halide (for example, $PdF_2$, $PdCl_2$, $PdBr_2$, $PdI_2$, etc.), a platinum halide (for example, $PtF_2$, $PtCl_2$, $PtBr_2$, $PtI_2$, etc.), a copper halide (for example, CuF, CuCl, CuBr, CuI, etc.), a silver halide (for example, AgF, AgCl, AgBr, AgI, etc.), a gold halide (for example, AUF, AuCl, AuBr, AuI, etc.), and the like.

Examples of the post-transition metal halide may include a zinc halide (for example, $ZnF_2$, $ZnCl_2$, $ZnBr_2$, $ZnI_2$, etc.), an indium halide (for example, $InI_3$, etc.), a tin halide (for example, $SnI_2$, etc.), and the like.

Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$ $SmBr_3$, YbI, $YbI_2$, $YbI_3$, $SmI_3$, and the like.

Examples of the metalloid halide may include an antimony halide (for example, $SbCl_5$, etc.) and the like.

Examples of the metal telluride may include an alkali metal telluride (for example, $Li_2Te$, a $na_2Te$, $K_2Te$, $Rb_2Te$, $Cs_2Te$, etc.), an alkaline earth metal telluride (for example, BeTe, MgTe, CaTe, SrTe, BaTe, etc.), a transition metal telluride (for example, $TiTe_2$, $ZrTe_2$, $HfTe_2$, $V_2Te_3$, $Nb_2Te_3$, $Ta_2Te_3$, $Cr_2Te_3$, $MozTe_3$, $W_2Te_3$, MnTe, TcTe, ReTe, FeTe, RuTe, OsTe, CoTe, RhTe, IrTe, NiTe, PdTe, PtTe, CuzTe, CuTe, $Ag_2Te$, AgTe, $Au_2Te$, etc.), a post-transition metal telluride (for example, ZnTe, etc.), a lanthanide metal telluride (for example, LaTe, CeTe, PrTe, NdTe, PmTe, EuTe, GdTe, TbTe, DyTe, HoTe, ErTe, TmTe, YbTe, LuTe, etc.), and the like.

[Emission Layer in Interlayer 130]

When the light-emitting device 10 is a full-color light-emitting device, the emission layer may be patterned into a red emission layer, a green emission layer, and/or a blue emission layer, according to a subpixel. In an embodiment, the emission layer may have a stacked structure of two or more layers of a red emission layer, a green emission layer, and a blue emission layer, in which the two or more layers may contact each other or may be separated from each other to emit white light. In embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

In the emission layer, an amount of the dopant may be in a range of about 0.01 parts by weight to about 15 parts by weight, based on 100 parts by weight of the host.

In embodiments, the emission layer may include a quantum dot.

In embodiments, the emission layer may include a delayed fluorescence material. The delayed fluorescence material may serve as a host or as a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within these ranges, excellent luminescence characteristics may be obtained without a substantial increase in driving voltage.

[Host]

In an embodiment, the host may include a compound represented by Formula 301:

$$[Ar_{301}]_{xb11}-[(L_{301})_{xb1}-R_{301}]_{xb21} \quad \text{[Formula 301]}$$

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, or —$P(=O)(Q_{301})(Q_{302})$, xb21 may be an integer from 1 to 5, and $Q_{301}$ to $Q_{303}$ may each independently be the same as described in connection with $Q_1$.

For example, in Formula 301, when xb11 is 2 or more, two or more of $Ar_{301}$ may be bonded to each other via a single bond.

In embodiments, the host may include a compound represented by Formula 301-1, a compound represented by Formula 301-2, or any combination thereof:

[Formula 301-1]

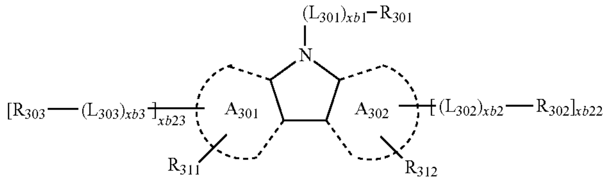

-continued

[Formula 301-2]

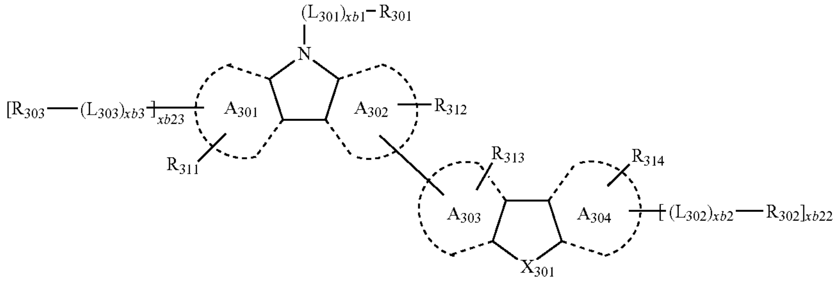

In Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[$(L_{304})_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ may each be the same as described herein, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each independently be the same as described in connection with $R_{301}$.

In embodiments, the host may include an alkali earth metal complex, a post-transition metal complex, or any combination thereof. In an embodiment, the host may include a Be complex (for example, Compound H55), an Mg complex, a Zn complex, or any combination thereof.

In an embodiment, the host may include one of Compounds H1 to H125, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

H1

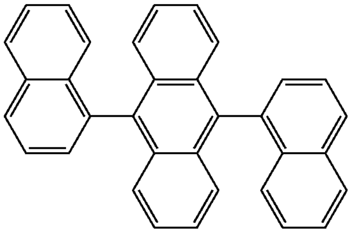

H2

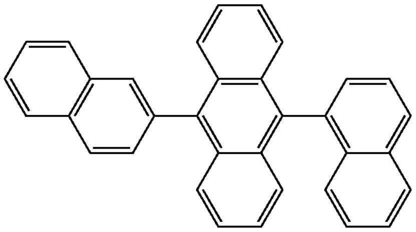

-continued

H3

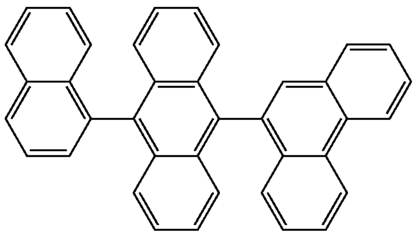

H4

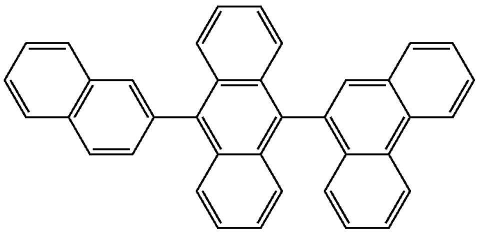

H5

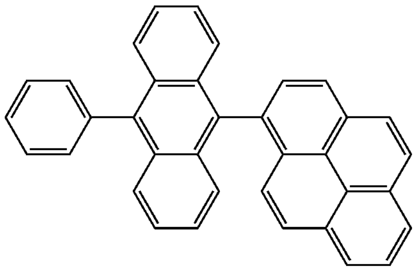

H6

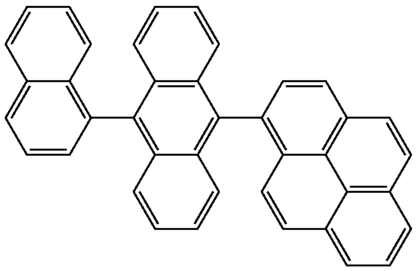

-continued
H7
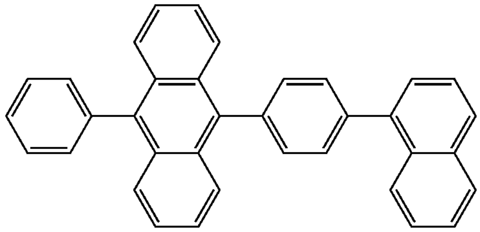
H8
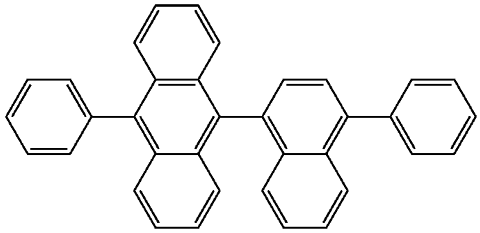
H9
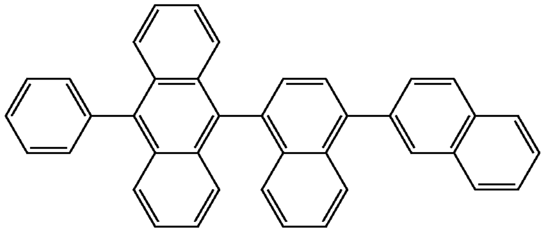
H10
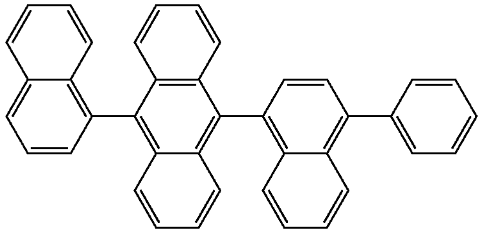
H11
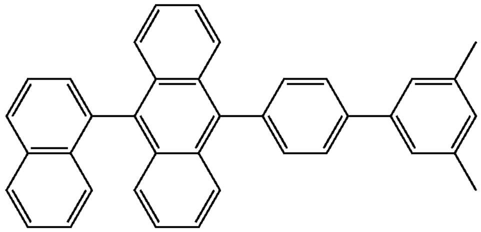
H12
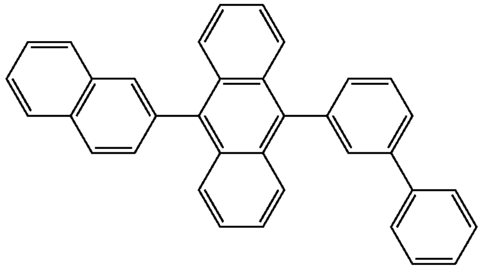
-continued
H13
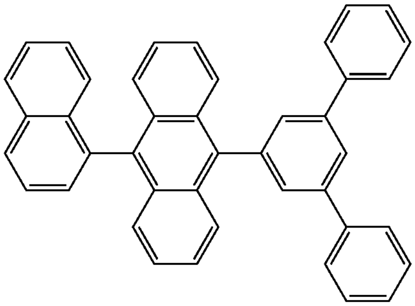
H14
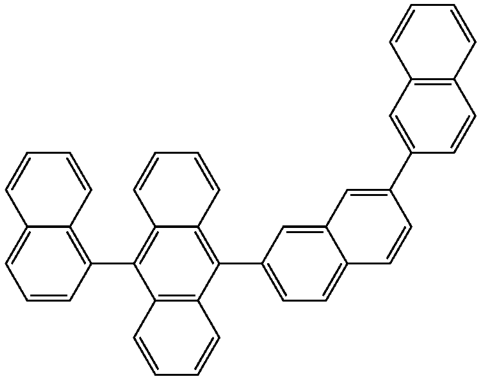
H15
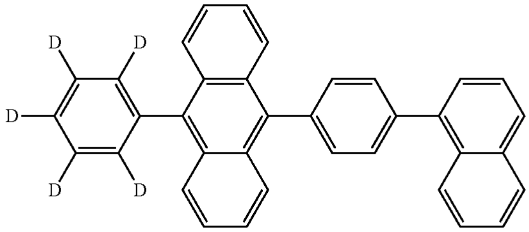
H16
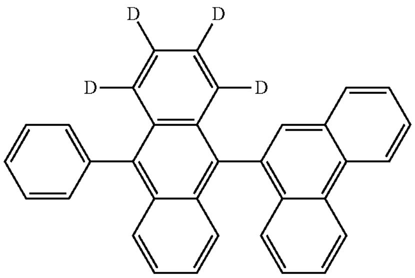
H17
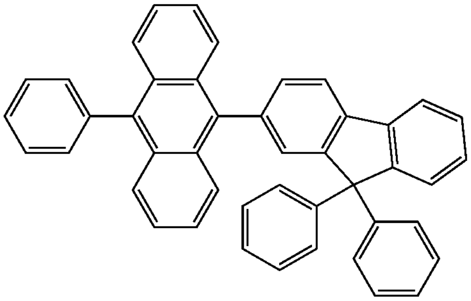

-continued
H18
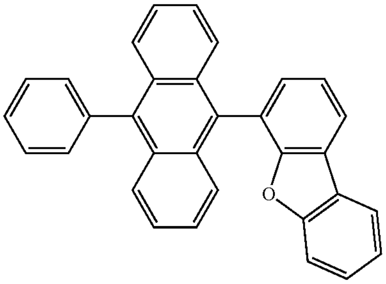
H19
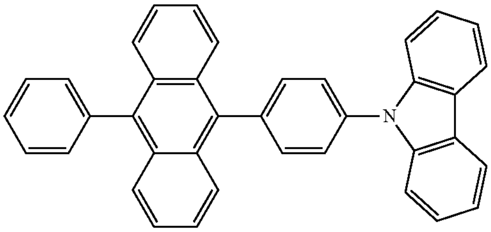
H20
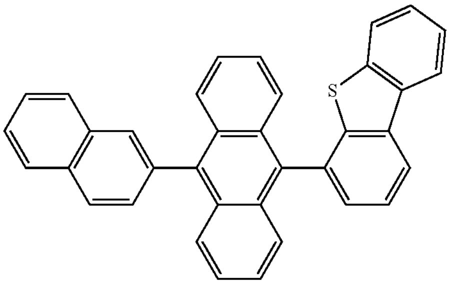
H21
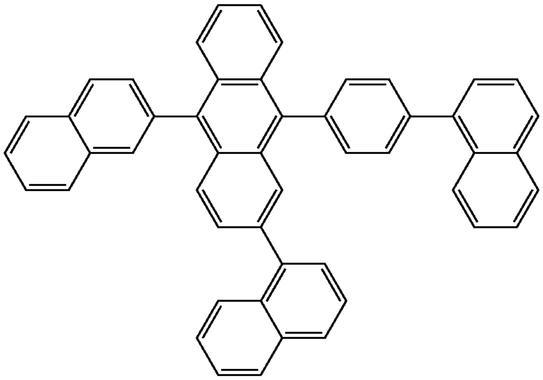
H22
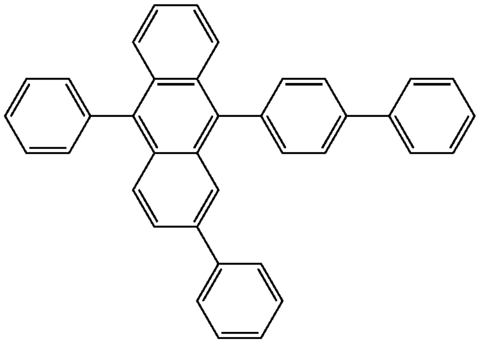
-continued
H23
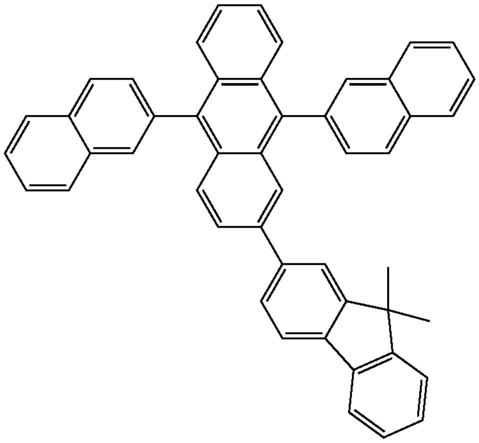
H24
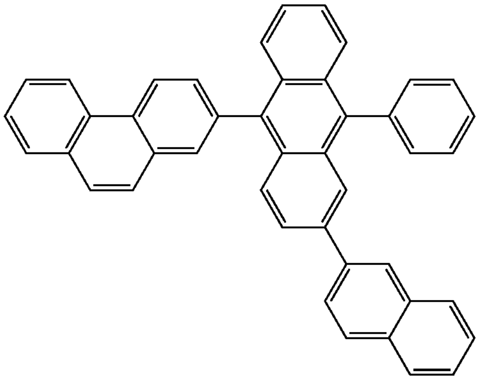
H25
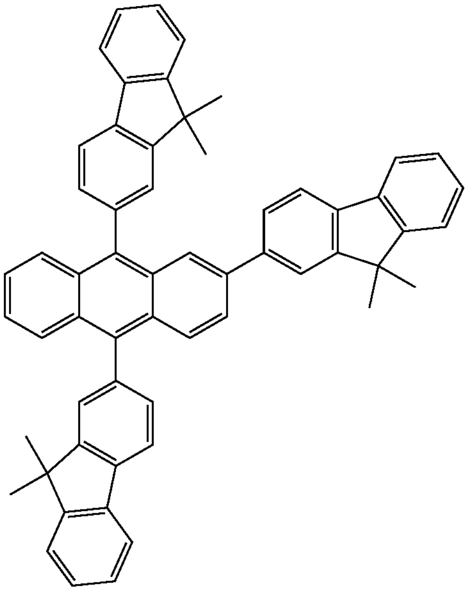

-continued
H26
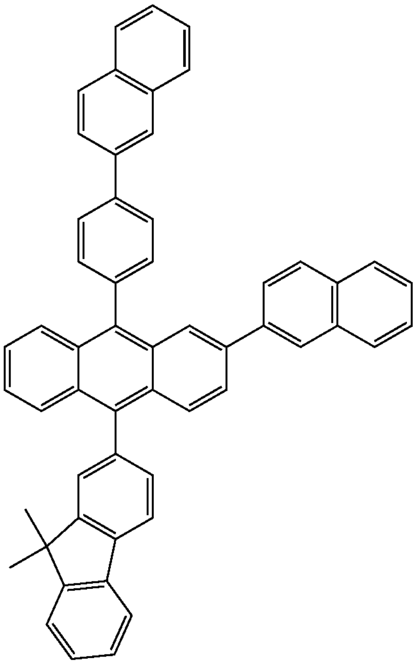
H27
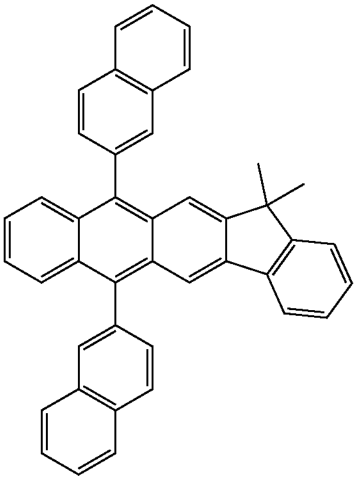
H28
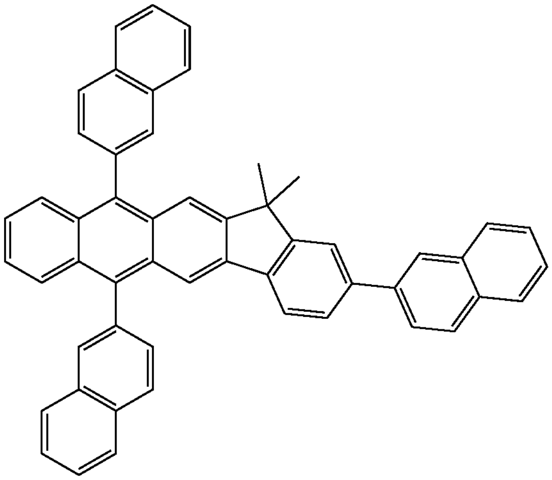
-continued
H29
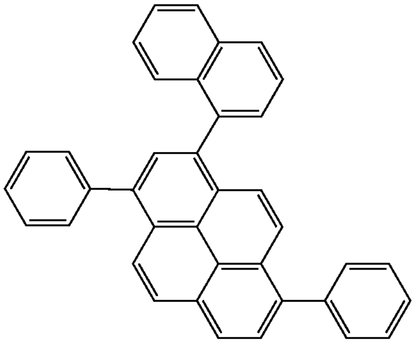
H30
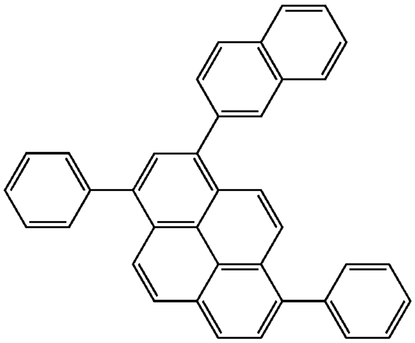
H31
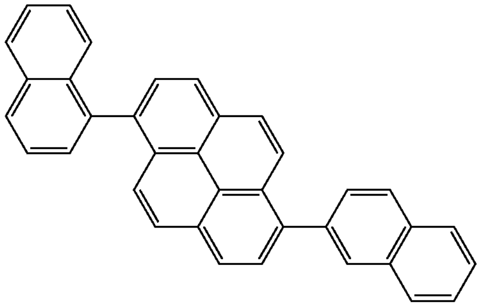
H32
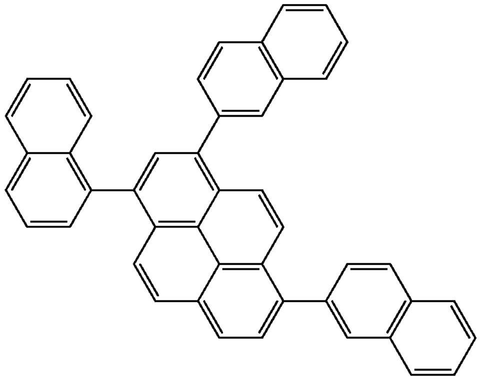
H33
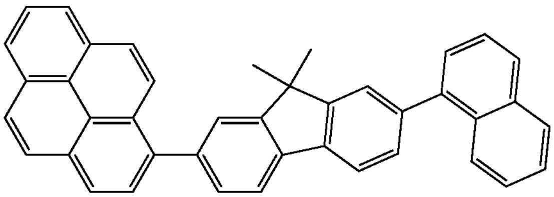

-continued
H34
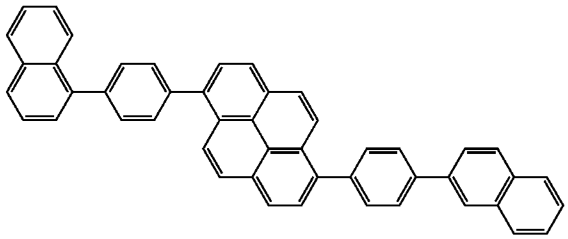
H35
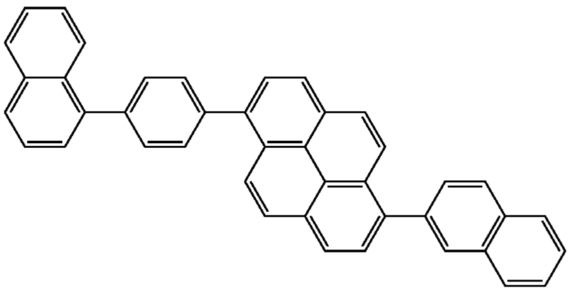
H36
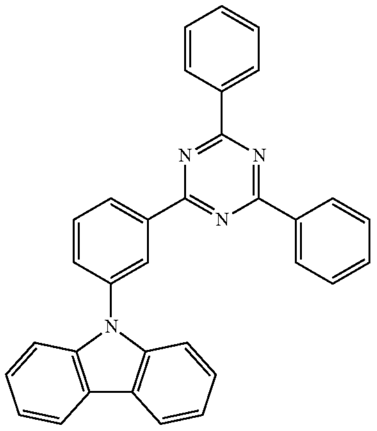
H37
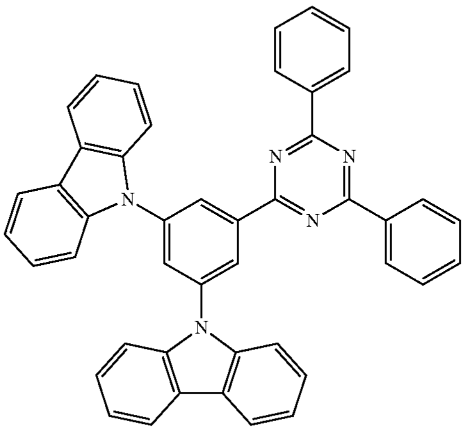
-continued
H38
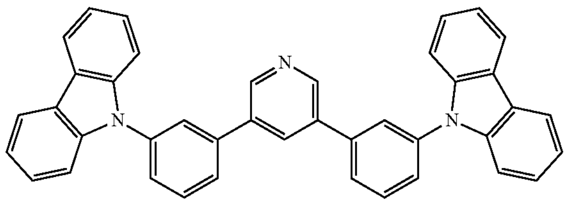
H39
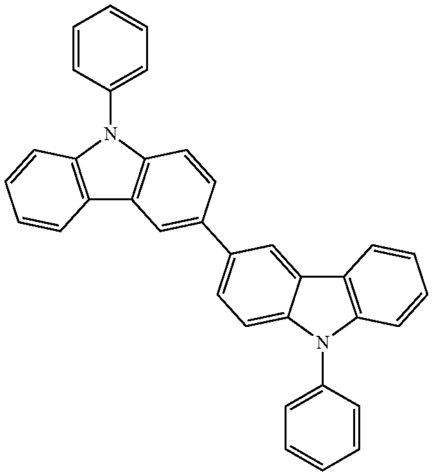
H40
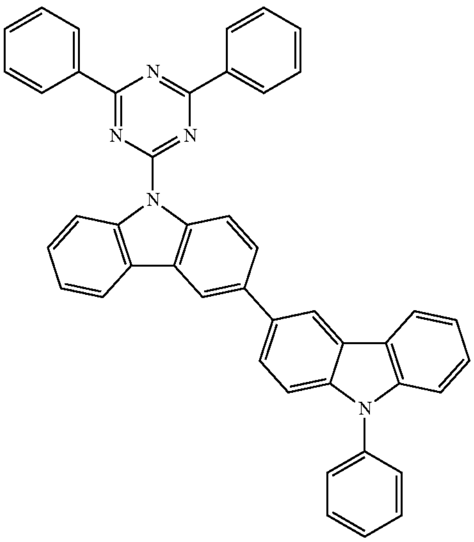

-continued
H41
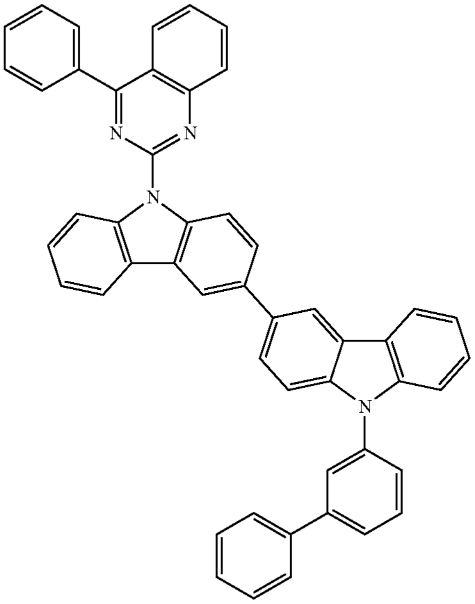
H42
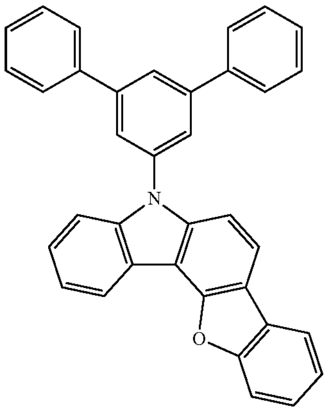
H43
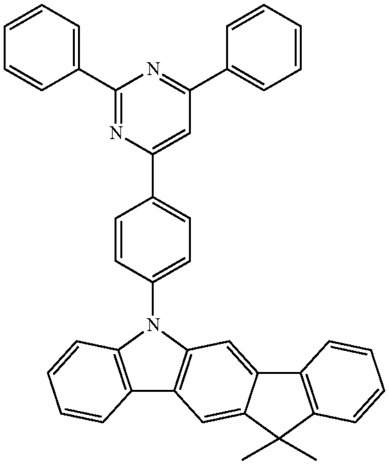
-continued
H44
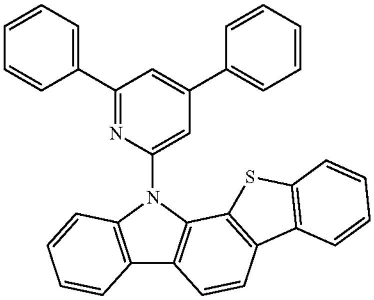
H45
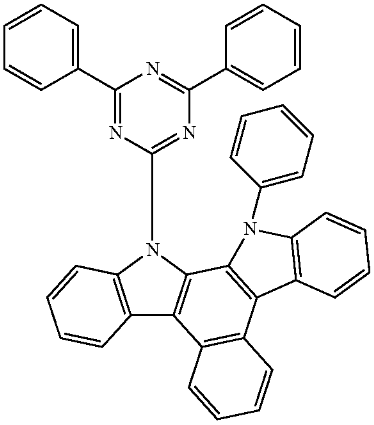
H46
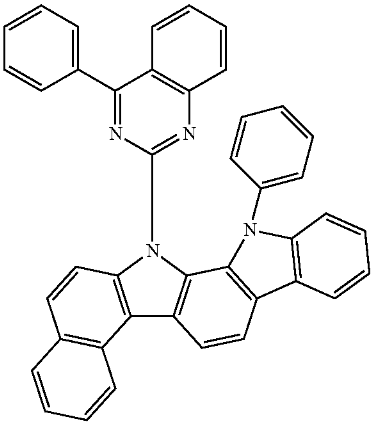
H47
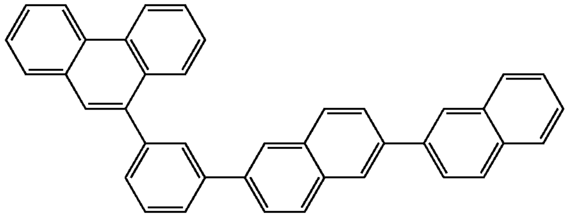
H48
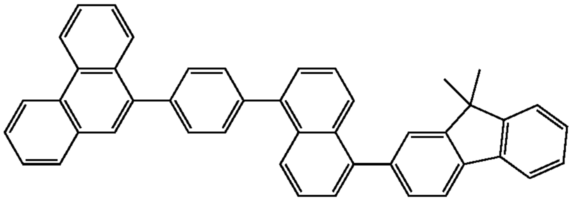

-continued
H49
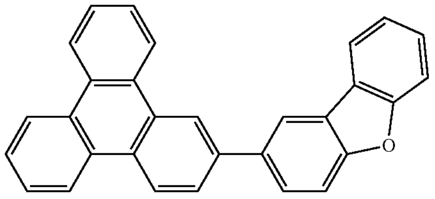
H50
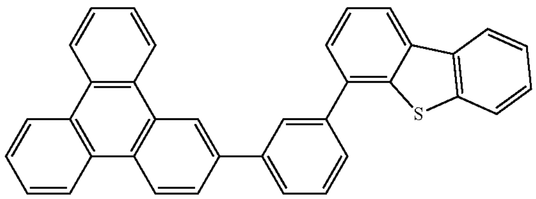
H51
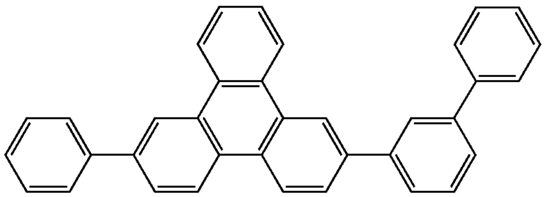
H52
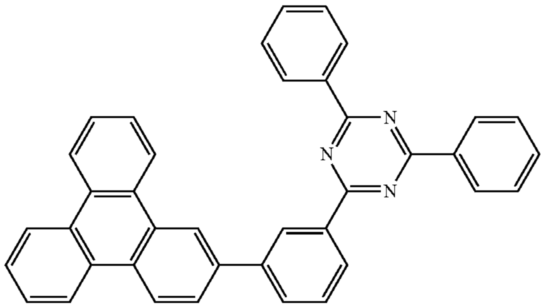
H53
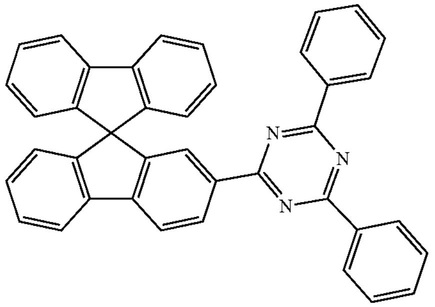
-continued
H54
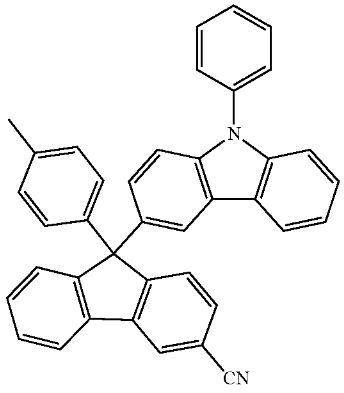
H55
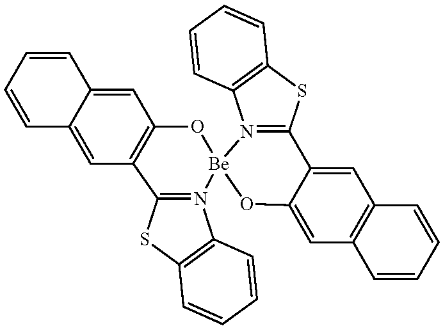
H56
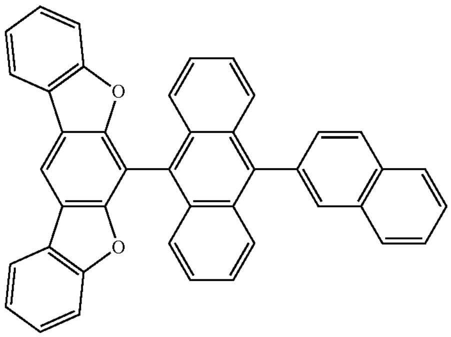
H57
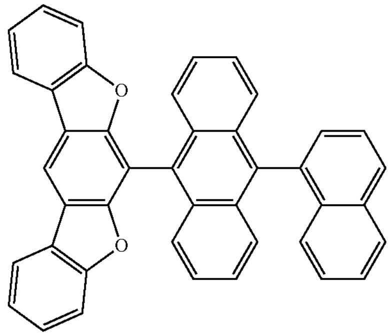

-continued
H58
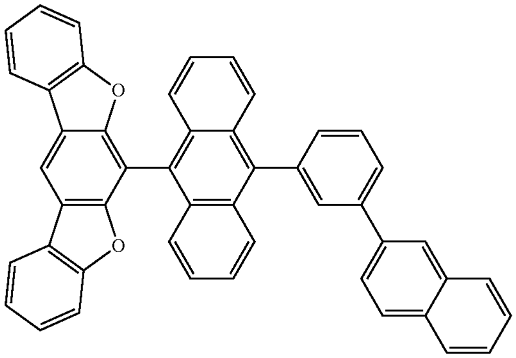
H59
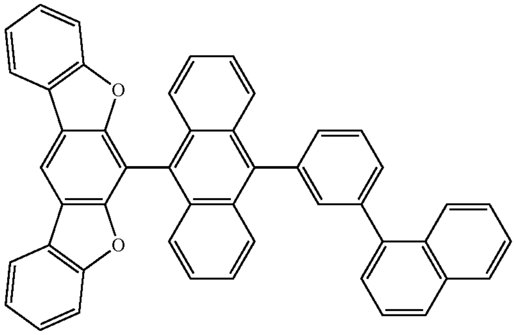
H60
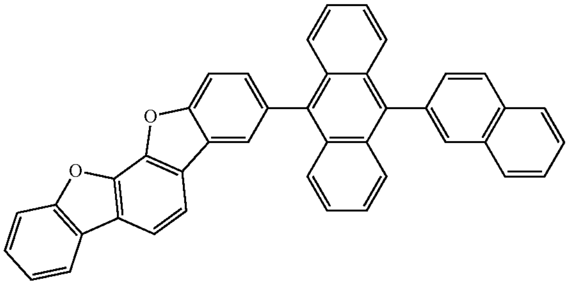
H61
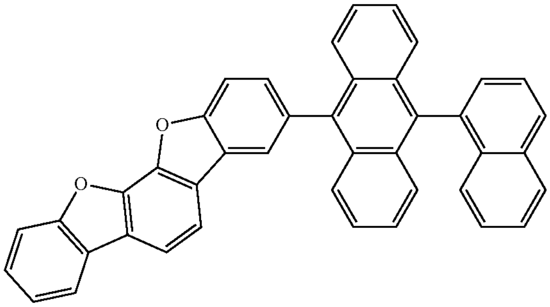
-continued
H62
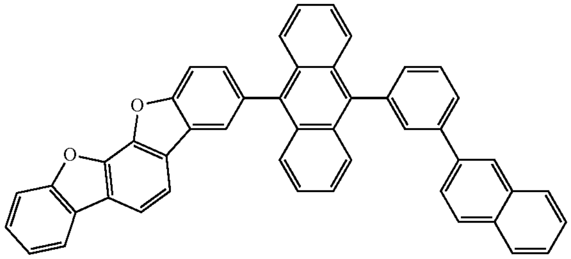
H63
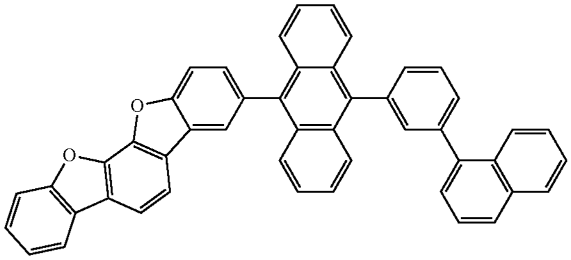
H64
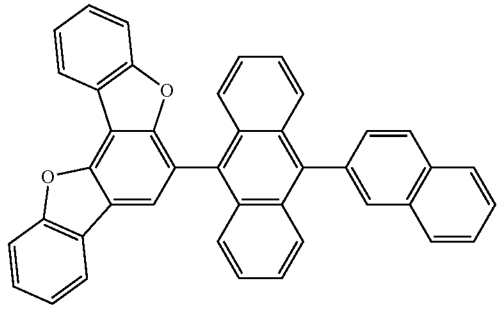
H65
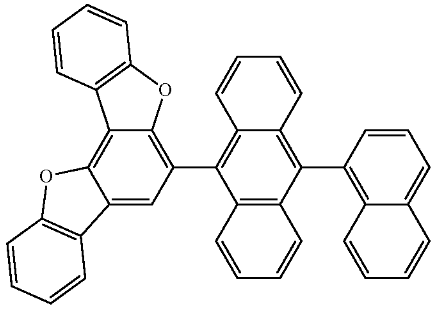
H66
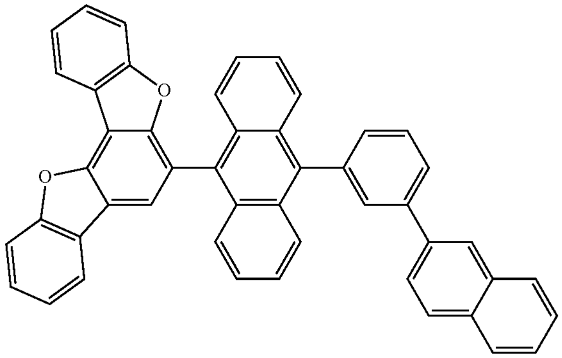

-continued
H67
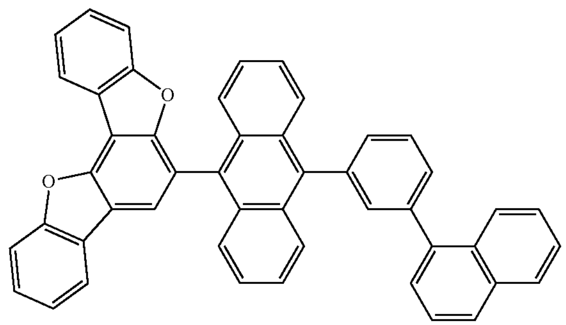
H68
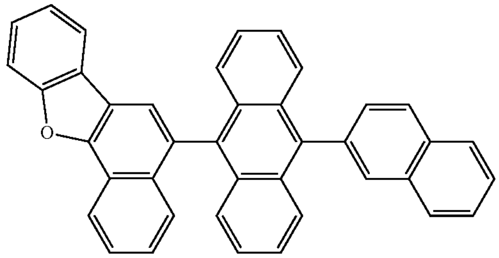
H69
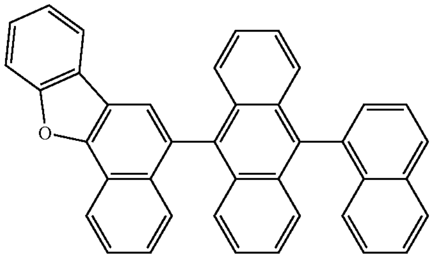
H70
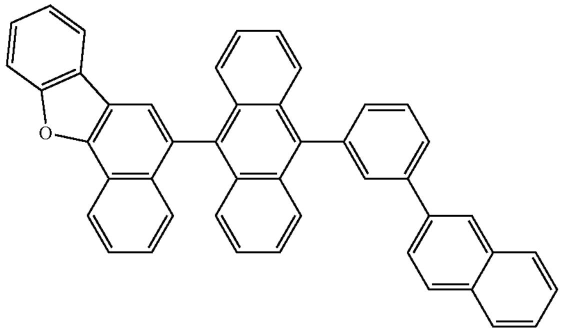
H71
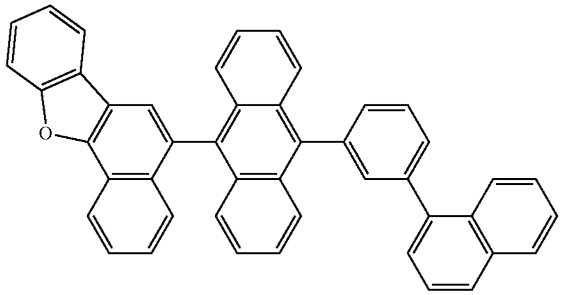
-continued
H72
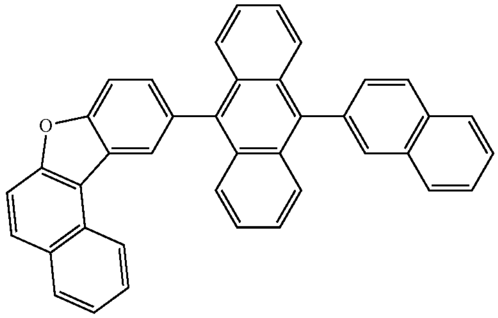
H73
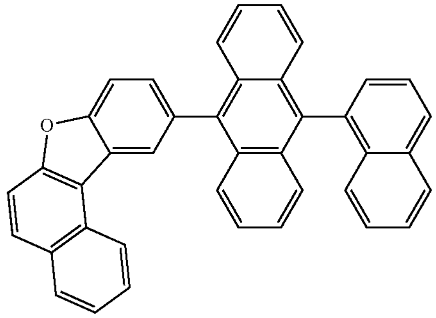
H74
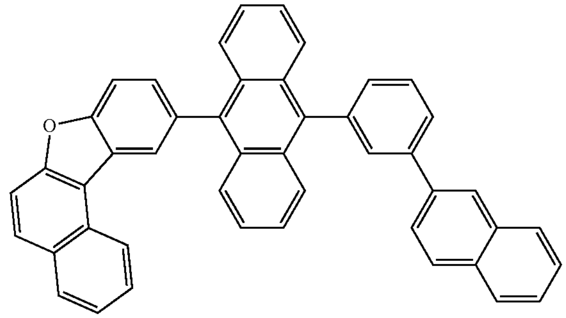
H75
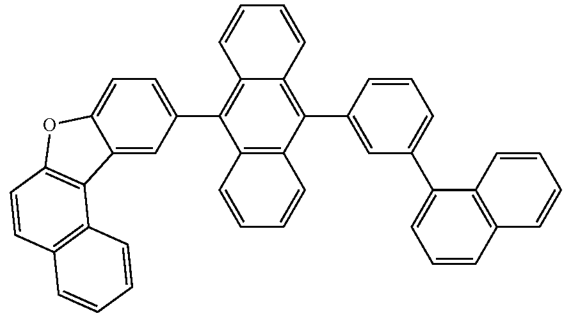
H76
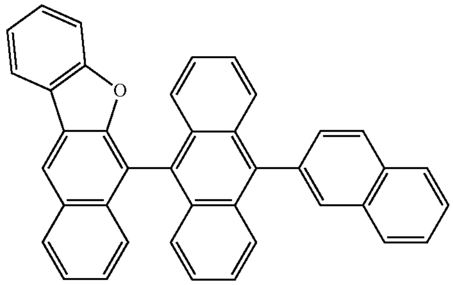

-continued
H77
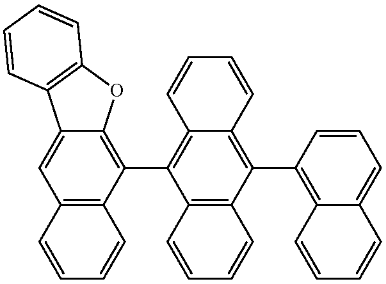
H78
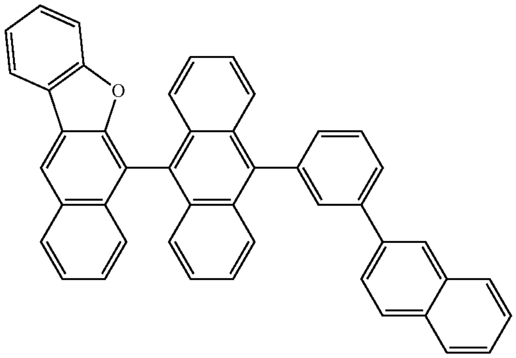
H79
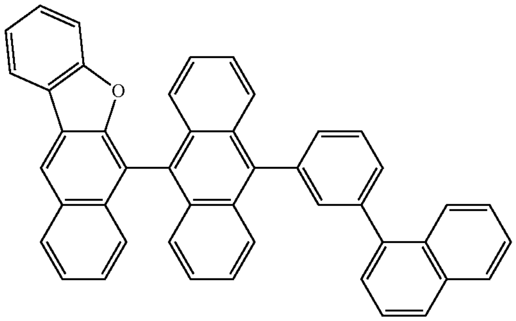
H80
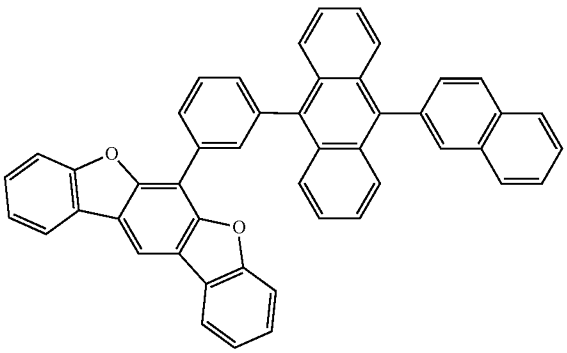
-continued
H81
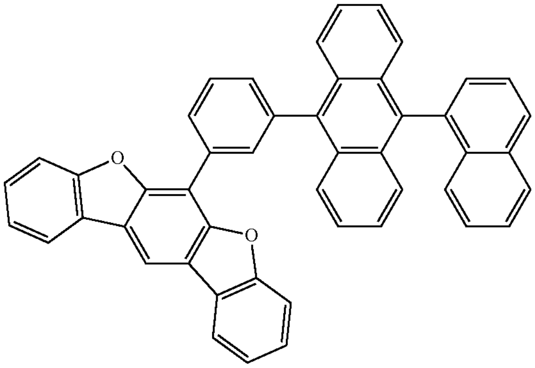
H82
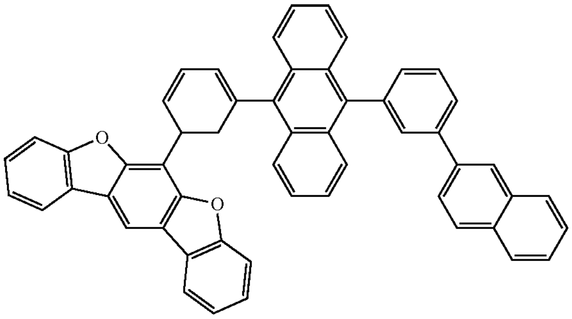
H83
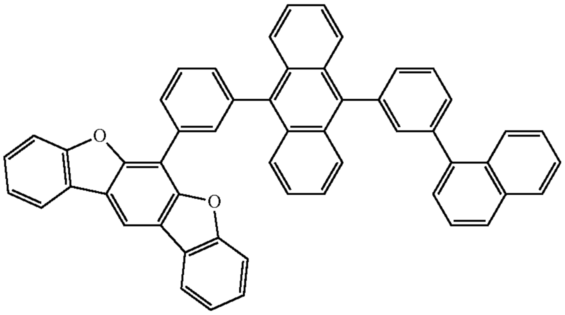
H84
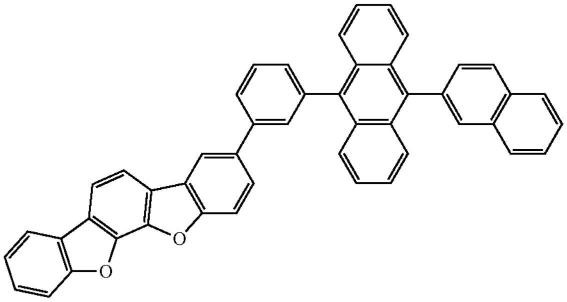

-continued
H85
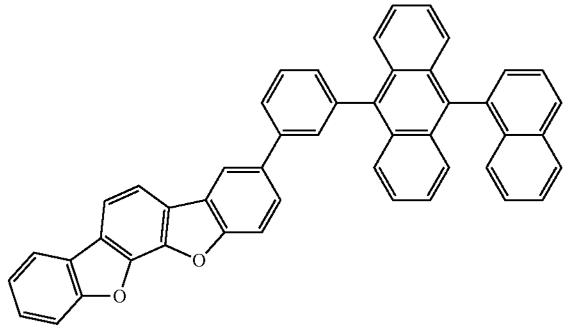
H86
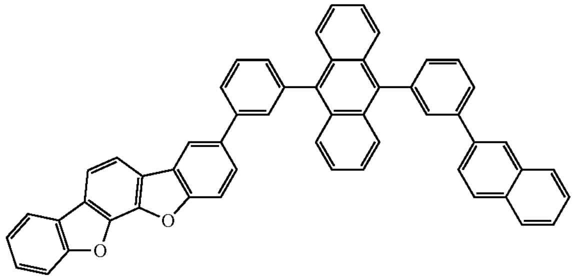
H87
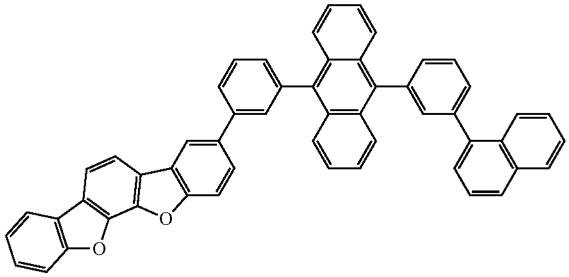
H88
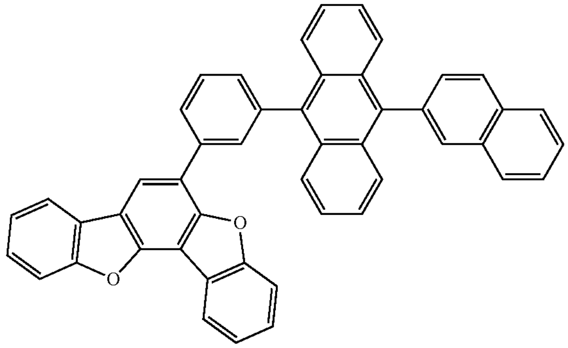
-continued
H89
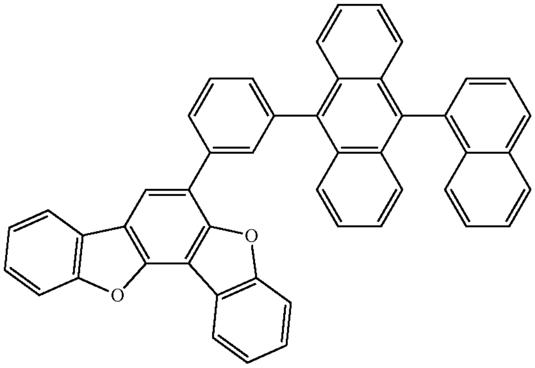
H90
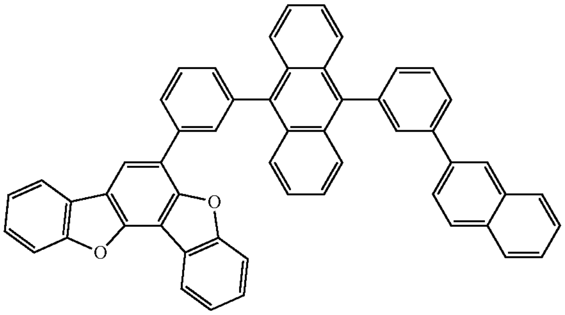
H91
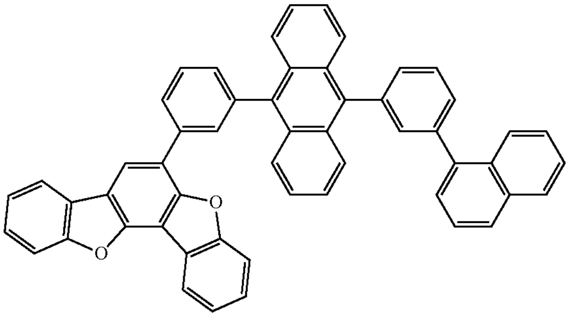
H92
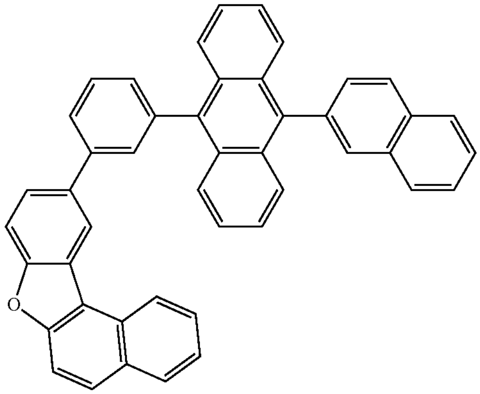

-continued
H93
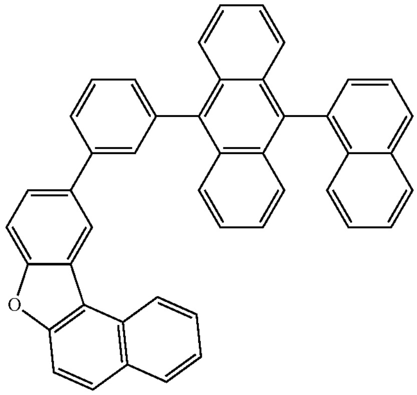
H94
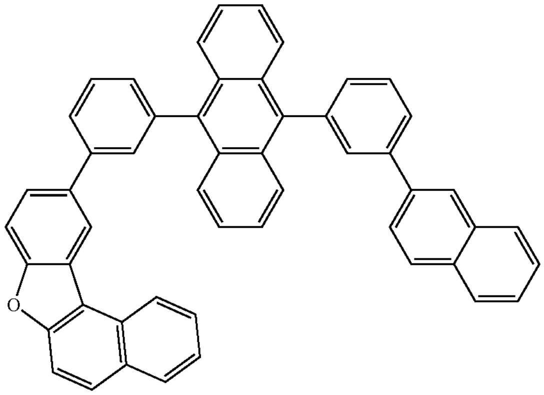
H95
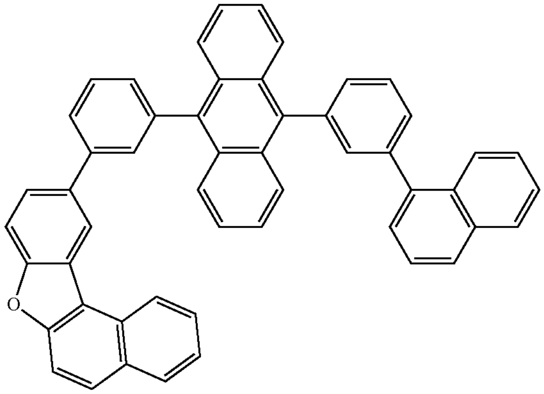
H96
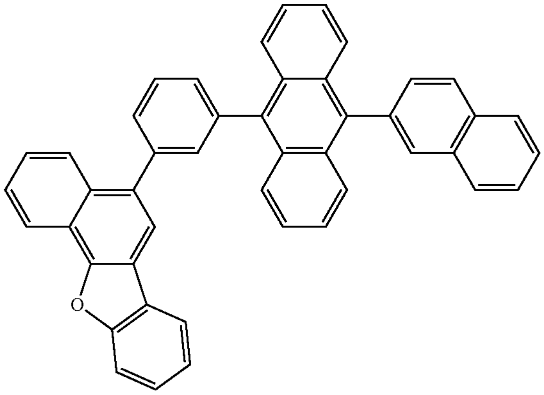
-continued
H97
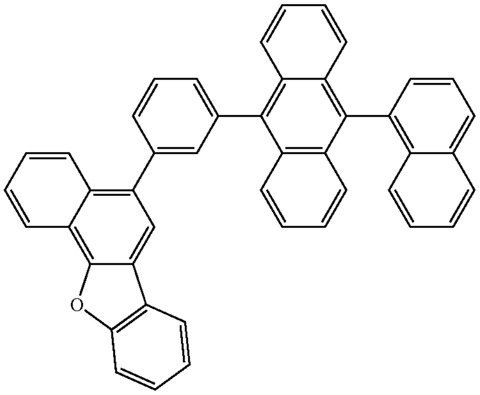
H98
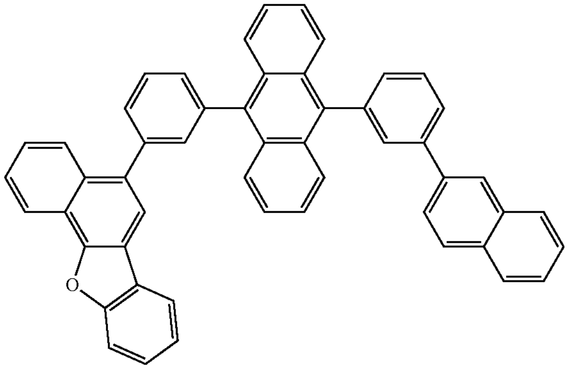
H99
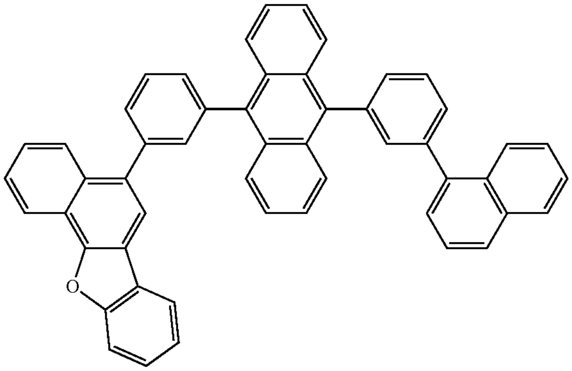
H100
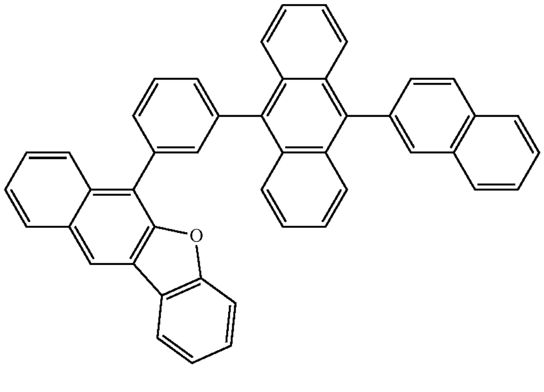

-continued
H101
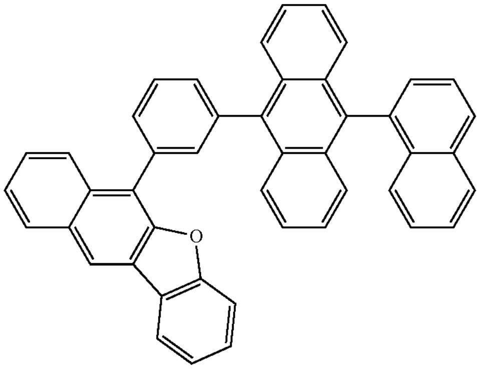
H102
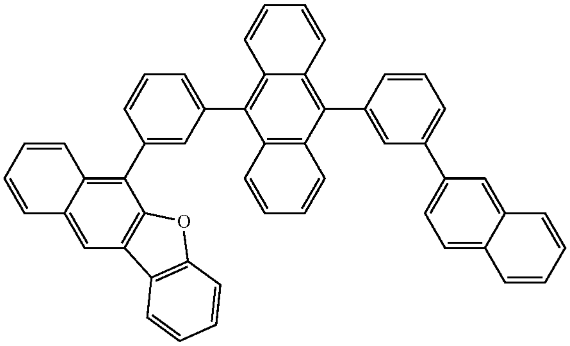
H103
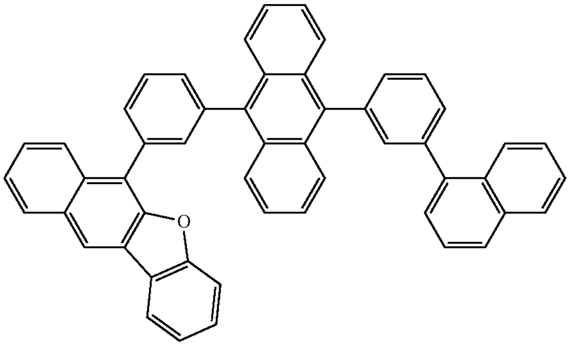
H104
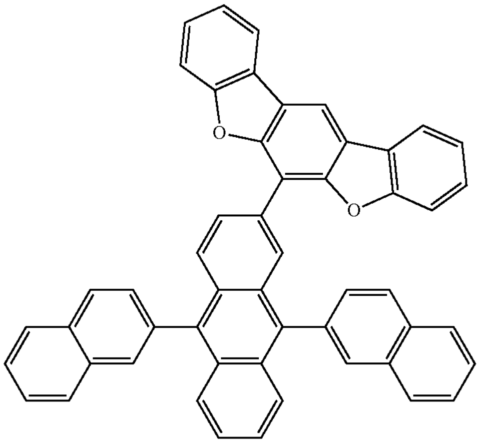
-continued
H105
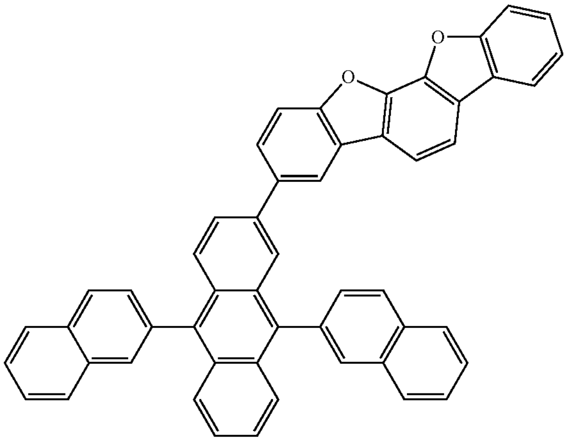
H106
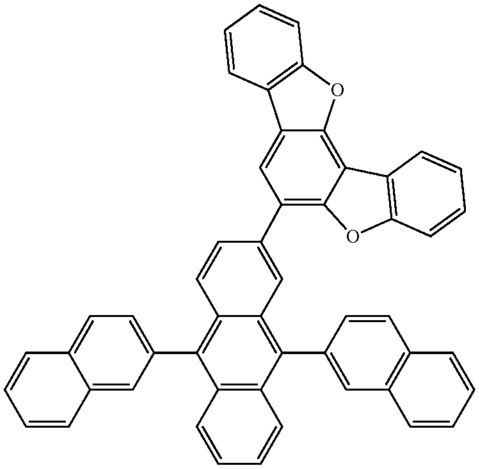
H107
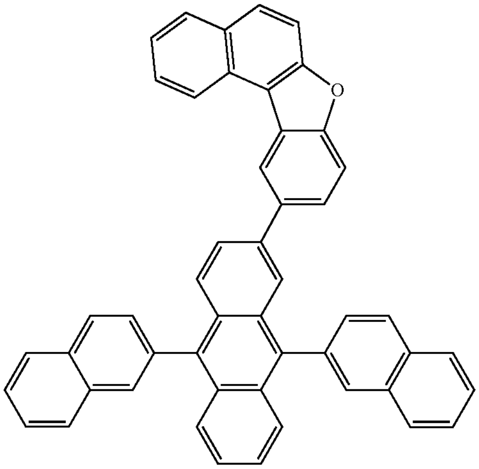

H108
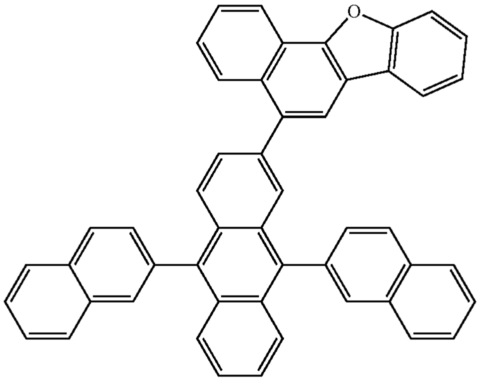
H109
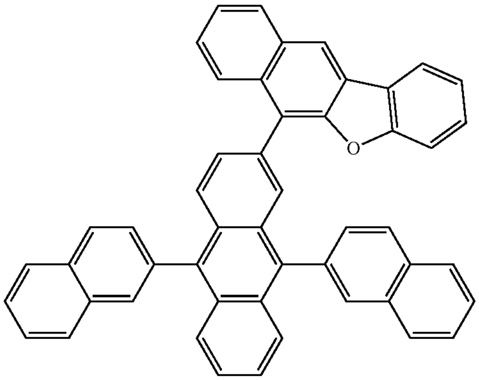
H110
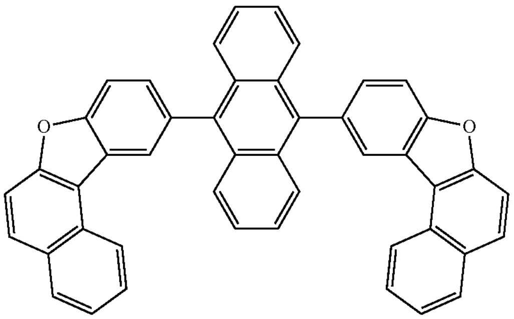
H111
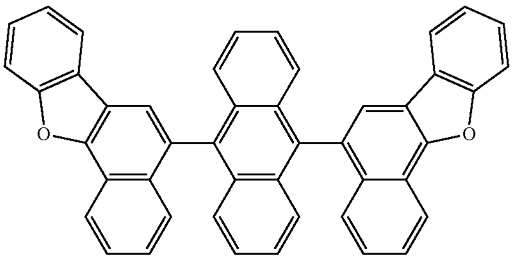
H112
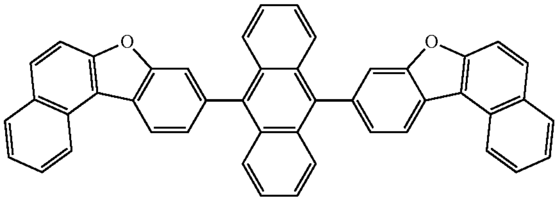
H113
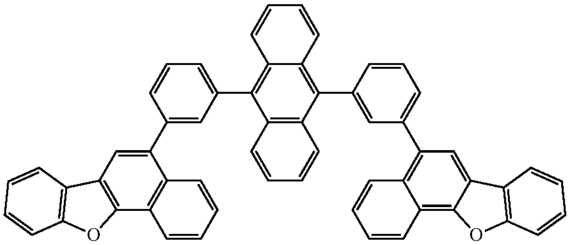
H114
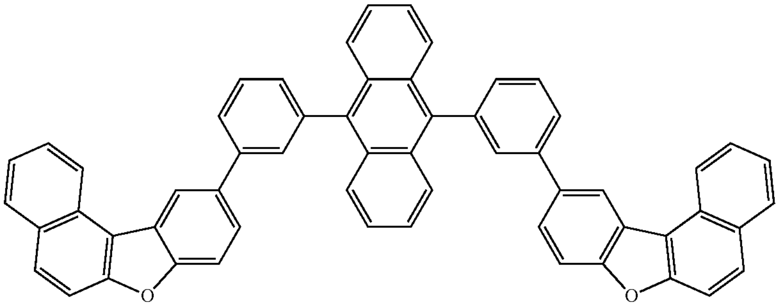

-continued
H115
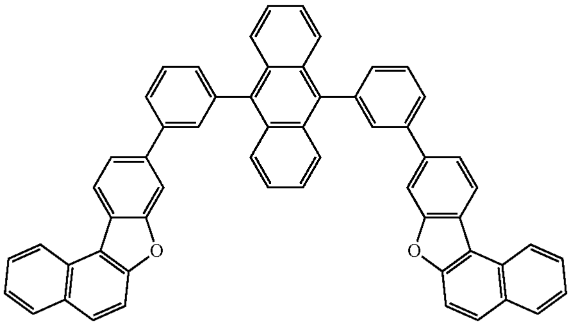
H116
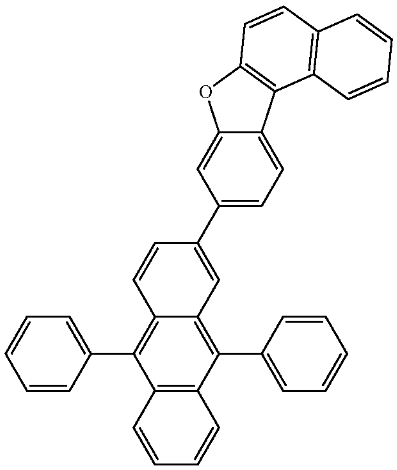
H117
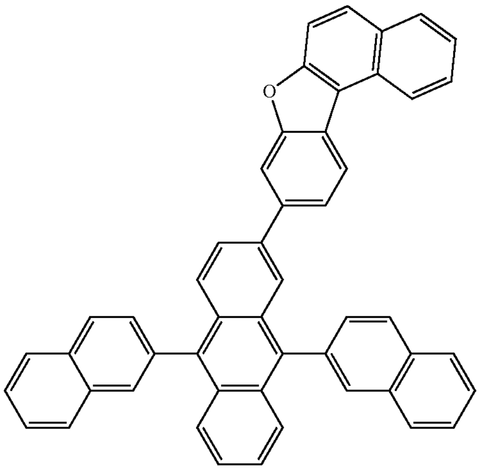
H118
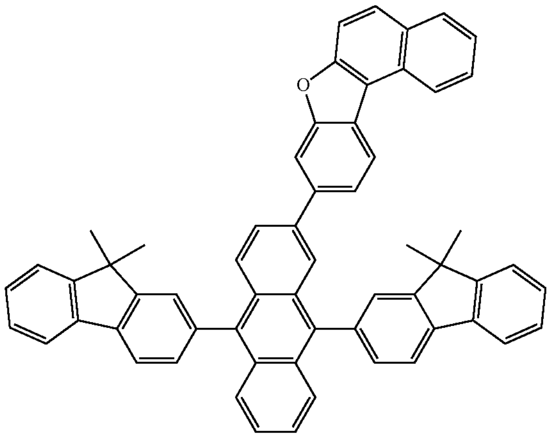
H119
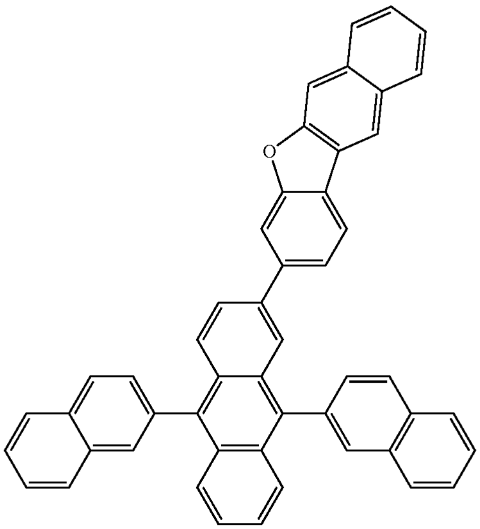
H120
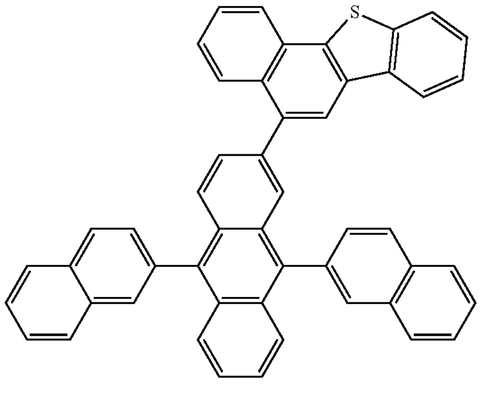

-continued
H121
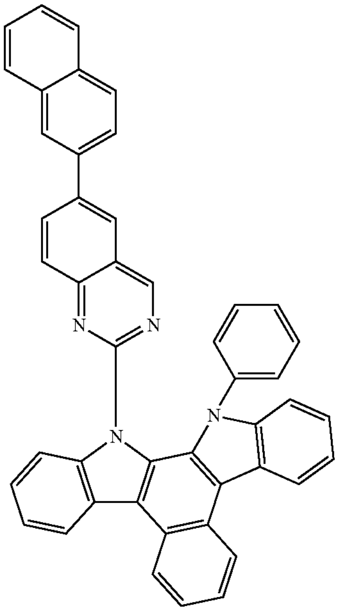
H122
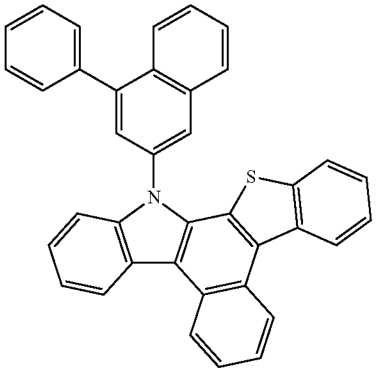
H123
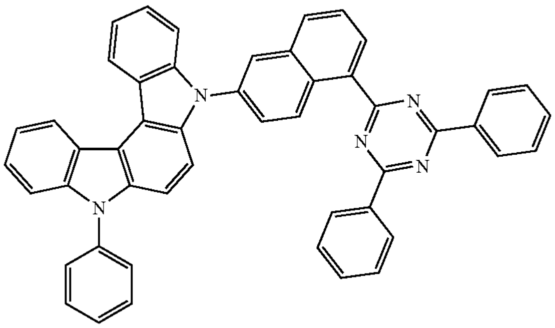
H124
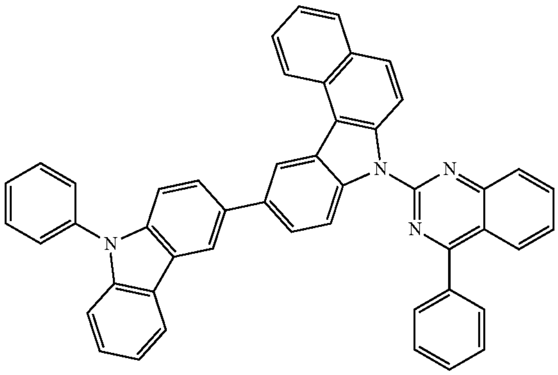
H125
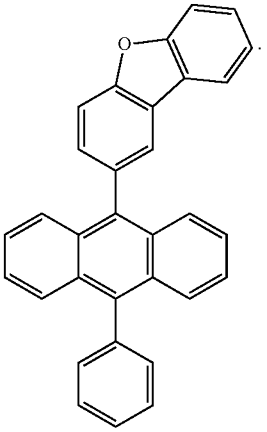

[Phosphorescent Dopant]

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

$M(L_{401})_{xc1}(L_{402})_{xc2}$ [Formula 401]

[Formula 402]

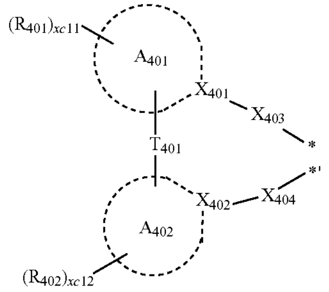

In Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is 2 or more, two or more of $L_{401}$ may be identical to or different from each other, $L_{402}$ may be an organic ligand, and xc2 may be 0, 1, 2, 3, or 4, wherein when xc2 is 2 or more, two or more of $L_{402}$ may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*, $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be the same as described in connection with $Q_1$, xc11 and xc12 may each independently be an integer from 0 to 10, and

* and *' in Formula 402 each indicate a binding site to M in Formula 401.

In an embodiment, in Formula 402, $X_{401}$ may be nitrogen and $X_{402}$ may be carbon, or $X_{401}$ and $X_{402}$ may each be nitrogen.

In an embodiment, in Formula 401, when xc1 is 2 or more, in two or more of $L_{401}$, two ring $A_{401}$(s) may optionally be linked to each other via $T_{402}$, which is a linking group, and two ring $A_{402}$(s) may optionally be linked to each other via $T_{403}$, which is a linking group (for example, see Compounds PD1 to PD4 and PD7). $T_{402}$ and $T_{403}$ may each independently be the same as described in connection with $T_{401}$.

In Formula 401, $L_{402}$ may be an organic ligand. For example, $L_{402}$ may include a halogen group, a diketone group (for example, an acetylacetonate group), a carboxylic acid group (for example, a picolinate group), —C(=O), an isonitrile group, a —CN group, a phosphorus group (for example, a phosphine group, a phosphite group, etc.), or any combination thereof.

The phosphorescent dopant may include, for example, one of Compounds PD1 to PD39, or any combination thereof:

PD1

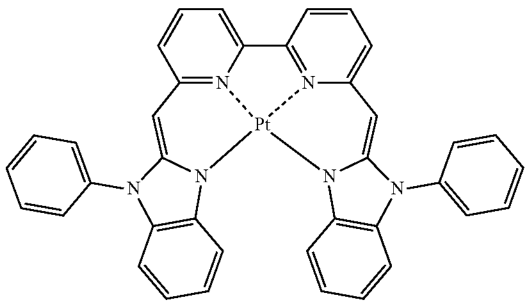

PD2

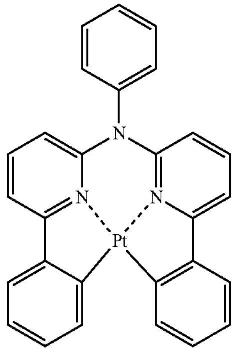

PD3

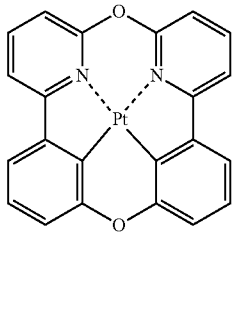

-continued
PD4
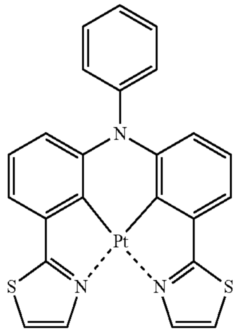
PD5
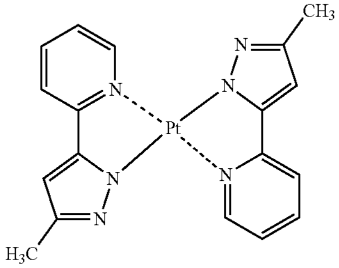
PD6
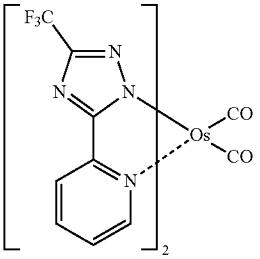
PD7
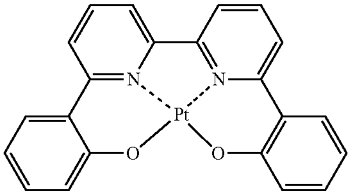
PD8
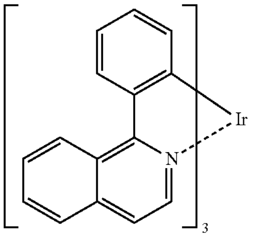
PD9
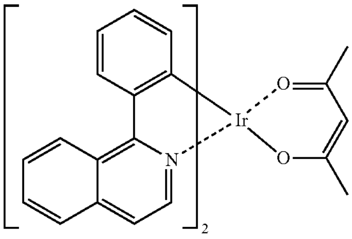
-continued
PD10
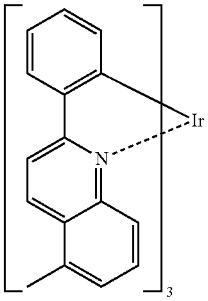
PD11
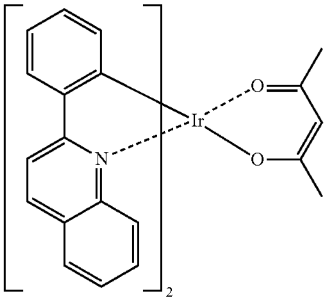
PD12
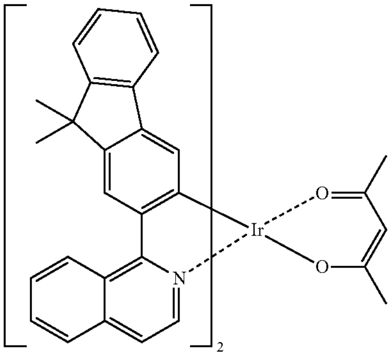
PD13
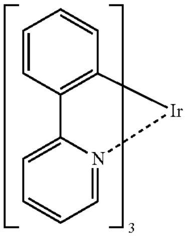
PD14
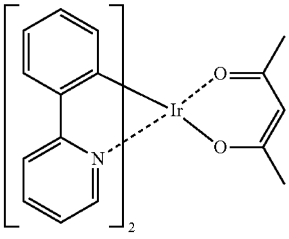

-continued
PD15
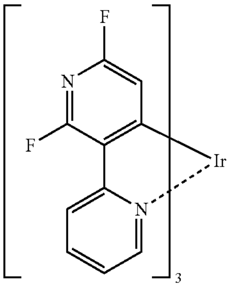
PD16
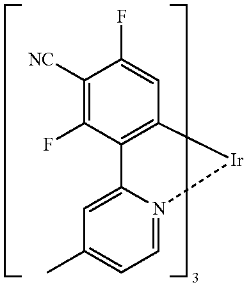
PD17
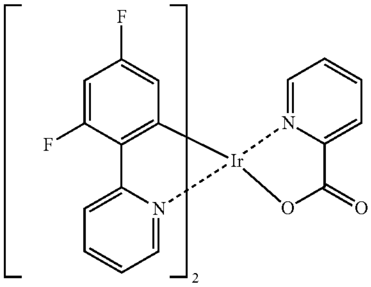
PD18
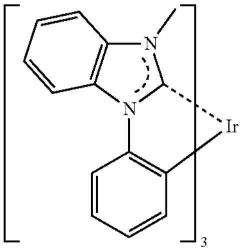
PD19
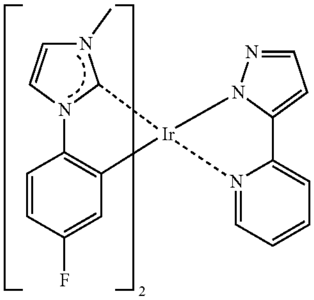
-continued
PD20
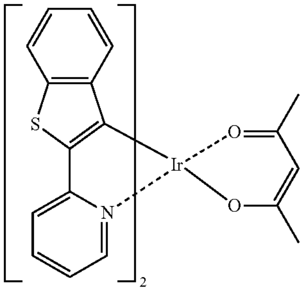
PD21
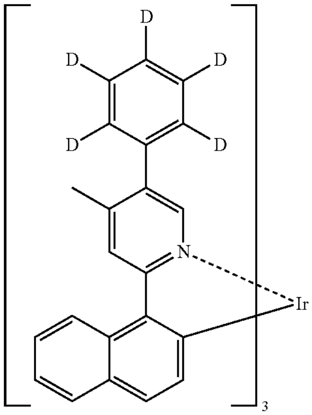
PD22
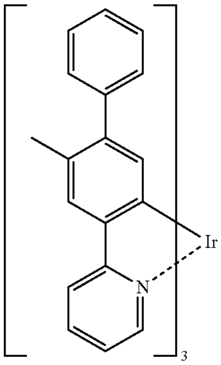
PD23
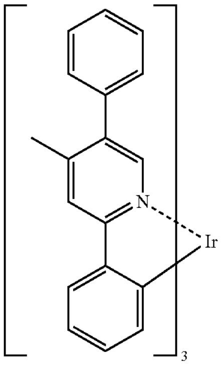

PD24
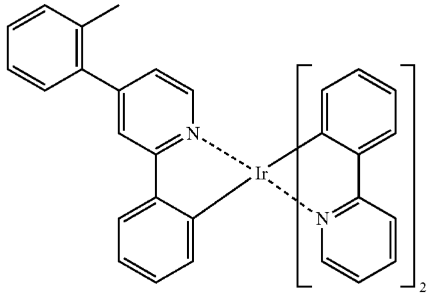
PD25
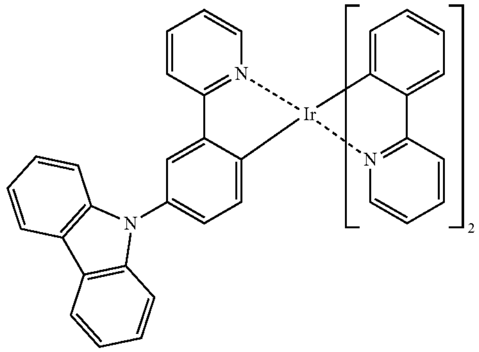
PD26
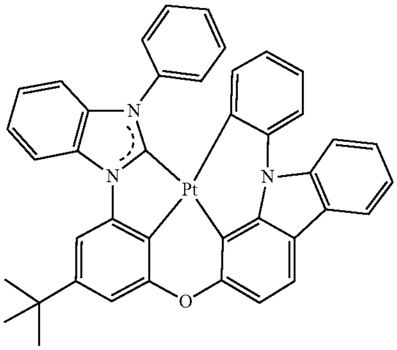
PD27
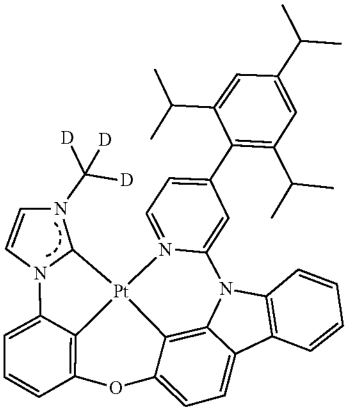
PD28
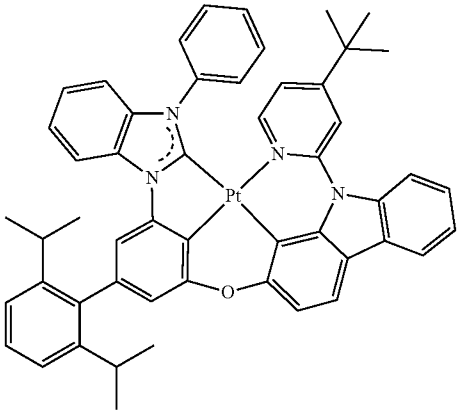
PD29
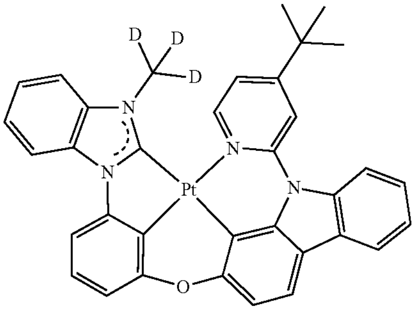
PD30
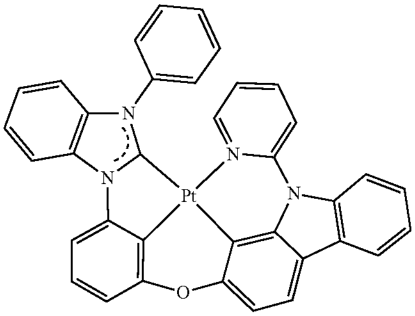
PD31
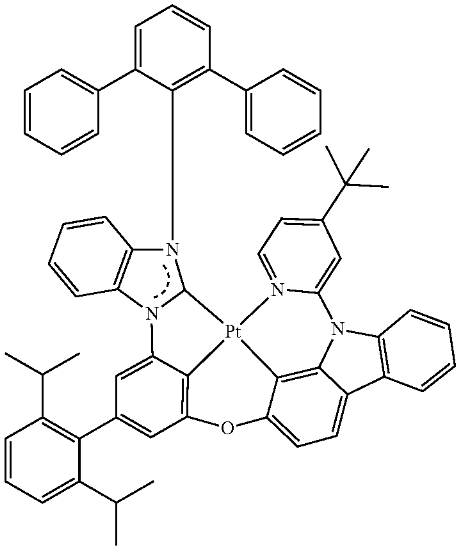

-continued
PD32
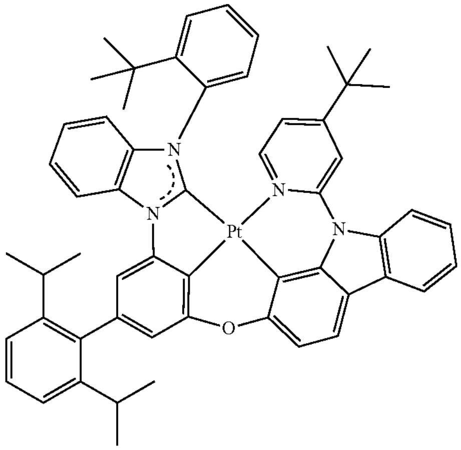
PD33
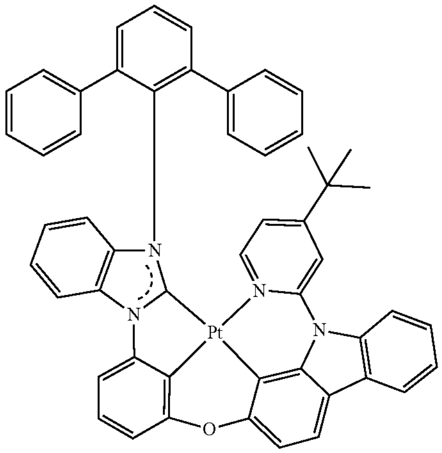
PD34
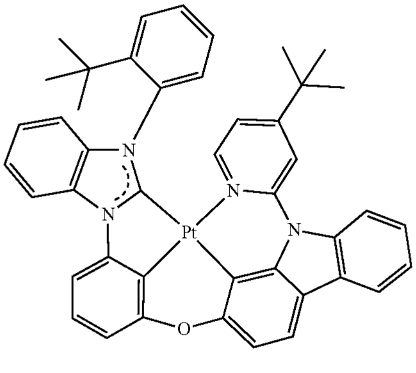
-continued
PD35
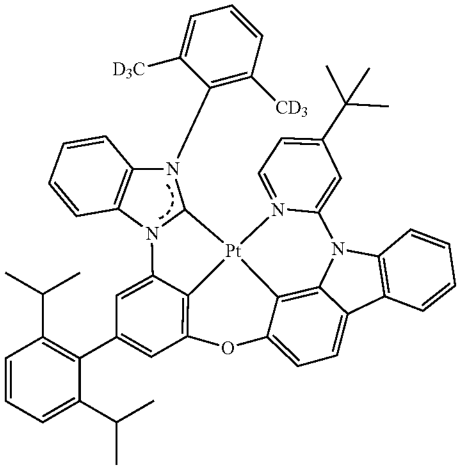
PD36
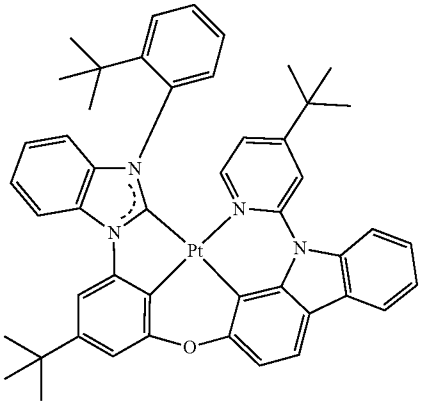
PD37
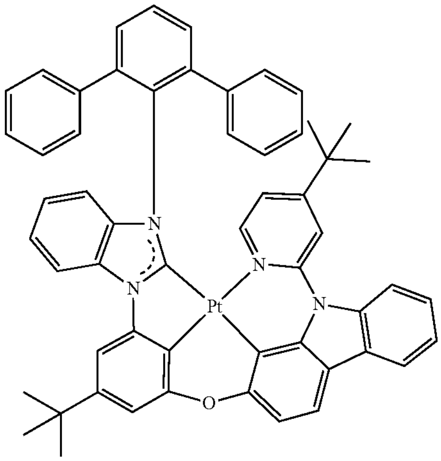

-continued

PD38

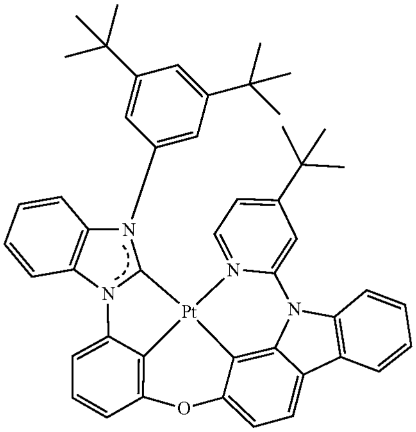

PD39

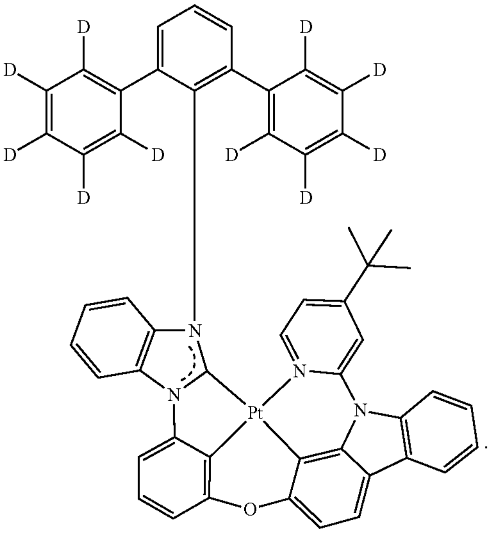

[Fluorescent Dopant]

The fluorescent dopant may include an amine group-containing compound, a styryl group-containing compound, or any combination thereof.

In an embodiment, the fluorescent dopant may include a compound represented by Formula 501:

[Formula 501]

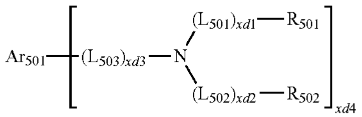

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, in Formula 501, $Ar_{501}$ may be a condensed cyclic group (for example, an anthracene group, a chrysene group, a pyrene group, etc.) in which three or more monocyclic groups are condensed together.

In an embodiment, in Formula 501, xd4 may be 2.

In an embodiment, the fluorescent dopant may include one of Compounds FD1 to FD36, DPVBi, DPAVBi, or any combination thereof:

FD1

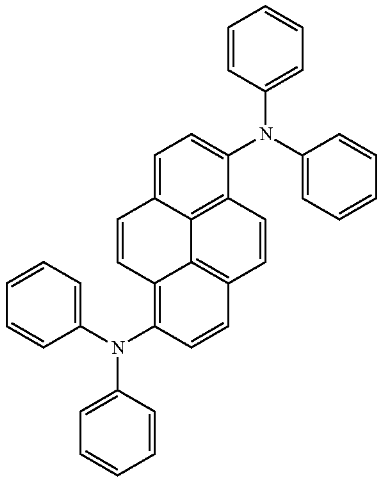

FD2

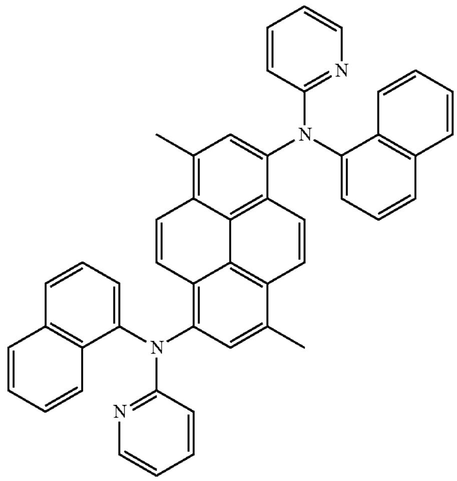

FD3

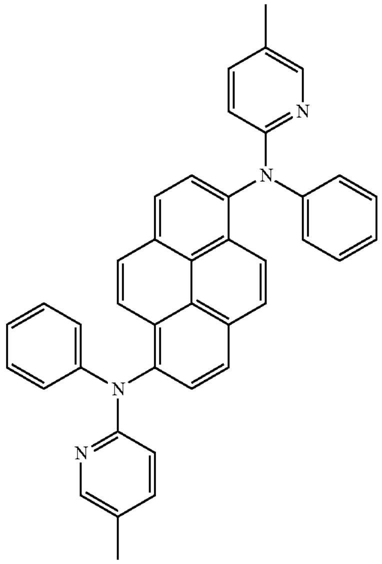

-continued
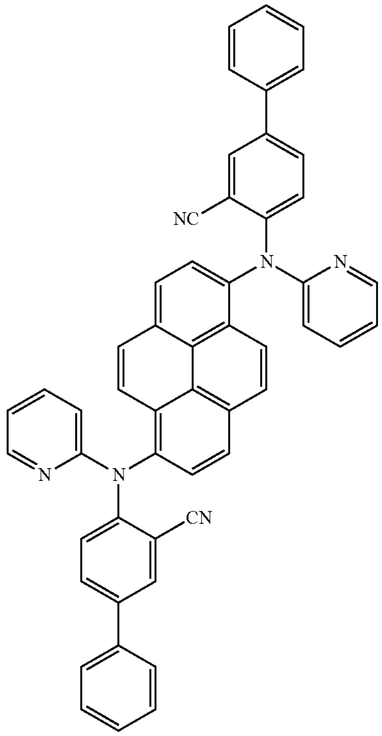
FD4
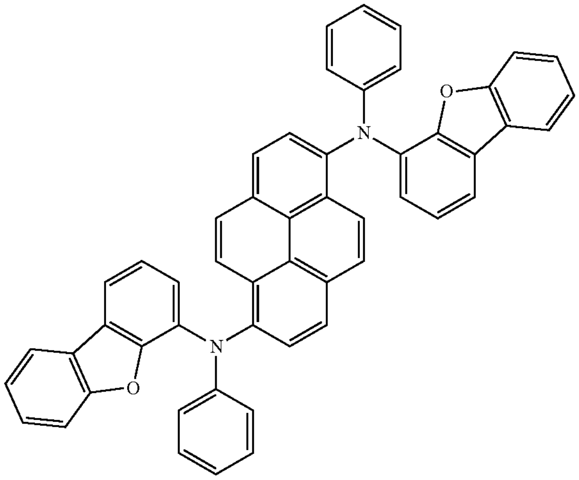
FD5
-continued
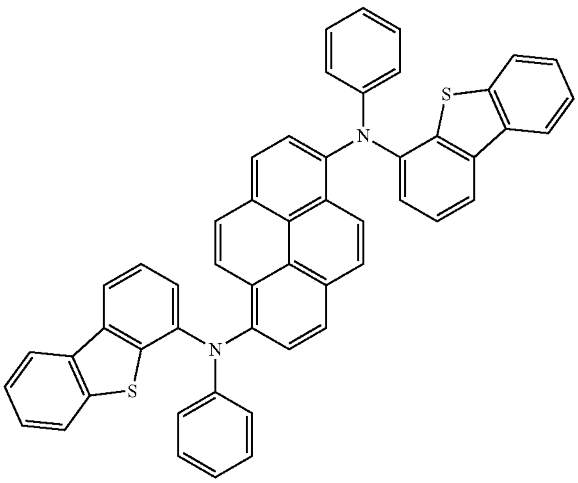
FD6
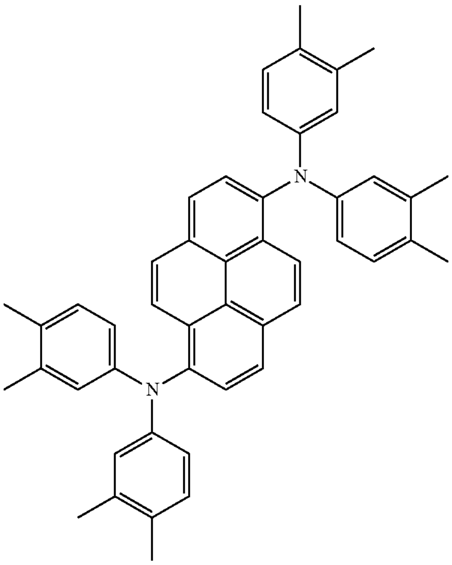
FD7
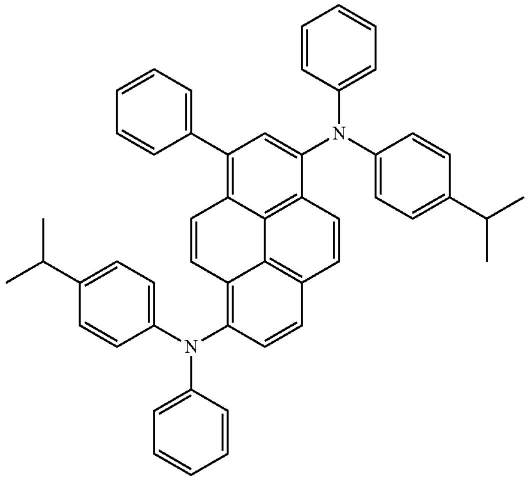
FD8

-continued
FD9
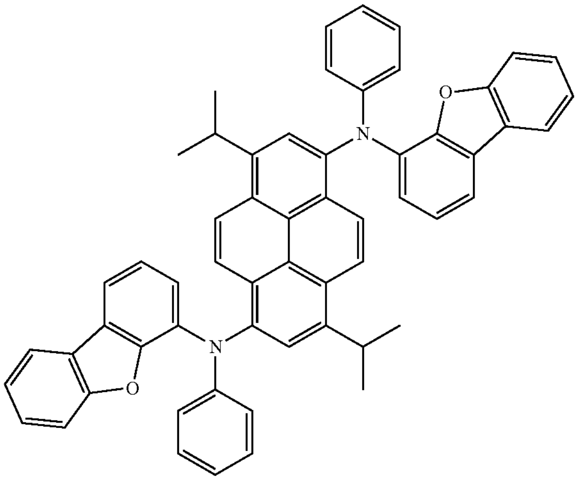
FD10
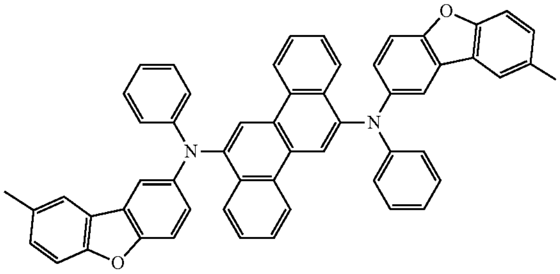
FD11
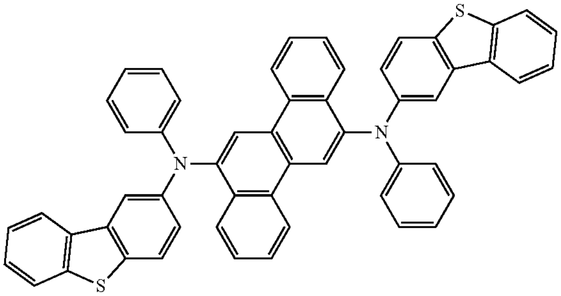
FD12
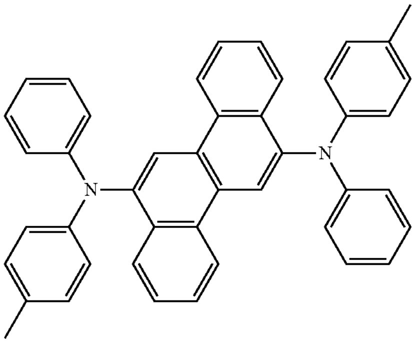
-continued
FD13
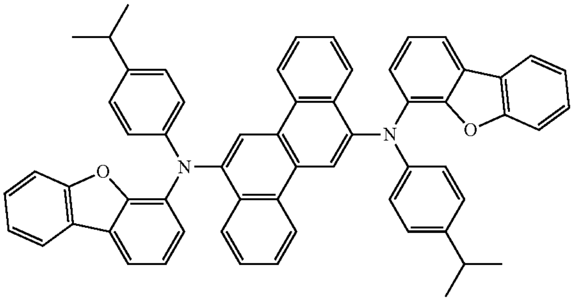
FD14
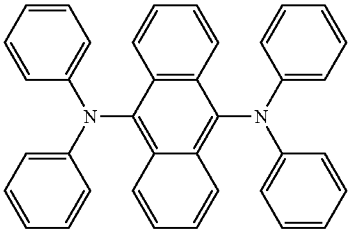
FD15
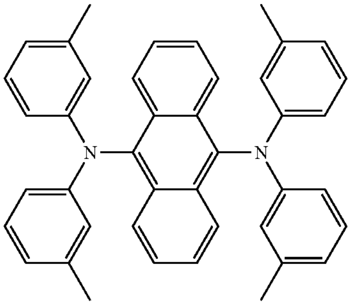
FD16
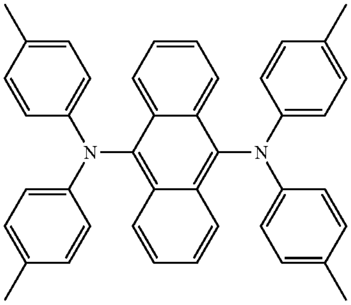
FD17
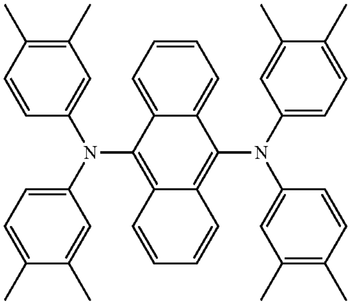

-continued
FD18
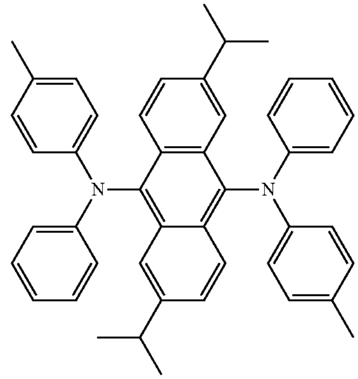
FD19
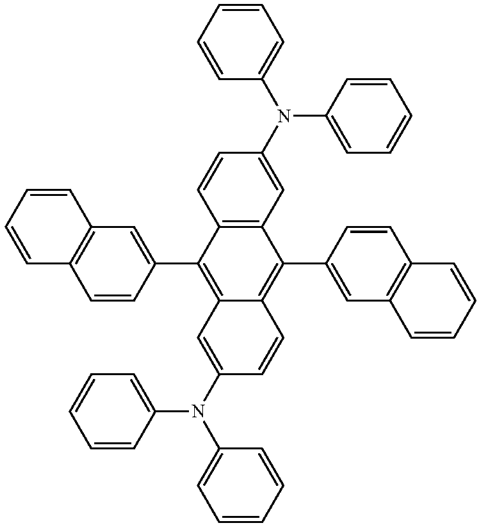
FD20
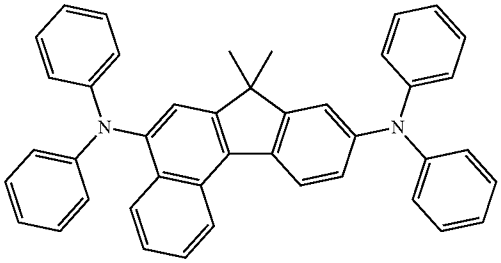
FD21
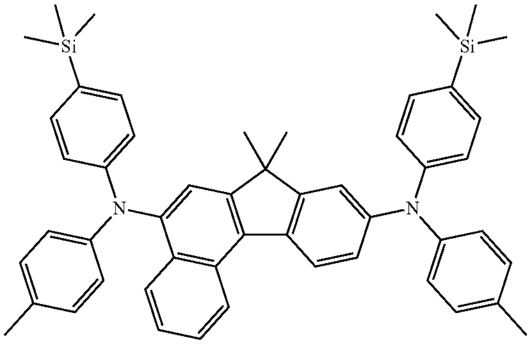
-continued
FD22
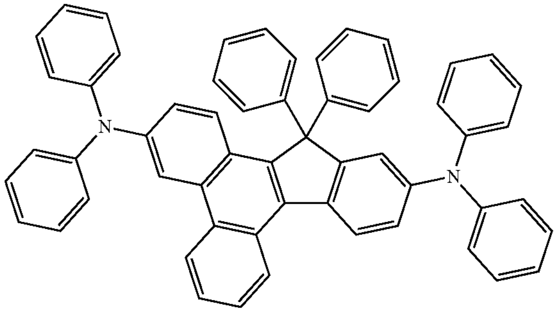
FD23
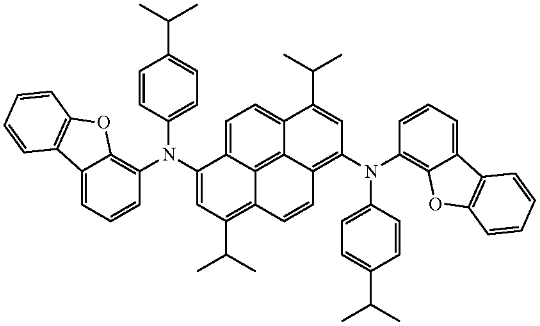
FD24
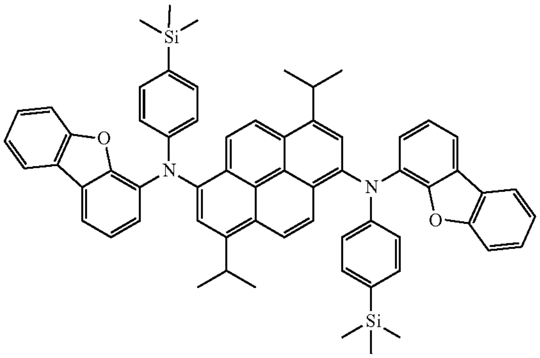
FD25
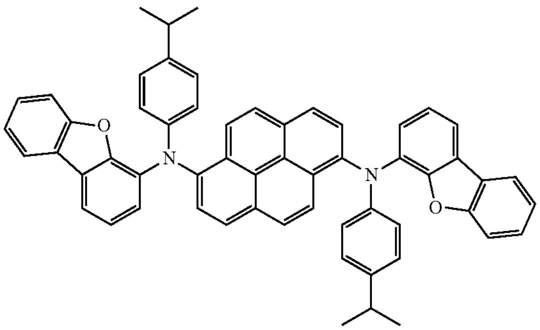

-continued
FD26
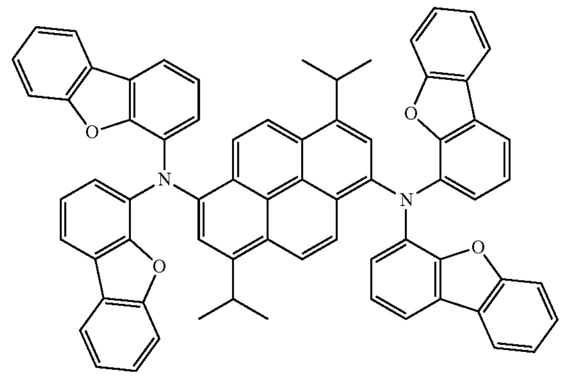
FD27
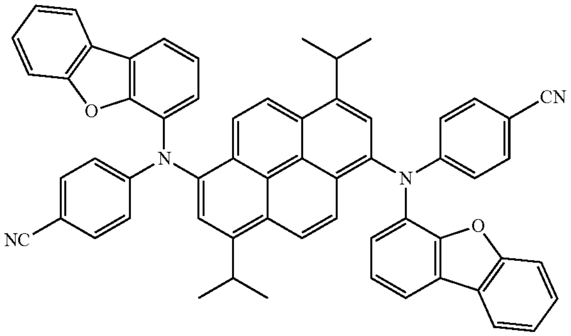
FD28
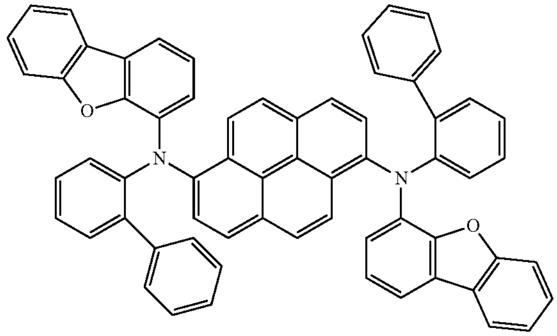
FD29
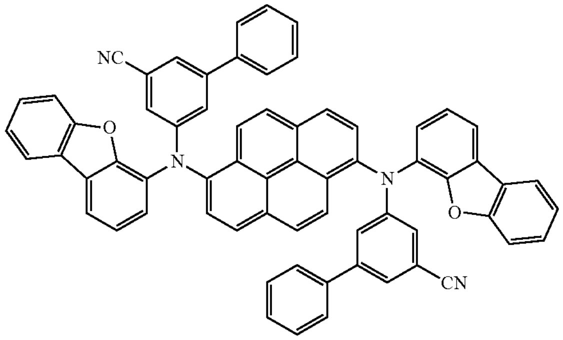
-continued
FD30
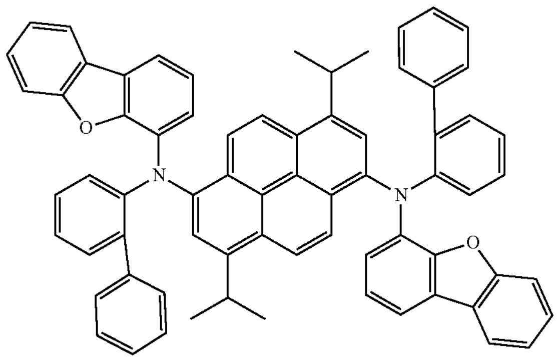
FD31
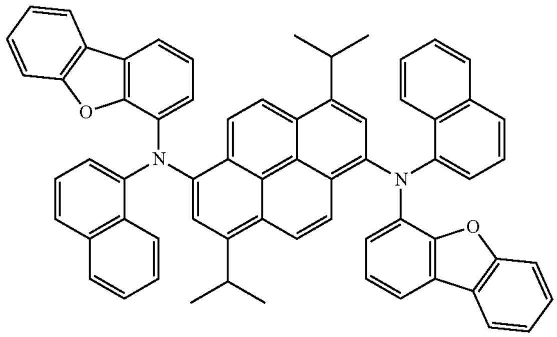
FD32
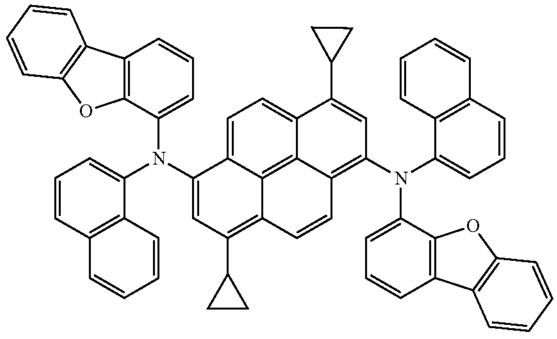
FD33
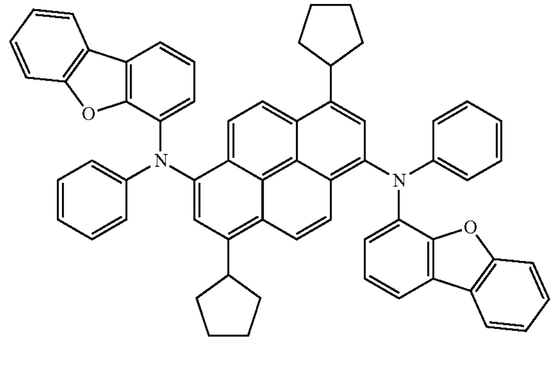

-continued

FD34

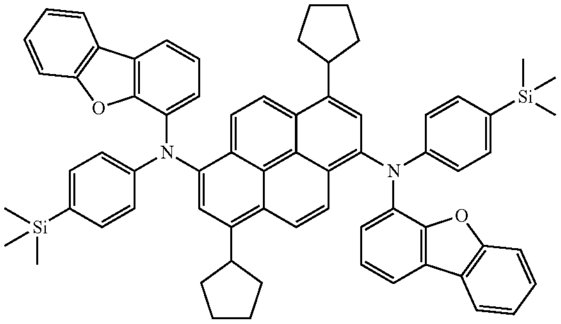

FD35

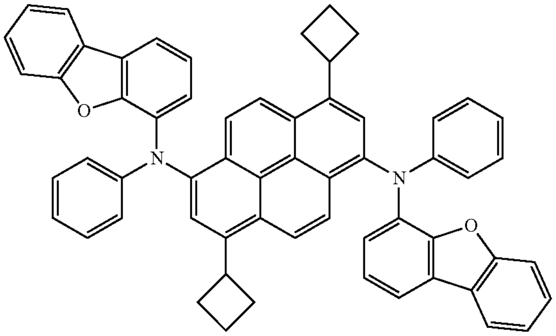

FD36

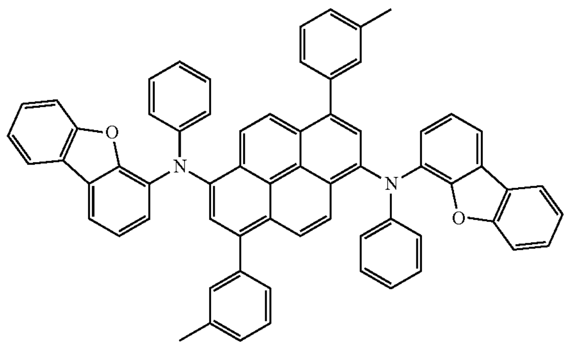

DPVBi

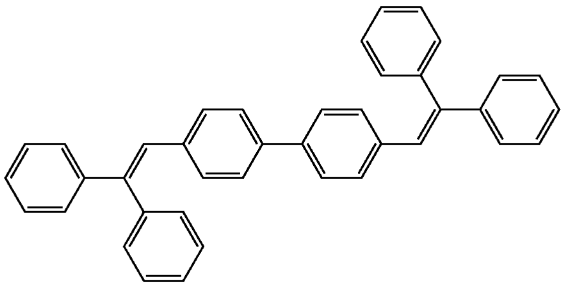

DPAVBi

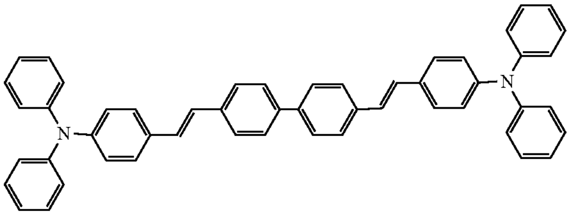
.

[Delayed Fluorescence Material]

The emission layer may include a delayed fluorescence material.

In the specification, the delayed fluorescence material may be selected from compounds capable of emitting delayed fluorescence based on a delayed fluorescence emission mechanism.

The delayed fluorescence material included in the emission layer may serve as a host or as a dopant, depending on the type of other materials included in the emission layer.

In an embodiment, a difference between a triplet energy level (eV) of the delayed fluorescence material and a singlet energy level (eV) of the delayed fluorescence material may be in a range of about 0 eV to about 0.5 eV. When the difference between the triplet energy level (eV) of the delayed fluorescence material and the singlet energy level (eV) of the delayed fluorescence material satisfies the range described above, up-conversion from the triplet state to the singlet state of the delayed fluorescence material may effectively occur, and thus, the light-emitting device 10 may have improved luminescence efficiency.

In an embodiment, the delayed fluorescence material may include: a material including at least one electron donor (for example, a π electron-rich $C_3$-$C_{60}$ cyclic group and the like, such as a carbazole group) and at least one electron acceptor (for example, a sulfoxide group, a cyano group, a π electron-deficient nitrogen-containing $C_1$-$C_{60}$ cyclic group, and the like); a material including a $C_8$-$C_{60}$ polycyclic group including at least two cyclic groups that are condensed to each other while sharing boron (B); or the like.

Examples of the delayed fluorescence material may include at least one of Compounds DF1 to DF10:

DF1

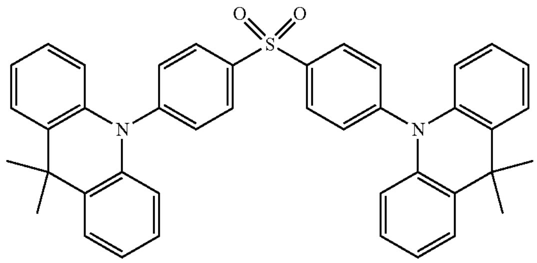

(DMAC-DPS)

DF2

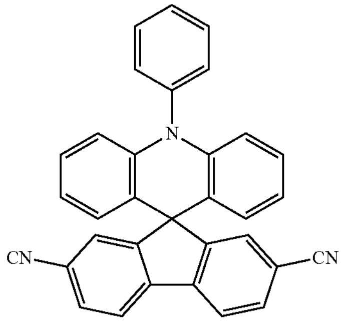

(ACRFLCN)

-continued
DF3
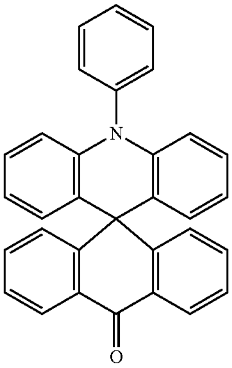
(ACRSA)
DF4
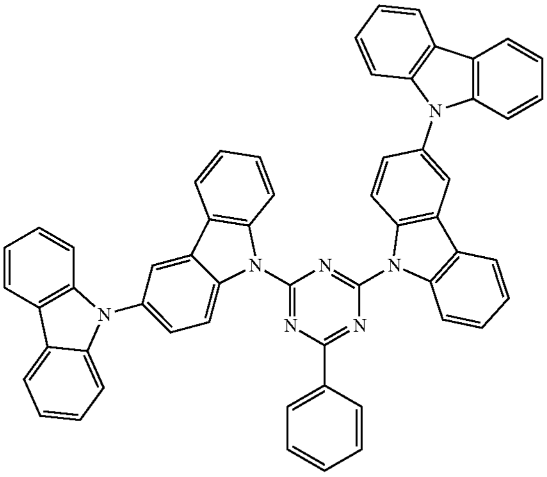
(CC2TA)
DF5
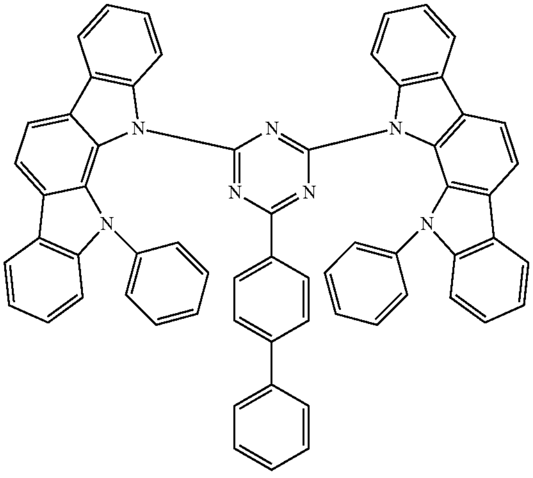
(PIC-TRZ)
-continued
DF6
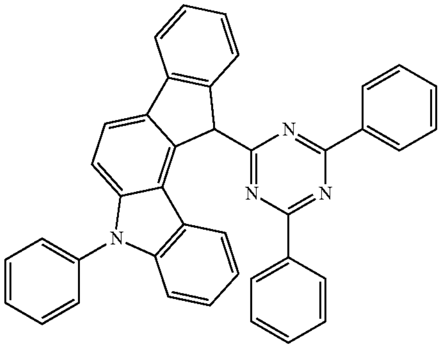
(PIC-TRZ2)
DF7
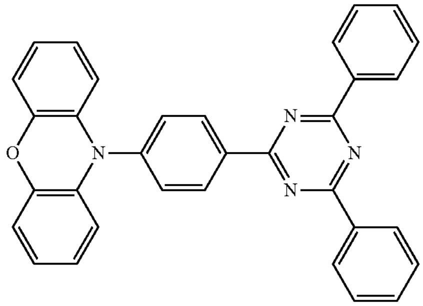
(PXZ-TRZ)
DF8
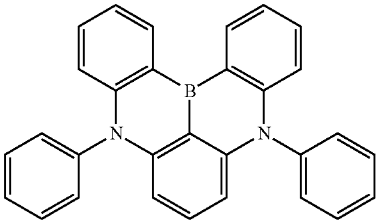
(DABNA-1)
DF9
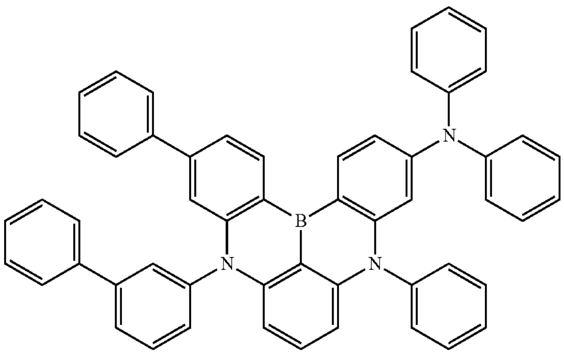
(DABNA-2)

-continued

DF10

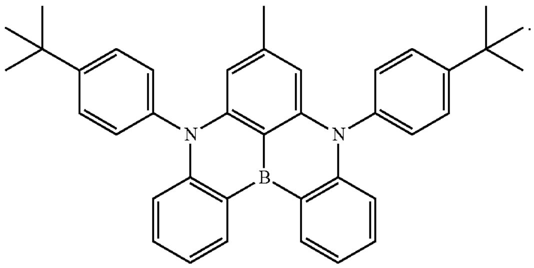

[Quantum Dot]

The emission layer may include a quantum dot.

In the specification, a quantum dot may be a crystal of a semiconductor compound, and may include any material capable of emitting light of various emission wavelengths according to a size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto.

The wet chemical process is a method that may include mixing a precursor material with an organic solvent and growing quantum dot particle crystals. When the crystal grows, the organic solvent naturally acts as a dispersant coordinated on the surface of the quantum dot crystal and controls the growth of the crystal so that the growth of quantum dot particles can be controlled through a process which costs less, and may be more readily performed than vapor deposition methods, such as metal organic chemical vapor deposition (MOCVD) or molecular beam epitaxy (MBE).

The quantum dot may include a Group II-VI semiconductor compound, a Group III-V semiconductor compound, a Group III-VI semiconductor compound, a Group I-III-VI semiconductor compound, a Group IV-VI semiconductor compound, a Group IV element or compound, or any combination thereof.

Examples of the Group II-VI semiconductor compound may include: a binary compound, such as CdS, CdSe, CdTe, ZnS, ZnSe, ZnTe, ZnO, HgS, HgSe, HgTe, MgSe, MgS, and the like; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and the like; a quaternary compound, such as CdZnSeS, CdZnSeTe, CdZnSTe, CdHgSeS, CdHgSeTe, CdHgSTe, HgZnSeS, HgZnSeTe, HgZnSTe, and the like; or any combination thereof.

Examples of the Group III-V semiconductor compound may include: a binary compound, such as GaN, GaP, GaAs, GaSb, AlN, AlP, AlAs, AlSb, InN, InP, InAs, InSb, and the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and the like; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and the like; or any combination thereof. In an embodiment, the Group III-V semiconductor compound may further include a Group II element. Examples of the Group III-V semiconductor compound further including a Group II element may include InZnP, InGaZnP, InAlZnP, and the like.

Examples of the Group III-VI semiconductor compound may include: a binary compound, such as GaS, GaSe, $Ga_2Se_3$, GaTe, InS, InSe, $In_2S_3$, $In_2Se_3$, InTe, and the like; a ternary compound, such as $InGaS_3$, $InGaSe_3$, and the like; or any combination thereof.

Examples of the Group I-III-VI semiconductor compound may include: a ternary compound, such as AgInS, $AgInS_2$, CuInS, $CuInS_2$, $CuGaO_2$, $AgGaO_2$, $AgAlO_2$, and the like; or any combination thereof.

Examples of the Group IV-VI semiconductor compound may include: a binary compound, such as SnS, SnSe, SnTe, PbS, PbSe, PbTe, and the like; a ternary compound, such as SnSeS, SnSeTe, SnSTe, PbSeS, PbSeTe, PbSTe, SnPbS, SnPbSe, SnPbTe, and the like; a quaternary compound, such as SnPbSSe, SnPbSeTe, SnPbSTe, and the like; or any combination thereof.

Examples of the Group IV element or compound may include: a single element material, such as Si, Ge, and the like; a binary compound, such as SiC, SiGe, and the like; or any combination thereof.

Each element included in a multi-element compound, such as a binary compound, a ternary compound, or a quaternary compound, may be present in a particle at a uniform concentration or at a non-uniform concentration.

In an embodiment, the quantum dot may have a single structure in which the concentration of each element in the quantum dot is uniform, or the quantum dot may have a core-shell structure. In an embodiment, in case that the quantum dot has a core-shell structure, a material included in the core and a material included in the shell may be different from each other.

The shell of the quantum dot may serve as a protective layer that prevents chemical denaturation of the core to maintain semiconductor characteristics, and/or may serve as a charging layer that imparts electrophoretic characteristics to the quantum dot. The shell may be a single layer or a multi-layer. An interface between the core and the shell may have a concentration gradient in which the concentration of a material that is present in the shell decreases toward the core.

Examples of the shell of the quantum dot may include a metal oxide, a metalloid oxide, a non-metal oxide, a semiconductor compound, or any combination thereof. Examples of the metal oxide, the metalloid oxide, or the non-metal oxide may include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, NiO, and the like; a ternary compound, such as $MgAl_2O_4$, $CoFe_2O_4$, $NiFe_2O_4$, $CoMn_2O_4$, and the like; or any combination thereof.

Examples of the semiconductor compound may include, as described herein, a Group II-VI semiconductor compound, a Group III-V semiconductor compound, a Group III-VI semiconductor compound, a Group I-III-VI semiconductor compound, a Group IV-VI semiconductor compound, or any combination thereof. Examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

The quantum dot may have a full width at half maximum (FWHM) of an emission wavelength spectrum equal to or less than about 45 nm. For example, the quantum dot may have a FWHM of an emission wavelength spectrum equal to or less than about 40 nm. For example, the quantum dot may have a FWHM of an emission wavelength spectrum equal to or less than about 30 nm. When the FWHM of the quantum dot is within any of these ranges, the quantum dot may have improved color purity or color reproducibility. Light emitted through the quantum dot may be emitted in all directions, so that a wide viewing angle may be improved.

In embodiments, the quantum dot may be in the form of a spherical particle, a pyramidal particle, a multi-arm particle, a cubic nanoparticle, a nanotube particle, a nanowire particle, a nanofiber particle, or a nanoplate particle.

Since the energy band gap may be adjusted by controlling the size of the quantum dot, light having various wavelength bands may be obtained from the quantum dot emission layer. Accordingly, by using quantum dots of different sizes, a light-emitting device that emits light of various wavelengths may be implemented. In an embodiment, the size of the quantum dot may be selected to emit red, green, and/or blue light. In an embodiment, the size of the quantum dot may be selected to emit white light by a combination of light of various colors.

[Electron Transport Region in Interlayer 130]

The electron transport region may have a structure consisting of a layer consisting of a single material, a structure consisting of a layer including multiple materials that are different from each other, or a structure including multiple layers including multiple materials that are different from each other.

The electron transport region may include a buffer layer, a hole blocking layer, an electron control layer, an electron transport layer, an electron injection layer, or any combination thereof.

In embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein the layers of each structure may be stacked from the emission layer in its respective stated order, but the structure of the electron transport region is not limited thereto.

In an embodiment, the electron transport region (for example, a buffer layer, a hole blocking layer, an electron control layer, or an electron transport layer in the electron transport region) may include a metal-free compound including at least one TT electron-deficient nitrogen-containing $C_1$-$C_{60}$ cyclic group.

In embodiments, the electron transport region may include a compound represented by Formula 601:

$$[Ar_{601}]_{xe11}\text{-}[(L_{601})_{xe1}\text{-}R_{601}]_{xe21}$$ [Formula 601]

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ may each independently be the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

For example, in Formula 601, when xe11 is 2 or more, two or more of $Ar_{601}$ may be linked to each other via a single bond.

In an embodiment, in Formula 601, $Ar_{601}$ may be a substituted or unsubstituted anthracene group.

In embodiments, the electron transport region may include a compound represented by Formula 601-1:

[Formula 601-1]

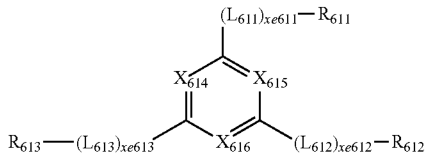

In Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may each be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, in Formulae 601 and 601-1, xe1 and xe611 to xe613 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, or any combination thereof:

ET1

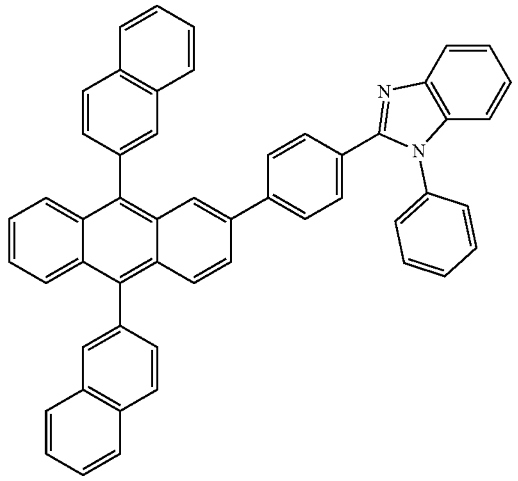

-continued
ET2
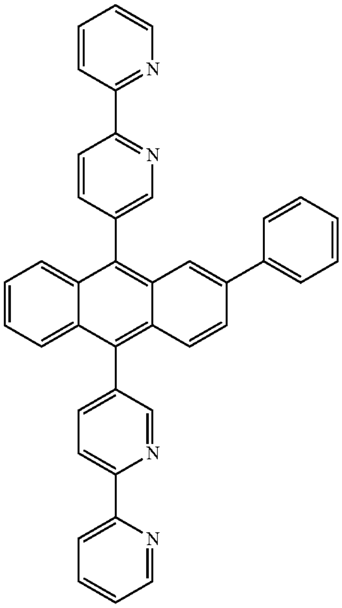
ET3
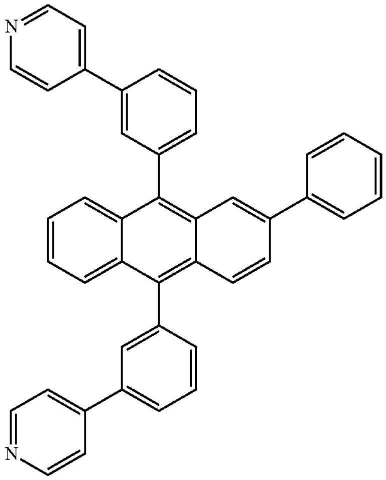
ET4
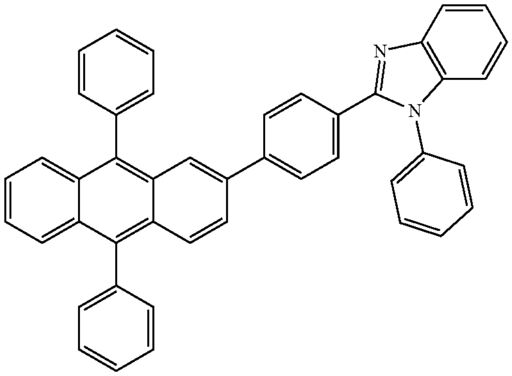
-continued
ET5
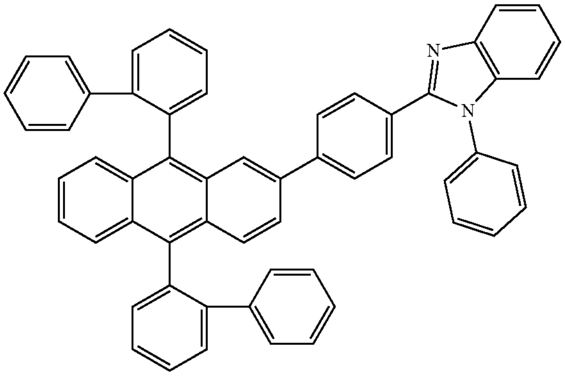
ET6
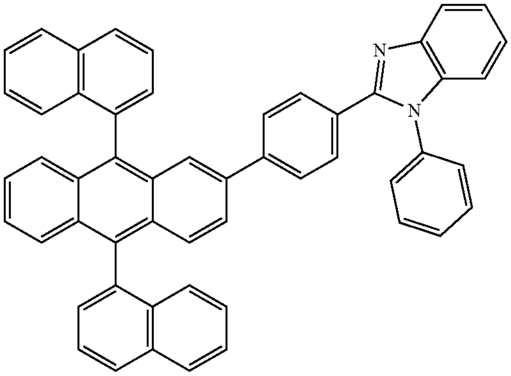
ET7
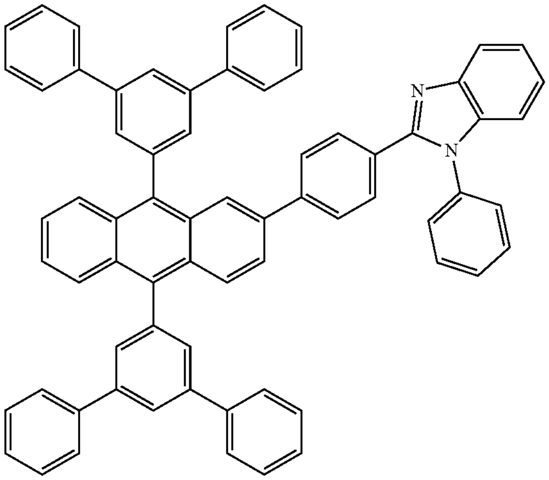

-continued
ET8
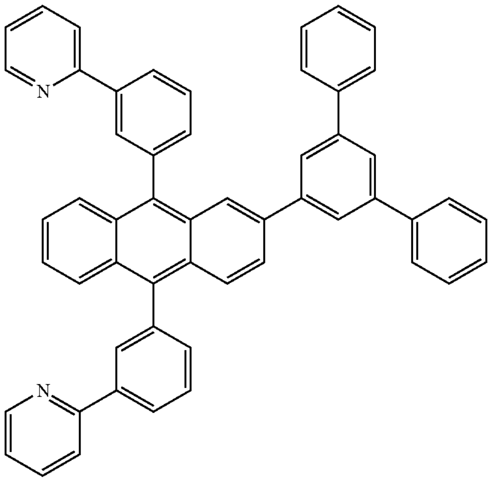
ET9
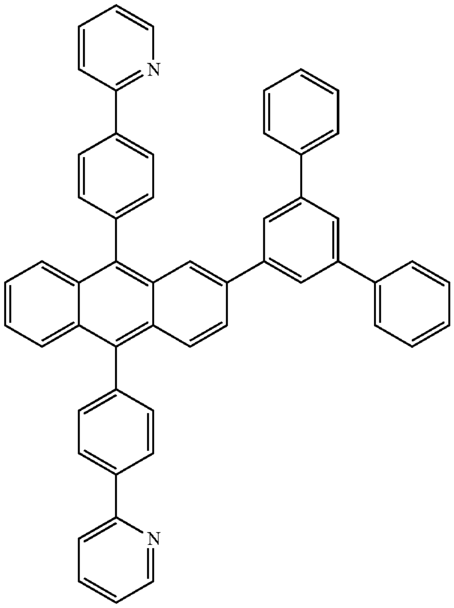
-continued
ET10
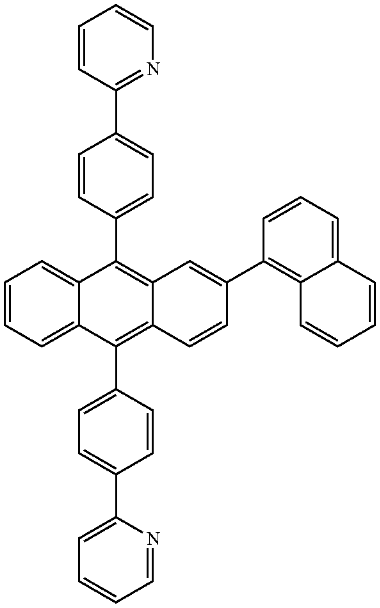
ET11
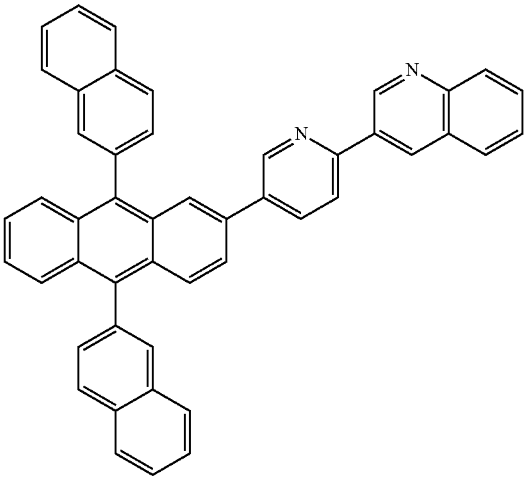
ET12
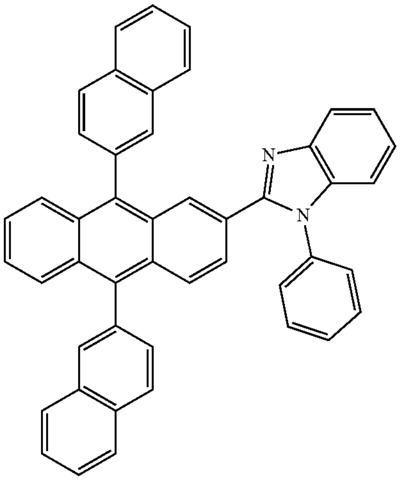

-continued
ET13
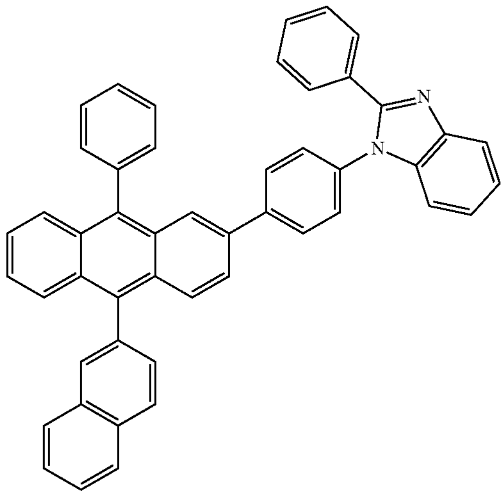
ET14
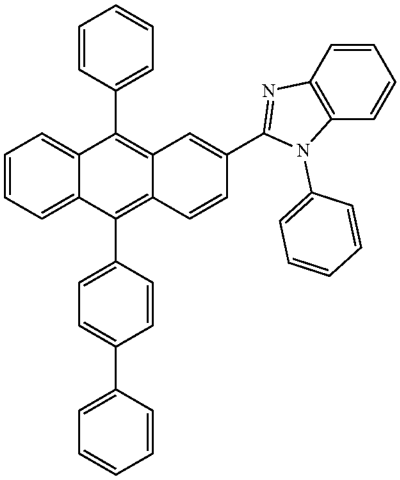
ET15
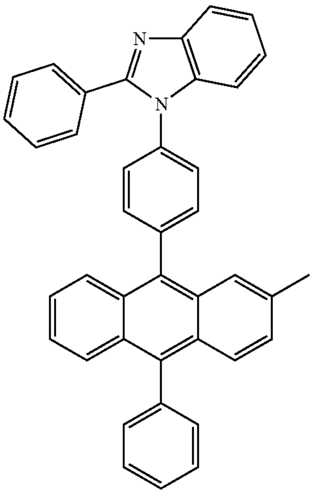
-continued
ET16
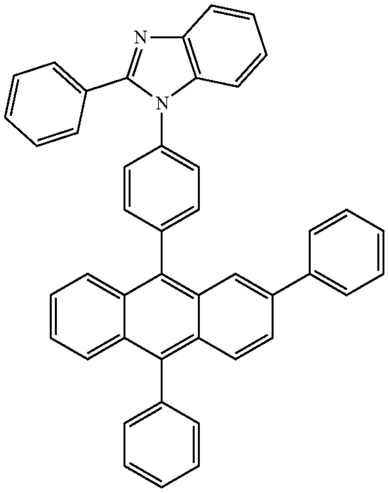
ET17
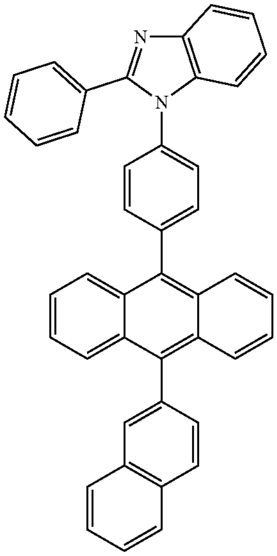
ET18
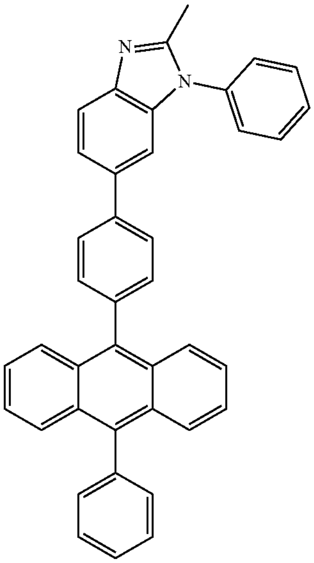

-continued
ET19
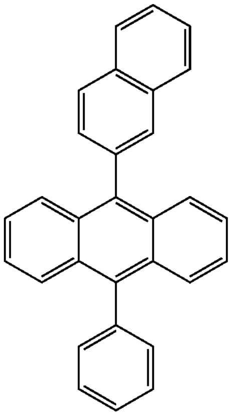
ET20
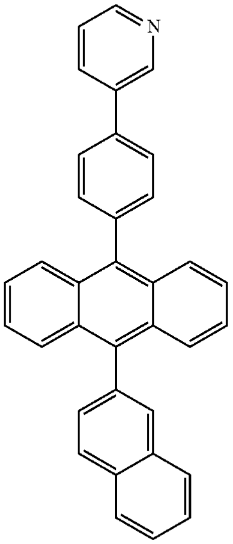
ET21
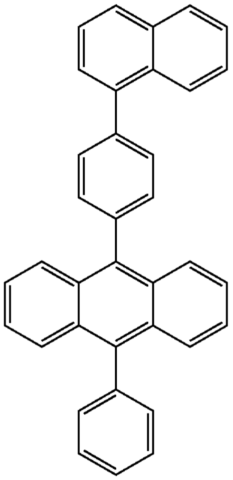
-continued
ET22
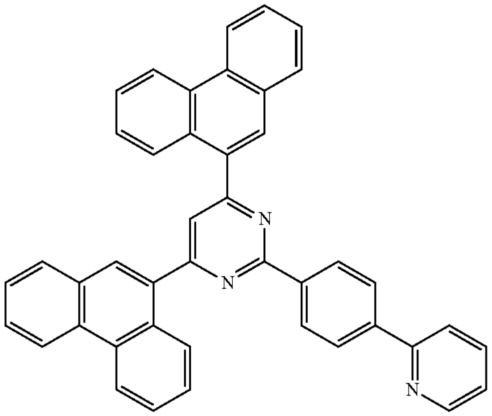
ET23
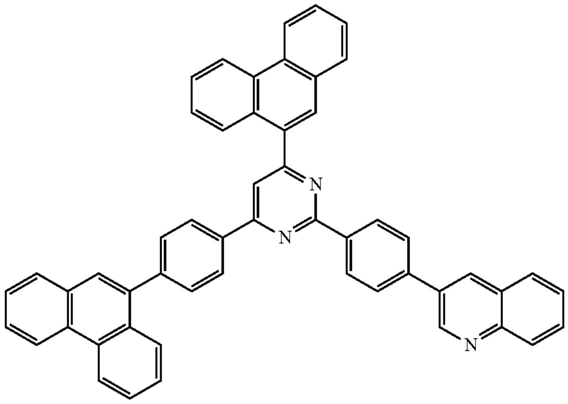
ET24
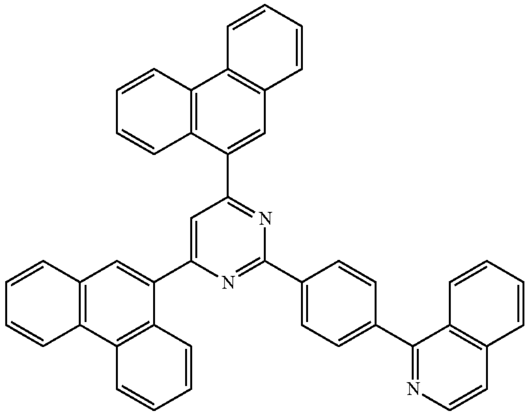

-continued
ET25
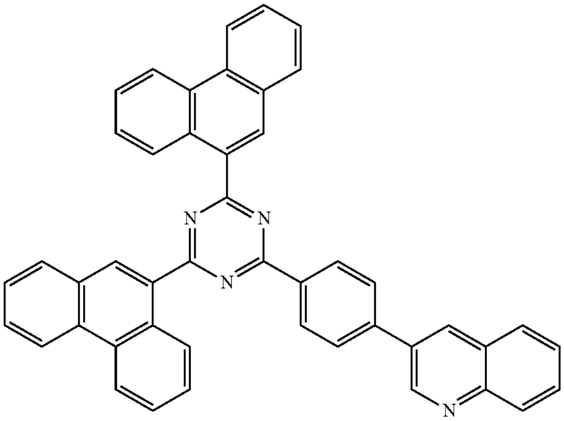
ET26
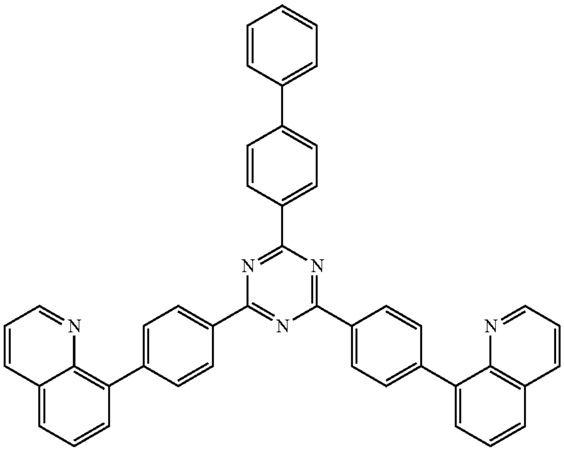
ET27
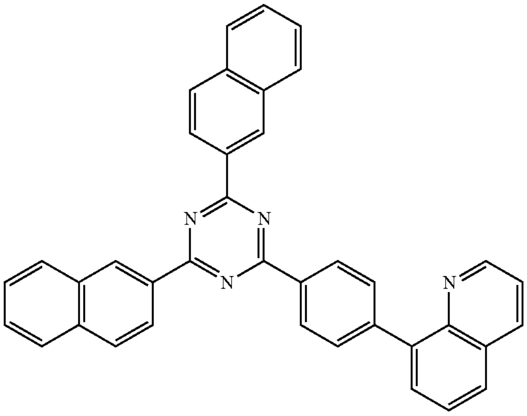
-continued
ET28
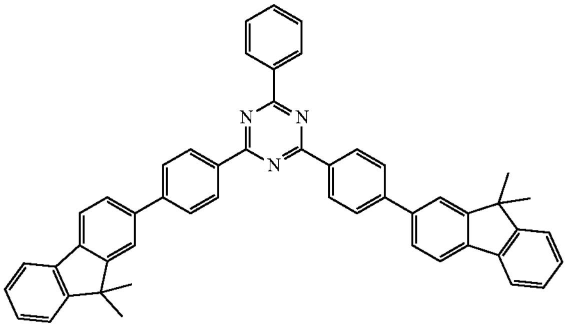
ET29
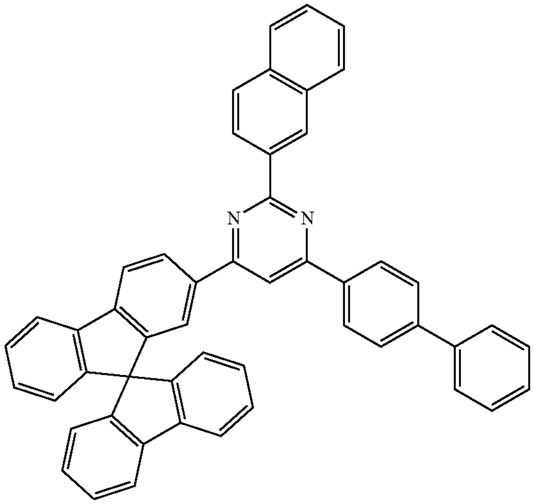
ET30
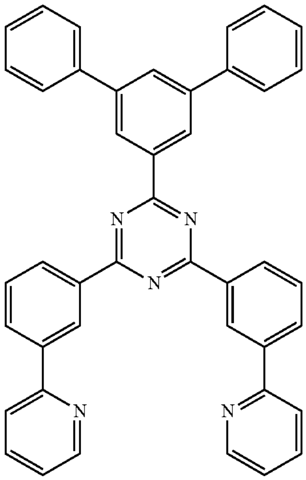

-continued
ET31
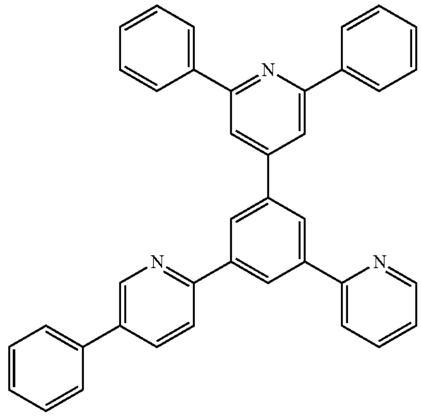
ET32
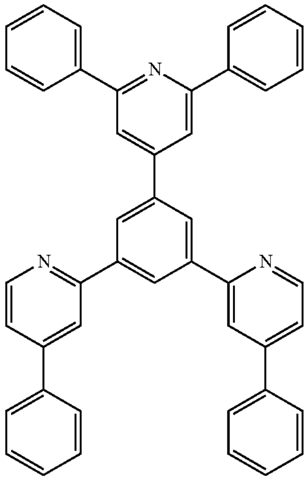
ET33
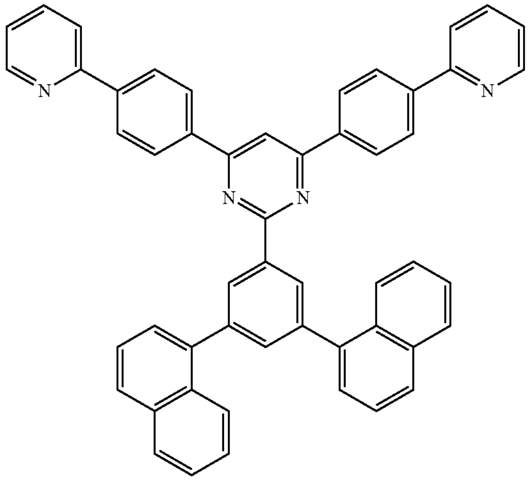
-continued
ET34
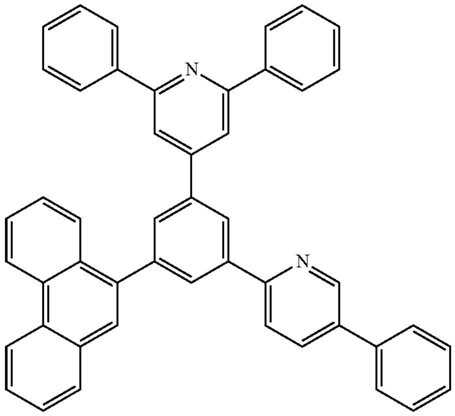
ET35
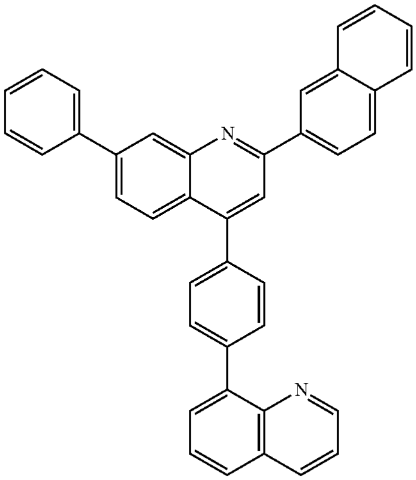
ET36
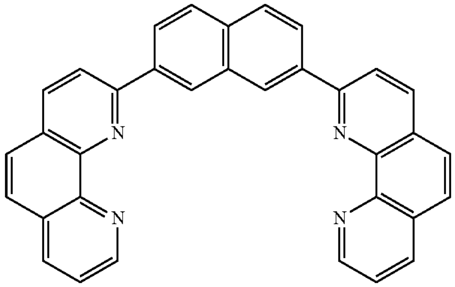
ET37
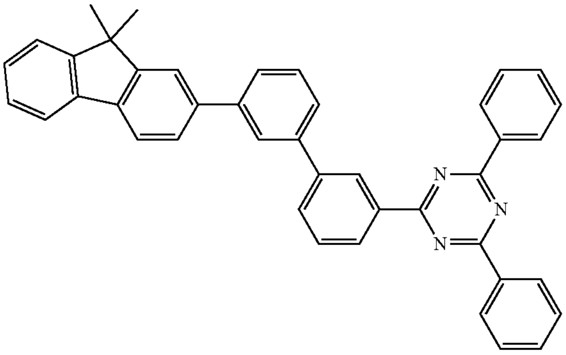

ET38
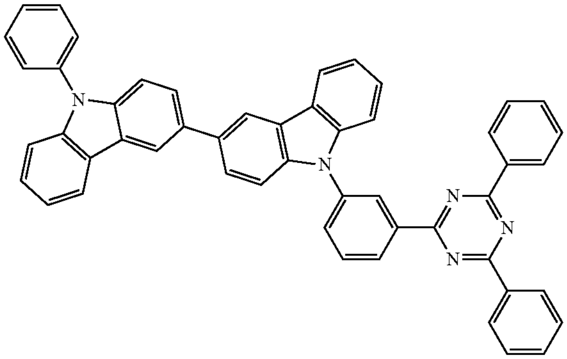
ET39
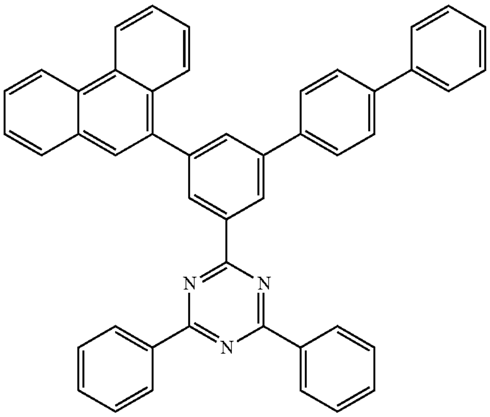
ET40
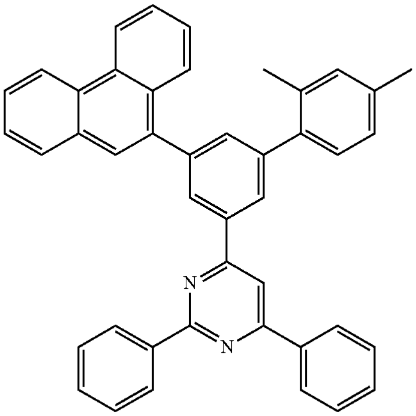
ET41
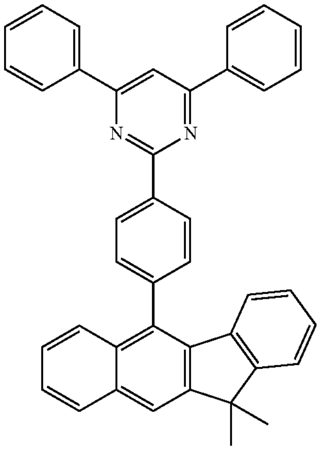
ET42
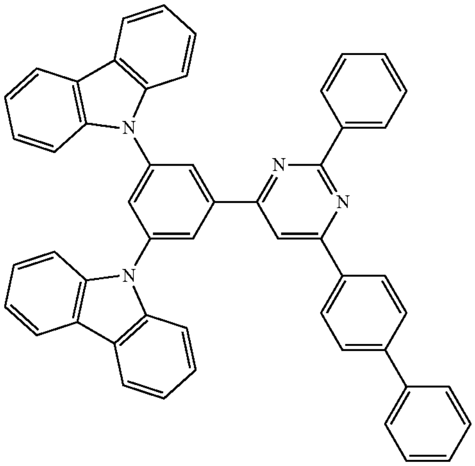
ET43
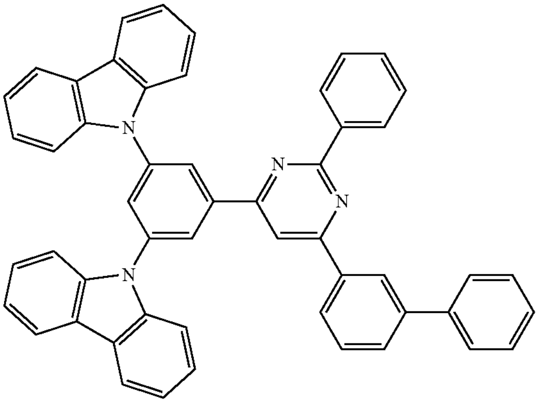

-continued

ET44

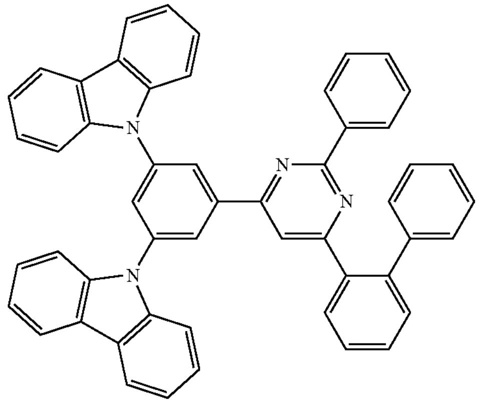

ET45

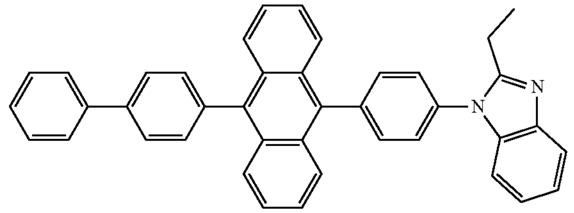

Alq3

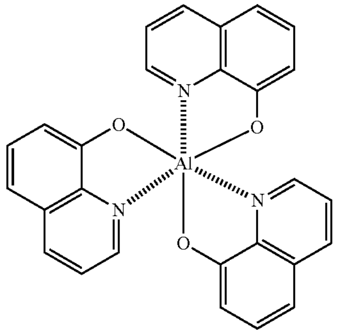

BAlq

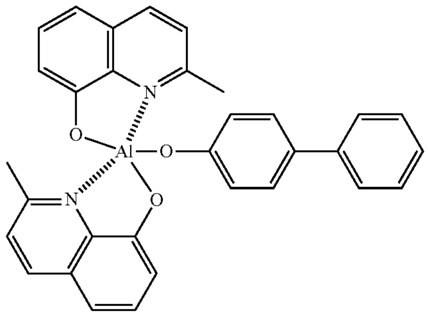

TAZ

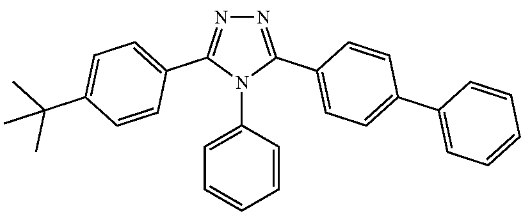

-continued

NTAZ

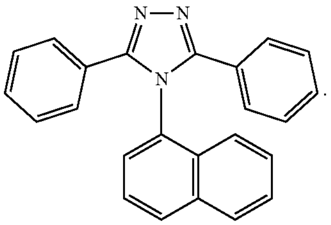

A thickness of the electron transport region may be in a range of about 100 Å to about 5,000 Å. For example, the thickness of the electron transport region may be in a range of about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, and a thickness of the electron transport layer may be in a range of about 100 Å to about 1,000 Å. For example, the thickness of the buffer layer, the hole blocking layer, or the electron control layer may each independently be in a range of about 30 Å to about 300 Å. For example, the thickness of the electron transport layer may be in a range of about 150 Å to about 500 Å. When the thicknesses of the buffer layer, the hole blocking layer, the electron control layer, the electron transport layer, and/or the electron transport region are within these ranges, satisfactory electron transporting characteristics may be obtained without a substantial increase in driving voltage.

The electron transport region (for example, an electron transport layer in the electron transport region) may further include, in addition to the materials described above, a metal-containing material.

The metal-containing material may include an alkali metal complex, an alkaline earth metal complex, or any combination thereof. A metal ion of an alkali metal complex may be a Li ion, a Na ion, a K ion, a Rb ion, or a Cs ion, and a metal ion of an alkaline earth metal complex may be a Be ion, a Mg ion, a Ca ion, a Sr ion, or a Ba ion.

A ligand coordinated with the metal ion of the alkali metal complex or with the metal ion of the alkaline earth-metal complex may each independently include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a lithium (Li) complex. The Li complex may include, for example, Compound ET-D1 (LiQ) or Compound ET-D2:

ET-D1

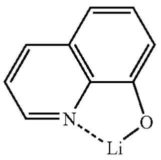

-continued

ET-D2

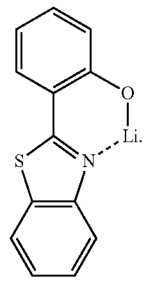

The electron transport region may include an electron injection layer that facilitates the injection of electrons from the second electrode 150. The electron injection layer may directly contact the second electrode 150.

The electron injection layer may have a structure consisting of a layer consisting of a single material, a structure consisting of a layer including different materials, or a structure including multiple layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, iodides, etc.), or tellurides of the alkali metal, the alkaline earth metal, the rare earth metal, or any combination thereof.

The alkali metal-containing compound may include: an alkali metal oxide, such as $Li_2O$, $Cs_2O$, $K_2O$, and the like; an alkali metal halide, such as LiF, NaF, CsF, KF, LiI, NaI, CsI, KI, and the like; or any combination thereof. The alkaline earth metal-containing compound may include an alkaline earth metal compound, such as BaO, SrO, CaO, $Ba_xSr_{1-x}O$ (wherein x is a real number satisfying $0<x<1$), $Ba_xCa_{1-x}O$ (wherein x is a real number satisfying $0<x<1$), and the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, $Lu_2Te_3$, and the like.

The alkali metal complex, the alkaline earth-metal complex, and the rare earth metal complex may include one of an alkali metal ion, an alkaline earth metal ion, and a rare earth metal ion, and a ligand bonded to the metal ion (for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenyl benzimidazole, a hydroxyphenylbenzothiazole, a bipyridine, a phenanthroline, a cyclopentadiene, or any combination thereof).

In an embodiment, the electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In embodiments, the electron injection layer may further include an organic material (for example, a compound represented by Formula 601).

In an embodiment, the electron injection layer may consist of an alkali metal-containing compound (for example, an alkali metal halide); or the electron injection layer may consist of an alkali metal-containing compound (for example, alkali metal halide), and an alkali metal, an alkaline earth metal, a rare earth metal, or any combination thereof. For example, the electron injection layer may be a KI:Yb co-deposited layer, an RbI:Yb co-deposited layer, and the like.

When the electron injection layer further includes an organic material, an alkali metal, an alkaline earth metal, a rare earth metal, an alkali metal-containing compound, an alkaline earth metal-containing compound, a rare earth metal-containing compound, an alkali metal complex, an alkaline earth-metal complex, a rare earth metal complex, or any combination thereof may be uniformly or non-uniformly dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within any of the ranges above, satisfactory electron injection characteristics may be obtained without a substantial increase in driving voltage.

[Second Electrode 150]

The second electrode 150 may be arranged on the interlayer 130 having a structure as described above. The second electrode 150 may be a cathode, which is an electron injection electrode. A material for forming the second electrode 150 may be a material having a low-work function, for example, a metal, an alloy, an electrically conductive compound, or any combination thereof.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure.

[Capping Layer]

The light-emitting device 10 may include a first capping layer arranged outside the first electrode 110, and/or a second capping layer arranged outside the second electrode 150. For example, the light-emitting device 10 may have a structure in which the first capping layer, the first electrode 110, the interlayer 130, and the second electrode 150 are stacked in this stated order, a structure in which the first electrode 110, the interlayer 130, the second electrode 150, and the second capping layer are stacked in this stated order, or a structure in which the first capping layer, the first electrode 110, the interlayer 130, the second electrode 150, and the second capping layer are stacked in this stated order.

Light generated in an emission layer of the interlayer 130 of the light-emitting device 10 may be extracted toward the outside through the first electrode 110, which may be a semi-transmissive electrode or a transmissive electrode, and through the first capping layer. Light generated in an emission layer of the interlayer 130 of the light-emitting device 10 may be extracted toward the outside through the second electrode 150, which may be a semi-transmissive electrode or a transmissive electrode, and through the second capping layer.

The first capping layer and the second capping layer may each increase external emission efficiency according to the principle of constructive interference. Accordingly, the light extraction efficiency of the light-emitting device 10 is increased, so that the luminescence efficiency of the light-emitting device 10 may be improved.

The first capping layer and the second capping layer may each include a material having a refractive index of greater than or equal to about 1.6 (with respect to a wavelength of about 589 nm).

The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include a carbocyclic compound, a heterocyclic compound, an amine group-containing compound, a porphine derivative, a phthalocyanine derivative, a naphthalocyanine derivative, an alkali metal complex, an alkaline earth metal complex, or any combination thereof. The carbocyclic compound, the heterocyclic compound, and the amine group-containing compound may optionally be substituted with a substituent including O, N, S, Se, Si, F, Cl, Br, I, or any combination thereof.

In an embodiment, at least one of the first capping layer and the second capping layer may each independently include an amine group-containing compound.

In embodiments, at least one of the first capping layer and the second capping layer may each independently include a compound represented by Formula 201, a compound represented by Formula 202, or any combination thereof.

In embodiments, at least one of the first capping layer and the second capping layer may each independently include one of Compounds HT28 to HT33, one of Compounds CP1 to CP6, β-NPB, or any combination thereof:

CP1

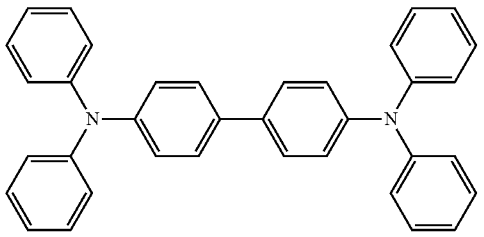

CP2

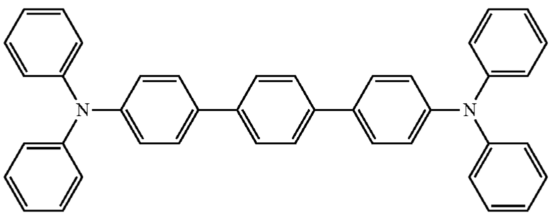

-continued

CP3

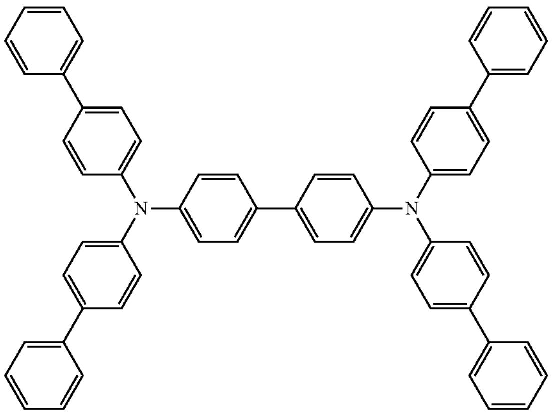

CP4

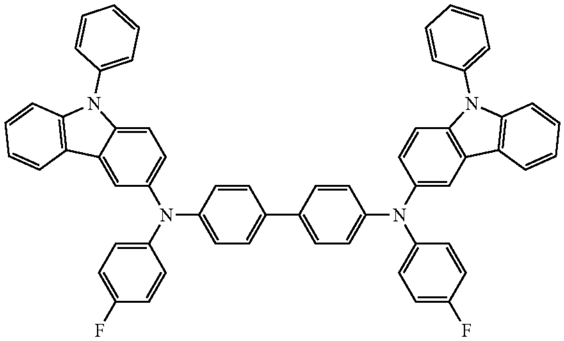

CP5

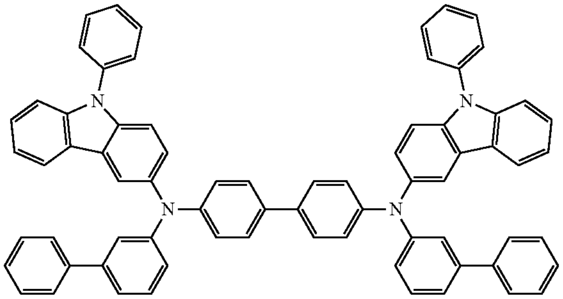

CP6

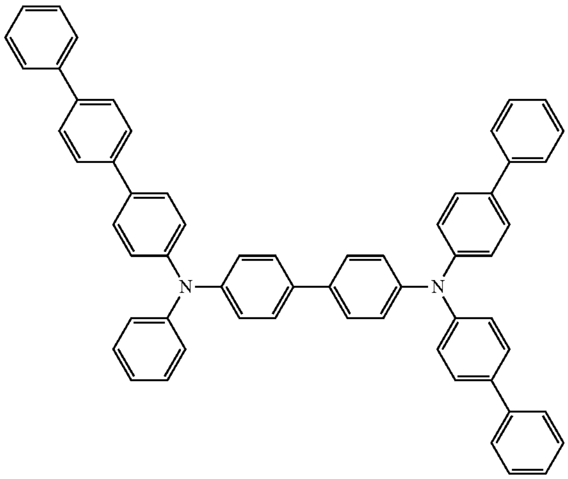

-continued

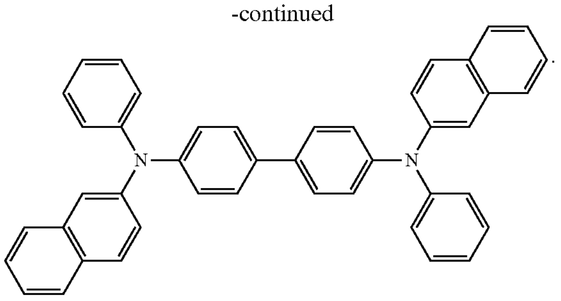

β-NPB

[Film]

At least one of the amine-based compounds represented by Formulae 1 to 4 may be included in various films. Accordingly, another aspect provides a film which may include at least one of the amine-based compounds represented by Formulae 1 to 4. The film may be, for example, an optical member (or a light control means) (for example, a color filter, a color conversion member, a capping layer, a light extraction efficiency enhancement layer, a selective light absorbing layer, a polarizing layer, a quantum dot-containing layer, or like), a light-blocking member (for example, a light reflective layer, a light absorbing layer, or the like), or a protective member (for example, an insulating layer, a dielectric layer, or the like).

[Electronic Apparatus]

The light-emitting device may be included in various electronic apparatuses. In an embodiment, an electronic apparatus including the light-emitting device may be a light-emitting apparatus, an authentication apparatus, and the like.

The electronic apparatus (for example, a light-emitting apparatus) may further include, in addition to the light-emitting device, a color filter, a color conversion layer, or a color filter and a color conversion layer. The color filter and/or the color conversion layer may be arranged in at least one traveling direction of light emitted from the light-emitting device. In an embodiment, light emitted from the light-emitting device may be blue light or white light. The light-emitting device may be the same as described herein. In an embodiment, the color conversion layer may include a quantum dot. The quantum dot may be, for example, a quantum dot as described herein.

The electronic apparatus may include a first substrate. The first substrate may include subpixels, the color filter may include color filter areas respectively corresponding to the subpixels, and the color conversion layer may include color conversion areas respectively corresponding to the subpixels.

A pixel-defining film may be arranged between the subpixels to define each subpixel.

The color filter may further include color filter areas and light-shielding patterns arranged between the color filter areas, and the color conversion layer may further include color conversion areas and light-shielding patterns arranged between the color conversion areas.

The color filter areas (or the color conversion areas) may include a first area emitting first color light, a second area emitting second color light, and/or a third area emitting third color light, wherein the first color light, the second color light, and/or the third color light may have different maximum emission wavelengths from one another. For example, the first color light may be red light, the second color light may be green light, and the third color light may be blue light. In an embodiment, the color filter areas (or the color conversion areas) may include quantum dots. For example, the first area may include a red quantum dot, the second area may include a green quantum dot, and the third area may not include a quantum dot. The quantum dot may be the same as described herein. The first area, the second area, and/or the third area may each further include a scatterer.

In an embodiment, the light-emitting device may emit first light, the first area may absorb the first light to emit first-first color light, the second area may absorb the first light to emit second-first color light, and the third area may absorb the first light to emit third-first color light. The first-first color light, the second-first color light, and the third-first color light may have different maximum emission wavelengths. For example, the first light may be blue light, the first-first color light may be red light, the second-first color light may be green light, and the third-first color light may be blue light.

The electronic apparatus may further include a thin-film transistor, in addition to the light-emitting device as described herein. The thin-film transistor may include a source electrode, a drain electrode, and an active layer, wherein any one of the source electrode and the drain electrode may be electrically connected to any one of the first electrode and the second electrode of the light-emitting device.

The thin-film transistor may further include a gate electrode, a gate insulating film, and the like.

The active layer may include crystalline silicon, amorphous silicon, an organic semiconductor, an oxide semiconductor, and the like.

The electronic apparatus may further include a sealing portion for sealing the light-emitting device. The sealing portion may be arranged between the color filter and/or the color conversion layer, and the light-emitting device. The sealing portion may allow light from the light-emitting device to be extracted to the outside, and may simultaneously prevent ambient air and moisture from penetrating into the light-emitting device. The sealing portion may be a sealing substrate including a transparent glass substrate or a plastic substrate. The sealing portion may be a thin-film encapsulation layer including an organic layer and/or an inorganic layer. When the sealing portion is a thin-film encapsulation layer, the electronic apparatus may be flexible.

Various functional layers may be further included on the sealing portion, in addition to the color filter and/or the color conversion layer, according to the use of the electronic apparatus. Examples of a functional layer may include a touch screen layer, a polarizing layer, an authentication apparatus, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device as described above, a biometric information collector.

The electronic apparatus may be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 2:
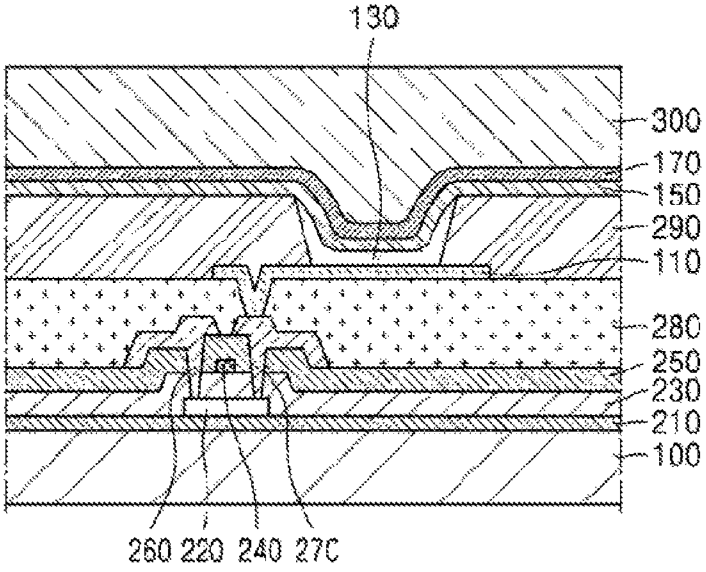
FIG. 2 is a schematic cross-sectional view of an electronic apparatus according to an embodiment.
Figure 3:
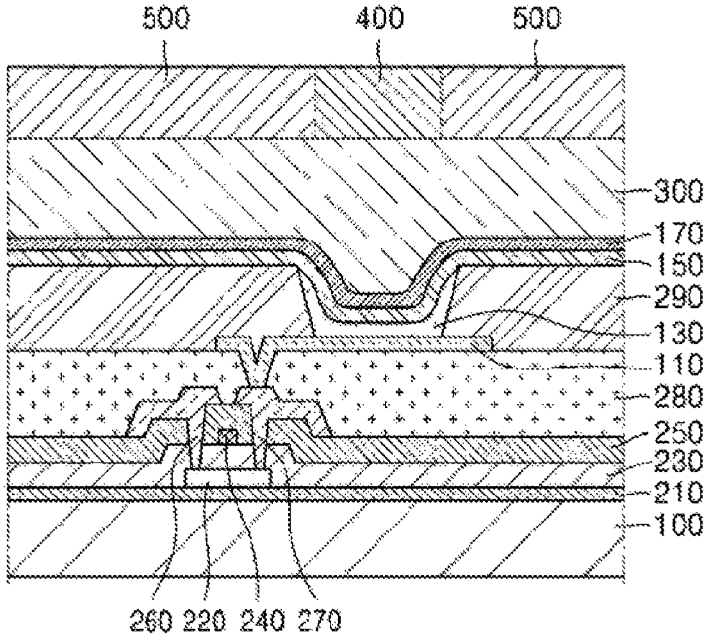
FIG. 3 is a schematic cross-sectional view of an electronic apparatus according to another embodiment.

[Description of FIGS. 2 and 3]

FIG. 2 is a schematic cross-sectional view of an electronic apparatus according to an embodiment.

The electronic apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be arranged on the substrate 100. The buffer layer 210 may prevent penetration of impurities through the substrate 100 and may provide a flat surface on the substrate 100.

A TFT may be arranged on the buffer layer 210. The TFT may include an active layer 220, a gate electrode 240, a source electrode 260, and a drain electrode 270.

The active layer 220 may include an inorganic semiconductor such as silicon or polysilicon, an organic semiconductor, or an oxide semiconductor, and may include a source region, a drain region, and a channel region.

A gate insulating film 230 for insulating the active layer 220 from the gate electrode 240 may be arranged on the active layer 220, and the gate electrode 240 may be arranged on the gate insulating film 230.

An interlayer insulating film 250 may be arranged on the gate electrode 240. The interlayer insulating film 250 may be arranged between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be arranged on the interlayer insulating film 250. The interlayer insulating film 250 and the gate insulating film 230 may be formed to expose the source region and the drain region of the active layer 220, and the source electrode 260 and the drain electrode 270 may respectively contact the exposed portions of the source region and the drain region of the active layer 220.

The TFT may be electrically connected to a light-emitting device to drive the light-emitting device, and may be covered and protected by a passivation layer 280. The passivation layer 280 may include an inorganic insulating film, an organic insulating film, or any combination thereof. A light-emitting device may be provided on the passivation layer 280. The light-emitting device may include a first electrode 110, an interlayer 130, and a second electrode 150.

The first electrode 110 may be arranged on the passivation layer 280. The passivation layer 280 may not completely cover the drain electrode 270 and may expose a portion of the drain electrode 270, and the first electrode 110 may be electrically connected to the exposed portion of the drain electrode 270.

A pixel defining layer 290 including an insulating material may be arranged on the first electrode 110. The pixel defining layer 290 may expose a region of the first electrode 110, and an interlayer 130 may be formed in the exposed region of the first electrode 110. The pixel defining layer 290 may be a polyimide or polyacrylic organic film. Although not shown in FIG. 2, at least some layers of the interlayer 130 may extend beyond the upper portion of the pixel defining layer 290 to be provided in the form of a common layer.

The second electrode 150 may be arranged on the interlayer 130, and a capping layer 170 may be further included on the second electrode 150. The capping layer 170 may be formed to cover the second electrode 150.

The encapsulation portion 300 may be arranged on the capping layer 170. The encapsulation portion 300 may be arranged on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, or the like), an epoxy-based resin (for example, aliphatic glycidyl ether (AGE), or the like), or any combination thereof; or any combination of the inorganic films and the organic films.

FIG. 3 is a schematic cross-sectional view of an electronic apparatus according to another embodiment.

The electronic apparatus of FIG. 3 may differ from the electronic apparatus of FIG. 2, at least in that a light-shielding pattern 500 and a functional region 400 are further included on the encapsulation portion 300. The functional region 400 may be a color filter area, a color conversion area, or a combination of the color filter area and the color conversion area. In an embodiment, the light-emitting device included in the electronic apparatus of FIG. 3 may be a tandem light-emitting device.

[Manufacturing Method]

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, laser-induced thermal imaging, and the like.

When respective layers included in the hole transport region, the emission layer, and respective layers included in the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

[Definitions of Terms]

The term "$C_3$-$C_{60}$ carbocyclic group" as used herein may be a cyclic group consisting of carbon as the only ring-forming atoms and having three to sixty carbon atoms, and the term "$C_1$-$C_{60}$ heterocyclic group" as used herein may be a cyclic group that has one to sixty carbon atoms and further has, in addition to carbon, at least one heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed with each other. For example, the number of ring-forming atoms in a $C_1$-$C_{60}$ heterocyclic group may be from 3 to 61.

The term "cyclic group" as used herein may include both the $C_3$-$C_{60}$ carbocyclic group or the $C_1$-$C_{60}$ heterocyclic group.

The term "π electron-rich $C_3$-$C_{60}$ cyclic group" as used herein may be a cyclic group that has three to sixty carbon atoms and may not include *—N=*' as a ring-forming moiety, and the term "π electron-deficient nitrogen-containing $C_1$-$C_{60}$ cyclic group" as used herein may be a heterocyclic group that has one to sixty carbon atoms and may include *—N=*' as a ring-forming moiety.

In embodiments, the $C_3$-$C_{60}$ carbocyclic group may be a T1 group or a group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be a T2 group, a group in which at least two T2 groups are condensed with each other, or a group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, or the like), the π electron-rich $C_3$-$C_{60}$ cyclic group may be a T1 group, a group in which at least two T1 groups are condensed with each other, a T3 group, a group in which at least two T3 groups are condensed with each other, or a group in which at least one T3 group and at least one T1 group are condensed with each other (for example, a $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, or the like), and the π electron-deficient nitrogen-containing $C_1$-$C_{60}$ cyclic group may be a T4 group, a group in which at least two T4 groups are condensed with each other, a group in which at least one T4 group and at least one T1 group are condensed with each other, a group in which at least one T4 group and at least one T3 group are condensed with each other, or a group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein may each be a group condensed to any cyclic group, a monovalent group, or a polyvalent group (for example, a divalent group, a trivalent group, a tetravalent group, etc.) according to the structure of a formula for which the corresponding term is used. For example, a "benzene group" may be a benzo group, a phenyl group, a phenylene group, or the like, which may be readily understood by one of ordinary skill in the art according to the structure of a formula including the "benzene group."

Examples of a monovalent $C_3$-$C_{60}$ carbocyclic group and a monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. Examples of a divalent $C_3$-$C_{60}$ carbocyclic group and a divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein may be a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein may be a divalent group having a same structure as the $C_1$-$C_{60}$ alkyl group.

The term "$C_2$-$C_{60}$ alkenyl group" as used herein may be a monovalent hydrocarbon group having at least one carbon-carbon double bond in the middle or at a terminus of a $C_2$-$C_{60}$ alkyl group, and examples thereof may include an ethenyl group, a propenyl group, a butenyl group, and the like. The term "$C_2$-$C_{60}$ alkenylene group" as used herein may be a divalent group having a same structure as the $C_2$-$C_{60}$ alkenyl group.

The term "$C_2$-$C_{60}$ alkynyl group" as used herein may be a monovalent hydrocarbon group having at least one carbon-carbon triple bond in the middle or at a terminus of a $C_2$-$C_{60}$ alkyl group, and examples thereof may include an ethynyl group, a propynyl group, and the like. The term "$C_2$-$C_{60}$ alkynylene group" as used herein may be a divalent group having a same structure as the $C_2$-$C_{60}$ alkynyl group.

The term "$C_1$-$C_{60}$ alkoxy group" as used herein may be a monovalent group represented by —O($A_{101}$) (wherein $A_{101}$ may be a $C_1$-$C_{60}$ alkyl group), and examples thereof may include a methoxy group, an ethoxy group, an isopropyloxy group, and the like.

The term "$C_3$-$C_{10}$ cycloalkyl group" as used herein may be a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, a bicyclo[2.2.2]octyl group, and the like. The term "$C_3$-$C_{10}$ cycloalkylene group" as used herein may be a divalent group having a same structure as the $C_3$-$C_{10}$ cycloalkyl group.

The term "$C_1$-$C_{10}$ heterocycloalkyl group" as used herein may be a monovalent cyclic group of 1 to 10 carbon atoms, further including, in addition to carbon atoms, at least one heteroatom, as ring-forming atoms, and examples thereof may include a 1,2,3,4-oxatriazolidinyl group, a tetrahydrofuranyl group, a tetrahydrothiophenyl group, and the like. The term "$C_1$-$C_{10}$ heterocycloalkylene group" as used herein may be a divalent group having a same structure as the $C_1$-$C_{10}$ heterocycloalkyl group.

The term "$C_3$-$C_{10}$ cycloalkenyl group" as used herein may be a monovalent cyclic group that has three to ten carbon atoms and at least one carbon-carbon double bond in the ring thereof and no aromaticity, and examples thereof may include a cyclopentenyl group, a cyclohexenyl group, a cycloheptenyl group, and the like. The term "$C_3$-$C_{10}$ cycloalkenylene group" as used herein may be a divalent group having a same structure as the $C_3$-$C_{10}$ cycloalkenyl group.

The term "$C_1$-$C_{10}$ heterocycloalkenyl group" as used herein may be a monovalent cyclic group of 1 to 10 carbon atoms, further including, in addition to carbon atoms, at least one heteroatom, as ring-forming atoms, and having at least one carbon-carbon double bond in the cyclic structure thereof. Examples of a $C_1$-$C_{10}$ heterocycloalkenyl group may include a 4,5-dihydro-1,2,3,4-oxatriazolyl group, a 2,3-dihydrofuranyl group, a 2,3-dihydrothiophenyl group, and the like. The term "$C_1$-$C_{10}$ heterocycloalkenylene group" as used herein may be a divalent group having a same structure as the $C_1$-$C_{10}$ heterocycloalkenyl group.

The term "$C_6$-$C_{60}$ aryl group" as used herein may be a monovalent group having a carbocyclic aromatic system of 6 to 60 carbon atoms, and the term "$C_6$-$C_{60}$ arylene group" as used herein may be a divalent group having a carbocyclic aromatic system of 6 to 60 carbon atoms. Examples of a $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, an ovalenyl group, and the like. When the $C_6$-$C_{60}$ aryl group and the $C_6$-$C_{60}$ arylene group each independently include two or more rings, the respective rings may be condensed with each other.

The term "$C_1$-$C_{60}$ heteroaryl group" as used herein may be a monovalent group having a heterocyclic aromatic system of 1 to 60 carbon atoms, further including, in addition to carbon atoms, at least one heteroatom, as ring-forming atoms. The term "$C_1$-$C_{60}$ heteroarylene group" as used herein may be a divalent group having a heterocyclic aromatic system of 1 to 60 carbon atoms, further including, in addition to carbon atoms, at least one heteroatom, as ring-forming atoms. Examples of a $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each independently include two or more rings, the respective rings may be condensed with each other.

The term "monovalent non-aromatic condensed polycyclic group" as used herein may be a monovalent group (for example, having 8 to 60 carbon atoms) having two or more rings condensed to each other, only carbon atoms as ring-forming atoms, and no aromaticity in its entire molecular structure. Examples of a monovalent non-aromatic condensed polycyclic group may include an indenyl group, a fluorenyl group, a spiro-bifluorenyl group, a benzofluorenyl group, an indenophenanthrenyl group, an indeno anthracenyl group, and the like. The term "divalent non-aromatic condensed polycyclic group" as used herein may be a divalent group having a same structure as the monovalent non-aromatic condensed polycyclic group described above.

The term "monovalent non-aromatic condensed heteropolycyclic group" as used herein may be a monovalent group (for example, having 1 to 60 carbon atoms) having two or more rings condensed to each other, further including, in addition to carbon atoms, at least one heteroatom, as ring-forming atoms, and having non-aromaticity in its entire molecular structure. Examples of a monovalent non-aromatic condensed heteropolycyclic group may include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indeno carbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein may be a divalent group having a same structure as the monovalent non-aromatic condensed heteropolycyclic group described above.

The term "$C_6$-$C_{60}$ aryloxy group" as used herein may be a group represented by —$O(A_{102})$ (wherein $A_{102}$ may be a $C_6$-$C_{60}$ aryl group), and the term "$C_6$-$C_{60}$ arylthio group" as used herein may be a group represented by —$S(A_{103})$ (wherein $A_{103}$ may be a $C_6$-$C_{60}$ aryl group).

The term "$C_7$-$C_{60}$ arylalkyl group" as used herein may be a group represented by -$(A_{104})(A_{105})$ (wherein $A_{104}$ may be a $C_1$-$C_{54}$ alkylene group, and $A_{105}$ may be a $C_6$-$C_{59}$ aryl group), and the term "$C_2$-$C_{60}$ heteroarylalkyl group" as used herein may be a group represented by -$(A_{106})(A_{107})$ (wherein $A_{106}$ may be a $C_1$-$C_{59}$ alkylene group, and $A_{107}$ may be a $C_1$-$C_{59}$ heteroaryl group).

In the specification, the group "$R_{10a}$" may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_6$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, or a $C_2$-$C_{60}$ heteroarylalkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

In the specification, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, a $C_7$-$C_{60}$ arylalkyl group, or a $C_2$-$C_{60}$ heteroarylalkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "heteroatom" as used herein may be any atom other than a carbon atom or a hydrogen atom. Examples of a heteroatom may include O, S, N, P, Si, B, Ge, Se, or any combination thereof.

The term "third-row transition metal" as used herein may include Hf, Ta, W, Re, Os, Ir, Pt, Au, or the like.

The term "Ph" as used herein refers to a phenyl group, the term "Me" as used herein refers to a methyl group, the term "Et" as used herein refers to an ethyl group, the terms "tert-Bu" or "But" as used herein each refer to a tert-butyl group, and the term "OMe" as used herein refers to a methoxy group.

The term "biphenyl group" as used herein may be a "phenyl group substituted with a phenyl group." For example, the "biphenyl group" may be a substituted phenyl group having a $C_6$-$C_{60}$ aryl group as a substituent.

The term "terphenyl group" as used herein may be a "phenyl group substituted with a biphenyl group." For example, the "terphenyl group" may be a substituted phenyl group having, as a substituent, a $C_6$-$C_{60}$ aryl group substituted with a $C_6$-$C_{60}$ aryl group.

The symbols * and *' as used herein, unless defined otherwise, each refer to a binding site to a neighboring atom in a corresponding formula or moiety.

Hereinafter, compounds according to embodiments and light-emitting devices according to embodiments will be described in detail with reference to the following Synthesis Examples and Examples. The wording "B was used instead of A" used in describing Synthesis Examples means that an identical molar equivalent of B was used in place of A.

EXAMPLES

Synthesis Examples

Synthesis Example 1: Synthesis of Compound 1

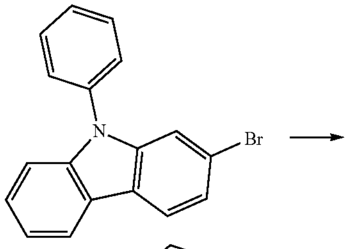

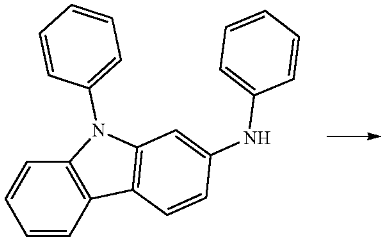

1a

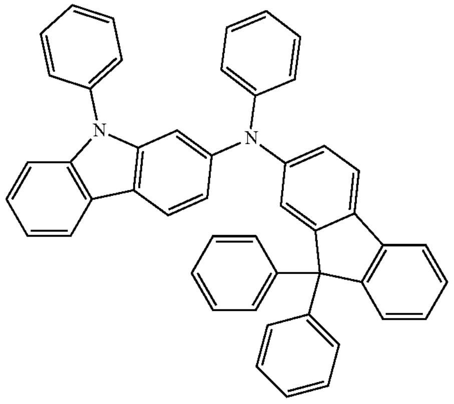

1

1. Synthesis of Intermediate 1a 2-bromo-9-phenyl-9H-carbazole (1 eq.), aniline (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred for 2 hours at 80° C. in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 1a. (Yield: 85%)

2. Synthesis of Compound 1

Intermediate 1a (1 eq.), 2-bromo-9,9-diphenyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred for 2 hours at 80° C. in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 1. (Yield: 86%, HRMS (ESI): calcd.: 650.2722; found: 650.2720).

Synthesis Example 2: Synthesis of Compound 3

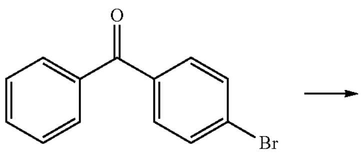

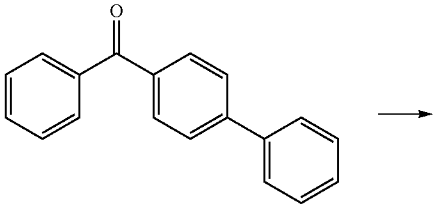

3a

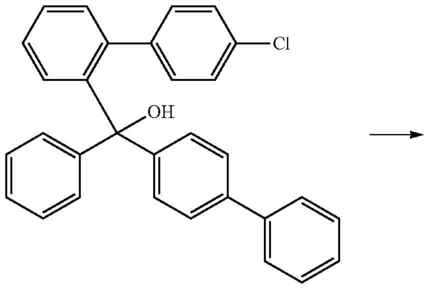

3b

-continued

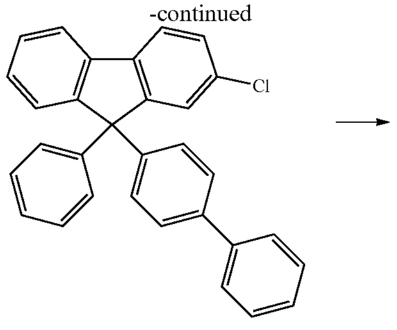

3c

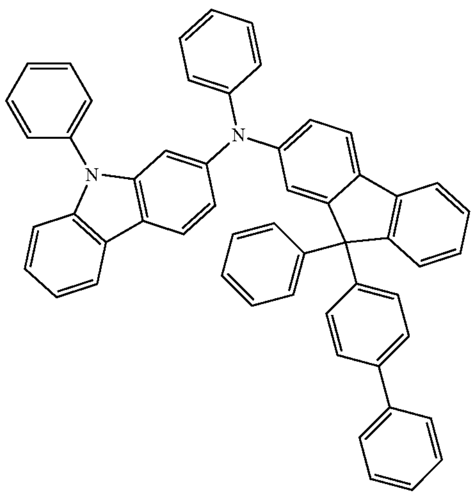

3

1. Synthesis of Intermediate 3a (4-bromophenyl)(phenyl)methanone (1.0 eq.), phenylboronic acid (1.0 eq.), tetrakis(triphenylphosphine)palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 3a. (Yield: 62%)

2. Synthesis of Intermediate 3b 2-bromo-4'-chloro-1,1'-biphenyl (1.0 eq.) and tetrahydrofuran were cooled to −78° C. while stirring. n-butyl lithium (1.1 eq.) was slowly added dropwise to the mixed solution and stirred at −78° C. for 1 hour. Intermediate 3a (1.1 eq.) was slowly added dropwise thereto at −78° C. and stirred at room temperature for 4 hours to obtain a reaction mixture. An extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 3b. (Yield: 69%)

3. Synthesis of Intermediate 3c

Intermediate 3b (1.0 eq.) was dissolved in a solution containing acetic acid and hydrochloric acid at a volume ratio of 9:1, and stirred at 80° C. for 2 hours in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 3c. (Yield: 69%)

4. Synthesis of Compound 3

Intermediate 3c (1 eq.), 1a (1 eq.), Intermediate tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 3. (Yield: 86% HRMS (ESI): calcd.: 726.3035; found: 726.3037).

Synthesis Example 3: Synthesis of Compound 7

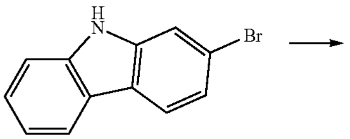

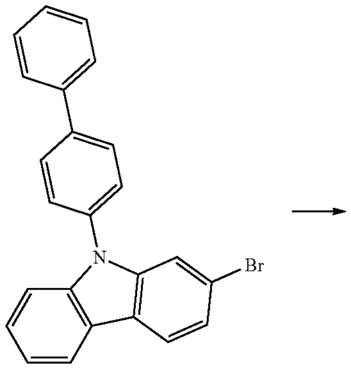

7a

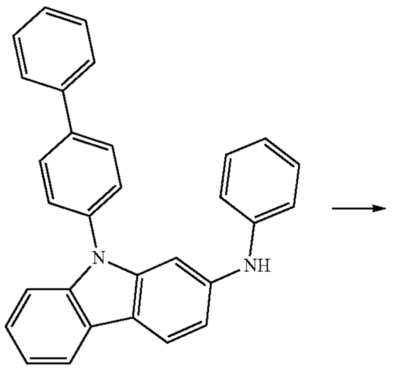

7b

-continued

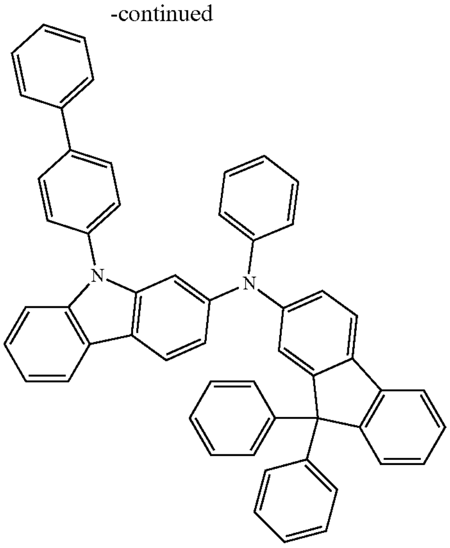

7

1. Synthesis of Intermediate 7a 2-bromo-9H-carbazole (1 eq.), 4-iodo-1,1'-biphenyl (1 eq.), copper iodide (0.03 eq.), and potassium carbonate (2.0 eq.) were dissolved in dimethyl formamide (DMF) and stirred in a nitrogen atmosphere at 120° C. for 8 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 7a.

2. Synthesis of Intermediate 7b

Intermediate 7a (1 eq.), aniline (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 7b. (Yield: 85%)

3. Synthesis of Compound 7

Intermediate 7a (1 eq.), 2-bromo-9,9-diphenyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 7. (Yield: 86%, HRMS (ESI): calcd.: 726.3035; found: 726.3030).

Synthesis Example 4: Synthesis of Compound 15

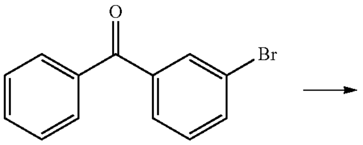

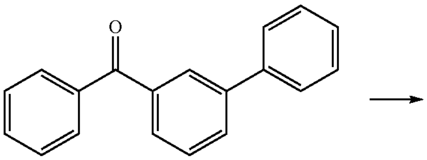

15a

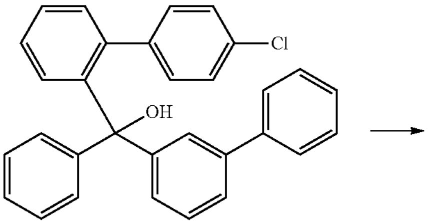

15b

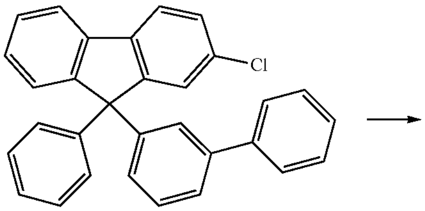

15c

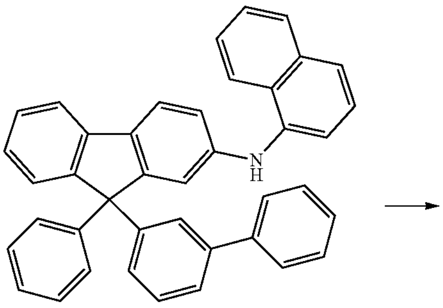

15d

-continued

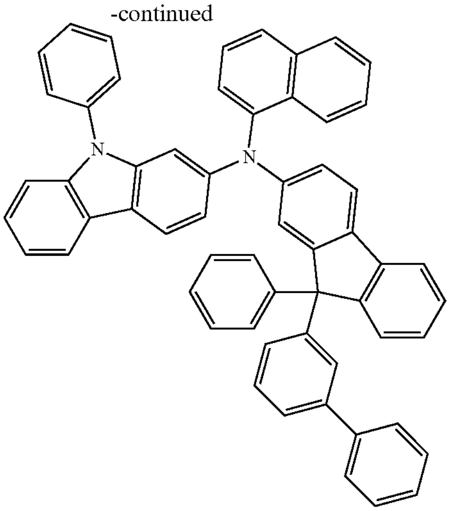

15

1. Synthesis of Intermediate 15a (3-bromophenyl)(phenyl)methanone (1.0 eq.), phenylboronic acid (1.0 eq.), tetrakis(triphenylphosphine)palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 15a. (Yield: 62%)

2. Synthesis of Intermediate 15b 2-bromo-4'-chloro-1,1'-biphenyl (1.0 eq.) and tetrahydrofuran were cooled to −78° C. while stirring. n-butyl lithium (1.1 eq) was slowly added dropwise to the mixed solution and stirred at −78° C. for 1 hour. Intermediate 15a (1.1 eq.) was slowly added dropwise thereto at −78° C. and stirred at room temperature for 4 hours to obtain a reaction mixture. An extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 15b. (Yield: 69%)

3. Synthesis of Intermediate 15c

Intermediate 15b (1.0 eq.) was dissolved in a solution containing acetic acid and hydrochloric acid at a volume ratio of 9:1, and stirred at 80° C. for 2 hours in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 15c. (Yield: 69%)

4. Synthesis of Intermediate 15d

Intermediate 15c (1 eq.), 1-aminonaphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 15d. (Yield: 85%)

5. Synthesis of Compound 15

Intermediate 15d (1 eq.), 2-bromo-9-phenyl-9H-carbazole (1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 15. (Yield: 86%, HRMS (ESI): calcd.: 776.3191; found: 776.3189).

Synthesis Example 5: Synthesis of Compound 83

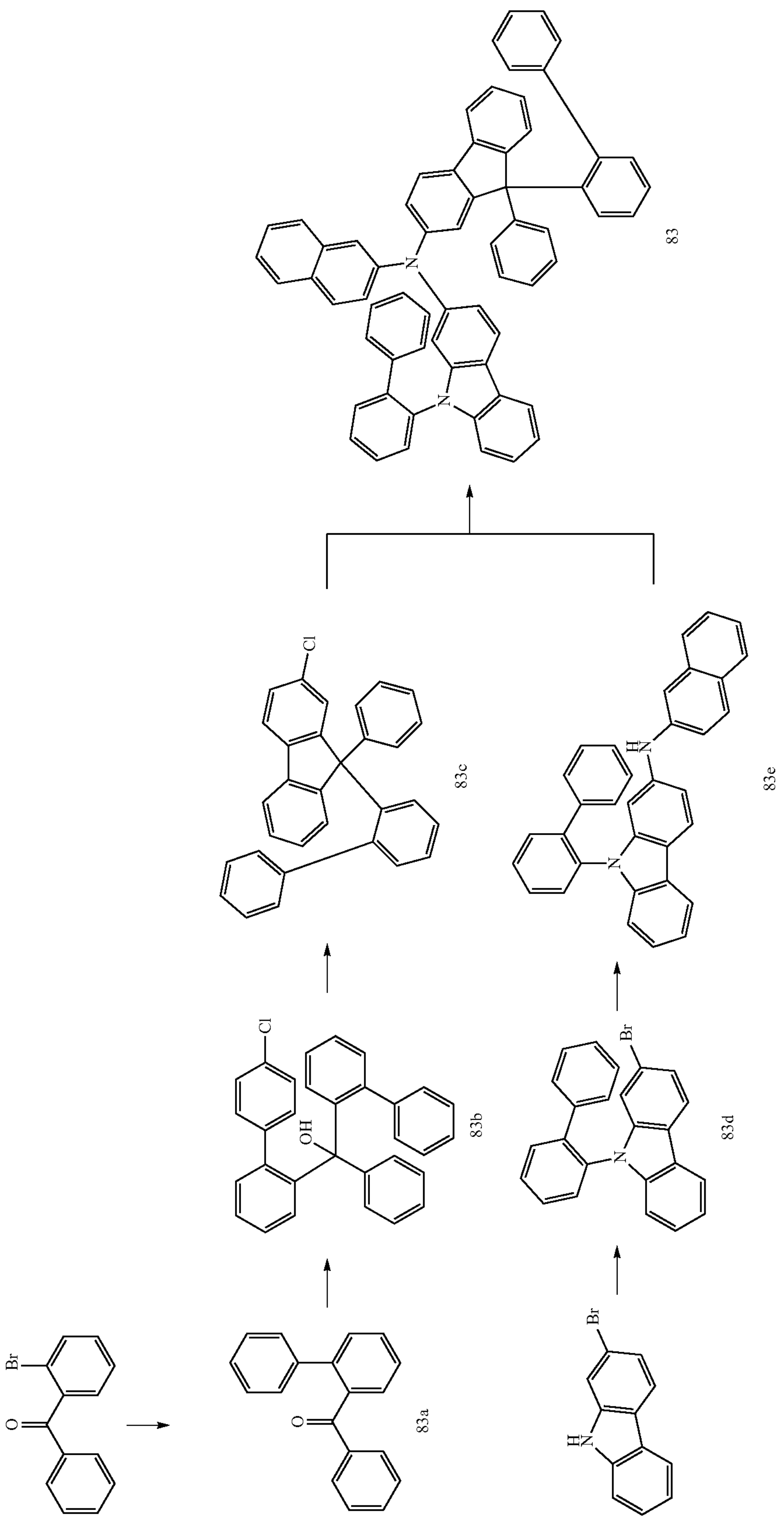
83
83c
83e
83b
83d
83a

1. Synthesis of Intermediate 83a (2-bromophenyl)(phenyl)methanone (1.0 eq.), phenylboronic acid (1.0 eq.), tetrakis(triphenylphosphine)palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 83a. (Yield: 62%)

2. Synthesis of Intermediate 83b 2-bromo-4'-chloro-1,1'-biphenyl (1.0 eq) and tetrahydrofuran were cooled to −78° C. while stirring. n-butyl lithium (1.1 eq) was slowly added dropwise to the mixed solution and stirred at −78° C. for 1 hour. Intermediate 83a (1.1 eq.) was slowly added dropwise thereto at −78° C. and stirred at room temperature for 4 hours to obtain a reaction mixture. An extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 83b. (Yield: 69%)

3. Synthesis of Intermediate 83c

Intermediate 83b (1.0 eq.) was dissolved in a solution containing acetic acid and hydrochloric acid at a volume ratio of 9:1, and stirred at 80° C. for 2 hours in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 83c. (Yield: 69%)

4. Synthesis of Intermediate 83d 2-bromo-9H-carbazole (1 eq.), 2-iodo-1,1'-biphenyl (1 eq.), copper(I) iodide (0.03 eq.), and potassium carbonate (2.0 eq.) were dissolved in DMF and stirred in a nitrogen atmosphere at 120° C. for 8 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 83d.

5. Synthesis of Intermediate 83e

Intermediate 83d (1 eq.), 2-aminonaphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 83e. (Yield: 85%)

6. Synthesis of Compound 83

Intermediate 83e (1 eq.), Intermediate 83c (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 83. (Yield: 86%, HRMS (ESI): calcd.: 852.3504; found: 852.3506).

Synthesis Example 6: Synthesis of Compound 92

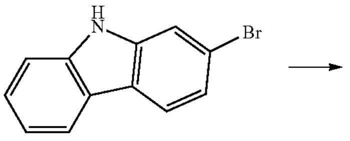

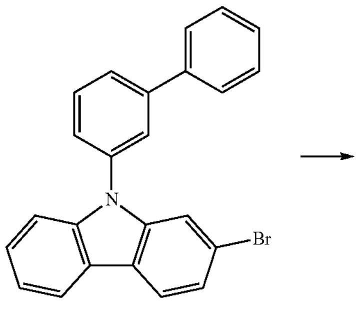

92a

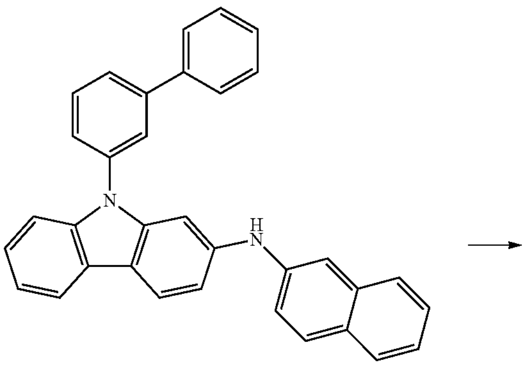

92b

-continued

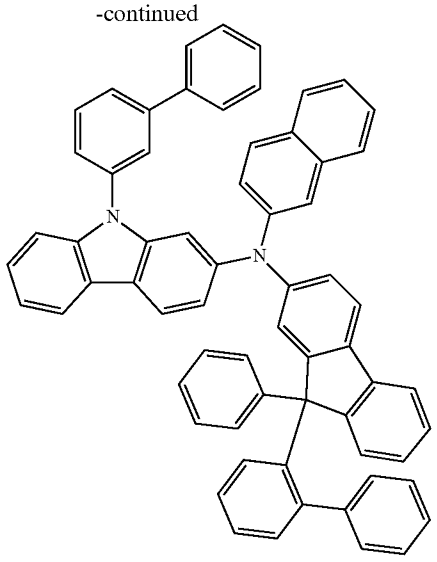

92

1. Synthesis of Intermediate 92a 2-bromo-9H-carbazole (1 eq.), 3-iodo-1,1'-biphenyl (1 eq.), copper iodide (0.03 eq.), and potassium carbonate (2.0 eq.) were dissolved in DMF and stirred in a nitrogen atmosphere at 120° C. for 8 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 92a.

2. Synthesis of Intermediate 92b

Intermediate 92a (1 eq.), 2-aminonaphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 92b. (Yield: 85%)

3. Synthesis of Compound 92

Intermediate 92b (1 eq.), Intermediate 83c (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 92. (Yield: 86%, HRMS (ESI): calcd.: 852.3504; found: 852.3508).

Synthesis Example 7: Synthesis of Compound 94

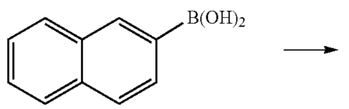

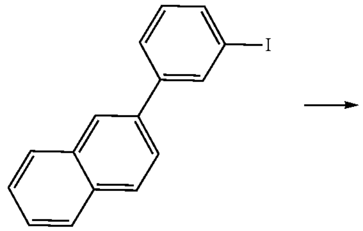

94a

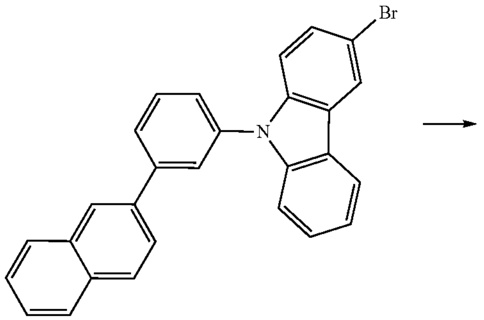

94b

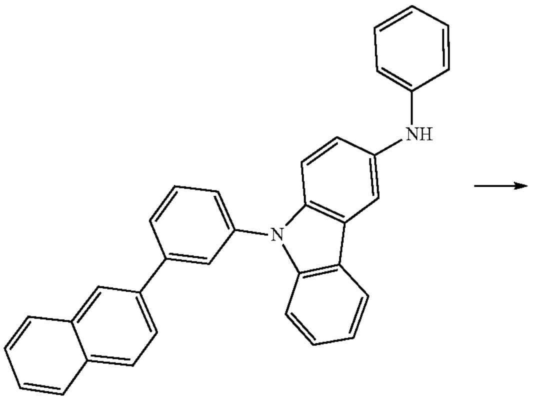

94c

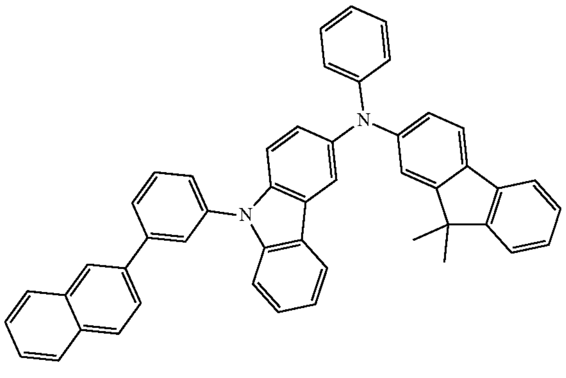

94

1. Synthesis of Intermediate 94a

Naphthalen-2-boronic acid (1.0 eq.), 1,3-diiodobenzene (1.0 eq.), tetrakis(triphenylphosphine)palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 94a. (Yield: 62%)

2. Synthesis of Intermediate 94b 3-bromo-9H-carbazole (1 eq.), Intermediate 94a (1 eq.), copper(I) iodide (0.03 eq.), and potassium carbonate (2.0 eq.) were dissolved in DMF and stirred in a nitrogen atmosphere at 120° C. for 8 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 94b.

3. Synthesis of Intermediate 94b

Intermediate 94b (1.1 eq.), aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 94c. (Yield: 86%)

4. Synthesis of Compound 94

Intermediate 94c (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 94. (Yield: 86%, HRMS (ESI): calcd.: 652.2878; found: 652.2880).

Synthesis Example 8: Synthesis of Compound 99

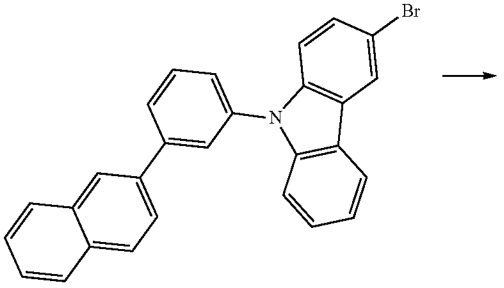

-continued

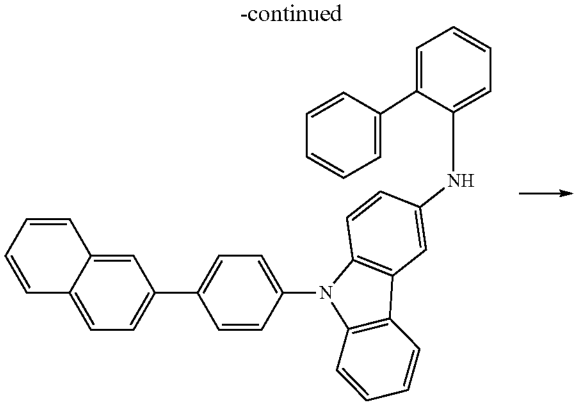

99a

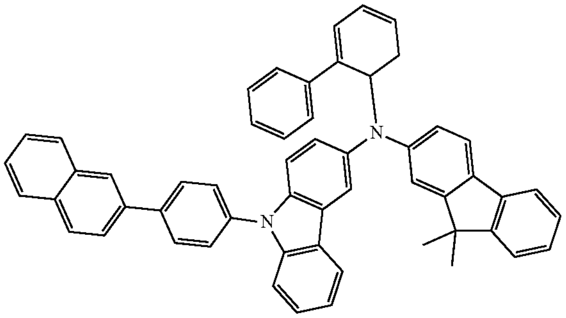

99

1. Synthesis of Intermediate 99a

Intermediate 94b (1.1 eq.), [1,1'-biphenyl]-2-amine (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 99a. (Yield: 86%)

2. Synthesis of Compound 99

Intermediate 99a (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 99. (Yield: 86%, HRMS (ESI): calcd.: 728.3191; found: 728.3195).

Synthesis Example 9: Synthesis of Compound 100

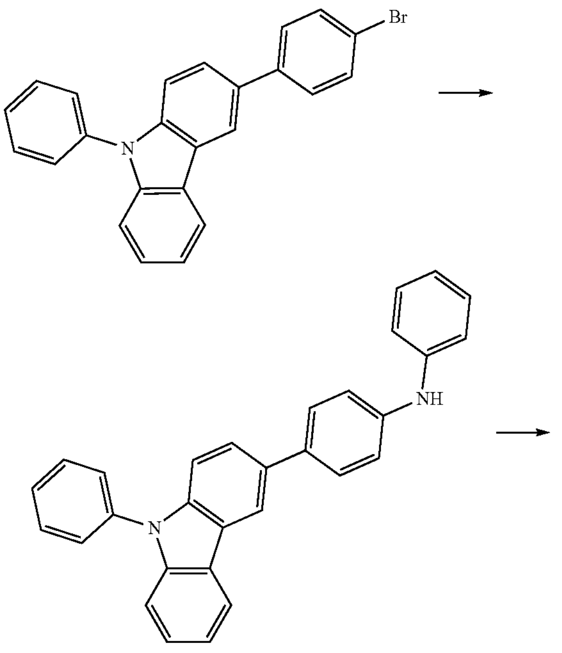

100a

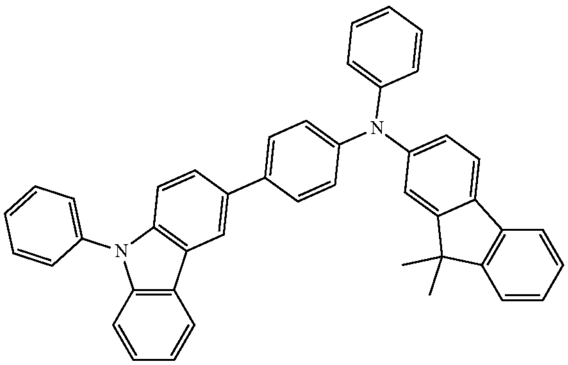

100

1. Synthesis of Intermediate 100a 3-(4-bromophenyl)-9-phenyl-9H-carbazole (1.1 eq.), aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 100a. (Yield: 86%)

2. Synthesis of Compound 100

Intermediate 100a (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 100. (Yield: 86%, HRMS (ESI): calcd.: 602.2722; found: 602.2724).

Synthesis Example 10: Synthesis of Compound 105

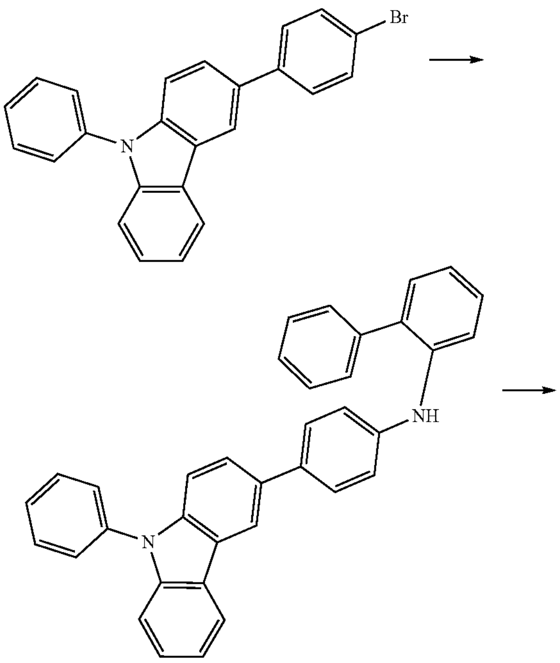

105a

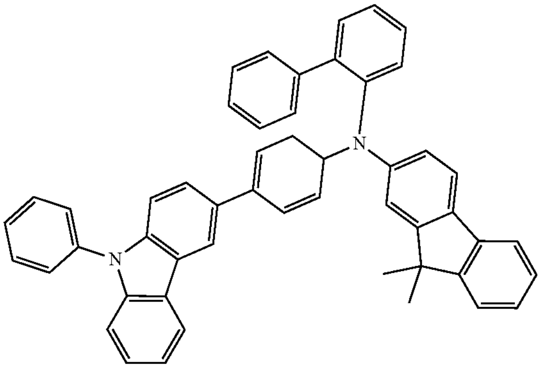

105

1. Synthesis of Intermediate 105a 3-(4-bromophenyl)-9-phenyl-9H-carbazole (1.1 eq.), [1,1'-biphenyl]-2-amine (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 105a. (Yield: 86%)

2. Synthesis of Compound 105

Intermediate 105a (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 105. (Yield: 86%, HRMS (ESI): calcd.: 678.3035; found: 678.3040).

Synthesis Example 11: Synthesis of Compound 110

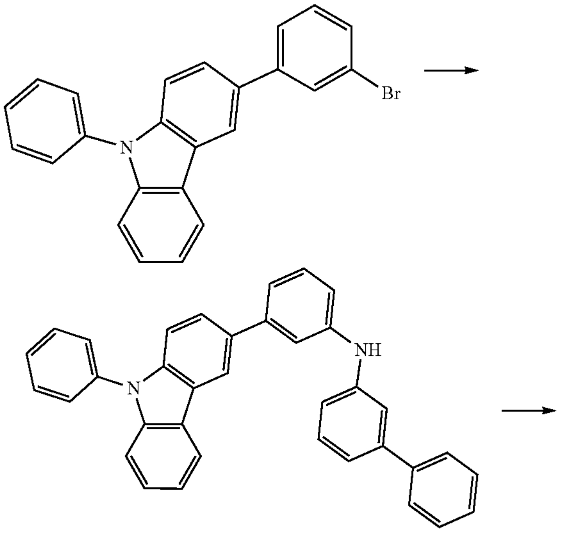

110a

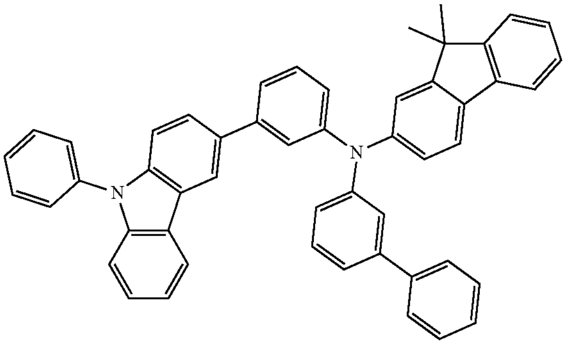

110

1. Synthesis of Intermediate 110a 3-(3-bromophenyl)-9-phenyl-9H-carbazole (1.1 eq.), [1,1'-biphenyl]-3-amine (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 110a. (Yield: 86%)

2. Synthesis of Compound 110

Intermediate 110a (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 110. (Yield: 86%, HRMS (ESI): calcd.: 678.3035; found: 678.3038).

Synthesis Example 12: Synthesis of Compound 113

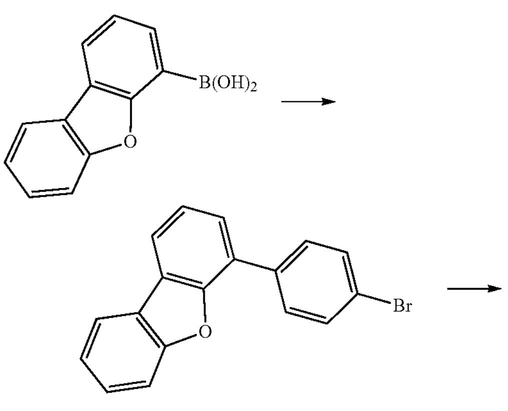

113a

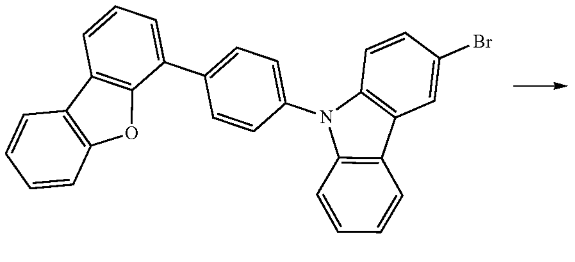

113b

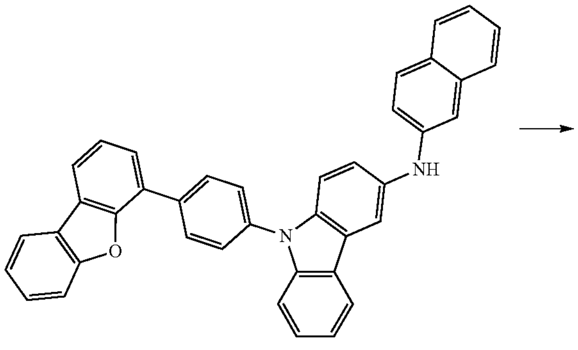

113c

-continued

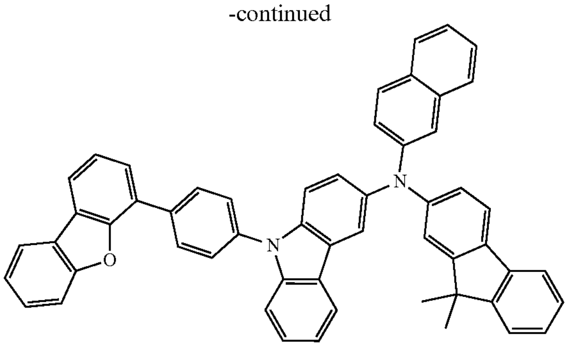

113

1. Synthesis of Intermediate 113a

Dibenzo[b,d]furan-4-ylboronic acid (1.0 eq.), 4-bromophenylboronic acid (1.0 eq.), tetrakis(triphenylphosphine) palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 113a. (Yield: 62%)

2. Synthesis of Intermediate 113b 3-bromo-9H-carbazole (1 eq.), Intermediate 113a (1 eq.), copper(I) iodide (0.03 eq.), and potassium carbonate (2.0 eq.) were dissolved in DMF and stirred in a nitrogen atmosphere at 120° C. for 8 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 113b.

3. Synthesis of Intermediate 113c

Intermediate 113b (1.1 eq.), 2-aminonaphthalene (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 113c. (Yield: 86%)

4. Synthesis of Compound 113

Intermediate 113c (1 eq.), 2-bromo-9,9-dimethyl-9H-fluorene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 113. (Yield: 86%, HRMS (ESI): calcd.: 742.2984; found: 742.2988).

Synthesis Example 13: Synthesis of Compound 124

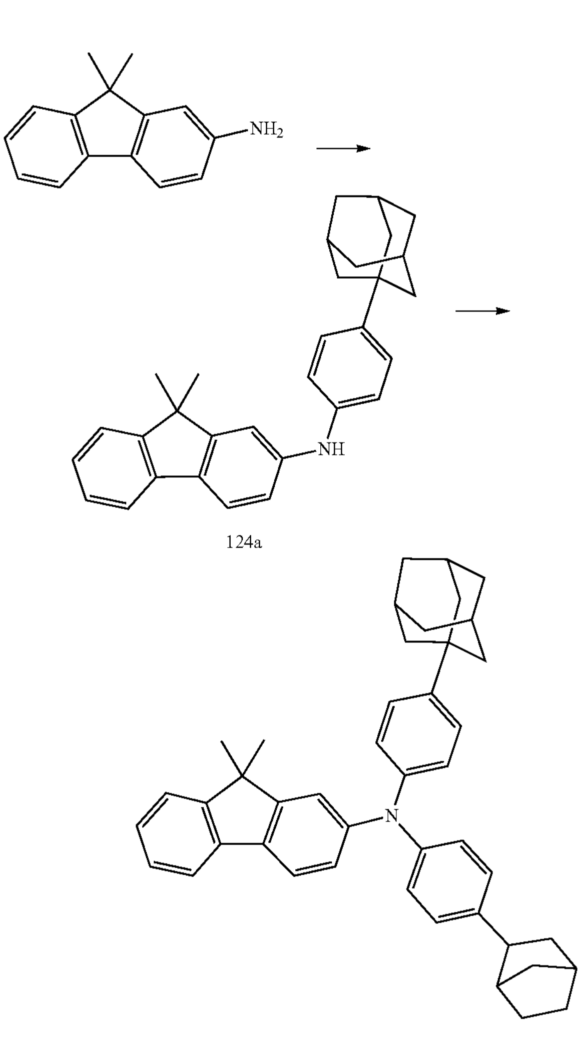

124a

124

1. Synthesis of Intermediate 124a 9,9-dimethyl-9H-fluoren-2-amine (1.0 eq.), 1-(4-bromophenyl) adamantane (1.0 eq.), tris(dibenzylideneacetone) dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 124a. (Yield: 86%)

2. Synthesis of Compound 124

Intermediate 124a (1.0 eq.), 2-(4-bromophenyl) bicyclo [2.2.1]heptane (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 124. (Yield: 86% HRMS (ESI): calcd.: 589.3709; found: 589.3713).

Synthesis Example 14: Synthesis of Compound 147

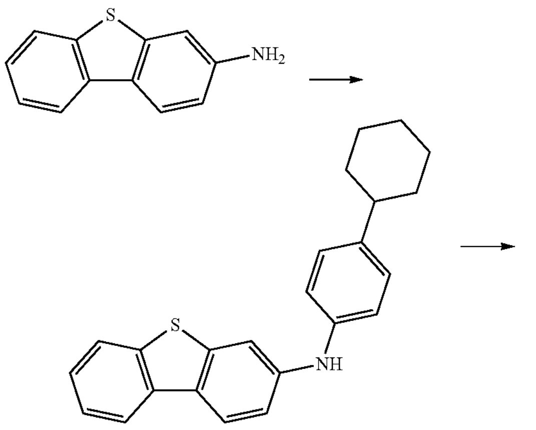

147a

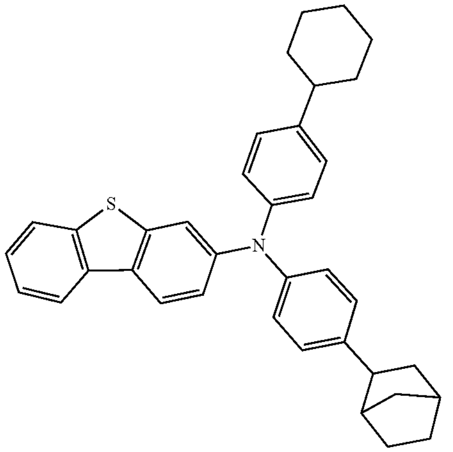

147

1. Synthesis of Intermediate 147a

Dibenzo[b,d]thiophen-3-amine (1.0 eq.), 1-bromo-4-cyclohexylbenzene (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 147a. (Yield: 86%)

2. Synthesis of Compound 147

Intermediate 147a (1.0 eq.), 2-(4-bromophenyl) bicyclo [2.2.1]heptane (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 147. (Yield: 86%, HRMS (ESI): calcd.: 527.2647; found: 527.2650).

Synthesis Example 15: Synthesis of Compound 163

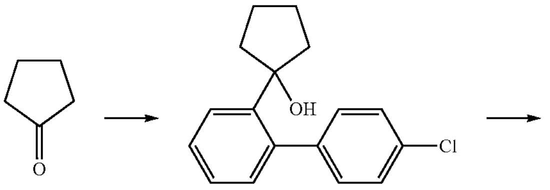

163a

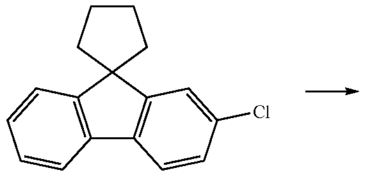

163b

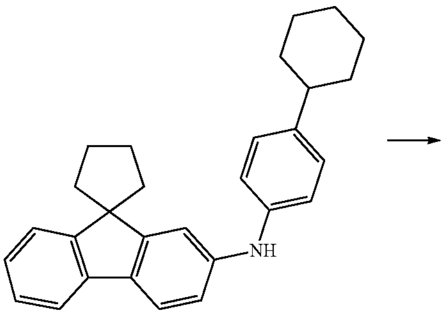

163c

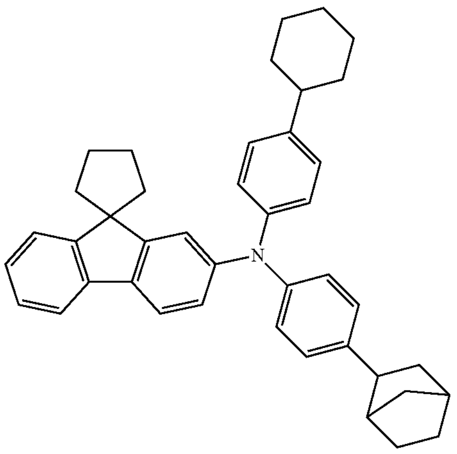

163

1. Synthesis of Intermediate 163a 2-bromo-4'-chloro-1,1'-biphenyl (1.0 eq) and tetrahydrofuran were cooled to −78° C. while stirring. n-butyl lithium (1.1 eq) was slowly added dropwise to the mixed solution and stirred at −78° C. for 1 hour. Cyclopentanone (1.1 eq.) was slowly added dropwise thereto at −78° C. and stirred at room temperature for 4 hours to obtain a reaction mixture. An extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 163a. (Yield: 69%)

2. Synthesis of Intermediate 163b

Intermediate 163a (1.0 eq.) was dissolved in a solution containing acetic acid and hydrochloric acid at a volume ratio of 9:1, and stirred at 80° C. for 2 hours in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 163b. (Yield: 69%)

3. Synthesis of Intermediate 163c

Intermediate 163b (1.1 eq.), 4-cyclohexylaniline (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 163c. (Yield: 85%)

4. Synthesis of Compound 163

Intermediate 163c (1 eq.), 2-(4-bromophenyl) bicyclo [2.2.1]heptane (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 163. (Yield: 86%, HRMS (ESI): calcd.: 563.3552; found: 563.3555).

Synthesis Example 16: Synthesis of Compound 181

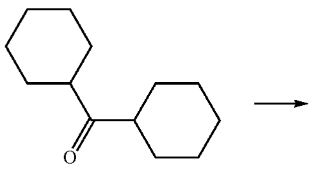

-continued

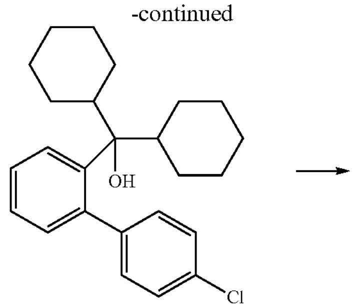

181a

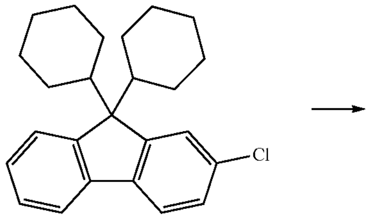

181b

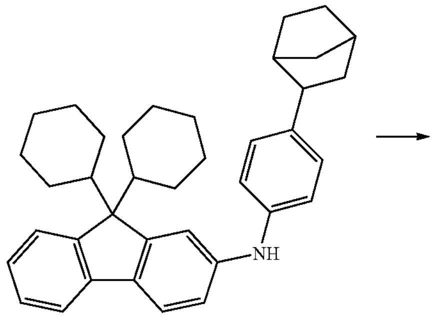

181c

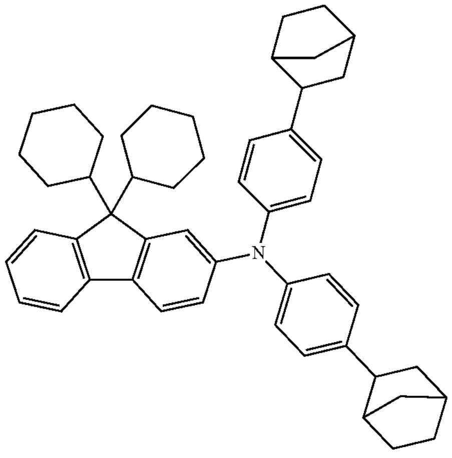

181

1. Synthesis of Intermediate 181a 2-bromo-4'-chloro-1,1'-biphenyl (1.0 eq) and tetrahydrofuran were cooled to −78° C. while stirring. n-butyl lithium (1.1 eq) was slowly added dropwise to the mixed solution and stirred at −78° C. for 1 hour. Dicyclohexylmethanone (1.1 eq.) was slowly added dropwise thereto at −78° C. and stirred at room temperature for 4 hours to obtain a reaction mixture. An extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 181a. (Yield: 69%)

2. Synthesis of Intermediate 181b

Intermediate 181 (1.0 eq.) was dissolved in a solution containing acetic acid and hydrochloric acid at a volume ratio of 9:1, and stirred at 80° C. for 2 hours in a nitrogen atmosphere to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 181b. (Yield: 69%)

3. Synthesis of Intermediate 181c

Intermediate 181b (1.1 eq.), 4-(bicyclo[2.2.1]heptan-2-yl) aniline (1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 181c. (Yield: 85%)

4. Synthesis of Compound 181

Intermediate 181c (1 eq.), 2-(4-bromophenyl) bicyclo [2.2.1]heptane (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 181. (Yield: 86%, HRMS (ESI): calcd.: 685.4648; found: 685.4650).

Synthesis Example 17: Synthesis of Compound 185

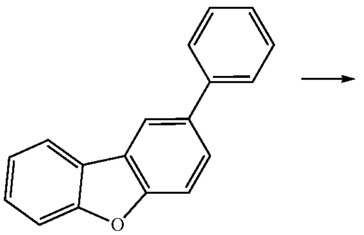

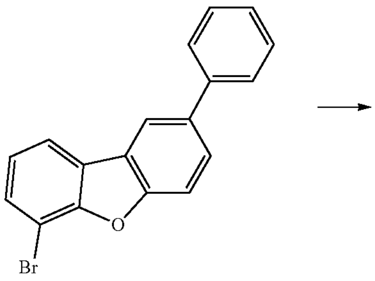

185a

-continued

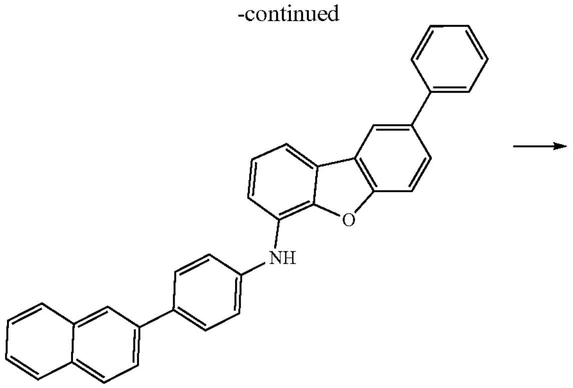

185b

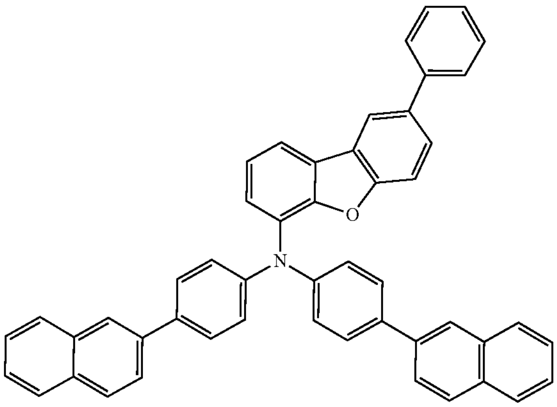

185

1. Synthesis of Intermediate 185a 2-phenyldibenzo[b,d]furan (1.0 eq.) and tetrahydrofuran were cooled to −78° C. while stirring. n-butyl lithium (1.1 eq) was slowly added dropwise to the mixed solution and stirred at −78° C. for 1 hour. Bromine (1.2 eq.) was slowly added dropwise thereto at −78° C. and stirred at room temperature for 4 hours to obtain a reaction mixture. After a sodium thiosulfate solution was added dropwise thereto, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 185a. (Yield: 49%)

2. Synthesis of Intermediate 185b

Intermediate 185a (1.1 eq.), 4-(naphthalen-2-yl) aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 185b. (Yield: 86%)

3. Synthesis of Compound 185

Intermediate 185b (1 eq.), 2-(4-bromophenyl) naphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 185. (Yield: 86%, HRMS (ESI): calcd.: 663.2562; found: 663.2565).

Synthesis Example 18: Synthesis of Compound 188

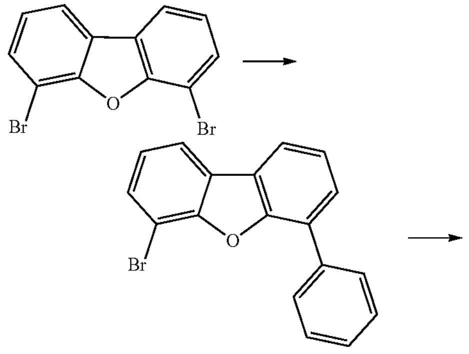

188a

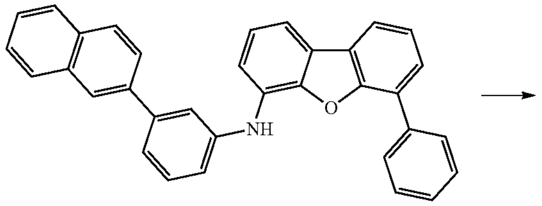

188b

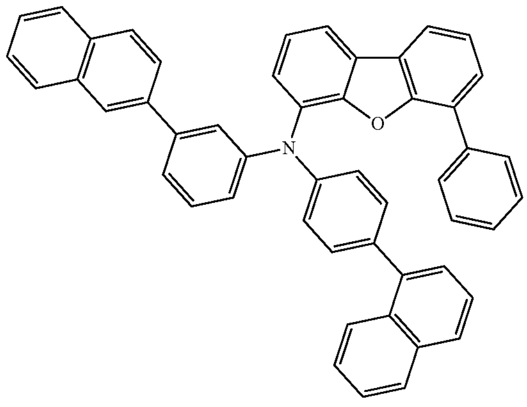

188

1. Synthesis of Intermediate 188a 4,6-dibromodibenzo[b,d]furan (1.0 eq), phenylboronic acid (1.0 eq.), tetrakis(triphenylphosphine)palladium (0.05 eq.), and potassium carbonate (2.0 eq.) were dissolved in a solution containing THF and $H_2O$ mixed at a volume ratio of 4:1, and stirred in a nitrogen atmosphere at 90° C. for 12 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 188a. (Yield: 62%)

2. Synthesis of Intermediate 188b

Intermediate 188a (1.1 eq.), 3-(naphthalen-2-yl) aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 188b. (Yield: 86%)

3. Synthesis of Compound 188

Intermediate 188a (1.0 eq.), 1-(4-bromophenyl) naphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 188. (Yield: 86%, HRMS (ESI): calcd.: 663.2562; found: 663.2560).

Synthesis Example 19: Synthesis of Compound 194

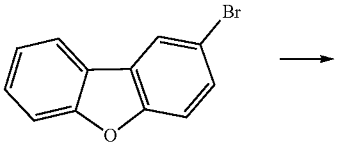

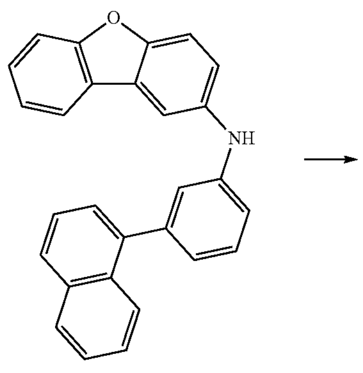

194a

-continued

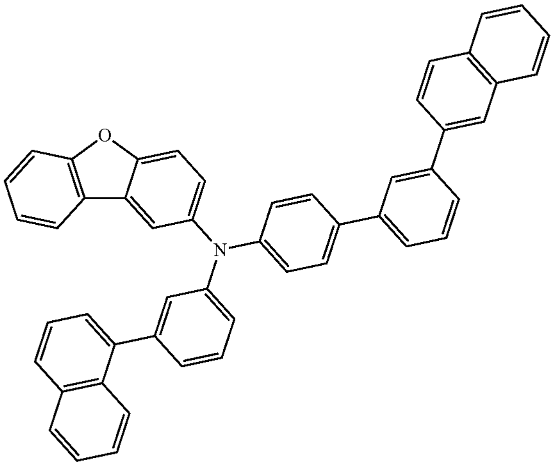

194

1. Synthesis of Intermediate 194a 2-bromodibenzo[b,d]furan (1.0 eq), 3-(naphthalen-1-yl) aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 194a. (Yield: 86%)

2. Synthesis of Compound 194

Intermediate 194a (1.0 eq.), 2-(4'-bromo-[1,1'-biphenyl]-3-yl) naphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 194. (Yield: 86%, HRMS (ESI): calcd.: 663.2562; found: 663.2559).

Synthesis Example 20: Synthesis of Compound 207

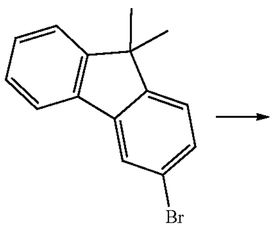

-continued

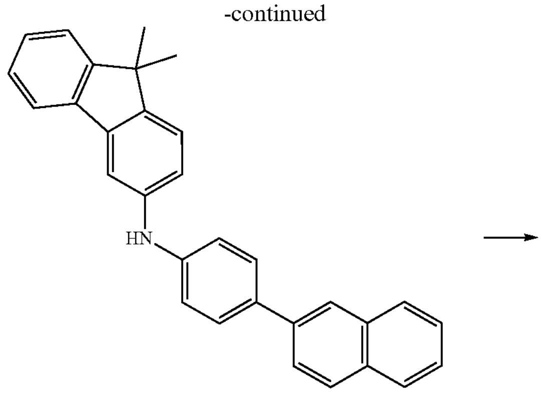

207a

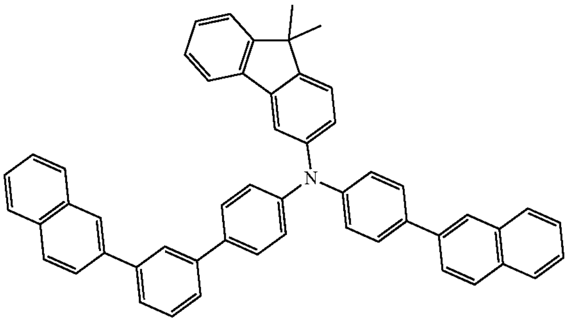

207

1. Synthesis of Intermediate 207a 3-bromo-9,9-dimethyl-9H-fluorene (1.1 eq), 4-(naphthalen-2-yl) aniline (1.0 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Intermediate 207a. (Yield: 86%)

2. Synthesis of Compound 207

Intermediate 207a (1.0 eq.), 2-(4'-bromo-[1,1'-biphenyl]-3-yl) naphthalene (1.1 eq.), tris(dibenzylideneacetone)dipalladium(0) (0.03 eq.), tri-tert-butylphosphine (0.06 eq.), and sodium tert-butoxide (2.0 eq.) were dissolved in toluene and stirred in a nitrogen atmosphere at 80° C. for 2 hours to obtain a reaction mixture. After cooling the reaction mixture, an extraction process was performed thereon by using ethyl acetate and water three times each, and an organic layer thus obtained was dried by using $MgSO_4$ first and dried again under reduced pressure. The resultant product was subjected to column chromatography, thereby obtaining Compound 207. (Yield: 86%, HRMS (ESI): calcd.: 689.3083; found: 689.3090).

Synthesis methods of compounds other than the compounds synthesized in Synthesis Examples may be readily recognized by those skilled in the art by referring to the synthesis paths and source materials.

Comparative Example 1

As an anode, a 15 Ω/$cm^2$ (1,200 Å) ITO glass substrate (product of Corning Co., Ltd) was cut to a size of 50 mm×50 mm×0.7 mm, sonicated in isopropyl alcohol and pure water for 5 minutes in each solvent, cleaned by irradiation of ultraviolet rays and exposure to ozone thereto for 30 minutes, and loaded onto a vacuum deposition apparatus.

N4,N4'-diphenyl-N4,N4'-bis(9-phenyl-9H-carbazol-3-yl)-[1,1'-biphenyl]-4,4'-diamine (hereinafter referred to as HIL 1) was vacuum-deposited on the anode to form a hole injection layer having a thickness of 200 Å, and Compound 103 was vacuum-deposited on the hole injection layer to form a hole transport layer having a thickness of 900 Å.

2-(10-phenylanthracen-9-yl)dibenzo[b,d]furan (hereinafter referred to as Host 1) as a host and 5,9-bis(4-(tert-butyl)phenyl)-7-methyl-5,9-dihydro-5,9-diaza-13b-boranaphtho[3,2,1-de]anthracene (hereinafter referred to as Dopant 1) as a dopant were co-deposited on the hole transport layer at a weight ratio of 98:2 to form an emission layer having a thickness of 250 Å.

$Alq_3$ was vacuum-deposited on the emission layer to form an electron transport layer having a thickness of 300 Å. LiF, which is a halogenated alkali metal, was vacuum-deposited on the electron transport layer to form an electron injection layer having a thickness of 100 Å, and Al was vacuum-deposited thereon to form a cathode having a thickness of 3,000 Å to thereby form a LiF/Al electrode, thereby completing manufacture of a light-emitting device.

HIL 1

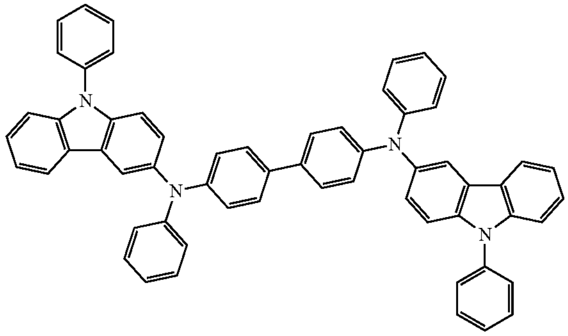

-continued

103

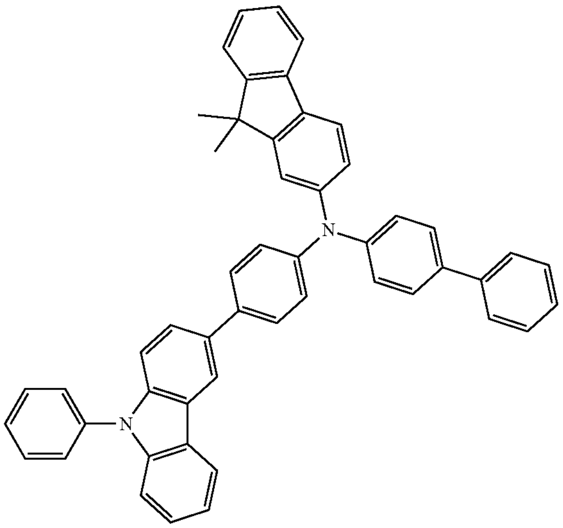

Host 1

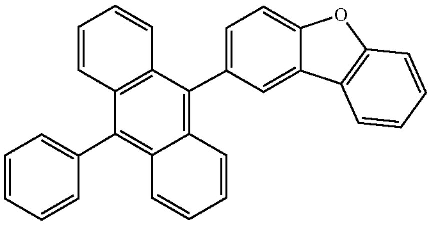

Dopant 1

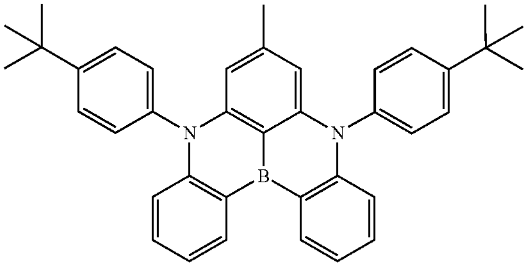

Comparative Example 2

A light-emitting device was manufactured in the same manner as in Comparative Example 1, except that, in forming a hole transport layer, a two-layer hole transport layer was formed by arranging a first hole transport layer and a second hole transport layer in the stated order from the anode by using compounds shown in Table 1.

1

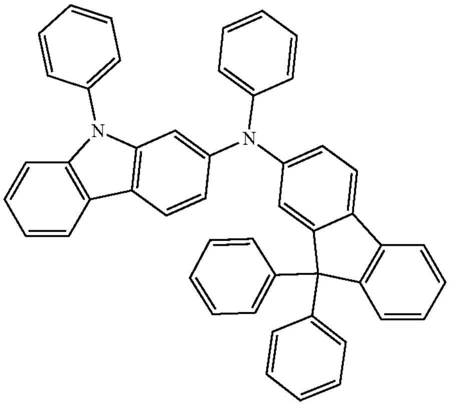

106

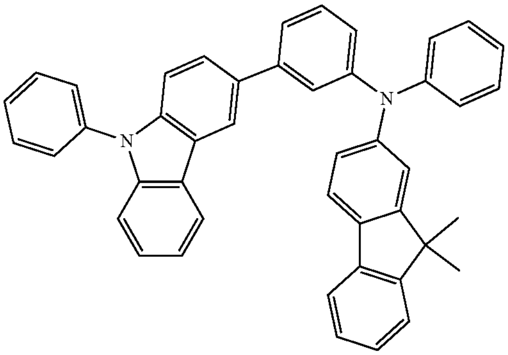

Examples 1 to 4

Light-emitting devices were each manufactured in the same manner as in Comparative Example 1, except that, in forming a hole transport layer, a three-layer hole transport layer was formed by arranging a first hole transport layer, a second hole transport layer, and a third hole transport layer in the stated order from the anode by using compounds shown in Table 1.

Examples 5 to 9

Light-emitting devices were each manufactured in the same manner as in Comparative Example 1, except that, in forming a hole transport layer, a four-layer hole transport layer was formed by arranging a first hole transport layer, a second hole transport layer, a third hole transport layer, and a fourth in the stated order from the anode by using compounds shown in Table 1.

Evaluation Example 1 (Evaluation of Characteristics of Light-Emitting Device)

To evaluate characteristics of the light-emitting devices of the Examples and the Comparative Examples above, the driving voltage (V) at a current density of 50 mA/cm$^2$, luminance (Cd/m$^2$), luminescence efficiency (Cd/A), and half lifespan of the light-emitting devices were each measured by utilizing a Keithley SMU 236 and a luminance meter PR650, and results thereof are shown in Table 2. In Table 2, the half lifespan is a measure of the time (hr) it takes for the luminance to each 50% of the initial luminance at a current density of 100 mA/cm$^2$.

TABLE 1

| | Hole injection layer | First hole transport layer | Second hole transport layer | Third hole transport layer | Fourth hole transport layer |
|---|---|---|---|---|---|
| Comparative Example 1 | HIL 1 | Compound 103 | — | — | — |
| Comparative Example 2 | HIL 1 | Compound 1 | Compound 106 | — | — |
| Example1 | HIL 1 | Compound 92 | Compound 99 | Compound 124 | — |
| Example 2 | HIL 1 | Compound 1 | Compound 94 | Compound 124 | — |
| Example 3 | HIL 1 | Compound 7 | Compound 94 | Compound 181 | — |
| Example 4 | HIL 1 | Compound 83 | Compound 113 | Compound 124 | — |
| Example 5 | HIL 1 | Compound 3 | Compound 110 | Compound 147 | Compound 194 |
| Example 6 | HIL 1 | Compound 15 | Compound 100 | Compound 163 | Compound 185 |
| Example 7 | HIL 1 | Compound 92 | Compound 105 | Compound 124 | Compound 188 |
| Example 8 | HIL 1 | Compound 1 | Compound 94 | Compound 124 | Compound 207 |
| Example 9 | HIL 1 | Compound 1 | Compound 94 | Compound 124 | Compound 185 |

TABLE 2
| | Driving voltage (V) | Current density (mA/cm$^2$) | Luminance (cd/m$^2$) | Efficiency (cd/A) | Emission color | Half-lifespan (hr @100 mA/cm$^2$) |
|---|---|---|---|---|---|---|
| Comparative Example 1 | 4.76 | 50 | 3363 | 7.5 | Blue | 374 |
| Comparative Example 2 | 4.36 | 50 | 4068 | 8.0 | Blue | 404 |
| Example1 | 4.12 | 50 | 4873 | 8.9 | Blue | 496 |
| Example 2 | 3.92 | 50 | 5076 | 8.6 | Blue | 454 |
| Example 3 | 4.01 | 50 | 5133 | 8.4 | Blue | 467 |
| Example 4 | 4.10 | 50 | 4280 | 8.3 | Blue | 468 |
| Example 5 | 3.88 | 50 | 5302 | 8.7 | Blue | 437 |
| Example 6 | 3.74 | 50 | 5714 | 9.1 | Blue | 499 |
| Example 7 | 3.82 | 50 | 6181 | 9.5 | Blue | 528 |
| Example 8 | 3.95 | 50 | 6332 | 9.6 | Blue | 573 |
| Example 9 | 3.70 | 50 | 6190 | 9.6 | Blue | 587 |
1
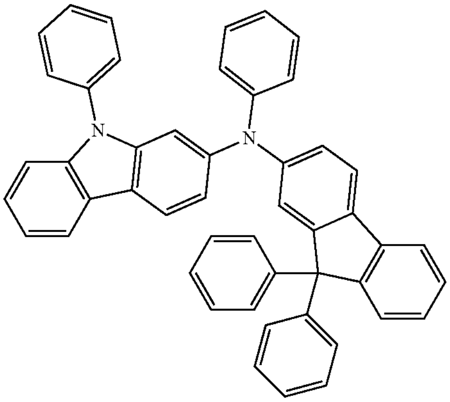
3
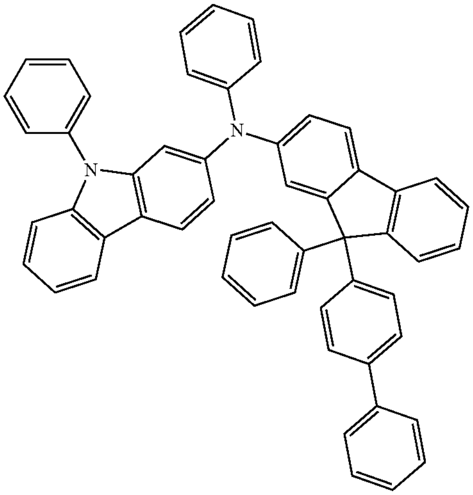
-continued
7
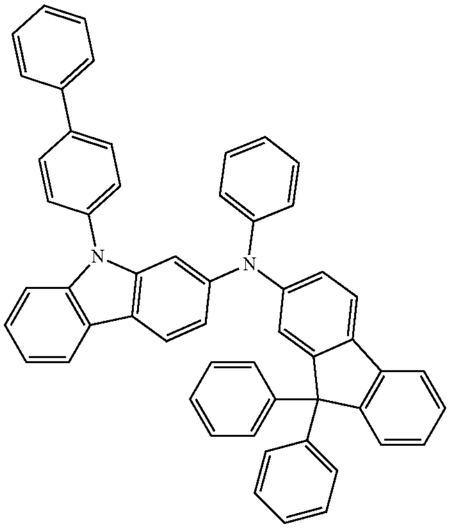
15
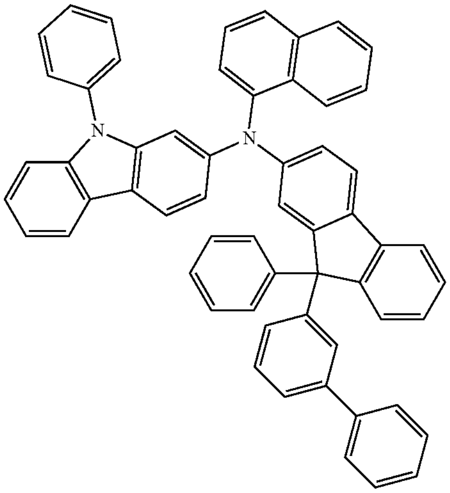
83
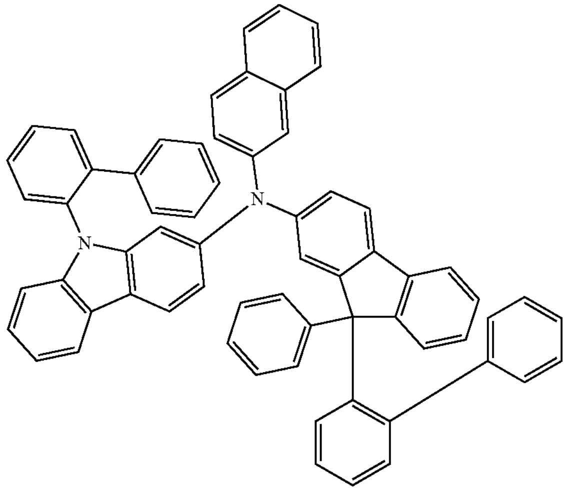

-continued
92
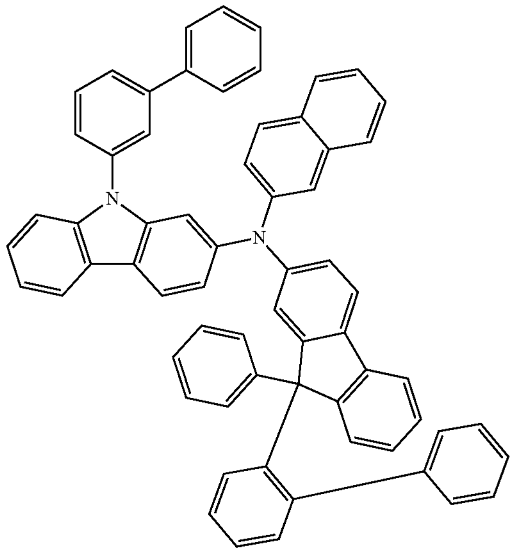
94
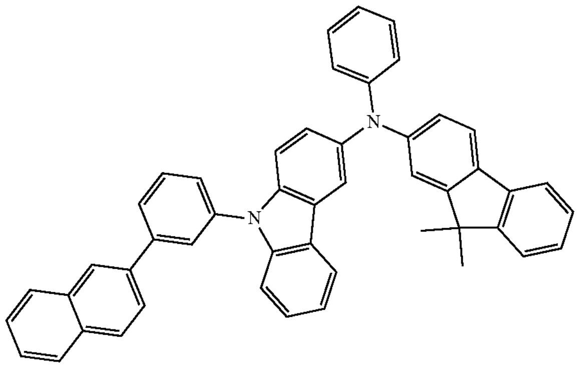
99
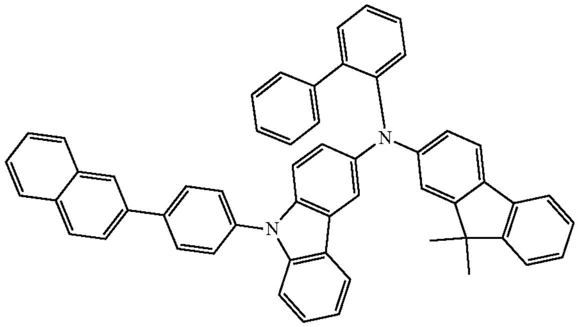
-continued
100
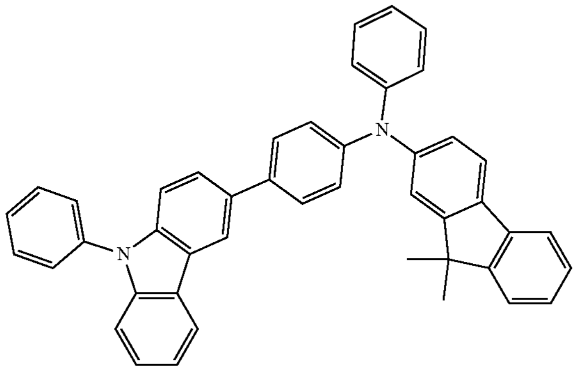
105
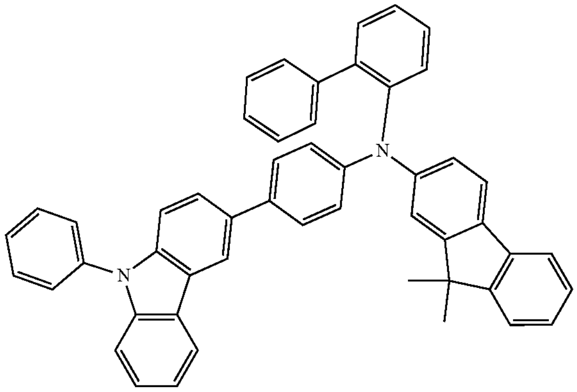
110
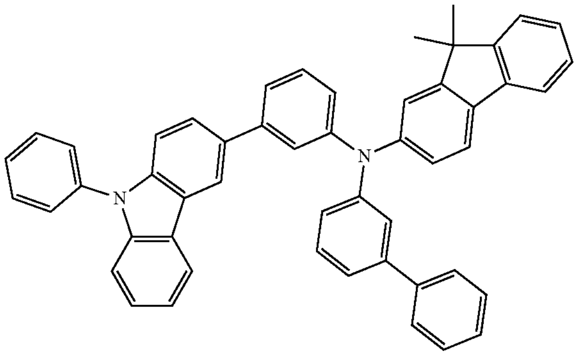
113
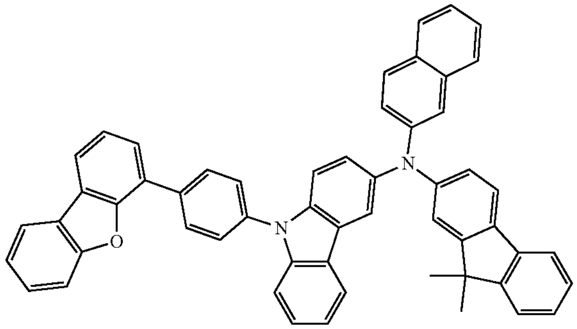

-continued
124
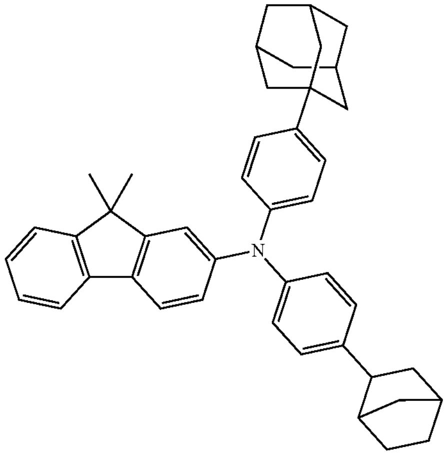
147
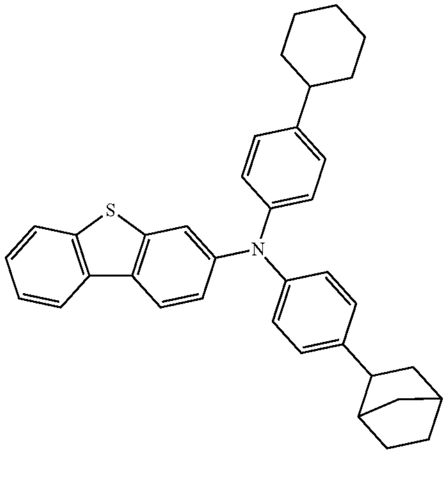
163
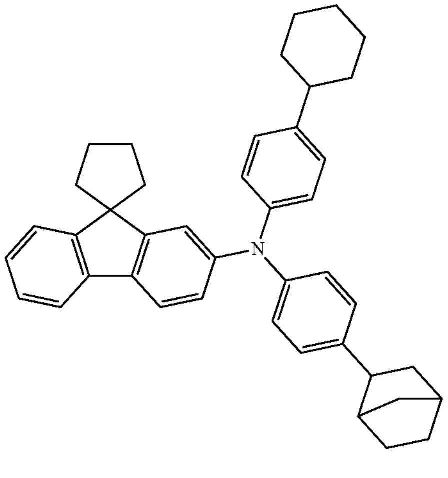
-continued
181
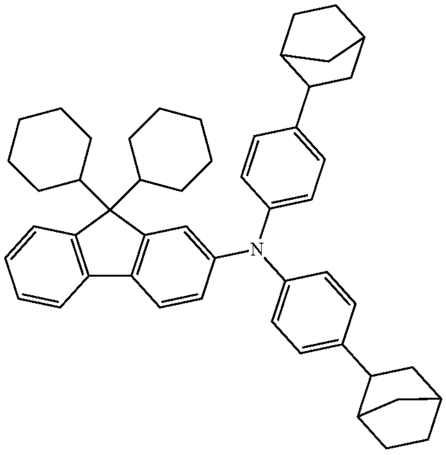
185
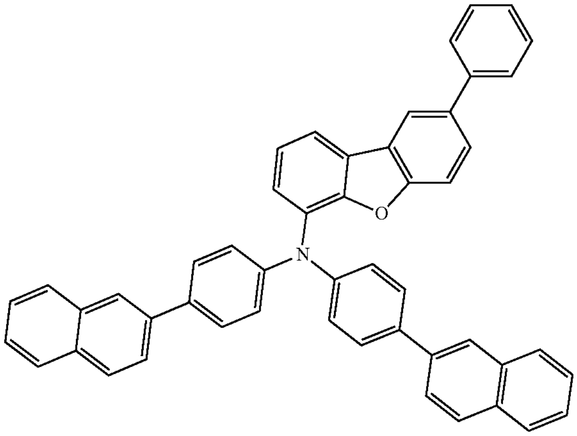
188
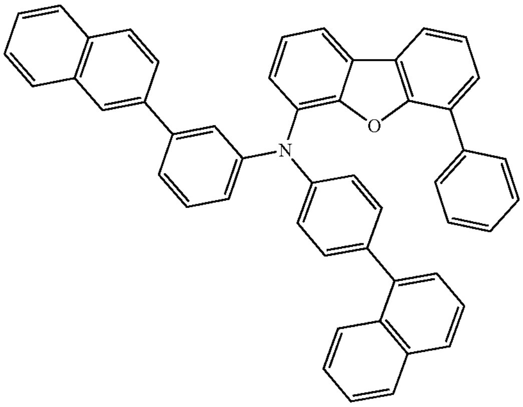

-continued

194

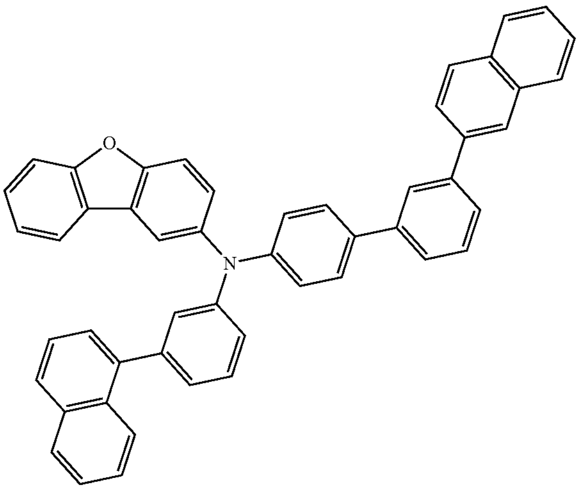

207

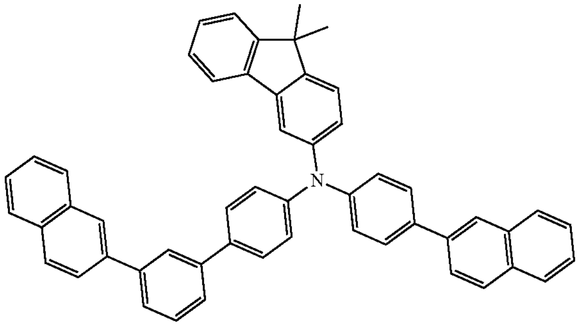

Referring to Table 2, it was confirmed that the light-emitting devices of Examples 1 to 9 using, as a hole-transporting material, the first compound; the second compound; and at least one of the third compound and the fourth compound had excellent characteristics in terms of a driving voltage, luminance, luminescence efficiency, and/or a half lifespan as compared to the light-emitting devices of Comparative Examples 1 and 2.

According to embodiments, a light-emitting device has a low driving voltage, high efficiency, and a long lifespan.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the claims.

What is claimed is:

1. A light-emitting device comprising:

a first electrode;

a second electrode facing the first electrode;

an interlayer between the first electrode and the second electrode and comprising an emission layer;

a first compound represented by Formula 1;

a second compound represented by Formula 2; and at least one of a third compound represented by Formula 3 and a fourth compound represented by Formula 4, wherein the first compound to the fourth compound are different from each other:

[Formula 1]

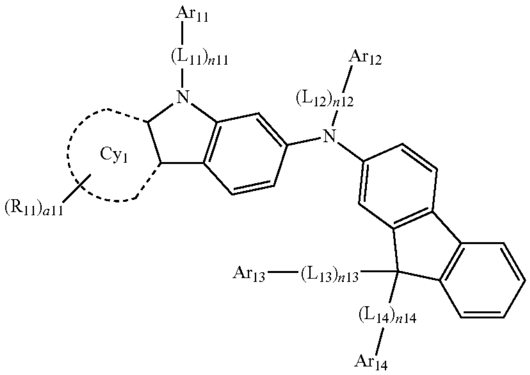

[Formula 2]

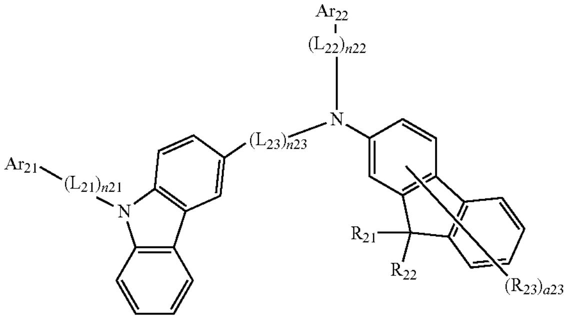

[Formula 3]

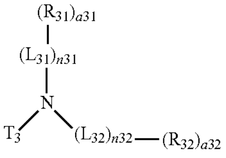

[Formula 4]

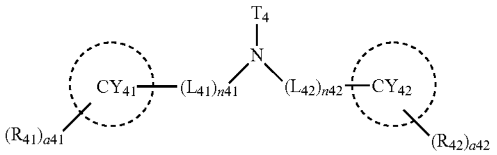

[Formula 5]

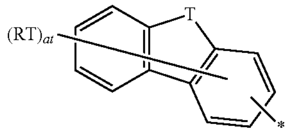

wherein in Formulae 1 to 4, $L_{11}$ to $L_{14}$, $L_{21}$ to $L_{23}$, $L_{31}$, $L_{32}$, $L_{41}$, and $L_{42}$ are each independently a single bond, a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, n11 to n14, n21 to n23, n31, n32, n41, and n42 are each independently an integer from 1 to 3, $Ar_{11}$ to $Ar_{14}$, $Ar_{21}$, and $Ar_{22}$ are each independently a $C_5$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{21}$ and $R_{22}$ are each independently a $C_1$-$C_{30}$ alkyl group or a $C_3$-$C_{30}$ cycloalkyl group, each unsubstituted or substituted with deuterium, —F, a cyano group, a $C_1$-$C_{10}$ alkyl group, or a combination thereof, $R_{31}$ and $R_{32}$ are each independently a $C_3$-$C_{30}$ cycloalkyl group that is unsubstituted or substituted with deuterium, —F, a cyano group, a $C_1$-$C_{10}$ alkyl group, or a combination thereof, $CY_1$ is a benzene group or a naphthalene group, $CY_{41}$ and $CY_{42}$ are each independently a $C_5$-$C_{30}$ carbocyclic group, and $T_3$ and $T_4$ are each independently a group represented by Formula 5, wherein in Formula 5, T is $C(X_1)(X_2)$, O, S, or $N(X_1)$, $X_1$ and $X_2$ are each independently a $C_1$-$C_{30}$ alkyl group unsubstituted or substituted with at least one $R_{10a}$, a $C_2$-$C_{30}$ alkenyl group unsubstituted or substituted with at least one $R_{10a}$, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, and $X_1$ and $X_2$ are optionally linked to each other to form a $C_5$-$C_{30}$ carbocyclic group that is unsubstituted or substituted with at least one $R_{10a}$ or a $C_1$-$C_{30}$ heterocyclic group that is unsubstituted or substituted with at least one $R_{10a}$, wherein in Formulae 1 to 5, $R_{11}$, $R_{23}$, $R_{41}$, $R_{42}$, and RT are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)_2(Q_1)$, or —$P(=O)(Q_1)(Q_2)$, a11 is an integer from 0 to 6, a23 is an integer from 0 to 7, a31 and a32 are each independently an integer from 1 to 5, a41 and a42 are each independently an integer from 0 to 9, at is an integer from 0 to 7,

* indicates a binding site to a neighboring atom, $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or a combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, or a $C_2$-$C_{60}$ heteroarylalkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ arylalkyl group, a $C_2$-$C_{60}$ heteroarylalkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or a combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group, a $C_1$-$C_{60}$ heterocyclic group, a $C_7$-$C_{60}$ arylalkyl group, or a $C_2$-$C_{60}$ heteroarylalkyl group, each unsubstituted or substituted with deuterium, —F, a cyano group, a $C_1$-$C_{60}$ alkyl group, a $C_1$-$C_{60}$ alkoxy group, a phenyl group, a biphenyl group, or a combination thereof.

2. The light-emitting device of claim 1, wherein the first electrode is an anode, the second electrode is a cathode, the interlayer further comprises:

a hole transport region between the emission layer and the first electrode; and an electron transport region between the emission layer and the second electrode, the hole transport region comprises a hole injection layer, a hole transport layer, an emission auxiliary layer, an electron blocking layer, or a combination thereof, and the electron transport region comprises a buffer layer, a hole blocking layer, an electron control layer, an electron transport layer, an electron injection layer, or a combination thereof.

3. The light-emitting device of claim 2, wherein the hole transport region comprises at least one of a hole injection layer, a hole transport layer, and an electron blocking layer, and the at least one of the hole injection layer, the hole transport layer, and the electron blocking layer comprises:

the first compound;

the second compound; and at least one of the third compound and the fourth compound.

4. The light-emitting device of claim 2, wherein the hole transport region comprises a hole transport layer, the hole transport layer comprises a first hole transport layer, a second hole transport layer, and a third hole transport layer, the first hole transport layer is between the first electrode and the second hole transport layer, the first hole transport layer comprises the first compound, the second hole transport layer is between the first hole transport layer and the third hole transport layer, the second hole transport layer comprises the second compound, and the third hole transport layer comprises at least one of the third compound and the fourth compound.

5. The light-emitting device of claim 2, wherein the hole transport region comprises a hole transport layer, the hole transport layer comprises a first hole transport layer, a second hole transport layer, a third hole transport layer, and a fourth hole transport layer, the first hole transport layer is between the first electrode and the second hole transport layer, the first hole transport layer comprises the first compound, the second hole transport layer is between the first hole transport layer and the third hole transport layer, the second hole transport layer comprises the second compound, the third hole transport layer is between the second hole transport layer and the fourth hole transport layer, the third hole transport layer comprises the third compound, and the fourth hole transport layer comprises the fourth compound.

6. The light-emitting device of claim 1, wherein in Formulae 1 to 4, $L_{11}$ to $L_{14}$, $L_{21}$ to $L_{23}$, $L_{31}$, $L_{32}$, $L_{41}$, and $L_{42}$ are each independently:

a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$, and $R_{10a}$ is the same as defined in Formulae 1 to 4.

7. The light-emitting device of claim 1, wherein in Formulae 1 to 4, $L_{11}$ to $L_{14}$, $L_{21}$ to $L_{23}$, $L_{31}$, $L_{32}$, $L_{41}$, and $L_{42}$ are each independently a single bond or phenylene.

8. The light-emitting device of claim 1, wherein in Formulae 1 and 2, $Ar_{11}$ to $Ar_{14}$, $Ar_{21}$, and $Ar_{22}$ are each independently:

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, a benzoisothiazolyl group, a benzoxazolyl group, a benzoisoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, $—P(=O)(Q_{31})(Q_{32})$, or a combination thereof, and $Q_{31}$ to $Q_{33}$ are each independently:

$—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, or $—CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, or a combination thereof.

9. The light-emitting device of claim 1, wherein in Formulae 1 and 2, $Ar_{11}$ to $Ar_{14}$, $Ar_{21}$, and $Ar_{22}$ are each independently a phenyl group, a naphthyl group, a phenanthrenyl group, an anthracenyl group, a dibenzothiophenyl group, or a dibenzofuranyl group, each unsubstituted or substituted with deuterium, —F, a cyano group, a $C_1$-$C_{20}$ alkyl group, a $C_1$-$C_{20}$ alkoxy group, a phenyl group, or a combination thereof.

10. The light-emitting device of claim 1, wherein in Formula 2, $R_{21}$ and $R_{22}$ are identical to each other.

11. The light-emitting device of claim 1, wherein in Formula 3, $R_{31}$ and $R_{32}$ are each independently a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, or a bicyclo[2.2.2]octyl group, each unsubstituted or substituted with deuterium, —F, a cyano group, a $C_1$-$C_{10}$ alkyl group, or a combination thereof.

12. The light-emitting device of claim 1, wherein in Formula 4, $CY_{41}$ and $CY_{42}$ are each a naphthalene group, or one of $CY_{41}$ and $CY_{42}$ is a naphthalene group, and the other of $CY_{41}$ and $CY_{42}$ is a benzene group or a phenanthrene group.

13. The light-emitting device of claim 1, wherein in Formulae 1, 2, and 4, $R_{11}$ is hydrogen, deuterium, or —F, and $R_{23}$, $R_{41}$, and $R_{42}$ are each independently:

hydrogen, deuterium, or —F; or a phenyl group that is unsubstituted or substituted with deuterium, —F, a cyano group, a $C_1$-$C_{20}$ alkyl group, or a combination thereof.

14. The light-emitting device of claim 1, wherein in Formula 5, $X_1$ and $X_2$ are each independently:

a $C_1$-$C_{10}$ alkyl group that is unsubstituted or substituted with deuterium, —F, a cyano group, or a combination thereof; or a $C_2$-$C_{10}$ alkenyl group, a cyclopropyl group, a cyclobutyl group, a cyclopentyl group, a cyclohexyl group, a cycloheptyl group, a cyclooctyl group, an adamantanyl group, a bicyclo[2.2.1]heptyl group, a bicyclo[1.1.1]pentyl group, a bicyclo[2.1.1]hexyl group, a bicyclo[2.2.2]octyl group, phenyl group, a naphthyl group, a pyridinyl group, a pyrimidinyl group, a pyrazinyl group, a pyridazinyl group, or a triazinyl group, each unsubstituted or substituted with deuterium, —F, a cyano group, a $C_1$-$C_{10}$ alkyl group, or a combination thereof.

15. The light-emitting device of claim 1, wherein in Formula 5, when T is $C(X_1)(X_2)$, $X_1$ and $X_2$ are identical to each other.

16. The light-emitting device of claim 1, wherein in Formula 5, RT is:

hydrogen, deuterium, —F, or a cyano group; or a $C_6$-$C_{10}$ aryl group that is unsubstituted or substituted with deuterium, —F, a cyano group, a $C_1$-$C_{10}$ alkyl group, a $C_1$-$C_{10}$ alkoxy group, or a combination thereof.

17. The light-emitting device of claim 1, wherein the emission layer emits blue light having a maximum emission wavelength in a range of about 430 nm to about 490 nm.

18. An electronic apparatus comprising the light-emitting device of claim 1.

19. The electronic apparatus of claim 18, further comprising a thin-film transistor, wherein the thin-film transistor comprises a source electrode and a drain electrode, and the first electrode of the light-emitting device is electrically connected to the source electrode or the drain electrode.

20. The electronic apparatus of claim 19, further comprising a color filter, a color conversion layer, a touch screen layer, a polarizing layer, or a combination thereof.

* * * * *